United States Patent
Wen et al.

(10) Patent No.: US 12,358,912 B2
(45) Date of Patent: Jul. 15, 2025

(54) CRYSTALLINE FORMS OR AMORPHOUS FORMS OF N-(PHENYL SULFONYL) BENZAMIDE COMPOUNDS OR ITS SALTS OR SOLVATES

(71) Applicants: ASCENTAGE PHARMA (SUZHOU) CO., LTD., Suzhou (CN); ASCENTAGE PHARMA GROUP CORP LIMITED, Hong Kong (CN)

(72) Inventors: Jianfeng Wen, Suzhou (CN); Jianpeng Feng, Suzhou (CN); Tianzhu Wu, Suzhou (CN); Weidong Li, Suzhou (CN); Yanqiong Lin, Suzhou (CN)

(73) Assignees: ASCENTAGE PHARMA (SUZHOU) CO., LTD., Jiangsu (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 118 days.

(21) Appl. No.: 17/423,745

(22) PCT Filed: Mar. 5, 2021

(86) PCT No.: PCT/CN2021/079392
§ 371 (c)(1),
(2) Date: Jul. 16, 2021

(87) PCT Pub. No.: WO2021/175321
PCT Pub. Date: Sep. 10, 2021

(65) Prior Publication Data
US 2023/0159518 A1 May 25, 2023

(30) Foreign Application Priority Data

Mar. 6, 2020 (WO) ................ PCT/CN2020/078266
Mar. 4, 2021 (CN) ......................... 202110237803.9

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
USPC ........................................................ 544/362
See application file for complete search history.

(56) References Cited

U.S. PATENT DOCUMENTS 10,221,174 B2    3/2019   Wang et al.

FOREIGN PATENT DOCUMENTS

| CN | 109311871 A | 2/2019 | |
|----|-------------|--------|---|
| CN | 110772639 A | 2/2020 | |
| CN | 110776507 A | 2/2020 | |
| WO | WO2018027097 A1 * | 2/2018 | ........... C07D 471/04 |

(Continued)

OTHER PUBLICATIONS

International Search Report issued in PCT/CN2021/079392, dated May 31, 2021.

(Continued)

*Primary Examiner* — Jeffrey S Lundgren
*Assistant Examiner* — Heather Dahlin
(74) *Attorney, Agent, or Firm* — Barnes & Thornburg LLP

(57) ABSTRACT

The present invention provides crystalline forms or amorphous forms of N-(phenylsulfonyl) benzoamide compound or its salts or solvates used as a Bcl-2 inhibitor, and the preparation method and the application thereof.

11 Claims, 139 Drawing Sheets

(56) References Cited

FOREIGN PATENT DOCUMENTS

WO     2020/024820 A1     2/2020
WO     2020/024834 A1     2/2020

OTHER PUBLICATIONS

Amundson, Sally A., et al. "An Informatics Approach Identifying Markers of Chemosensitivity in Human Cancer Cell Lines", Nov. 1, 2000, pp. 6101-6110, vol. 60, No. 21.
Danial, Nika N., et al. "Cell Death: Critical Control Points", Cell, Jan. 23, 2004, pp. 205-219, vol. 116.
Kirkin, V., et al. "The role of Bcl-2 family members in tumorigenesis", Biochimica et Biophysica Acta, 2004, pp. 229-249, vol. 1644.
Zhang, Jason Y. "Apoptosis-based anticancer drugs." Nature Reviews. Drug Discovery 1.2 (2002): 101.

\* cited by examiner

CRYSTALLINE FORMS OR AMORPHOUS FORMS OF N-(PHENYL SULFONYL) BENZAMIDE COMPOUNDS OR ITS SALTS OR SOLVATES

CROSS REFERENCE TO RELATED APPLICATIONS

This application is a national phase of International Patent Application No. PCT/CN2021/079392, filed Mar. 5, 2021, which claims priority to Chinese Patent Application No. 202110237803.9, filed Mar. 4, 2021, and to International Patent Application No. PCT/CN2020/078266, filed Mar. 6, 2020, all of which are incorporated by reference herein in their entirety.

FIELD OF THE INVENTION

The invention relates to the field of pharmaceutical chemistry, in particular to a crystalline form or amorphous form of N-(phenyl sulfonyl) benzamide compound or its salt and solvant used as a Bcl-2 inhibitor, as well as a preparation method and an application thereof.

BACKGROUND OF THE INVENTION

Apoptosis is a process of programmed cell death and an essential biological process for tissue homeostasis. In mammals, it has been shown to regulate early embryonic development. Toward the end of life, cell death is a default mechanism by whcih potentially dangerous cells are eliminated such as cells carrying cancer defects. Several apoptotic pathways are known. One of the most important apoptotic pathways involves the Bcl-2 protein family, which is a key regulator of the mitochondrial (also known as "intrinsic") pathway of apoptosis. See Danial and Korsmeyer, Cell 776:205-219 (2004). BH1, BH2, BH3 and BH4 of structural homologous domains are characteristics of the Bcl-2 family of proteins. The Bcl-2 protein family can be further divided into three subgroups. It depends on how many homologous domains and biological activities each protein has, that is whether it has pro-apoptotic or anti-apoptotic functions.

The first subgroup of Bcl-2 proteins contains proteins with all four homologous domains, namely BH1, BH2, BH3, and BH4. Their general function is anti-apoptosis, that is which protects cells from starting the process of cell death. Proteins such as Bcl-2, Bcl-W, Bcl-XL, Mel-1, and BFL-1/AL are members of the first subgroup. The proteins belonging to the second subgroup of Bcl-2 protein contain three homologous domains of BH1, BH2 and BH3, and have effects of promoting apoptosis. The two main representative proteins of the second subgroup are Bax and Bak. The third subgroup of Bcl-2 protein consists of proteins containing only the BH3 domain, and members of this subgroup are often referred to as "BH3-only proteins". Their biological effects on cells are pro-apoptotic. BIM, BID, BAD, BIK, NOXA, HRK, BMF, and PUMA are examples of the third subgroup of protein family.

The disordered apoptotic pathway involes pathologies of many important diseases, such as neurodegenerative disorders (up-regulated apoptosis), such as Alzheimer's disease; And proliferative diseases (down-regulated apoptosis), such as cancers, autoimmune diseases, and prothrombotic disorders.

Downregulated apoptosis (more specifically, the Bcl-2 protein family) can be involved in the onset of cancerous malignancies. Studies have shown, for example, that the anti-apoptotic proteins Bcl-2 and Bcl-XL are overexpressed in many cancer cell types. See Zhang, Nature Reviews Drug Discovery 1:101 (2002); Kirkin et al., Biochimica et Biophysica Acta 1644:229-249 (2004); And Amundson et al., Cancer Research 60:6101-6110(2000). The effects of the disorder are to alter the survival of cells that would otherwise undergo apoptosis under normal conditions. Replication of defects associated with unregulated proliferation is thought to be the starting point of cancer evolution.

These findings make possible new strategies for drug discovery that target cancer. WO2018/027097A1 discloses N-(phenylsulfonyl) benzoamide and related compounds for the treatment of diseases, disorders or conditions (e.g., cancer) that respond to BCl-2 protein inhibition, and specifically discloses representative compound: (S)—N-((4-(((1,4-dioxan-2-yl) methyl) amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide (Compound 1), its structure formula is as follows:

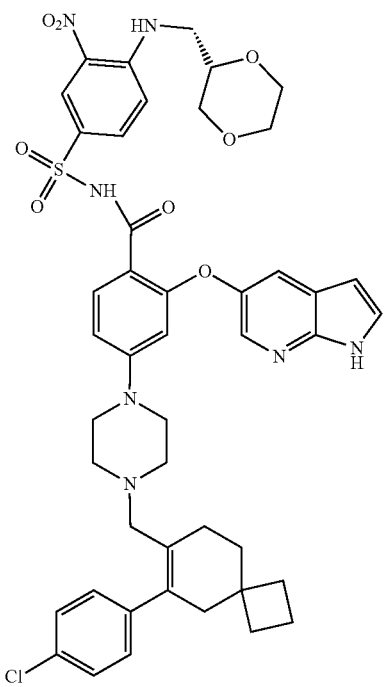

However, the current literature including the patent application, mainly reported the structure and pharmacological activity of the compounds without any studies and reports on polymorphs, amorphous and other structural forms.

Due to the influence of various factors such as configuration, conformation, molecular arrangement, molecular interaction and eutectic mixtures of molecular structure of solid matter, the arrangement of molecular lattice space is different and two or more different crystal structures are formed. This Phenomenon is called "Polymorphism Phenomenon" or "allomorphism". "Polymorphism phenomenon" widely exists in solid drugs. Physical and chemical properties between different crystal forms of the same drug can exist differences, such as appearance, density, hardness, melting point, solubility, stability, dissolution, dissolution rate and bioavailability can be significantly different. This phenomenon is particularly evident in oral solid preparations. Further more, the existent forms and quantities of polycrystalline compounds are unpredictable. Different crystalline forms of the same drug have significant differences in solubility, melting point, density, stability, etc., which affect the uniformity, bioavailability, efficacy and safety etc. of the drug to different degrees.

In addition to polycrystalline form, some solid compounds may have amorphous forms. The amorphous refers to the structure of some amorphous regions (amorphous regions) of incomplete crystals or forms of some amorphous solids (amorphous regions). For a specific solid drug, the existent forms and quantities of its amorphous form are also unpredictable, and may also have a significant impact on the solubility, melting point, density, stability, etc.

Therefore, in the process of new drug research and development, it is necessary to considery multiple factors to carry out comprehensive screening of drug compounds in crystalline forms and amorphous forms. In particular, for the above compound of Formula 1 as inhibitor of BCL-2, there are potential medicinal values and clinical values to develop crystalline or amorphous forms with possible medical values of the compound or their salts and solvates, to improve the stability, solubility, bioavailability and other properties of the compounds.

SUMMARY OF THE INVENTION

The present invention provides crystalline forms or amorphous forms of N-(phenyl sulfonyl) benzoamide compounds or their salts and solvates used as BCl-2 inhibitors, as well as preparation methods and applications thereof. The crystalline forms or amorphous forms of the invention are of great values for drug development, preparation development and production.

In the following descriptions, certain specific details are described to provide thorough understandings of the various embodiments of the invention. However, the persons skilled in the art will understand that the invention can be practiced without the details. The following descriptions of several embodiments are done with the understanding that the present disclosure is regarded as an example of the subject matter for which protection is sought, and is not intended to limit the attached claims to the particular embodiments shown. The headings used throughout the invention are provided for convenience only and shall not be construed as limiting claims in any way. The embodiments shown under any heading may be combined with the embodiments shown under any other heading.

In addition, when referring to, for example, XRPD patterns, DSC curves, TGA plots, etc., the terms "substantially as shown" mean that they are not necessarily the same as those described herein, but when considered by ordinary persons skilled in the art, the spectrum falls within the limits of experimental error or deviation.

In the first aspect, the present invention provides the amorphous or crystalline forms of the compound 1 below or its salts or solvates thereof:

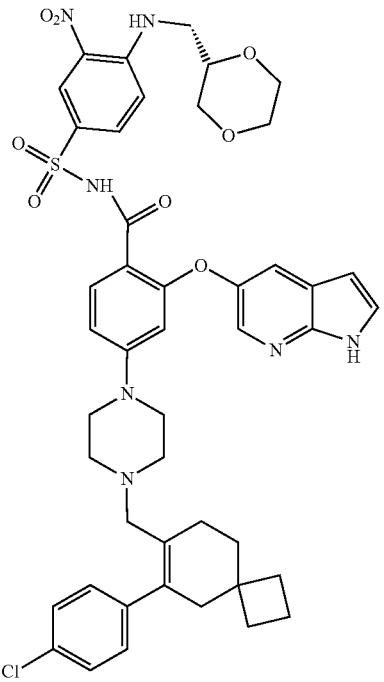

compound 1

The chemical name of the compound is (S)—N-((4-(((1, 4-dioxan-2-yl) methyl) amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl) benzamide.

Specifically, the form may be the following specific forms:

1) The Crystalline Form I of Compound 1

In one embodiment, the form is the crystalline form I of the compound 1, which is characterized by having at least three, at least four, at least five, at least six or seven characteristic peaks at the following positions in the X-ray powder diffraction (XRPD) pattern represented by angle 2θ: 7.57±0.2°, 16.41±0.2°, 17.76±0.2°, 18.44±0.2°, 19.39±0.2°, 20.34±0.2° and 21.08±0.2°.

In some preferred embodiments, the form also has one or more characteristic peaks at the following positions in the XRPD pattern represented by angle 2θ: 4.39±0.2°, 11.23±0.2°, 14.59±0.2°, 15.17±0.2°, 15.87±0.2°, 21.69±0.2°, and 27.65±0.2°.

In some preferred embodiments, the form has XRPD characteristic peaks at the positions substantially as shown in Table 1 below and/or an X-ray powder diffraction (XRPD) pattern substantially as shown in FIG. 1.

TABLE 1

| Angle[°2θ] ± 0.2° | d-value[Å] | Relative intensity [%] |
|---|---|---|
| 4.398789 | 20.08838 | 30.77 |
| 7.578719 | 11.66521 | 100.00 |
| 11.238130 | 7.87361 | 27.91 |
| 13.137090 | 6.73945 | 16.03 |
| 14.596170 | 6.06887 | 38.83 |
| 15.172880 | 5.83947 | 43.81 |
| 15.878410 | 5.58155 | 47.72 |
| 16.418210 | 5.39924 | 86.91 |
| 17.760590 | 4.99407 | 60.85 |
| 18.445950 | 4.81003 | 65.18 |

TABLE 1-continued

| Angle[°2θ] ± 0.2° | d-value[Å] | Relative intensity [%] |
|---|---|---|
| 19.396030 | 4.57651 | 51.88 |
| 20.347790 | 4.36455 | 62.66 |
| 21.085680 | 4.21345 | 51.26 |
| 21.692670 | 4.09690 | 48.84 |
| 22.778780 | 3.90396 | 15.22 |
| 24.749620 | 3.59737 | 10.92 |
| 25.395710 | 3.50729 | 19.00 |
| 25.964140 | 3.43178 | 18.56 |
| 27.651780 | 3.22605 | 38.42 |

In some preferred embodiments, they also have the following characteristics:
1) In the thermogravimetric analysis (TGA) plot, there is a weight loss of 2.4±0.2% by weight before 150° C.;
2) In the DSC curve, there are three endothermic peaks at the peak temperature of 81.6±2.0° C. and the initial temperature of 148.9±2.0° C. and 179.9±2.0° C.;
3) the TGA plot substantially as shown in FIG. 2; and/or
4) the DSC curve substantially as shown in FIG. 3.

2) The Crystalline Form II of Compound 1

In one embodiment, the form is the crystalline form II of the compound 1, which is characterized by having at least three, at least four or five characteristic peaks at the following positions in the XRPD pattern represented by angle 2θ: 7.22±0.2°, 14.48±0.2°, 18.73±0.2°, 19.08±0.2° and 20.50±0.2°.

In some preferred embodiments, the form has XRPD characteristic peaks at the positions substantially as shown in Table 2 below and/or an XRPD pattern substantially as shown in FIG. 4.

TABLE 2

| Angle[°2θ] ± 0.2° | d-value[Å] | Relative intensity [%] |
|---|---|---|
| 6.222398 | 14.20454 | 17.57 |
| 7.229177 | 12.22843 | 100.00 |
| 7.971669 | 11.09105 | 12.06 |
| 11.349910 | 7.79632 | 16.18 |
| 12.762840 | 6.93621 | 2.43 |
| 13.259160 | 6.67767 | 6.11 |
| 13.697400 | 6.46499 | 13.28 |
| 14.488100 | 6.11389 | 30.52 |
| 15.677430 | 5.65265 | 5.73 |
| 16.022260 | 5.53177 | 7.51 |
| 17.179410 | 5.16168 | 5.80 |
| 17.879770 | 4.96105 | 14.52 |
| 18.737960 | 4.73572 | 23.56 |
| 19.087960 | 4.64967 | 28.67 |
| 19.933120 | 4.45439 | 8.99 |
| 20.504600 | 4.33152 | 22.48 |
| 21.079760 | 4.21462 | 10.79 |
| 21.999300 | 4.04049 | 12.95 |
| 23.071660 | 3.85506 | 3.88 |
| 23.477170 | 3.78938 | 4.85 |
| 24.142830 | 3.68639 | 6.42 |
| 25.724490 | 3.46321 | 5.77 |
| 26.138000 | 3.40935 | 6.54 |
| 27.692480 | 3.22140 | 3.24 |
| 29.250890 | 3.05323 | 1.80 |
| 33.365200 | 2.68554 | 1.46 |

In some preferred embodiments, they also have the following characteristics:
1) In the TGA plot, there is a weight loss of 3.5±0.2% by weight before 150° C.;
2) In the DSC curve, there are four endothermic peaks at the peak temperatures of 68.9±2.0° C. and 140.3±2.0° C., and the initial temperatures of 148.6±2.0° C. and 181.8±2.0° C.;
3) the TGA plot substantially as shown in FIG. 5; and/or
4) the DSC curve substantially as shown in FIG. 6.

3) The Crystalline Form III of Compound 1

In one embodiment, the form is the crystalline form III of the compound 1, which is characterized by having at least three, at least four or five characteristic peaks at the following positions in the XRPD pattern represented by angle 2θ: 5.97±0.2°, 18.01±0.2°, 21.57±0.2°, 24.56±0.2° and 28.59±0.2°.

In some preferred embodiments, the form also has one or more characteristic peaks at the following positions in the XRPD pattern represented by angle 2θ: 13.28±0.2°, 16.30±0.2°, 16.67±0.2°, 17.61±0.2°, 18.59±0.2°, 18.91±0.2°, 19.67±0.2° and 20.86±0.2°.

In some preferred embodiments, the form has XRPD characteristic peaks at the positions substantially as shown in Table 3 below and/or an XRPD pattern substantially as shown in FIG. 7.

TABLE 3

| Angle[°2θ] ± 0.2° | d-value[Å] | Relative intensity [%] |
|---|---|---|
| 5.975145 | 14.79176 | 47.52 |
| 6.717507 | 13.15867 | 9.24 |
| 8.190475 | 10.79524 | 5.00 |
| 9.408436 | 9.40031 | 17.14 |
| 9.796705 | 9.02861 | 7.09 |
| 12.438820 | 7.11616 | 19.19 |
| 13.288440 | 6.66302 | 34.01 |
| 13.475320 | 6.57104 | 17.29 |
| 15.800150 | 5.60903 | 13.09 |
| 16.304870 | 5.43651 | 34.15 |
| 16.675740 | 5.31643 | 27.97 |
| 17.619110 | 5.03385 | 34.95 |
| 18.018940 | 4.92304 | 41.87 |
| 18.590560 | 4.77294 | 27.20 |
| 18.914260 | 4.69198 | 31.06 |
| 19.670020 | 4.51338 | 21.59 |
| 20.032360 | 4.43255 | 11.67 |
| 20.274080 | 4.38025 | 16.97 |
| 20.865780 | 4.25735 | 29.78 |
| 21.575430 | 4.11890 | 100.00 |
| 22.252120 | 3.99515 | 10.58 |
| 22.750500 | 3.90875 | 8.91 |
| 23.106110 | 3.84939 | 7.10 |
| 24.081160 | 3.69569 | 9.51 |
| 24.561610 | 3.62448 | 67.94 |
| 25.214900 | 3.53203 | 17.60 |
| 25.925200 | 3.43685 | 3.65 |
| 26.898120 | 3.31471 | 3.21 |
| 28.022590 | 3.18420 | 3.65 |
| 28.595660 | 3.12168 | 35.57 |
| 29.692590 | 3.00881 | 5.12 |
| 30.419620 | 2.93853 | 2.65 |
| 33.853320 | 2.64793 | 0.95 |
| 34.955410 | 2.56693 | 3.59 |
| 37.904080 | 2.37375 | 1.69 |

In some preferred embodiments, they also have the following characteristics:
1) In the TGA plot, there is a weight loss of 1.0±0.2% by weight before 150° C.;
2) In the DSC curve, there are two endothermic peaks at the initial temperatures of 169.9±2.0° C. and 232.0±2.0° C.;
3) the TGA plot substantially as shown in FIG. 8; and/or
4) the DSC curve substantially as shown in FIG. 9.

4) the 1, 4-Dioxane Solvate Crystalline Form IV of Compound 1

In one embodiment, the form is the 1, 4-dioxane solvate crystalline form IV of the compound 1, which is characterized by having at least three, at least four, at least five or six characteristic peaks at the following positions in the XRPD pattern represented by angle 2θ: 4.31±0.2°, 18.31±0.2°, 19.52±0.2°, 19.71±0.2°, 21.15±0.2° and 21.78±0.2°.

In some preferred embodiments, the form also has one or more characteristic peaks at the following positions in the XRPD pattern represented by angle 2θ: 8.50±0.2°, 15.95±0.2°, 16.54±0.2°, 17.45±0.2° and 20.42±0.2°.

In some preferred embodiments, the form has XRPD characteristic peaks at the positions substantially as shown in Table 4 below and/or an XRPD pattern substantially as shown in FIG. 10.

TABLE 4

| Angle[°2θ] ± 0.2° | d-value[Å] | Relative intensity [%] |
|---|---|---|
| 4.312485 | 20.49021 | 78.81 |
| 8.508758 | 10.39213 | 40.46 |
| 13.923320 | 6.36059 | 21.12 |
| 15.950660 | 5.55644 | 40.41 |
| 16.540260 | 5.35967 | 47.83 |
| 17.451310 | 5.08187 | 45.73 |
| 18.319830 | 4.84286 | 100.00 |
| 19.529070 | 4.54563 | 87.47 |
| 19.711060 | 4.50407 | 88.13 |
| 20.425160 | 4.34819 | 52.14 |
| 21.153840 | 4.20002 | 85.74 |
| 21.787240 | 4.07933 | 73.67 |
| 22.910060 | 3.88188 | 21.49 |
| 24.367900 | 3.65285 | 12.53 |
| 25.922770 | 3.43717 | 24.88 |

In some preferred embodiments, they also have the following characteristics:
1) In the TGA plot, there is a weight loss of 12.8±0.2% by weight before 150° C.;
2) In the DSC curve, there are two endothermic peaks at the initial temperatures of 120.6±2.0° C. and 206.2±2.0° C.;
3) the TGA plot substantially as shown in FIG. 11; and/or
4) the DSC curve substantially as shown in FIG. 12.

5) The Ethyl Acetate Solvate Crystalline Form V of Compound 1

In one embodiment, the form is the ethyl acetate solvate crystalline form V of the compound 1, which is characterized by having at least three, at least four or five characteristic peaks at the following positions in the XRPD pattern represented by angle 2θ: 7.17±0.2°, 13.75±0.2°, 18.40±0.2°, 18.69±0.2° and 19.96±0.2°.

In some preferred embodiments, the form also has one or more characteristic peaks at the following positions in the XRPD pattern represented by angle 2θ: 7.64±0.2°, 14.34±0.2° and 15.78±0.2°.

In some preferred embodiments, the form has XRPD characteristic peaks at the positions substantially as shown in Table 5 below and/or an XRPD pattern substantially as shown in FIG. 13.

TABLE 5

| Angle[°2θ] ± 0.2° | d-value[Å] | Relative intensity [%] |
|---|---|---|
| 7.172810 | 12.32440 | 100.00 |
| 7.641418 | 11.56963 | 21.10 |
| 11.335770 | 7.80601 | 12.96 |
| 12.074100 | 7.33028 | 1.42 |
| 13.757680 | 6.43680 | 29.91 |
| 14.343160 | 6.17535 | 20.82 |
| 15.315150 | 5.78554 | 16.33 |
| 15.780080 | 5.61611 | 21.88 |
| 17.872990 | 4.96291 | 13.40 |
| 18.406510 | 4.82025 | 27.90 |
| 18.699270 | 4.74543 | 34.32 |
| 19.465670 | 4.56029 | 18.96 |

TABLE 5-continued

| Angle[°2θ] ± 0.2° | d-value[Å] | Relative intensity [%] |
|---|---|---|
| 19.969240 | 4.44642 | 25.78 |
| 20.732010 | 4.28452 | 10.54 |
| 21.553970 | 4.12295 | 12.88 |
| 21.826540 | 4.07208 | 11.77 |
| 23.280790 | 3.82090 | 12.00 |
| 24.033230 | 3.70295 | 2.74 |
| 24.892100 | 3.57710 | 5.27 |
| 25.379920 | 3.50944 | 12.18 |
| 28.958110 | 3.08343 | 9.76 |

In some preferred embodiments, they also have the following characteristics:
1) In the TGA plot, there is a weight loss of 1.88±0.2% by weight before 150° C.;
2) In the DSC curve, there are three endothermic peaks at the peak temperatures of 103.8±2.0° C. and the initial temperatures of 141.9±2.0° C. and 182.6±2.0° C.;
3) the TGA plot substantially as shown in FIG. 14; and/or
4) the DSC curve substantially as shown in FIG. 15.

6) The Methylbenzene Solvate Crystalline Form VI of Compound 1

In one embodiment, the form is the methylbenzene solvate crystalline form VI of the compound 1, which is characterized by having at least three, at least four or five characteristic peaks at the following positions in the XRPD pattern represented by angle 2θ: 7.16±0.2°, 18.02±0.2°, 18.76±0.2°, 19.97±0.2° and 20.64±0.2°.

In some preferred embodiments, the form has XRPD characteristic peaks at the positions substantially as shown in Table 6 below and/or an XRPD pattern substantially as shown in FIG. 16.

TABLE 6

| Angle[°2θ] ± 0.2° | d-value[Å] | Relative intensity [%] |
|---|---|---|
| 7.164968 | 12.33787 | 100.00 |
| 7.642807 | 11.56753 | 17.15 |
| 11.238760 | 7.87317 | 9.75 |
| 14.277000 | 6.20381 | 14.82 |
| 15.329030 | 5.78033 | 14.07 |
| 15.697340 | 5.64553 | 11.79 |
| 18.021390 | 4.92238 | 26.26 |
| 18.769620 | 4.72781 | 32.94 |
| 19.973060 | 4.44558 | 34.67 |
| 20.642610 | 4.30287 | 18.73 |
| 21.526950 | 4.12806 | 13.57 |
| 25.393740 | 3.50756 | 10.64 |
| 28.886500 | 3.09091 | 5.57 |

In some preferred embodiments, they also have the following characteristics:
1) In the TGA plot, there is a weight loss of 3.7±0.2% by weight before 150° C.;
2) In the DSC curve, there are two endothermic peaks at the initial temperatures of 140.9±2.0° C. and 181.3±2.0° C.;
3) the TGA plot substantially as shown in FIG. 17; and/or
4) the DSC curve substantially as shown in FIG. 18.

7) The Methylbenzene Solvate Crystalline Form VII of Compound 1

In one embodiment, the form is the methylbenzene solvate crystalline form VII of the compound 1, which is characterized by having at least three, at least four or five characteristic peaks at the following positions in the XRPD pattern represented by angle 2θ: 5.80±0.2°, 17.81±0.2°, 18.59±0.2°, 20.10±0.2° and 21.65±0.2°.

In some preferred embodiments, the form also has one or more characteristic peaks at the following positions in the XRPD pattern represented by angle 2θ: 7.52±0.2°, 16.48±0.2°, 20.60±0.2° and 22.67±0.2°.

In some preferred embodiments, the form has XRPD characteristic peaks at the positions substantially as shown in Table 7 below and/or an XRPD pattern substantially as shown in FIG. 19.

TABLE 7

| Angle[°2θ] ± 0.2° | d-value[Å] | Relative intensity [%] |
|---|---|---|
| 5.803095 | 15.22991 | 100.00 |
| 7.529270 | 11.74171 | 29.89 |
| 10.426180 | 8.48488 | 17.97 |
| 11.601380 | 7.62789 | 13.02 |
| 14.268860 | 6.20733 | 23.10 |
| 15.214400 | 5.82363 | 19.97 |
| 16.489410 | 5.37609 | 25.00 |
| 16.889090 | 5.24975 | 15.83 |
| 17.815320 | 4.97885 | 34.09 |
| 18.599270 | 4.77072 | 55.32 |
| 19.701340 | 4.50627 | 21.50 |
| 20.108540 | 4.41593 | 36.04 |
| 20.601230 | 4.31142 | 29.11 |
| 20.925900 | 4.24526 | 22.23 |
| 21.653950 | 4.10414 | 39.86 |
| 22.672100 | 3.92208 | 25.61 |
| 23.583180 | 3.77259 | 18.94 |
| 24.384570 | 3.65039 | 16.07 |
| 25.132610 | 3.54341 | 23.91 |
| 27.619650 | 3.22973 | 10.74 |
| 29.565150 | 3.02148 | 3.93 |
| 30.415650 | 2.93891 | 6.78 |

In some preferred embodiments, they also have the following characteristics:
1) In the TGA plot, there is a weight loss of 10.0±0.2% by weight before 150° C.;
2) In the DSC curve, there are two endothermic peaks at the initial temperatures of 64.6±2.0° C. and 134.8±2.0° C.;
3) the TGA plot substantially as shown in FIG. 20; and/or
4) the DSC curve substantially as shown in FIG. 21.

8) The Chloroform Solvate Crystalline Form VIII of Compound 1

In one embodiment, the form is the chloroform solvate crystalline form VIII of the compound 1, which is characterized by having at least three, at least four or five characteristic peaks at the following positions in the XRPD pattern represented by angle 2θ: 5.37±0.2°, 19.83±0.2°, 21.15±0.2°, 21.49±0.2° and 22.93±0.2°.

In some preferred embodiments, the form has XRPD characteristic peaks at the positions substantially as shown in Table 8 below and/or an XRPD pattern substantially as shown in FIG. 22.

TABLE 8

| Angle[°2θ] ± 0.2° | d-value[Å] | Relative intensity [%] |
|---|---|---|
| 5.379363 | 16.42859 | 100.00 |
| 7.654765 | 11.54949 | 7.24 |
| 15.995650 | 5.54091 | 14.41 |
| 16.895780 | 5.24769 | 19.16 |
| 19.835830 | 4.47602 | 51.31 |
| 21.158350 | 4.19914 | 31.56 |
| 21.492740 | 4.13456 | 47.81 |
| 22.930980 | 3.87839 | 35.17 |
| 24.981970 | 3.56443 | 21.26 |
| 26.943120 | 3.30927 | 11.33 |
| 28.064460 | 3.17955 | 13.03 |
| 30.290330 | 2.95078 | 6.88 |

In some preferred embodiments, they also have the following characteristics:
1) In the TGA plot, there is a weight loss of 2.7±0.2% by weight before 70° C., a weight loss of 11.0±0.2% by weight between 70° C. and 150° C.;
2) In the DSC curve, there is an endothermic peak at the initial temperature of 138.2±2.0° C.;
3) the TGA plot substantially as shown in FIG. 23; and/or
4) the DSC curve substantially as shown in FIG. 24.

9) The Methyl Tert-Butyl Ether Solvate Crystalline Form IX of Compound 1

In one embodiment, the form is the methyl tert-butyl ether solvate crystalline form IX of the compound 1, which is characterized by having at least three, at least four or five characteristic peaks at the following positions in the XRPD pattern represented by angle 2θ: 5.92±0.2°, 7.42±0.2°, 13.11±0.2°, 15.87±0.2° and 18.95±0.2°.

In some preferred embodiments, the form has XRPD characteristic peaks at the positions substantially as shown in Table 9 below and/or an XRPD pattern substantially as shown in FIG. 25.

TABLE 9

| Angle[°2θ] ± 0.2° | d-value[Å] | Relative intensity [%] |
|---|---|---|
| 5.921207 | 14.92638 | 56.46 |
| 7.422888 | 11.90974 | 100.00 |
| 13.117090 | 6.74967 | 20.56 |
| 15.876100 | 5.58236 | 27.04 |
| 18.957900 | 4.68127 | 38.94 |

In some preferred embodiments, they also have the following characteristics:
1) In the TGA plot, there is a weight loss of 10.6±0.2% by weight before 150° C.;
2) In the DSC curve, there are three endothermic peaks at the peak temperatures of 50.5±2.0° C. and 136.0±2.0° C., and the initial temperature of 180.9±2.0° C.;
3) the TGA plot substantially as shown in FIG. 26; and/or
4) the DSC curve substantially as shown in FIG. 27.

10) The 2-Methyltetrahydrofuran Solvate Crystalline Form X of Compound 1

In one embodiment, the form is the 2-methyltetrahydrofuran solvate crystalline form X of the compound 1, which is characterized by having at least three, at least four, at least five or six characteristic peaks at the following positions in the XRPD pattern represented by angle 2θ: 5.85±0.2°, 7.42±0.2°, 16.64±0.2°, 18.88±0.2°, 19.68±0.2° and 22.37±0.2°.

In some preferred embodiments, the form has XRPD characteristic peaks at the positions substantially as shown in Table 10 below and/or an XRPD pattern substantially as shown in FIG. 28.

TABLE 10

| Angle[°2θ] ± 0.2° | d-value[Å] | Relative intensity [%] |
|---|---|---|
| 5.854990 | 15.09504 | 74.88 |
| 7.422709 | 11.91003 | 27.25 |
| 11.958840 | 7.40067 | 9.24 |
| 13.126820 | 6.74470 | 10.51 |
| 14.352660 | 6.17128 | 13.92 |
| 15.159070 | 5.84476 | 14.54 |
| 16.647690 | 5.32533 | 100.00 |
| 17.521520 | 5.06166 | 18.13 |
| 18.888170 | 4.69840 | 58.85 |
| 19.686100 | 4.50973 | 33.61 |
| 21.591600 | 4.11585 | 16.49 |

TABLE 10-continued

| Angle[°2θ] ± 0.2° | d-value[Å] | Relative intensity [%] |
|---|---|---|
| 22.374300 | 3.97361 | 30.48 |
| 28.953770 | 3.08388 | 6.73 |

In some preferred embodiments, they also have the following characteristics:
1) In the TGA plot, there is a weight loss of 10.7±0.2% by weight before 150° C.;
2) In the DSC curve, there are two endothermic peaks at the initial temperatures of 111.1±2.0° C. and 217.4±2.0° C.;
3) the TGA plot substantially as shown in FIG. 29; and/or
4) the DSC curve substantially as shown in FIG. 30.

11) The Crystalline Form XI of Compound 1

In one embodiment, the form is the crystalline form XI of the compound 1, which is characterized by having at least three, at least four, at least five or six characteristic peaks at the following positions in the XRPD pattern represented by angle 2θ: 5.48±0.2°, 13.58±0.2°, 15.65±0.2°, 20.72±0.2°, 21.79±0.2° and 22.40±0.2°.

In some preferred embodiments, the form also has one or more characteristic peaks at the following positions in the XRPD pattern represented by angle 2θ: 14.42±0.2°, 18.72±0.2°, 19.07±0.2°, 23.64±0.2° and 26.20±0.2°.

In some preferred embodiments, the form has XRPD characteristic peaks at the positions substantially as shown in Table 11 below and/or an XRPD pattern substantially as shown in FIG. 31.

TABLE 11

| Angle[°2θ] ± 0.2° | d-value[Å] | Relative intensity [%] |
|---|---|---|
| 5.484990 | 16.11245 | 95.80 |
| 7.062830 | 12.51606 | 28.21 |
| 9.208320 | 9.60414 | 24.77 |
| 10.861810 | 8.14554 | 21.79 |
| 12.421030 | 7.12631 | 31.96 |
| 13.589810 | 6.51593 | 100.00 |
| 14.423790 | 6.14101 | 43.94 |
| 15.651250 | 5.66205 | 68.01 |
| 16.475610 | 5.38056 | 35.91 |
| 17.295420 | 5.12732 | 37.55 |
| 18.729450 | 4.73786 | 58.96 |
| 19.070380 | 4.65392 | 50.29 |
| 20.336380 | 4.36697 | 28.22 |
| 20.720330 | 4.28691 | 74.73 |
| 21.287200 | 4.17401 | 39.82 |
| 21.796110 | 4.07769 | 81.98 |
| 22.400240 | 3.96907 | 74.98 |
| 23.093490 | 3.85146 | 17.18 |
| 23.642120 | 3.76331 | 40.34 |
| 25.370340 | 3.51074 | 17.65 |
| 25.697150 | 3.46683 | 26.83 |
| 26.204600 | 3.40084 | 51.20 |
| 28.470660 | 3.13510 | 11.23 |
| 30.785420 | 2.90445 | 14.02 |
| 31.469770 | 2.84283 | 11.83 |

In some preferred embodiments, they also have the following characteristics:
1) In the TGA plot, there is a weight loss of 2.5±0.2% by weight before 150° C.;
2) In the DSC curve, there is an endothermic peaks at the initial temperature of 145.9±2.0° C.;
3) the TGA plot substantially as shown in FIG. 32; and/or
4) the DSC curve substantially as shown in FIG. 33.

12) The Acetone Solvate Crystalline Form XII of Compound 1

In one embodiment, the form is the acetone solvate crystalline form XII of the compound 1, which is characterized by having at least three, at least four or five characteristic peaks at the following positions in the XRPD pattern represented by angle 2θ: 5.42±0.2°, 13.62±0.20° 15.64±0.2°, 21.62±0.2° and 22.19±0.2°.

In some preferred embodiments, the form also has one or more characteristic peaks at the following positions in the XRPD pattern represented by angle 2θ: 18.50±0.2°, 19.08±0.2° and 20.51±0.2°.

In some preferred embodiments, the form has XRPD characteristic peaks at the positions substantially as shown in Table 12 below and/or an XRPD pattern substantially as shown in FIG. 34.

TABLE 12

| Angle[°2θ] ± 0.2° | d-value[Å] | Relative intensity [%] |
|---|---|---|
| 5.427239 | 16.28377 | 100.00 |
| 7.035403 | 12.56480 | 15.62 |
| 9.591051 | 9.22173 | 8.09 |
| 10.766550 | 8.21740 | 8.17 |
| 12.324840 | 7.18171 | 21.10 |
| 13.628900 | 6.49733 | 98.45 |
| 14.414280 | 6.14504 | 25.42 |
| 15.649520 | 5.66267 | 63.12 |
| 16.334140 | 5.42684 | 23.32 |
| 17.057810 | 5.19821 | 7.53 |
| 18.085580 | 4.90505 | 12.55 |
| 18.502160 | 4.79554 | 43.18 |
| 19.083620 | 4.65072 | 43.82 |
| 20.519820 | 4.32834 | 35.71 |
| 21.629670 | 4.10869 | 55.92 |
| 22.197940 | 4.00478 | 50.10 |
| 23.495830 | 3.78641 | 22.34 |
| 25.117810 | 3.54546 | 12.00 |
| 25.961090 | 3.43218 | 24.72 |
| 30.208900 | 2.95855 | 4.13 |

In some preferred embodiments, they also have the following characteristics:
1) In the TGA plot, there is a weight loss of 1.0±0.2% by weight before 90° C., a weight loss of 3.6±0.2% by weight between 90° C. and 150° C.;
2) In the DSC curve, there are two endothermic peaks at the peak temperature of 59.1±2.0° C., and the initial temperature of 146.2±2.0° C.;
3) the TGA plot substantially as shown in FIG. 35; and/or
4) the DSC curve substantially as shown in FIG. 36.

13) The Crystalline Form XIII of Compound 1

In one embodiment, the form is the crystalline form XIII of the compound 1, which is characterized by having characteristic peaks at the following positions in the XRPD pattern represented by angle 2θ: 6.24±0.2°, 8.15±0.2° and 18.06±0.2°.

In some preferred embodiments, the form also has one or more characteristic peaks at the following positions in the XRPD pattern represented by angle 2θ: 12.49±0.2°, 16.78±0.2°, 19.47±0.2 and 22.11±0.2°.

In some preferred embodiments, the form has XRPD characteristic peaks at the positions substantially as shown in Table 13 below and/or an XRPD pattern substantially as shown in FIG. 37.

TABLE 13

| Angle[°2θ] ± 0.2° | d-value[Å] | Relative intensity [%] |
|---|---|---|
| 6.243906 | 14.15566 | 100.00 |
| 8.151101 | 10.84730 | 43.46 |
| 12.495670 | 7.08391 | 13.26 |
| 13.756630 | 6.43729 | 9.10 |

TABLE 13-continued

| Angle[°2θ] ± 0.2° | d-value[Å] | Relative intensity [%] |
|---|---|---|
| 16.787310 | 5.28135 | 15.24 |
| 18.063500 | 4.91100 | 38.05 |
| 19.472620 | 4.55868 | 16.40 |
| 20.725150 | 4.28592 | 8.76 |
| 22.111080 | 4.02031 | 17.52 |
| 24.029790 | 3.70347 | 4.06 |
| 27.171430 | 3.28198 | 4.31 |

In some preferred embodiments, they also have the following characteristics:
1) In the TGA plot, there is a weight loss of 2.6±0.2% by weight before 150° C.;
2) In the DSC curve, there are two endothermic peaks at the peak temperature of 87.0±2.0° C., and the initial temperature of 142.8±2.0° C.;
3) the TGA plot substantially as shown in FIG. 38; and/or
4) the DSC curve substantially as shown in FIG. 39.

14) The Crystalline Form XIV of Compound 1

In one embodiment, the form is the crystalline form XIV of the compound 1, which is characterized by having at least three, at least four or five characteristic peaks at the following positions in the XRPD pattern represented by angle 2θ: 5.13±0.2°, 10.56±0.2°, 16.08±0.2°, 18.17±0.2° and 20.77±0.2°.

In some preferred embodiments, the form has XRPD characteristic peaks at the positions substantially as shown in Table 14 below and/or an XRPD pattern substantially as shown in FIG. 40.

TABLE 14

| Angle[°2θ] ± 0.2° | d-value[Å] | Relative intensity [%] |
|---|---|---|
| 5.134706 | 17.21081 | 100.00 |
| 10.560930 | 8.37692 | 23.64 |
| 16.080350 | 5.51191 | 33.44 |
| 18.173090 | 4.88163 | 17.73 |
| 20.775140 | 4.27572 | 25.29 |

In some preferred embodiments, they also have the following characteristics:
1) In the TGA plot, there is a weight loss of 8.4±0.2% by weight before 150° C.;
2) In the DSC curve, there is an endothermic peaks at the initial temperature of 127.8±2.0° C.;
3) the TGA plot substantially as shown in FIG. 41; and/or
4) the DSC curve substantially as shown in FIG. 42.

15) The Crystalline Form XV of Compound 1

In one embodiment, the form is the crystalline form XV of the compound 1, which is characterized by having at least three, at least four or five characteristic peaks at the following positions in the XRPD pattern represented by angle 2θ: 4.53±0.2°, 6.17±0.2°, 9.90±0.2°, 16.71±0.2° and 17.83±0.2°.

In some preferred embodiments, the form has XRPD characteristic peaks at the positions substantially as shown in Table 15 below and/or an XRPD pattern substantially as shown in FIG. 43.

TABLE 15

| Angle[°2θ] ± 0.2° | d-value[Å] | Relative intensity [%] |
|---|---|---|
| 4.533975 | 19.48973 | 100.00 |
| 6.171669 | 14.32118 | 41.94 |

TABLE 15-continued

| Angle[°2θ] ± 0.2° | d-value[Å] | Relative intensity [%] |
|---|---|---|
| 7.324262 | 12.06989 | 8.87 |
| 9.908910 | 8.92662 | 20.00 |
| 15.469880 | 5.72802 | 11.95 |
| 16.717670 | 5.30319 | 19.12 |
| 17.833560 | 4.97380 | 41.68 |
| 19.729100 | 4.49999 | 13.54 |
| 21.674970 | 4.10021 | 12.35 |
| 22.913390 | 3.88133 | 10.66 |
| 25.223830 | 3.53080 | 4.51 |

In some preferred embodiments, they also have the following characteristics:
1) In the TGA plot, there is a weight loss of 1.6±0.2% by weight before 150° C.;
2) In the DSC curve, there are three endothermic peaks at the peak temperature of 71.2±2.0° C., and the initial temperatures of 134.1±2.0° C. and 151.6±2.0° C.;
3) the TGA plot substantially as shown in FIG. 44; and/or
4) the DSC curve substantially as shown in FIG. 45.

16) The N,N-Dimethylformamide Solvate Crystalline Form XVI of Compound 1

In one embodiment, the form is the N,N-dimethylformamide solvate crystalline form XVI of the compound 1, which is characterized by having at least three, at least four, at least five or six characteristic peaks at the following positions in the XRPD pattern represented by angle 2θ: 6.13±0.2°, 6.97±0.2°, 13.84±0.2°, 18.35±0.2°, 19.00±0.2° and 19.55±0.2°.

In some preferred embodiments, the form has XRPD characteristic peaks at the positions substantially as shown in Table 16 below and/or an XRPD pattern substantially as shown in FIG. 46.

TABLE 16

| Angle[°2θ] ± 0.2° | d-value[Å] | Relative intensity [%] |
|---|---|---|
| 6.136095 | 14.40413 | 61.33 |
| 6.974022 | 12.67525 | 75.93 |
| 9.308429 | 9.50108 | 14.18 |
| 11.538670 | 7.66920 | 22.55 |
| 13.840300 | 6.39856 | 71.19 |
| 14.585040 | 6.07347 | 39.01 |
| 17.021680 | 5.20916 | 20.82 |
| 18.351910 | 4.83446 | 58.82 |
| 19.003900 | 4.67005 | 100.00 |
| 19.552870 | 4.54015 | 53.22 |
| 22.508360 | 3.95024 | 15.78 |
| 29.090570 | 3.06969 | 15.86 |

In some preferred embodiments, they also have the following characteristics:
1) In the TGA plot, there is a weight loss of 5.2±0.2% by weight before 150° C.;
2) In the DSC curve, there are two endothermic peaks at the initial temperatures of 79.9±2.0° C. and 137.6±2.0° C.;
3) the TGA plot substantially as shown in FIG. 47; and/or
4) the DSC curve substantially as shown in FIG. 48.

17) The Crystalline Form XVII of Compound 1

In one embodiment, the form is the crystalline form XVII of the compound 1, which is characterized by having at least three, at least four, at least five or six characteristic peaks at the following positions in the XRPD pattern represented by angle 2θ: 4.50±0.2°, 7.33±0.2°, 15.20±0.2°, 17.55±0.2°, 18.06±0.2° and 19.49±0.2°.

In some preferred embodiments, the form has XRPD characteristic peaks at the positions substantially as shown in Table 17 below and/or an XRPD pattern substantially as shown in FIG. 49.

TABLE 17

| Angle[°2θ] ± 0.2° | d-value[Å] | Relative intensity [%] |
|---|---|---|
| 4.503521 | 19.62145 | 100.00 |
| 7.332149 | 12.05693 | 3.18 |
| 15.205640 | 5.82696 | 3.99 |
| 17.553090 | 5.05263 | 11.43 |
| 18.066850 | 4.91010 | 25.07 |
| 19.496320 | 4.55319 | 4.68 |
| 23.484990 | 3.78814 | 2.67 |

In some preferred embodiments, they also have the following characteristics:
1) In the TGA plot, there is a weight loss of 1.4±0.2% by weight before 150° C.;
2) In the DSC curve, there are two endothermic peaks at the peak temperature of 54.2±2.0° C., and at the initial temperature of 152.8±2.0° C.;
3) the TGA plot substantially as shown in FIG. 50; and/or
4) the DSC curve substantially as shown in FIG. 51.

18) The Crystalline Form XVIII of Compound 1

In one embodiment, the form is the crystalline form XVIII of the compound 1, which is characterized by having at least three, at least four, at least five or six characteristic peaks at the following positions in the XRPD pattern represented by angle 2θ: 5.93±0.2°, 8.61±0.2°, 17.28±0.2°, 20.60±0.2°, 21.45±0.2° and 21.76±0.2°.

In some preferred embodiments, the form has XRPD characteristic peaks at the positions substantially as shown in Table 18 below and/or an XRPD pattern substantially as shown in FIG. 52.

TABLE 18

| Angle[°2θ] ± 0.2° | d-value[Å] | Relative intensity [%] |
|---|---|---|
| 5.933129 | 14.89642 | 100.00 |
| 8.614887 | 10.26434 | 24.28 |
| 13.205550 | 6.70466 | 11.46 |
| 15.472060 | 5.72722 | 13.01 |
| 15.900780 | 5.57375 | 10.00 |
| 17.285050 | 5.13038 | 24.52 |
| 19.085030 | 4.65038 | 18.86 |
| 19.934790 | 4.45402 | 7.05 |
| 20.605150 | 4.31061 | 21.19 |
| 21.457360 | 4.14129 | 23.19 |
| 21.760920 | 4.08421 | 26.20 |
| 23.304920 | 3.81700 | 5.11 |
| 25.214420 | 3.53210 | 5.22 |
| 26.444540 | 3.37052 | 7.27 |
| 27.284040 | 3.26869 | 7.04 |

In some preferred embodiments, they also have the following characteristics:
1) In the TGA plot, there is a weight loss of 0.3±0.2% by weight before 150° C.;
2) In the DSC curve, there is an endothermic peak at the initial temperature of 206.7±2.0° C.;
3) the TGA plot substantially as shown in FIG. 53; and/or
4) the DSC curve substantially as shown in FIG. 54.

19) The Hydrochloride Crystalline Form XIX of Compound 1

In one embodiment, the form is the hydrochloride crystalline form XIX of the compound 1, which is characterized by having at least three, at least four or five characteristic peaks at the following positions in the XRPD pattern represented by angle 2θ: 9.53±0.2°, 16.70±0.20° 20.56±0.2°, 21.23±0.2° and 23.79±0.2°.

In some preferred embodiments, the form also has one or more characteristic peaks at the following positions in the XRPD pattern represented by angle 2θ: 11.07±0.2°, 15.44±0.2°, 19.78±0.2° and 28.81±0.2°.

In some preferred embodiments, the form has XRPD characteristic peaks at the positions substantially as shown in Table 19 below and/or an XRPD pattern substantially as shown in FIG. 55.

TABLE 19

| Angle[°2θ] ± 0.2° | d-value[Å] | Relative intensity [%] |
|---|---|---|
| 9.539562 | 9.27139 | 100.00 |
| 11.075690 | 7.98872 | 33.00 |
| 12.564500 | 7.04525 | 18.68 |
| 15.440520 | 5.73885 | 45.22 |
| 16.708640 | 5.30604 | 92.75 |
| 19.540860 | 4.54292 | 12.89 |
| 19.781710 | 4.48814 | 52.96 |
| 20.569680 | 4.31796 | 61.79 |
| 21.230820 | 4.18497 | 70.60 |
| 22.153050 | 4.01279 | 27.10 |
| 22.721560 | 3.91366 | 25.15 |
| 23.793660 | 3.73969 | 60.64 |
| 24.863470 | 3.58115 | 23.72 |
| 26.604090 | 3.35067 | 10.95 |
| 28.818910 | 3.09800 | 35.30 |

In some preferred embodiments, they also have the following characteristics:
1) In the TGA plot, there is a weight loss of 2.3±0.2% by weight before 150° C., and a weight loss of 4.4±0.2% by weight between 150° C. and 200° C.;
2) In the DSC curve, there is an endothermic peak at the initial temperature of 189.5±2.0° C.;
3) the TGA plot substantially as shown in FIG. 56; and/or
4) the DSC curve substantially as shown in FIG. 57.

20) The Sulphate Crystalline Form XX of Compound 1

In one embodiment, the form is the sulphate crystalline form XX of the compound 1, which is characterized by having characteristic peaks at the following positions in the XRPD pattern represented by angle 2θ: 15.62±0.2°, 19.69±0.2° and 23.33±0.2°.

In some preferred embodiments, the form also has one or more characteristic peaks at the following positions in the XRPD pattern represented by angle 2θ: 8.34±0.2°, 16.56±0.2°, 18.12±0.2° and 26.64±0.2°.

In some preferred embodiments, the form has XRPD characteristic peaks at the positions substantially as shown in Table 20 below and/or an XRPD pattern substantially as shown in FIG. 58.

TABLE 20

| Angle[°2θ] ± 0.2° | d-value[Å] | Relative intensity [%] |
|---|---|---|
| 7.585601 | 11.65464 | 19.74 |
| 8.340707 | 10.60113 | 38.62 |
| 9.747928 | 9.07367 | 19.81 |
| 13.496060 | 6.56098 | 15.26 |
| 15.620950 | 5.67296 | 51.20 |
| 16.566680 | 5.35119 | 43.32 |
| 18.128790 | 4.89346 | 38.04 |
| 19.697750 | 4.50709 | 100.00 |
| 20.760740 | 4.27865 | 23.25 |
| 23.336240 | 3.81194 | 53.41 |
| 24.729300 | 3.60028 | 17.45 |
| 26.640530 | 3.34617 | 44.27 |
| 27.280030 | 3.26916 | 21.13 |

In some preferred embodiments, they also have the following characteristics:
1) In the TGA plot, there is a weight loss of 6.0±0.2% by weight before 150° C.;

2) In the DSC curve, there are two endothermic peaks at the initial temperature of 89.2±2.0° C. and 176.1±2.0° C.;
3) the TGA plot substantially as shown in FIG. 59; and/or
4) the DSC curve substantially as shown in FIG. 60.

21) The Mesylate Crystalline Form XXI of Compound 1

In one embodiment, the form is the mesylate crystalline form XXI of the compound 1, which is characterized by having characteristic peaks at the following positions in the XRPD pattern represented by angle 2θ: 4.63±0.2°, 9.80±0.2° and 16.06±0.2°.

In some preferred embodiments, the form has XRPD characteristic peaks at the positions substantially as shown in Table 21 below and/or an XRPD pattern substantially as shown in FIG. 61.

TABLE 21

| Angle[°2θ] ± 0.2° | d-value[Å] | Relative intensity [%] |
|---|---|---|
| 4.638124 | 19.05231 | 29.06 |
| 9.803409 | 9.02245 | 100.00 |
| 16.066760 | 5.51654 | 31.60 |

In some preferred embodiments, they also have the following characteristics:
1) In the TGA plot, there is a weight loss of 4.2±0.2% by weight before 150° C.;
2) In the DSC curve, there are two endothermic peaks at the peak temperature of 86.4±2.0° C., and at the initial temperature of 168.4±2.0° C.;
3) the TGA plot substantially as shown in FIG. 62; and/or
4) the DSC curve substantially as shown in FIG. 63.

22) The Mesylate Crystalline Form XXII of Compound 1

In one embodiment, the form is the mesylate crystalline form XXII of the compound 1, which is characterized by having at least three, at least four or five characteristic peaks at the following positions in the XRPD pattern represented by angle 2θ: 6.15±0.2°, 7.80±0.2°, 14.56±0.2°, 17.28±0.2° and 18.48±0.2°.

In some preferred embodiments, the form also has one or more characteristic peaks at the following positions in the XRPD pattern represented by angle 2θ: 21.83±0.2° and 24.61±0.2°.

In some preferred embodiments, the form has XRPD characteristic peaks at the positions substantially as shown in Table 22 below and/or an XRPD pattern substantially as shown in FIG. 64.

TABLE 22

| Angle[°2θ] ± 0.2° | d-value[Å] | Relative intensity [%] |
|---|---|---|
| 6.152556 | 14.36563 | 100.00 |
| 7.806105 | 11.32591 | 48.55 |
| 8.861501 | 9.97923 | 25.22 |
| 11.152830 | 7.93364 | 11.64 |
| 12.325510 | 7.18132 | 26.89 |
| 14.563390 | 6.08245 | 45.89 |
| 17.282420 | 5.13115 | 53.33 |
| 18.482060 | 4.80071 | 66.00 |
| 19.802230 | 4.48354 | 24.55 |
| 21.830550 | 4.07134 | 35.39 |
| 22.721290 | 3.91370 | 18.42 |
| 24.617090 | 3.61643 | 34.16 |
| 29.276030 | 3.05066 | 7.43 |

In some preferred embodiments, they also have the following characteristics:
1) In the TGA plot, there is a weight loss of 2.6±0.2% by weight before 150° C.;
2) In the DSC curve, there are two endothermic peaks at the peak temperature of 102.6±2.0° C., and at the initial temperature of 181.3±2.0° C.;
3) the TGA plot substantially as shown in FIG. 65; and/or
4) the DSC curve substantially as shown in FIG. 66.

23) The Maleate Crystalline Form XXIII of Compound 1

In one embodiment, the form is the maleate crystalline form XXIII of the compound 1, which is characterized by having at least three, at least four, at least five or six characteristic peaks at the following positions in the XRPD pattern represented by angle 2θ: 5.32±0.2°, 8.73±0.2°, 13.02±0.2°, 18.94±0.2°, 22.85±0.2° and 25.20±0.2°.

In some preferred embodiments, the form has XRPD characteristic peaks at the positions substantially as shown in Table 23 below and/or an XRPD pattern substantially as shown in FIG. 67.

TABLE 23

| Angle[°2θ] ± 0.2° | d-value[Å] | Relative intensity [%] |
|---|---|---|
| 5.329199 | 16.58312 | 47.67 |
| 8.734749 | 10.12376 | 80.53 |
| 10.681700 | 8.28247 | 22.28 |
| 13.024280 | 6.79756 | 53.14 |
| 14.909210 | 5.94214 | 22.54 |
| 15.484520 | 5.72264 | 21.90 |
| 16.017330 | 5.53346 | 27.30 |
| 17.075090 | 5.19298 | 16.48 |
| 18.948690 | 4.68353 | 100.00 |
| 19.738370 | 4.49790 | 29.28 |
| 21.420210 | 4.14839 | 6.51 |
| 22.858420 | 3.89054 | 44.54 |
| 25.208590 | 3.53290 | 60.84 |
| 26.260470 | 3.39373 | 24.04 |

In some preferred embodiments, they also have the following characteristics:
1) In the TGA plot, there is a weight loss of 3.2±0.2% by weight before 150° C., and a weight loss of 8.6±0.2% by weight between 150° C. and 220° C.;
2) In the DSC curve, there are two endothermic peaks at the peak temperature of 90.2±2.0° C. and at the initial temperature of 174.8±2.0° C.;
3) the TGA plot substantially as shown in FIG. 68; and/or
4) the DSC curve substantially as shown in FIG. 69.

24) The Maleate Crystalline Form XXIV of Compound 1

In one embodiment, the form is the maleate crystalline form XXIV of the compound 1, which is characterized by having at least three, at least four or five characteristic peaks at the following positions in the XRPD pattern represented by angle 2θ: 4.77±0.2°, 12.50±0.20° 15.33±0.2°, 18.73±0.2° and 22.28±0.2°.

In some preferred embodiments, the form has XRPD characteristic peaks at the positions substantially as shown in Table 24 below and/or an XRPD pattern substantially as shown in FIG. 70.

TABLE 24

| Angle[°2θ] ± 0.2° | d-value[Å] | Relative intensity [%] |
|---|---|---|
| 4.774768 | 18.50738 | 100.00 |
| 7.619892 | 11.60227 | 8.51 |
| 8.129279 | 10.87637 | 8.70 |
| 9.512488 | 9.29772 | 16.46 |
| 11.797940 | 7.50124 | 11.89 |
| 12.500530 | 7.08117 | 19.98 |
| 14.342810 | 6.17550 | 8.70 |
| 14.815180 | 5.97964 | 6.52 |
| 15.336490 | 5.77754 | 38.49 |

TABLE 24-continued

| Angle[°2θ] ± 0.2° | d-value[Å] | Relative intensity [%] |
|---|---|---|
| 15.899480 | 5.57421 | 6.37 |
| 16.421160 | 5.39828 | 6.67 |
| 17.826810 | 4.97566 | 14.35 |
| 18.734350 | 4.73663 | 54.62 |
| 20.725170 | 4.28592 | 10.47 |
| 21.380980 | 4.15592 | 12.16 |
| 22.286330 | 3.98909 | 21.48 |
| 22.976860 | 3.87075 | 16.21 |
| 24.604320 | 3.61828 | 16.37 |
| 26.930830 | 3.31076 | 10.38 |
| 29.843420 | 2.99394 | 4.68 |

In some preferred embodiments, they also have the following characteristics:

1) In the TGA plot, there is a weight loss of 1.7±0.2% by weight before 150° C., and a weight loss of 9.1±0.2% by weight between 150° C. and 220° C.;
2) In the DSC curve, there are two endothermic peaks at the peak temperature of 70.5±2.0° C. and at the initial temperature of 190.0±2.0° C.;
3) the TGA plot substantially as shown in FIG. 71; and/or
4) the DSC curve substantially as shown in FIG. 72.

25) The Amorphous Form XXV of Compound 1

In one embodiment, the form is the amorphous form XXV of the compound 1,

In some preferred embodiments, they also have the following characteristics:

1) In the TGA plot, there is a weight loss of 3.0±0.2% by weight before 150° C.;
2) In the DSC curve, there is a glassy transition temperature at the midpoint temperature of 121.5±2.0° C.;
3) the XRPD pattern substantially as shown in FIG. 73;
4) the TGA plot substantially as shown in FIG. 74; and/or
5) the DSC curve substantially as shown in FIG. 75.

26) The Acetone Solvate Crystalline Form XXVI of Compound 1

In one embodiment, the form is the acetone solvate crystalline form XXVI of the compound 1, which is characterized by having at least three, at least four, at least five or six characteristic peaks at the following positions in the XRPD pattern represented by angle 2θ: 6.12±0.2°, 8.07±0.2°, 16.79±0.2°, 17.90±0.2°, 19.09±0.2° and 22.39±0.2°.

In some preferred embodiments, the form has XRPD characteristic peaks at the positions substantially as shown in Table 25 below and/or an XRPD pattern substantially as shown in FIG. 76.

TABLE 25

| Angle[°2θ] ± 0.2° | d-value[Å] | Relative intensity [%] |
|---|---|---|
| 6.129 | 14.4079 | 100 |
| 8.073 | 10.9432 | 51.3 |
| 8.422 | 10.4904 | 14.3 |
| 11.178 | 7.9093 | 10.7 |
| 12.212 | 7.2418 | 23.5 |
| 13.105 | 6.7502 | 19.4 |
| 15.707 | 5.6373 | 19.8 |
| 16.799 | 5.2732 | 39.3 |
| 17.908 | 4.9492 | 61.8 |
| 18.295 | 4.8453 | 19.0 |
| 18.685 | 4.7449 | 16.6 |
| 19.09 | 4.6451 | 42.4 |
| 19.696 | 4.5037 | 23.8 |
| 20.393 | 4.3512 | 27.9 |
| 20.80 | 4.267 | 21.4 |
| 21.635 | 4.1043 | 11.90 |
| 22.396 | 3.9664 | 61.0 |
| 23.387 | 3.8006 | 23.20 |
| 24.325 | 3.6561 | 10.0 |
| 24.942 | 3.567 | 11.80 |
| 25.252 | 3.5239 | 17.0 |
| 29.682 | 3.0072 | 16.1 |

In some preferred embodiments, they also have the following characteristics:

1) In the TGA plot, there is a weight loss of 0.18±0.02% by weight before 74.2° C., and a weight loss of 5.0±0.2% by weight between 74.2° C. and 168.55° C.;
2) In the DSC curve, there is an endothermic peaks at the peak temperature of 152.3±2.0° C.;
3) the TGA plot substantially as shown in FIG. 77; and/or
4) the DSC curve substantially as shown in FIG. 78.

27) The Benzene Sulfonate Crystalline Form XXVII of Compound 1

In one embodiment, the form is the benzene sulfonate crystalline Form XXVII of the compound 1, which is characterized by having at least three, at least four or five characteristic peaks at the following positions in the XRPD pattern represented by angle 2θ: 10.03±0.2°, 17.22±0.2°, 17.68±0.2°, 18.79±0.2°, 20.43±0.2°, 21.69±0.2°, 24.83±0.2°.

In some preferred embodiments, the form has XRPD characteristic peaks at the positions substantially as shown in Table 26 below and/or an XRPD pattern substantially as shown in FIG. 79.

In some preferred embodiments, they also have the following characteristics:

1) In the TGA plot, there is a weight loss of 2.4±0.2% by weight before 190.8° C.;
2) In the DSC curve, there is an endothermic peak at the initial temperature of 250.2±2.0° C.;
3) the TGA plot substantially as shown in FIG. 80; and/or
4) the DSC curve substantially as shown in FIG. 81.

TABLE 26

| Angle[°2θ] ± 0.2° | d-value[Å] | Relative intensity [%] |
|---|---|---|
| 6.8 | 12.9889 | 27 |
| 9.021 | 9.7945 | 19.1 |
| 10.032 | 8.81 | 98.9 |
| 11.02 | 8.0221 | 7.9 |
| 12.019 | 7.3574 | 31.7 |
| 12.503 | 7.0739 | 14.6 |
| 13.44 | 6.5826 | 47.3 |
| 14.043 | 6.3012 | 44.8 |
| 15.817 | 5.5982 | 16.7 |
| 16.421 | 5.3938 | 36.6 |
| 17.22 | 5.1452 | 59.8 |
| 17.686 | 5.0106 | 97.6 |
| 18.799 | 4.7164 | 63.9 |
| 20.434 | 4.3425 | 75.2 |
| 21.699 | 4.0922 | 100 |
| 22.812 | 3.895 | 22.5 |
| 23.492 | 3.7838 | 43.4 |
| 24.838 | 3.5817 | 72.3 |
| 25.326 | 3.5138 | 42.3 |
| 25.848 | 3.444 | 23.5 |
| 26.978 | 3.3022 | 14.4 |
| 27.446 | 3.247 | 12.9 |
| 28.399 | 3.1402 | 14.6 |
| 29.278 | 3.0479 | 38.1 |
| 30.466 | 2.9316 | 19.9 |
| 32.005 | 2.7941 | 11.9 |

28) The p-Toluenesulfonate Crystalline Form XXVIII of Compound 1

In one embodiment, the form is the p-toluenesulfonate crystalline Form XXVIII of the compound 1, which is characterized by having at least three, at least four or five characteristic peaks at the following positions in the XRPD pattern represented by angle 2θ: 6.66±0.2°, 9.25±0.2°, 9.48±0.2°, 10.18±0.2°, 13.53±0.2°, 14.14±0.2°, 17.06±0.2°, 18.03±0.2°, 18.44±0.2°, 19.24±0.2°, 19.79±0.2°, 20.35±0.2°, 21.83±0.2°, 24.95±0.2°.

In some preferred embodiments, the form has XRPD characteristic peaks at the positions substantially as shown in Table 27 below and/or an XRPD pattern substantially as shown in FIG. 82.

In some preferred embodiments, they also have the following characteristics:
1) In the TGA plot, there is a weight loss of 2.4±0.2% by weight before 113.0° C.; and a weight loss of 1.8±0.2% by weight between 113.0-200.7° C.;
2) In the DSC curve, there is an endothermic peak at the initial temperature of 165.2±2.0° C.;
3) the TGA plot substantially as shown in FIG. 83; and/or
4) the DSC curve substantially as shown in FIG. 84.

TABLE 27

| Angle[°2θ] ± 0.2° | d-value[Å] | Relative intensity [%] |
|---|---|---|
| 6.337 | 13.9366 | 26.1 |
| 6.662 | 13.2559 | 63.2 |
| 8.181 | 10.798 | 38.5 |
| 8.727 | 10.1245 | 32.2 |
| 9.252 | 9.5504 | 96.5 |
| 9.485 | 9.3164 | 58.5 |
| 10.188 | 8.6756 | 51 |
| 11.493 | 7.6928 | 9.6 |
| 12.524 | 7.062 | 35.7 |
| 13.538 | 6.5352 | 77.4 |
| 14.143 | 6.2568 | 74.1 |
| 15.818 | 5.5979 | 38.2 |
| 17.062 | 5.1925 | 78.1 |
| 17.24 | 5.1392 | 39.6 |
| 18.038 | 4.9137 | 77.2 |
| 18.447 | 4.8057 | 100 |
| 19.244 | 4.6083 | 86.2 |
| 19.791 | 4.4822 | 73.4 |
| 20.356 | 4.3591 | 68.5 |
| 20.872 | 4.2525 | 9.1 |
| 21.837 | 4.0667 | 83.9 |
| 24.953 | 3.5655 | 51.7 |
| 29.162 | 3.0597 | 33.1 |

29) The p-Toluenesulfonate Crystalline Form XXIX of Compound 1

In one embodiment, the form is the p-toluenesulfonate crystalline Form XXIX of the compound 1, which is characterized by having at least three, at least four or five characteristic peaks at the following positions in the XRPD pattern represented by angle 2θ: 9.99±0.2°, 17.21±0.2°, 19.38±0.2°, 19.85±0.2°, 22.57±0.2°.

In some preferred embodiments, the form has XRPD characteristic peaks at the positions substantially as shown in Table 28 below and/or an XRPD pattern substantially as shown in FIG. 85.

In some preferred embodiments, they also have the following characteristics:
1) In the TGA plot, there is a weight loss of 0.12±0.02% by weight before 236.4° C.;
2) In the DSC curve, there is an endothermic peak at the initial temperature of 222.7±2.0° C.;
3) the TGA plot substantially as shown in FIG. 86; and/or
4) the DSC curve substantially as shown in FIG. 87.

TABLE 28

| Angle[°2θ] ± 0.2° | d-value[Å] | Relative intensity [%] |
|---|---|---|
| 6.701 | 13.1804 | 22.8 |
| 7.051 | 12.5256 | 16.1 |
| 7.577 | 11.6582 | 13.8 |
| 8.59 | 10.2853 | 17.3 |
| 9.718 | 9.0938 | 12.6 |
| 9.993 | 8.8446 | 70.9 |
| 10.677 | 8.2792 | 6.2 |
| 11.391 | 7.7614 | 14.2 |
| 12.876 | 6.8696 | 9.3 |
| 13.244 | 6.6794 | 10 |
| 13.85 | 6.3885 | 6.6 |
| 15.017 | 5.8947 | 25.1 |
| 15.253 | 5.804 | 8.4 |
| 15.543 | 5.6965 | 38.9 |
| 15.973 | 5.5441 | 8.1 |
| 17.217 | 5.146 | 98.9 |
| 17.627 | 5.0272 | 9.9 |
| 18.253 | 4.8562 | 14.4 |
| 18.544 | 4.7807 | 40.1 |
| 18.743 | 4.7305 | 14.1 |
| 19.03 | 4.6598 | 39.1 |
| 19.381 | 4.5762 | 100 |
| 19.852 | 4.4685 | 47.6 |
| 20.433 | 4.3428 | 23.7 |
| 20.882 | 4.2505 | 13.6 |
| 21.291 | 4.1696 | 25.8 |
| 21.72 | 4.0884 | 22.9 |
| 22.108 | 4.0175 | 20.2 |
| 22.578 | 3.9349 | 65.1 |
| 23.492 | 3.7837 | 15.3 |
| 24.058 | 3.6961 | 30.6 |
| 24.271 | 3.6641 | 12.1 |
| 24.836 | 3.582 | 15.7 |
| 25.013 | 3.5571 | 6.3 |
| 25.305 | 3.5167 | 18.1 |
| 25.89 | 3.4385 | 12.7 |
| 27.25 | 3.2699 | 17.2 |
| 27.661 | 3.2222 | 7.1 |
| 28.227 | 3.1589 | 10.1 |
| 28.537 | 3.1253 | 19 |
| 28.987 | 3.0778 | 10.3 |
| 29.493 | 3.0261 | 14.5 |
| 29.785 | 2.9971 | 7.1 |
| 30.113 | 2.9653 | 12.3 |
| 30.642 | 2.9152 | 8 |
| 31.967 | 2.7974 | 7.3 |
| 32.844 | 2.7246 | 2.3 |
| 33.463 | 2.6756 | 5.7 |
| 33.644 | 2.6617 | 3.1 |
| 33.977 | 2.6363 | 2.1 |
| 35.139 | 2.5518 | 2.4 |
| 35.842 | 2.5033 | 7 |
| 37.321 | 2.4074 | 2.7 |

30) The Sulphate Crystalline Form XXX of Compound 1

In one embodiment, the form is the sulphate crystalline Form XXX of the compound 1, which is characterized by having at least three, at least four or five characteristic peaks at the following positions in the XRPD pattern represented by angle 2θ: 8.22±0.2°, 15.38±0.2°, 17.68±0.2°, 18.48±0.2°, 19.07±0.2°, 21.03±0.2°, 21.92±0.2°, 24.8±0.2°.

In some preferred embodiments, the form has XRPD characteristic peaks at the positions substantially as shown in Table 29 below and/or an XRPD pattern substantially as shown in FIG. 88.

In some preferred embodiments, they also have the following characteristics:
1) In the TGA plot, there is a weight loss of 0.13±0.02% by weight before 81.9° C.; a weight loss of 5.8±0.2% by weight between 81.9° C.-204.3° C.; and a weight loss of 4.0±0.2% by weight between 204.3° C.-242.7° C.;

2) In the DSC curve, there are two endothermic peaks at the initial temperature of 134.5±2.0° C. and 212.3±2.0° C.;

3) the TGA plot substantially as shown in FIG. 89; and/or 4) the DSC curve substantially as shown in FIG. 90.

TABLE 29

| Angle[°2θ] ± 0.2° | d-value[Å] | Relative intensity [%] |
|---|---|---|
| 4.809 | 18.3592 | 5.2 |
| 7.6 | 11.6232 | 8.8 |
| 8.22 | 10.7474 | 29.2 |
| 9.629 | 9.1774 | 12.1 |
| 10.121 | 8.733 | 3.7 |
| 10.31 | 8.5727 | 2.9 |
| 11.947 | 7.4014 | 8.9 |
| 12.62 | 7.0087 | 17.1 |
| 13.9 | 6.3657 | 3 |
| 14.36 | 6.1628 | 17 |
| 15.38 | 5.7563 | 26.6 |
| 16.259 | 5.4471 | 9.4 |
| 16.51 | 5.3647 | 1.9 |
| 17.18 | 5.157 | 14.2 |
| 17.68 | 5.0124 | 84.3 |
| 18.481 | 4.7969 | 27.5 |
| 19.07 | 4.6501 | 100 |
| 19.46 | 4.5578 | 5.8 |
| 19.98 | 4.4402 | 4.1 |
| 20.329 | 4.3647 | 6.9 |
| 20.72 | 4.2833 | 10.2 |
| 21.03 | 4.2209 | 32.3 |
| 21.92 | 4.0515 | 42.8 |
| 22.27 | 3.9885 | 5.1 |
| 22.88 | 3.8836 | 21.7 |
| 23.141 | 3.8404 | 4.4 |
| 23.42 | 3.7952 | 8 |
| 23.71 | 3.7496 | 9 |
| 23.959 | 3.7111 | 4.1 |
| 24.8 | 3.5871 | 59.8 |
| 25.259 | 3.5229 | 11.3 |
| 25.672 | 3.4672 | 1.9 |
| 26.1 | 3.4113 | 22.5 |
| 26.64 | 3.3434 | 14.2 |
| 27.43 | 3.2489 | 6.2 |
| 27.73 | 3.2144 | 1.4 |
| 28.1 | 3.1729 | 2.1 |
| 28.89 | 3.0879 | 1.7 |
| 29.5 | 3.0254 | 3.8 |
| 29.939 | 2.982 | 2 |
| 30.349 | 2.9427 | 1.6 |
| 30.708 | 2.9091 | 2.1 |
| 31.658 | 2.8239 | 2.2 |
| 32.6 | 2.7445 | 6.6 |
| 32.9 | 2.7201 | 3.2 |
| 33.62 | 2.6635 | 4.3 |
| 34.709 | 2.5824 | 2.1 |
| 35.08 | 2.5559 | 4.5 |
| 35.459 | 2.5294 | 1.9 |
| 36.34 | 2.4701 | 2.5 |
| 36.871 | 2.4358 | 2.1 |
| 38.761 | 2.3212 | 2.2 |

31) The Sulphate Crystalline Form XXXI of Compound 1

In one embodiment, the form is the sulphate crystalline Form XXXI of the compound 1, which is characterized by having at least three, at least four or five characteristic peaks at the following positions in the XRPD pattern represented by angle 2θ: 4.28±0.2°, 8.45±0.2°, 10.20±0.2°, 17.94±0.2°, 18.21±0.2°, 18.89±0.2°, 19.07±0.2°, 20.45±0.2°, 20.82±0.2°, 21.27±0.2°, 22.20±0.2°, 24.79±0.2°, 26.35±0.2°.

In some preferred embodiments, the form has XRPD characteristic peaks at the positions substantially as shown in Table 30 below and/or an XRPD pattern substantially as shown in FIG. 91.

In some preferred embodiments, they also have the following characteristics:

1) In the TGA plot, there is a weight loss of 0.05±0.02% by weight before 195.4° C.; and a weight loss of 1.1±0.2% by weight between 195.4° C.-219.2° C.;

2) In the DSC curve, there is an endothermic peak at the initial temperature of 192.7±2.0° C.;

3) the TGA plot substantially as shown in FIG. 92; and/or 4) the DSC curve substantially as shown in FIG. 93.

TABLE 30

| Angle[°2θ] ± 0.2° | d-value[Å] | Relative intensity [%] |
|---|---|---|
| 4.284 | 20.61 | 49.9 |
| 7.17 | 12.3192 | 18.4 |
| 8.453 | 10.4515 | 49.3 |
| 9.763 | 9.0523 | 33.1 |
| 10.209 | 8.6579 | 59.2 |
| 11.335 | 7.8001 | 26.7 |
| 12.196 | 7.2512 | 28.5 |
| 12.584 | 7.0286 | 21.6 |
| 13.461 | 6.5725 | 34.7 |
| 14.239 | 6.2151 | 27.7 |
| 15.372 | 5.7593 | 13.3 |
| 15.992 | 5.5373 | 26.7 |
| 16.795 | 5.2746 | 30.4 |
| 16.989 | 5.2146 | 38.1 |
| 17.942 | 4.9397 | 48.8 |
| 18.216 | 4.8661 | 100 |
| 18.892 | 4.6934 | 65.1 |
| 19.071 | 4.6498 | 62.4 |
| 19.597 | 4.5261 | 28 |
| 20.456 | 4.3381 | 53.3 |
| 20.822 | 4.2625 | 57.9 |
| 21.276 | 4.1726 | 46.9 |
| 22.206 | 3.9999 | 66.9 |
| 22.77 | 3.9022 | 27.7 |
| 23.608 | 3.7654 | 37.9 |
| 23.786 | 3.7377 | 31.7 |
| 24.798 | 3.5874 | 53.6 |
| 25.599 | 3.477 | 14.9 |
| 26.354 | 3.379 | 59.2 |
| 26.958 | 3.3046 | 28 |
| 28.343 | 3.1463 | 12 |
| 28.912 | 3.0856 | 10.1 |
| 29.414 | 3.0341 | 20.3 |
| 30.214 | 2.9556 | 14.7 |
| 30.704 | 2.9094 | 12.3 |
| 32.356 | 2.7646 | 20.5 |

32) The Sulphate Crystalline Form XXXII of Compound 1

In one embodiment, the form is the sulphate crystalline Form XXXII of the compound 1, which is characterized by having at least three, at least four or five characteristic peaks at the following positions in the XRPD pattern represented by angle 2θ: 4.28±0.2°, 16.71±0.2°, 16.92±0.2°, 20.82±0.2°, 21.32±0.2°.

In some preferred embodiments, the form has XRPD characteristic peaks at the positions substantially as shown in Table 31 below and/or an XRPD pattern substantially as shown in FIG. 94.

In some preferred embodiments, they also have the following characteristics:

1) In the TGA plot, there is a weight loss of 1.6±0.2% by weight before 162.0° C.; and a weight loss of 1.4±0.2% by weight between 162.0° C.-223.5° C.;

2) In the DSC curve, there is an endothermic peak at the initial temperature of 181.2±2.0° C.;

3) the TGA plot substantially as shown in FIG. 95; and/or 4) the DSC curve substantially as shown in FIG. 96.

TABLE 31

| Angle[°2θ] ± 0.2° | d-value[Å] | Relative intensity [%] |
|---|---|---|
| 4.286 | 20.6007 | 100 |
| 6.076 | 14.5342 | 3.3 |
| 6.587 | 13.4081 | 6.8 |
| 6.802 | 12.9834 | 6.3 |
| 7.09 | 12.4578 | 4.4 |
| 7.867 | 11.2284 | 3.6 |
| 8.417 | 10.496 | 4.1 |
| 9.152 | 9.6551 | 5.2 |
| 10.034 | 8.8077 | 7 |
| 15.876 | 5.5778 | 4.6 |
| 16.714 | 5.2999 | 21.4 |
| 16.926 | 5.2338 | 23.4 |
| 18.117 | 4.8924 | 13.3 |
| 18.543 | 4.7811 | 10.8 |
| 19.065 | 4.6512 | 6 |
| 20.048 | 4.4253 | 6.2 |
| 20.826 | 4.2618 | 20.6 |
| 21.329 | 4.1625 | 19.9 |
| 23.102 | 3.8469 | 5.1 |
| 23.883 | 3.7227 | 12.8 |
| 24.472 | 3.6344 | 5.5 |
| 28.087 | 3.1744 | 8.4 |

33) The Mesylate Crystalline Form XXXIII of Compound 1

In one embodiment, the form is the mesylate crystalline Form XXXIII of the compound 1, which is characterized by having at least three, at least four or five characteristic peaks at the following positions in the XRPD pattern represented by angle 2θ: 7.93±0.2°, 15.28±0.2°, 17.57±0.2°, 18.78±0.2°, 21.86±0.2°, 22.89±0.2°, 24.86±0.2°, 26.00±0.2θ.

In some preferred embodiments, the form has XRPD characteristic peaks at the positions substantially as shown in Table 32 below and/or an XRPD pattern substantially as shown in FIG. 97.

In some preferred embodiments, they also have the following characteristics:

1) In the TGA plot, there is a weight loss of 0.5±0.2% by weight before 69.0° C.; and a weight loss of 5.6±0.2% by weight between 69.0° C.-216.2° C.;
2) In the DSC curve, there is an endothermic peak at the initial temperature of 190.6±2.0° C.;
3) the TGA plot substantially as shown in FIG. 98; and/or
4) the DSC curve substantially as shown in FIG. 99.

TABLE 32

| Angle[°2θ] ± 0.2° | d-value[Å] | Relative intensity [%] |
|---|---|---|
| 4.871 | 18.1276 | 22.2 |
| 7.6 | 11.622 | 8.6 |
| 7.93 | 11.1399 | 38.9 |
| 9.5 | 9.302 | 14.2 |
| 9.74 | 9.0729 | 11.2 |
| 10.237 | 8.634 | 4.5 |
| 10.35 | 8.5396 | 4.1 |
| 11.73 | 7.5378 | 14.7 |
| 12.66 | 6.9865 | 15.7 |
| 14.24 | 6.2144 | 9 |
| 14.52 | 6.0953 | 10.4 |
| 15.289 | 5.7903 | 60.7 |
| 15.79 | 5.6079 | 18.4 |
| 16.69 | 5.3073 | 5.6 |
| 17.19 | 5.1542 | 25 |
| 17.36 | 5.1042 | 15.3 |
| 17.579 | 5.0408 | 65.9 |
| 18.32 | 4.8387 | 17.5 |
| 18.78 | 4.7213 | 100 |
| 19.079 | 4.6478 | 6.3 |
| 19.449 | 4.5603 | 8.6 |
| 19.9 | 4.458 | 5.6 |
| 20.5 | 4.3288 | 14 |
| 20.79 | 4.269 | 13.9 |
| 21.14 | 4.1991 | 20.9 |
| 21.481 | 4.1332 | 3.4 |
| 21.86 | 4.0624 | 39.8 |
| 22.89 | 3.8819 | 34.3 |
| 23.1 | 3.8471 | 8.7 |
| 23.281 | 3.8177 | 7.4 |
| 23.621 | 3.7635 | 10.2 |
| 24.28 | 3.6627 | 15.1 |
| 24.52 | 3.6275 | 16.5 |
| 24.86 | 3.5786 | 42.9 |
| 25.2 | 3.5311 | 2.7 |
| 25.72 | 3.4609 | 6.8 |
| 26.009 | 3.423 | 31.1 |
| 26.34 | 3.3808 | 4.7 |
| 26.668 | 3.3399 | 2.5 |
| 27.19 | 3.2769 | 1.6 |
| 27.61 | 3.2281 | 12 |
| 27.9 | 3.1952 | 4.6 |
| 28.08 | 3.1751 | 4.2 |
| 28.59 | 3.1196 | 3.7 |
| 29.85 | 2.9908 | 4 |
| 30.451 | 2.9331 | 2.2 |
| 30.94 | 2.8879 | 4.3 |
| 31.65 | 2.8247 | 4.8 |
| 32.229 | 2.7752 | 2.7 |
| 32.561 | 2.7477 | 2.2 |
| 32.949 | 2.7161 | 3.4 |
| 33.533 | 2.6702 | 1.7 |
| 34.242 | 2.6165 | 1.3 |
| 34.69 | 2.5837 | 2.2 |
| 35.07 | 2.5566 | 3.4 |
| 35.387 | 2.5344 | 1.3 |
| 35.919 | 2.4981 | 1.7 |
| 36.79 | 2.4409 | 2.2 |
| 37.4 | 2.4026 | 1.4 |
| 37.81 | 2.3774 | 1.7 |
| 38.14 | 2.3576 | 2.6 |
| 38.8 | 2.319 | 2.9 |

34) The Mesylate Crystalline Form XXXIV of Compound 1

In one embodiment, the form is the mesylate crystalline Form XXXIV of the compound 1, which is characterized by having at least three, at least four or five characteristic peaks at the following positions in the XRPD pattern represented by angle 2θ: 10.57±0.2°, 13.48±0.2°, 14.65±0.2°, 16.30±0.2°, 16.92±0.2°, 18.23±0.2°, 19.89±0.2°, 21.89±0.2°, 22.16±0.2°, 24.70±0.2°.

In some preferred embodiments, the form has XRPD characteristic peaks at the positions substantially as shown in Table 33 below and/or an XRPD pattern substantially as shown in FIG. 100.

In some preferred embodiments, they also have the following characteristics:

1) In the TGA plot, there is a weight loss of 0.2±0.1% by weight before 224.2° C.;
2) In the DSC curve, there is an endothermic peak at the initial temperature of 207.1±2.0° C.;
3) the TGA plot substantially as shown in FIG. 101; and/or
4) the DSC curve substantially as shown in FIG. 102.

TABLE 33

| Angle[°2θ] ± 0.2° | d-value[Å] | Relative intensity [%] |
|---|---|---|
| 6.802 | 12.9852 | 23.2 |
| 9.176 | 9.6302 | 4.4 |
| 10.578 | 8.3567 | 99.1 |
| 11.394 | 7.7593 | 20.1 |
| 12.604 | 7.0175 | 37.5 |

TABLE 33-continued

| Angle[°2θ] ± 0.2° | d-value[Å] | Relative intensity [%] |
|---|---|---|
| 13.481 | 6.5628 | 42.4 |
| 13.892 | 6.3695 | 27.8 |
| 14.65 | 6.0417 | 54.4 |
| 16.305 | 5.4318 | 50.1 |
| 16.927 | 5.2338 | 43 |
| 17.241 | 5.1389 | 13.8 |
| 17.688 | 5.0102 | 11.6 |
| 17.924 | 4.9446 | 22.9 |
| 18.233 | 4.8615 | 100 |
| 19.285 | 4.5986 | 16.3 |
| 19.694 | 4.5042 | 18.1 |
| 19.89 | 4.4602 | 44.7 |
| 20.412 | 4.3472 | 21.8 |
| 20.958 | 4.2352 | 20.3 |
| 21.136 | 4.2 | 14.2 |
| 21.525 | 4.1249 | 13.4 |
| 21.893 | 4.0563 | 89.2 |
| 22.169 | 4.0065 | 61.1 |
| 22.712 | 3.912 | 29 |
| 22.967 | 3.8691 | 15.8 |
| 23.745 | 3.744 | 6 |
| 24.041 | 3.6986 | 5.6 |
| 24.701 | 3.6012 | 39.2 |
| 25.224 | 3.5277 | 7.1 |
| 25.538 | 3.4851 | 0.7 |
| 26.007 | 3.4234 | 5.1 |
| 26.22 | 3.396 | 9.1 |
| 26.706 | 3.3353 | 13 |
| 27.388 | 3.2538 | 9.9 |
| 27.756 | 3.2114 | 6.7 |
| 27.934 | 3.1914 | 13 |
| 28.205 | 3.1613 | 11.5 |
| 28.667 | 3.1114 | 4.5 |
| 28.945 | 3.0822 | 28.8 |
| 29.511 | 3.0243 | 7.8 |
| 30.56 | 2.9229 | 6.7 |
| 31.03 | 2.8797 | 3.3 |
| 31.714 | 2.8191 | 4.4 |
| 32.161 | 2.7809 | 5.6 |
| 32.547 | 2.7488 | 12.5 |
| 33.199 | 2.6963 | 6.1 |
| 34.074 | 2.629 | 3.4 |
| 35.364 | 2.536 | 4.8 |
| 36.217 | 2.4782 | 3.2 |
| 36.68 | 2.448 | 5.6 |
| 37.888 | 2.3727 | 5.4 |
| 38.181 | 2.3551 | 5.2 |
| 39.763 | 2.265 | 3.4 |

35) The Mesylate Crystalline Form XXXV of Compound 1

In one embodiment, the form is the mesylate crystalline Form XXXV of the compound 1, which is characterized by having at least three, at least four or five characteristic peaks at the following positions in the XRPD pattern represented by angle 2θ: 9.54±0.2°, 16.47±0.2°, 16.69±0.2°, 16.94±0.2°, 18.71±0.2°, 19.71±0.2°, 20.33±0.2°, 20.98±0.2°, 21.75±0.2°.

In some preferred embodiments, the form has XRPD characteristic peaks at the positions substantially as shown in Table 34 below and/or an XRPD pattern substantially as shown in FIG. 103.

In some preferred embodiments, they also have the following characteristics:

1) In the TGA plot, there is a weight loss of 2.3±0.2% by weight before 85.2° C.; a weight loss of 3.4±0.2% by weight between 85.2° C.-131.5° C.; a weight loss of 2.7±0.2% by weight between 131.5° C.-188.8° C.; and a weight loss of 0.9±0.2% by weight between 188.8° C.-236.1° C.;

2) In the DSC curve, there are two endothermic peaks at the initial temperature of 169.5±2.0° C. and 234.0±2.0° C.;

3) the TGA plot substantially as shown in FIG. 104; and/or 4) the DSC curve substantially as shown in FIG. 105.

TABLE 34

| Angle[°2θ] ± 0.2° | d-value[Å] | Relative intensity [%] |
|---|---|---|
| 8.999 | 9.8191 | 31.5 |
| 9.545 | 9.2585 | 93.5 |
| 9.9 | 8.9267 | 10.8 |
| 10.169 | 8.6916 | 35 |
| 11.317 | 7.8124 | 29.3 |
| 12.798 | 6.9114 | 29.3 |
| 13.362 | 6.6209 | 13.5 |
| 14.104 | 6.2741 | 19.3 |
| 14.571 | 6.0743 | 26.2 |
| 15.447 | 5.7317 | 22.7 |
| 16.479 | 5.3749 | 67.8 |
| 16.694 | 5.3062 | 52 |
| 16.949 | 5.2269 | 100 |
| 17.613 | 5.0313 | 22.5 |
| 17.936 | 4.9415 | 39.3 |
| 18.719 | 4.7365 | 82.8 |
| 19.716 | 4.4992 | 60.7 |
| 20.336 | 4.3634 | 69.8 |
| 20.98 | 4.2309 | 78.3 |
| 21.47 | 4.1354 | 22.5 |
| 21.759 | 4.0811 | 50 |
| 23.554 | 3.7739 | 36.2 |
| 24.016 | 3.7024 | 8.7 |
| 24.68 | 3.6043 | 33.3 |
| 25.948 | 3.431 | 32 |
| 27.33 | 3.2605 | 23.5 |
| 28.101 | 3.1728 | 7.5 |
| 28.654 | 3.1128 | 34.3 |
| 29.784 | 2.9973 | 16.5 |

36) The Citrate Crystalline Form XXXVI of Compound 1

In one embodiment, the form is the citrate crystalline Form XXXVI of the compound 1, which is characterized by having at least three, at least four or five characteristic peaks at the following positions in the XRPD pattern represented by angle 2θ: 15.99±0.2°, 18.62±0.2°, 19.13±0.2°, 19.28±0.2°, 22.13±0.2°, 24.1±0.2°, 26.82±0.2°.

In some preferred embodiments, the form has XRPD characteristic peaks at the positions substantially as shown in Table 35 below and/or an XRPD pattern substantially as shown in FIG. 106

In some preferred embodiments, they also have the following characteristics:

1) In the TGA plot, there is a weight loss of 0.4±0.2% by weight before 106.7° C.; and a weight loss of 19.4±0.2% by weight between 106.7° C.-231.8° C.;

2) In the DSC curve, there are two endothermic peaks at the initial temperature of 157.7±2.0° C. and 222.2±2.0° C.;

3) the TGA plot substantially as shown in FIG. 107; and/or 4) the DSC curve substantially as shown in FIG. 108.

TABLE 35

| Angle[°2θ] ± 0.2° | d-value[Å] | Relative intensity [%] |
|---|---|---|
| 4.77 | 18.5099 | 23.8 |
| 7.001 | 12.6157 | 12.2 |
| 7.98 | 11.0697 | 32.3 |
| 8.95 | 9.8725 | 33.9 |
| 9.19 | 9.6147 | 2.1 |
| 9.59 | 9.215 | 6.7 |
| 10.619 | 8.3239 | 5.2 |
| 11.139 | 7.9368 | 12.6 |
| 12.281 | 7.2013 | 17 |
| 12.53 | 7.0586 | 6.4 |

TABLE 35-continued

| Angle[°2θ] ± 0.2° | d-value[Å] | Relative intensity [%] |
|---|---|---|
| 13.85 | 6.3889 | 11 |
| 14.12 | 6.267 | 19.9 |
| 14.279 | 6.1977 | 7.2 |
| 14.999 | 5.9017 | 13.8 |
| 15.17 | 5.8355 | 12.3 |
| 15.38 | 5.7562 | 26.3 |
| 15.81 | 5.6007 | 13.5 |
| 15.99 | 5.538 | 44.3 |
| 16.24 | 5.4536 | 15.6 |
| 16.59 | 5.3391 | 2.9 |
| 16.739 | 5.2918 | 3 |
| 17.5 | 5.0635 | 19.1 |
| 18 | 4.924 | 24.9 |
| 18.62 | 4.7614 | 37.3 |
| 18.823 | 4.7105 | 5.2 |
| 19.13 | 4.6356 | 100 |
| 19.289 | 4.5978 | 41.3 |
| 19.579 | 4.5302 | 18 |
| 19.77 | 4.487 | 3 |
| 20.161 | 4.4009 | 12.8 |
| 20.561 | 4.3162 | 2 |
| 21.13 | 4.201 | 31.9 |
| 21.34 | 4.1603 | 22.7 |
| 21.631 | 4.105 | 4.3 |
| 21.8 | 4.0735 | 4.5 |
| 22.13 | 4.0136 | 69.4 |
| 22.965 | 3.8694 | 1.1 |
| 23.25 | 3.8226 | 6.1 |
| 23.619 | 3.7637 | 24.8 |
| 24.1 | 3.6897 | 44.7 |
| 24.729 | 3.5972 | 2.6 |
| 25.121 | 3.542 | 2.2 |
| 25.67 | 3.4675 | 15.2 |
| 26.122 | 3.4086 | 1.1 |
| 26.829 | 3.3202 | 43 |
| 27.46 | 3.2454 | 7.9 |
| 28.09 | 3.174 | 2.5 |
| 28.35 | 3.1455 | 7 |
| 28.88 | 3.0889 | 2.7 |
| 29.37 | 3.0385 | 5 |
| 29.94 | 2.982 | 9.7 |
| 30.11 | 2.9655 | 16.2 |
| 30.379 | 2.9398 | 3.2 |
| 31.05 | 2.8779 | 4.3 |
| 31.37 | 2.8492 | 2.2 |
| 31.928 | 2.8007 | 2.4 |
| 32.52 | 2.751 | 5.5 |
| 32.97 | 2.7145 | 3.5 |
| 33.481 | 2.6742 | 1.8 |
| 33.829 | 2.6475 | 3.2 |
| 34.119 | 2.6257 | 3.2 |
| 34.849 | 2.5723 | 3 |
| 35.262 | 2.5432 | 2.8 |
| 36.459 | 2.4623 | 5.7 |
| 37.209 | 2.4144 | 1.5 |
| 37.848 | 2.3751 | 1.6 |
| 38.2 | 2.354 | 2.5 |
| 38.859 | 2.3156 | 3 |
| 39.24 | 2.294 | 1.3 |

37) The Citrate Crystalline Form XXXVII of Compound 1

In one embodiment, the form is the citrate crystalline Form XXXVII of the compound 1, which is characterized by having at least three, at least four or five characteristic peaks at the following positions in the XRPD pattern represented by angle 2θ: 5.96±0.2°, 15.31±0.2°, 16.92±0.2°, 17.94±0.2°, 18.77±0.2°, 19.01±0.2°, 20.06±0.2°, 21.03±0.2°, 21.75±0.2°, 22.96±0.2°.

In some preferred embodiments, the form has XRPD characteristic peaks at the positions substantially as shown in Table 36 below and/or an XRPD pattern substantially as shown in FIG. 109.

In some preferred embodiments, they also have the following characteristics:

1) In the TGA plot, there is a weight loss of 0.9±0.2% by weight before 128.2° C.; and a weight loss of 8.3±0.2% by weight between 128.2° C.-232.40° C.;

2) In the DSC curve, there are three endothermic peaks at the initial temperature of 138.8±2.0° C., 179.5±2.0° C. and 229.3±2.0° C.;

3) the TGA plot substantially as shown in FIG. 110; and/or 4) the DSC curve substantially as shown in FIG. 111.

TABLE 36

| Angle[°2θ] ± 0.2° | d-value[Å] | Relative intensity [%] |
|---|---|---|
| 5.377 | 16.4223 | 36.4 |
| 5.96 | 14.8155 | 100 |
| 7.656 | 11.5375 | 43.1 |
| 8.277 | 10.6731 | 40.7 |
| 9.564 | 9.2396 | 33.2 |
| 10.538 | 8.3883 | 35.5 |
| 11.669 | 7.5774 | 5.4 |
| 12.428 | 7.1163 | 39.8 |
| 13.536 | 6.5361 | 36.1 |
| 14.357 | 6.1642 | 45.9 |
| 15.312 | 5.782 | 51 |
| 15.856 | 5.5846 | 25.5 |
| 16.928 | 5.2334 | 63.6 |
| 17.94 | 4.9402 | 79.1 |
| 18.777 | 4.7219 | 90 |
| 19.012 | 4.6642 | 61.3 |
| 19.267 | 4.6031 | 21.3 |
| 20.066 | 4.4215 | 87.8 |
| 20.726 | 4.2822 | 27.1 |
| 21.038 | 4.2193 | 60.1 |
| 21.759 | 4.081 | 67.7 |
| 22.344 | 3.9756 | 37.9 |
| 22.965 | 3.8694 | 72 |
| 23.766 | 3.7409 | 33.4 |
| 24.505 | 3.6296 | 46.8 |
| 24.739 | 3.5959 | 13.1 |
| 25.343 | 3.5115 | 48.3 |
| 26.045 | 3.4184 | 28.2 |
| 27.795 | 3.207 | 6.7 |
| 28.809 | 3.0964 | 29.1 |
| 29.745 | 3.001 | 18 |
| 30.548 | 2.924 | 12.1 |
| 30.955 | 2.8865 | 9.8 |
| 31.206 | 2.8638 | 22.7 |
| 31.812 | 2.8106 | 17.6 |
| 33.309 | 2.6876 | 17.7 |

38) The Citrate Crystalline Form XXXVIII of Compound 1

In one embodiment, the form is the citrate crystalline Form XXXVIII of the compound 1, which is characterized by having at least three, at least four or five characteristic peaks at the following positions in the XRPD pattern represented by angle 2θ: 7.79±0.2°, 9.54±0.2°, 9.87±0.2°, 17.61±0.2°, 17.80±0.2°, 22.48±0.2°.

In some preferred embodiments, the form has XRPD characteristic peaks at the positions substantially as shown in Table 37 below and/or an XRPD pattern substantially as shown in FIG. 112.

In some preferred embodiments, they also have the following characteristics:

1) In the TGA plot, there is a weight loss of 2.2±0.2% by weight before 142.1° C.; and a weight loss of 15.1±0.2% by weight between 142.1° C.-230.1° C.;

2) In the DSC curve, there are two endothermic peaks at the initial temperature of 135.3±2.0° C. and 160.9±2.0° C.;

3) the TGA plot substantially as shown in FIG. 113; and/or 4) the DSC curve substantially as shown in FIG. 114.

TABLE 37

| Angle[°2θ] ± 0.2° | d-value[Å] | Relative intensity [%] |
|---|---|---|
| 3.994 | 22.1028 | 33.5 |
| 7.308 | 12.0861 | 12.5 |
| 7.791 | 11.3374 | 70.5 |
| 9.077 | 9.7343 | 31.8 |
| 9.545 | 9.2582 | 59.3 |
| 9.876 | 8.9486 | 60.5 |
| 10.206 | 8.6598 | 19.8 |
| 11.473 | 7.7062 | 9.3 |
| 11.805 | 7.4905 | 25.5 |
| 13.304 | 6.6498 | 19.7 |
| 13.769 | 6.4259 | 9.6 |
| 14.142 | 6.2572 | 14.7 |
| 14.512 | 6.0986 | 23 |
| 15.696 | 5.6411 | 13.5 |
| 16.19 | 5.47 | 17.8 |
| 16.615 | 5.3313 | 16.5 |
| 17.611 | 5.0319 | 81.4 |
| 17.804 | 4.9778 | 100 |
| 18.819 | 4.7116 | 46 |
| 19.4 | 4.5716 | 35.1 |
| 20.048 | 4.4254 | 29.2 |
| 20.355 | 4.3593 | 27.2 |
| 20.764 | 4.2743 | 11.2 |
| 21.66 | 4.0995 | 47.2 |
| 22.481 | 3.9516 | 56.4 |
| 22.707 | 3.9128 | 42.9 |
| 23.222 | 3.8272 | 10.1 |
| 23.683 | 3.7537 | 4.9 |
| 24.25 | 3.6672 | 22.1 |
| 25.15 | 3.538 | 6 |
| 25.674 | 3.4669 | 19.5 |
| 26.239 | 3.3935 | 21.2 |
| 26.651 | 3.342 | 11.3 |
| 27.563 | 3.2335 | 8.6 |
| 27.817 | 3.2046 | 9.7 |
| 28.126 | 3.17 | 7.1 |
| 28.59 | 3.1197 | 6.3 |
| 28.949 | 3.0817 | 10.9 |
| 29.533 | 3.0221 | 15.3 |
| 29.94 | 2.982 | 32.8 |
| 30.666 | 2.913 | 5.8 |
| 31.052 | 2.8776 | 7.9 |
| 32.574 | 2.7466 | 3.8 |
| 33.429 | 2.6783 | 5.5 |
| 33.801 | 2.6497 | 4.9 |
| 36.375 | 2.4679 | 4.1 |
| 37.885 | 2.3728 | 5.7 |

39) The Citrate Crystalline Form XXXIX of Compound 1

In one embodiment, the form is the citrate crystalline Form XXXIX of the compound 1, which is characterized by having at least three, at least four or five characteristic peaks at the following positions in the XRPD pattern represented by angle 2θ: 8.49±0.2°, 12.81±0.2°, 13.85±0.2°, 16.30±0.2°, 17.08±0.2°, 17.89±0.2°, 18.68±0.2°, 19.84±0.2°, 21.62±0.2°, 22.98±0.2°, 25.20±0.2°, 26.61±0.2°.

In some preferred embodiments, the form has XRPD characteristic peaks at the positions substantially as shown in Table 38 below and/or an XRPD pattern substantially as shown in FIG. 115.

In some preferred embodiments, they also have the following characteristics:

1) In the TGA plot, there is a weight loss of 0.02±0.010% by weight before 124.6° C.; and a weight loss of 21.6±0.2% by weight between 124.6° C.-232.1° C.;

2) In the DSC curve, there is an endothermic peak at the initial temperature of 165.6±2.0° C.;

3) the TGA plot substantially as shown in FIG. 116; and/or 4) the DSC curve substantially as shown in FIG. 117.

TABLE 38

| Angle[°2θ] ± 0.2° | d-value[Å] | Relative intensity [%] |
|---|---|---|
| 5.206 | 16.9615 | 6.1 |
| 5.53 | 15.9672 | 16.4 |
| 7.698 | 11.4755 | 41.2 |
| 8.493 | 10.4029 | 55 |
| 8.848 | 9.9856 | 32.1 |
| 8.919 | 9.9063 | 33.9 |
| 10.011 | 8.8287 | 21.9 |
| 10.892 | 8.1164 | 21.9 |
| 11.742 | 7.5301 | 15.4 |
| 12.39 | 7.1379 | 12.8 |
| 12.818 | 6.9004 | 52.8 |
| 13.212 | 6.6957 | 21.3 |
| 13.851 | 6.3883 | 49.7 |
| 14.34 | 6.1713 | 9.8 |
| 14.731 | 6.0084 | 15.2 |
| 15.316 | 5.7804 | 8.3 |
| 15.923 | 5.5614 | 7.6 |
| 16.304 | 5.4323 | 50.7 |
| 16.713 | 5.3001 | 33.9 |
| 17.083 | 5.1861 | 50.1 |
| 17.35 | 5.107 | 5.2 |
| 17.899 | 4.9515 | 75.7 |
| 18.177 | 4.8763 | 31 |
| 18.682 | 4.7457 | 98.8 |
| 18.992 | 4.669 | 41.5 |
| 19.482 | 4.5526 | 10.8 |
| 19.848 | 4.4695 | 100 |
| 20.237 | 4.3845 | 37.4 |
| 20.746 | 4.2779 | 20.8 |
| 21.076 | 4.2117 | 38.2 |
| 21.622 | 4.1067 | 78.2 |
| 22.654 | 3.9218 | 22.2 |
| 22.986 | 3.866 | 93.4 |
| 23.237 | 3.8248 | 37 |
| 23.488 | 3.7844 | 40.6 |
| 23.684 | 3.7535 | 16.9 |
| 24.333 | 3.655 | 32.8 |
| 24.779 | 3.5902 | 19.4 |
| 25.207 | 3.5302 | 62.1 |
| 25.612 | 3.4752 | 14.3 |
| 26.021 | 3.4215 | 7 |
| 26.61 | 3.3471 | 58.8 |
| 27.212 | 3.2744 | 11.1 |
| 28.733 | 3.1044 | 20.1 |
| 29.376 | 3.038 | 23.7 |
| 30.016 | 2.9746 | 6.5 |
| 30.278 | 2.9495 | 9.5 |
| 30.76 | 2.9043 | 12.8 |
| 31.338 | 2.852 | 8.6 |
| 31.605 | 2.8286 | 6.8 |
| 31.906 | 2.8025 | 16.3 |
| 32.688 | 2.7372 | 8.6 |
| 32.982 | 2.7136 | 11.9 |
| 33.231 | 2.6938 | 8.3 |
| 33.931 | 2.6398 | 10.8 |
| 34.226 | 2.6177 | 9.9 |
| 35.219 | 2.5461 | 7 |
| 35.555 | 2.5229 | 8.3 |
| 35.824 | 2.5045 | 9.2 |
| 36.817 | 2.4392 | 5 |
| 37.401 | 2.4025 | 7 |
| 38.432 | 2.3404 | 8.6 |

40) The Maleate Crystalline Form XL of Compound 1

In one embodiment, the form is the maleate crystalline Form XL of the compound 1, which is characterized by having at least three, at least four or five characteristic peaks at the following positions in the XRPD pattern represented by angle 2θ: 5.06±0.2°, 15.63±0.2°, 16.43±0.2°, 19.03±0.2°, 20.48±0.2°, 20.72±0.2°, 20.97±0.2°, 26.03±0.2°.

In some preferred embodiments, the form has XRPD characteristic peaks at the positions substantially as shown in Table 39 below and/or an XRPD pattern substantially as shown in FIG. 118

In some preferred embodiments, they also have the following characteristics:

1) In the TGA plot, there is a weight loss of 0.12±0.02% by weight before 81.6° C.; and a weight loss of 15.6±0.2% by weight between 81.6° C.-224.8° C.;

2) In the DSC curve, there are two endothermic peaks at the initial temperature of 154.5±2.0° C. and 220.3±2.0° C.;

3) the TGA plot substantially as shown in FIG. 119; and/or 4) the DSC curve substantially as shown in FIG. 120.

TABLE 39

| Angle[°2θ] ± 0.2° | d-value[Å] | Relative intensity [%] |
|---|---|---|
| 5.06 | 17.4513 | 100 |
| 8.44 | 10.4678 | 2.3 |
| 8.821 | 10.0164 | 3.6 |
| 9.529 | 9.2736 | 4.5 |
| 10.07 | 8.7769 | 8.3 |
| 10.76 | 8.2154 | 6 |
| 11.469 | 7.709 | 7 |
| 11.581 | 7.6348 | 5 |
| 12.459 | 7.0985 | 5 |
| 14.18 | 6.2407 | 4.3 |
| 14.557 | 6.0799 | 2.8 |
| 15.63 | 5.665 | 29 |
| 15.88 | 5.5764 | 14 |
| 16.43 | 5.3909 | 24.7 |
| 16.831 | 5.2633 | 12.4 |
| 17.08 | 5.187 | 11.2 |
| 17.691 | 5.0092 | 6.1 |
| 18.591 | 4.7687 | 11.5 |
| 19.03 | 4.6597 | 35.7 |
| 19.609 | 4.5234 | 8.9 |
| 20.157 | 4.4017 | 3.6 |
| 20.48 | 4.333 | 27.5 |
| 20.72 | 4.2833 | 52.5 |
| 20.97 | 4.2329 | 28.5 |
| 21.4 | 4.1487 | 13.1 |
| 21.85 | 4.0642 | 8.8 |
| 22.96 | 3.8703 | 14.6 |
| 23.29 | 3.8162 | 3.1 |
| 23.607 | 3.7656 | 1.5 |
| 24.11 | 3.6882 | 3.2 |
| 24.4 | 3.645 | 9.9 |
| 24.811 | 3.5855 | 3.6 |
| 25.359 | 3.5093 | 3 |
| 26.03 | 3.4204 | 27.9 |
| 26.86 | 3.3164 | 2.2 |
| 27.37 | 3.2558 | 9.6 |
| 27.719 | 3.2156 | 2.7 |
| 28.32 | 3.1488 | 2.8 |
| 29.669 | 3.0086 | 6.2 |
| 30.512 | 2.9274 | 2.9 |
| 31.31 | 2.8546 | 2.9 |
| 31.719 | 2.8186 | 3.9 |
| 32.759 | 2.7315 | 4.2 |
| 33.58 | 2.6665 | 2.1 |
| 34.059 | 2.6301 | 2.3 |
| 34.802 | 2.5757 | 1.6 |
| 35.351 | 2.5369 | 0.7 |
| 35.921 | 2.498 | 1.6 |
| 37.677 | 2.3855 | 1.4 |
| 38.27 | 2.3499 | 1.5 |
| 39.21 | 2.2957 | 1.3 |

41) The Maleate Crystalline Form XLI of Compound 1

In one embodiment, the form is the maleate crystalline Form XLI of the compound 1, which is characterized by having at least three, at least four or five characteristic peaks at the following positions in the XRPD pattern represented by angle 2θ: 5.12±0.2°, 8.12±0.2°, 14.68±0.2°, 16.83±0.2°, 18.35±0.2°, 19.32±0.2°, 21.11±0.2°, 23.66±0.2°.

In some preferred embodiments, the form has XRPD characteristic peaks at the positions substantially as shown in Table 40 below and/or an XRPD pattern substantially as shown in FIG. 121.

In some preferred embodiments, they also have the following characteristics:

1) In the TGA plot, there is a weight loss of 1.4±0.2% by weight before 154.0° C.; and a weight loss of 8.3±0.2% by weight between 154.0-227.8° C.;

2) In the DSC curve, there is an endothermic peak at the initial temperature of 193.6±2.0° C.;

3) the TGA plot substantially as shown in FIG. 122; and/or 4) the DSC curve substantially as shown in FIG. 123.

TABLE 40

| Angle[°2θ] ± 0.2° | d-value[Å] | Relative intensity [%] |
|---|---|---|
| 5.122 | 17.2402 | 49.8 |
| 7.596 | 11.6281 | 11.1 |
| 8.124 | 10.8747 | 46.1 |
| 9.333 | 9.4684 | 7.5 |
| 10.013 | 8.8266 | 26.4 |
| 10.89 | 8.1176 | 11.8 |
| 11.299 | 7.8244 | 16.9 |
| 12.546 | 7.0495 | 13.2 |
| 13.129 | 6.7377 | 29.9 |
| 14.688 | 6.0259 | 100 |
| 15.74 | 5.6254 | 10.5 |
| 16.093 | 5.5029 | 24.1 |
| 16.83 | 5.2636 | 52.1 |
| 17.025 | 5.2036 | 38.1 |
| 18.351 | 4.8305 | 50.7 |
| 19.324 | 4.5895 | 71.6 |
| 19.599 | 4.5258 | 17.5 |
| 19.966 | 4.4434 | 10.2 |
| 20.61 | 4.306 | 10.9 |
| 21.117 | 4.2037 | 51.5 |
| 21.721 | 4.0881 | 40.1 |
| 22.17 | 4.0063 | 30.1 |
| 22.478 | 3.9521 | 30.9 |
| 23.084 | 3.8498 | 9.4 |
| 23.667 | 3.7562 | 96.4 |
| 24.274 | 3.6637 | 9 |
| 24.913 | 3.5711 | 9.5 |
| 25.185 | 3.5331 | 10.5 |
| 26.065 | 3.4158 | 31.2 |
| 26.572 | 3.3517 | 16.3 |
| 27.934 | 3.1913 | 24.2 |
| 28.512 | 3.1279 | 3.8 |
| 29.104 | 3.0657 | 21.1 |
| 29.578 | 3.0176 | 3.3 |
| 30.001 | 2.976 | 16.1 |
| 30.697 | 2.9101 | 3.8 |
| 31.672 | 2.8227 | 10.1 |
| 32.338 | 2.7661 | 5 |
| 33.156 | 2.6997 | 9 |
| 33.949 | 2.6384 | 6.4 |
| 34.91 | 2.568 | 4.8 |
| 35.747 | 2.5097 | 3.2 |
| 36.332 | 2.4707 | 3.6 |
| 37.164 | 2.4172 | 3.7 |
| 37.634 | 2.3881 | 6.7 |
| 38.75 | 2.3219 | 4.9 |
| 39.429 | 2.2834 | 4.9 |

42) The Maleate Crystalline Form XLII of Compound 1

In one embodiment, the form is the maleate crystalline Form XLII of the compound 1, which is characterized by having at least three, at least four or five characteristic peaks at the following positions in the XRPD pattern represented by angle 2θ: 5.2±0.2°, 16.80±0.2°, 19.36±0.2°, 19.65±0.2°, 21.00±0.2°, 26.04±0.2°.

In some preferred embodiments, the form has XRPD characteristic peaks at the positions substantially as shown in Table 41 below and/or an XRPD pattern substantially as shown in FIG. 124.

In some preferred embodiments, they also have the following characteristics:

1) In the TGA plot, there is a weight loss of 1.6±0.2% by weight before 122.6° C.; a weight loss of 7.6±0.2% by weight between 122.6° C.-188.40° C.; and a weight loss of 5.0±0.2% by weight between 188.40° C.-228.10° C.;

2) In the DSC curve, there are three endothermic peaks at the initial temperature of 157.8±2.0° C. 184.3±2.0° C. and 218.8±2.0° C.;

3) the TGA plot substantially as shown in FIG. 125; and/or 4) the DSC curve substantially as shown in FIG. 126.

TABLE 41

| Angle[°2θ] ± 0.2° | d-value[Å] | Relative intensity [%] |
|---|---|---|
| 5.2 | 16.9819 | 76 |
| 8.222 | 10.7443 | 11 |
| 8.531 | 10.3563 | 6.5 |
| 9.075 | 9.7371 | 12.3 |
| 9.839 | 8.9824 | 17.2 |
| 10.927 | 8.0903 | 14.5 |
| 11.981 | 7.3805 | 15.9 |
| 12.525 | 7.0614 | 18.3 |
| 12.622 | 7.0072 | 17.2 |
| 13.42 | 6.5926 | 4.5 |
| 14.159 | 6.2499 | 9.6 |
| 14.526 | 6.0929 | 11.5 |
| 15.364 | 5.7624 | 10.2 |
| 16.128 | 5.4911 | 14.3 |
| 16.807 | 5.2707 | 29.8 |
| 17.257 | 5.1344 | 22.5 |
| 17.652 | 5.0203 | 14.7 |
| 18.076 | 4.9034 | 10.1 |
| 18.914 | 4.688 | 15.4 |
| 19.362 | 4.5806 | 38.9 |
| 19.653 | 4.5133 | 31.5 |
| 21.001 | 4.2267 | 100 |
| 22.087 | 4.0212 | 16.4 |
| 23.103 | 3.8467 | 24.5 |
| 24.665 | 3.6064 | 16.4 |
| 25.088 | 3.5466 | 7.6 |
| 26.045 | 3.4183 | 41.5 |
| 27.158 | 3.2808 | 7.6 |
| 27.805 | 3.2059 | 9.3 |
| 28.342 | 3.1464 | 11.2 |
| 29.655 | 3.01 | 12.4 |
| 30.153 | 2.9614 | 6.3 |
| 33.642 | 2.6618 | 6.3 |

43) The Maleate Crystalline Form XLIII of Compound 1

In one embodiment, the form is the maleate crystalline Form XLIII of the compound 1, which is characterized by having at least three, at least four or five characteristic peaks at the following positions in the XRPD pattern represented by angle 2θ: 5.18±0.2°, 15.60±0.2°, 15.99±0.2°, 17.04±0.2°, 19.18±0.2°, 20.86±0.2°, 25.98±0.2°.

In some preferred embodiments, the form has XRPD characteristic peaks at the positions substantially as shown in Table 42 below and/or an XRPD pattern substantially as shown in FIG. 127.

In some preferred embodiments, they also have the following characteristics:

1) In the TGA plot, there is a weight loss of 11.5±0.2% by weight before 187.4° C.; and a weight loss of 5.2±0.2% by weight between 187.4° C.-227.8° C.;

2) In the DSC curve, there are three endothermic peaks at the initial temperature of 148.0±2.0° C., 180.2±2.0° C. and 214.9±2.0° C.;

3) the TGA plot substantially as shown in FIG. 128; and/or 4) the DSC curve substantially as shown in FIG. 129.

TABLE 42

| Angle[°2θ] ± 0.2° | d-value[Å] | Relative intensity [%] |
|---|---|---|
| 5.181 | 17.0431 | 100 |
| 8.919 | 9.907 | 4.4 |
| 9.561 | 9.2424 | 4.3 |
| 10.167 | 8.6929 | 10.1 |
| 11 | 8.0365 | 5.3 |
| 11.648 | 7.5911 | 9.2 |
| 12.446 | 7.1061 | 5.6 |
| 13.651 | 6.4814 | 2.2 |
| 14.383 | 6.1532 | 6.7 |
| 15.602 | 5.6749 | 27.7 |
| 15.993 | 5.5372 | 31.1 |
| 16.266 | 5.4447 | 16.8 |
| 17.046 | 5.1973 | 25.2 |
| 17.771 | 4.9869 | 7.5 |
| 18.606 | 4.765 | 13.3 |
| 19.189 | 4.6215 | 37.7 |
| 19.912 | 4.4552 | 6.9 |
| 20.862 | 4.2545 | 75.7 |
| 21.481 | 4.1333 | 12.3 |
| 21.838 | 4.0665 | 9.6 |
| 22.97 | 3.8686 | 14.4 |
| 24.662 | 3.6069 | 18.5 |
| 25.542 | 3.4845 | 7.1 |
| 25.987 | 3.4259 | 33.4 |
| 27.586 | 3.2308 | 14.9 |
| 28.208 | 3.161 | 8.2 |
| 28.599 | 3.1186 | 4.5 |
| 29.571 | 3.0183 | 8.9 |
| 30.583 | 2.9207 | 5.4 |
| 31.694 | 2.8208 | 5.1 |
| 37.944 | 2.3693 | 4.8 |

44) The Maleate Crystalline Form XLIV of Compound 1

In one embodiment, the form is the maleate crystalline Form XLIV of the compound 1, which is characterized by having at least three, at least four or five characteristic peaks at the following positions in the XRPD pattern represented by angle 2θ: 5.20±0.2°, 6.03±0.2°, 13.5±0.2°, 16.88±0.2°, 17.70±0.2°, 18.75±0.2°, 19.16±0.2°, 19.77±0.2°, 20.97±0.2°, 21.72±0.2°, 24.77±0.2°, 28.65±0.2°.

In some preferred embodiments, the form has XRPD characteristic peaks at the positions substantially as shown in Table 43 below and/or an XRPD pattern substantially as shown in FIG. 130.

In some preferred embodiments, they also have the following characteristics:

1) In the TGA plot, there is a weight loss of 0.2±0.10% by weight before 102.1° C.; a weight loss of 5.0±0.2% by weight between 102.1° C.-188.8° C.; and a weight loss of 2.4±0.2% by weight between 188.8° C.-228.5° C.;

2) In the DSC curve, there are two endothermic peaks at the initial temperature of 192.0±2.0° C. and 228.0±2.0° C.;

3) the TGA plot substantially as shown in FIG. 131; and/or 4) the DSC curve substantially as shown in FIG. 132.

TABLE 43

| Angle[°2θ] ± 0.2° | d-value[Å] | Relative intensity [%] |
|---|---|---|
| 5.203 | 16.97 | 100 |
| 6.039 | 14.6236 | 87.2 |
| 6.7 | 13.1815 | 24.5 |
| 9.58 | 9.2242 | 38.3 |
| 12.252 | 7.2178 | 32.7 |
| 12.585 | 7.0277 | 37.8 |
| 13.5 | 6.5537 | 58.2 |
| 14.303 | 6.1875 | 14.3 |
| 15.108 | 5.8595 | 20.4 |
| 15.993 | 5.5371 | 27.6 |
| 16.541 | 5.3548 | 36.7 |

TABLE 43-continued

| Angle[°2θ] ± 0.2° | d-value[Å] | Relative intensity [%] |
|---|---|---|
| 16.889 | 5.2452 | 68.9 |
| 17.709 | 5.0044 | 59.7 |
| 18.194 | 4.8719 | 30.1 |
| 18.758 | 4.7267 | 78.6 |
| 19.164 | 4.6274 | 50 |
| 19.773 | 4.4863 | 81.1 |
| 20.979 | 4.231 | 99.5 |
| 21.72 | 4.0883 | 79.1 |
| 22.442 | 3.9583 | 42.3 |
| 22.97 | 3.8686 | 14.8 |
| 24.779 | 3.5902 | 90.8 |
| 25.419 | 3.5011 | 23 |
| 26.141 | 3.4061 | 18.9 |
| 28.656 | 3.1125 | 60.7 |
| 33.937 | 2.6394 | 17.9 |

45) The Tartrate Crystalline Form XLV of Compound 1

In one embodiment, the form is the tartrate crystalline Form XLV of the compound 1, which is characterized by having at least three, at least four or five characteristic peaks at the following positions in the XRPD pattern represented by angle 2θ: 3.88±0.2°, 5.91±0.2°, 15.6±0.2°, 18.04±0.2°, 18.4±0.2°, 19.44±0.2°.

In some preferred embodiments, the form has XRPD characteristic peaks at the positions substantially as shown in Table 44 below and/or an XRPD pattern substantially as shown in FIG. 133.

In some preferred embodiments, they also have the following characteristics:
1) In the TGA plot, there is a weight loss of 1.1±0.2% by weight before 76.6° C.; a weight loss of 1.4±0.2% by weight between 76.6° C.-155.7° C.; and a weight loss of 12.6±0.2% by weight between 155.7° C.-242.0° C.;
2) In the DSC curve, there is an endothermic peak at the initial temperature of 155.9±2.0° C.;
3) the TGA plot substantially as shown in FIG. 134; and/or
4) the DSC curve substantially as shown in FIG. 135.

TABLE 44

| Angle[°2θ] ± 0.2° | d-value[Å] | Relative intensity [%] |
|---|---|---|
| 3.88 | 22.7539 | 100 |
| 5.919 | 14.9181 | 46.6 |
| 7.771 | 11.3679 | 18.3 |
| 8.92 | 9.9055 | 19.9 |
| 10.209 | 8.6574 | 13.8 |
| 11.879 | 7.4439 | 9.4 |
| 12.31 | 7.184 | 9 |
| 14.04 | 6.3026 | 12 |
| 14.513 | 6.0984 | 6.5 |
| 15.6 | 5.6757 | 36.1 |
| 16.02 | 5.528 | 28.8 |
| 16.549 | 5.3523 | 23.1 |
| 18.04 | 4.9131 | 67 |
| 18.4 | 4.8177 | 61.2 |
| 19.44 | 4.5623 | 74.9 |
| 20.199 | 4.3926 | 25 |
| 21.839 | 4.0662 | 11.6 |
| 22.368 | 3.9713 | 11.2 |
| 22.9 | 3.8802 | 17.1 |
| 23.87 | 3.7248 | 15 |
| 25.63 | 3.4728 | 18 |
| 27.621 | 3.2269 | 11.9 |
| 29 | 3.0765 | 10.1 |

46) The Hydrochloride Crystalline Form XLVI of Compound 1

In one embodiment, the form is the hydrochloride crystalline Form XLVI of the compound 1, which is characterized by having at least three, at least four or five characteristic peaks at the following positions in the XRPD pattern represented by angle 2θ: 5.09±0.2°, 8.45±0.2°, 12.77±0.2°, 13.45±0.2°, 15.36±0.2°, 18.82±0.2°, 21.42±0.2°, 22.53±0.2°, 23.73±0.2°, 25.73±0.2°.

In some preferred embodiments, the form has XRPD characteristic peaks at the positions substantially as shown in Table 45 below and/or an XRPD pattern substantially as shown in FIG. 136.

In some preferred embodiments, they also have the following characteristics:
1) In the TGA plot, there is a weight loss of 3.9±0.2% by weight before 83.9° C.; and a weight loss of 3.6±0.2% by weight between 83.9° C.-200.0° C.;
2) In the DSC curve, there are two endothermic peaks at the initial temperature of 43.4±2.0° C. and 170.1±2.0° C.;
3) the TGA plot substantially as shown in FIG. 137; and/or
4) the DSC curve substantially as shown in FIG. 138.

TABLE 45

| Angle[°2θ] ± 0.2° | d-value[Å] | Relative intensity [%] |
|---|---|---|
| 5.098 | 17.3194 | 100 |
| 7.585 | 11.6449 | 19.2 |
| 7.958 | 11.101 | 4.9 |
| 8.457 | 10.4469 | 42.8 |
| 9.079 | 9.7324 | 3.2 |
| 9.449 | 9.3518 | 5.2 |
| 9.995 | 8.8427 | 6.2 |
| 10.364 | 8.528 | 3.5 |
| 10.969 | 8.0594 | 22.6 |
| 11.763 | 7.5169 | 8.2 |
| 12.487 | 7.0828 | 4 |
| 12.777 | 6.9229 | 43.9 |
| 13.456 | 6.575 | 49 |
| 14.66 | 6.0376 | 11.6 |
| 15.011 | 5.8969 | 10.9 |
| 15.361 | 5.7635 | 72.1 |
| 16.118 | 5.4945 | 26.2 |
| 16.366 | 5.4116 | 3 |
| 16.759 | 5.2858 | 14.5 |
| 17.05 | 5.1961 | 29.4 |
| 17.651 | 5.0205 | 36.9 |
| 18.272 | 4.8512 | 11.6 |
| 18.821 | 4.7111 | 77.4 |
| 19.52 | 4.544 | 8.1 |
| 19.847 | 4.4697 | 16.1 |
| 20.271 | 4.3771 | 7.4 |
| 20.527 | 4.3232 | 2 |
| 20.842 | 4.2586 | 10.6 |
| 21.153 | 4.1966 | 27.7 |
| 21.426 | 4.1438 | 41.7 |
| 21.889 | 4.0572 | 7.5 |
| 22.531 | 3.943 | 38.5 |
| 23.112 | 3.8451 | 8.8 |
| 23.736 | 3.7455 | 54.1 |
| 24.279 | 3.6629 | 7.5 |
| 24.632 | 3.6112 | 16.7 |
| 24.844 | 3.5808 | 4.4 |
| 25.14 | 3.5394 | 4.5 |
| 25.321 | 3.5145 | 4.7 |
| 25.739 | 3.4583 | 32.6 |
| 26.01 | 3.4229 | 16.8 |
| 26.324 | 3.3828 | 13.8 |
| 27.022 | 3.2969 | 7.6 |
| 27.625 | 3.2264 | 9.7 |
| 27.959 | 3.1886 | 3.1 |
| 28.518 | 3.1273 | 16.6 |
| 29.101 | 3.066 | 5.8 |
| 30.206 | 2.9563 | 8.4 |
| 30.539 | 2.9249 | 1.9 |
| 30.907 | 2.8909 | 4.2 |
| 31.165 | 2.8675 | 8.8 |
| 32.271 | 2.7717 | 5.7 |
| 32.592 | 2.7452 | 3.1 |

TABLE 45-continued

| Angle[°2θ] ± 0.2° | d-value[Å] | Relative intensity [%] |
|---|---|---|
| 33.842 | 2.6465 | 8.3 |
| 35.046 | 2.5583 | 2.6 |
| 36.336 | 2.4704 | 2.8 |
| 37.246 | 2.4121 | 3.1 |
| 37.497 | 2.3965 | 3.5 |
| 38.18 | 2.3552 | 4.2 |

47) The Hydrochloride Crystalline Form XLVII of Compound 1

In one embodiment, the form is the hydrochloride crystalline Form XLVII of the compound 1, which is characterized by having at least three, at least four or five characteristic peaks at the following positions in the XRPD pattern represented by angle 2θ: 5.9±0.2°, 11.79±0.2°, 14.45±0.2°, 16.65±0.2°, 20.46±0.2°.

In some preferred embodiments, the form has XRPD characteristic peaks at the positions substantially as shown in Table 46 below and/or an XRPD pattern substantially as shown in FIG. 139.

In some preferred embodiments, they also have the following characteristics:

1) In the TGA plot, there is a weight loss of 0.54±0.2% by weight before 149.0° C.; and a weight loss of 1.86±0.2% by weight between 149.0° C.-208.3° C.;
2) In the DSC curve, there is an endothermic peak at the initial temperature of 196.6±2.0° C.;
3) the TGA plot substantially as shown in FIG. 140; and/or
4) the DSC curve substantially as shown in FIG. 141.

TABLE 46

| Angle[°2θ] ± 0.2° | d-value[Å] | Relative intensity [%] |
|---|---|---|
| 5.9 | 14.9683 | 100 |
| 9.19 | 9.615 | 1.8 |
| 10.119 | 8.7339 | 2.3 |
| 11.799 | 7.4939 | 7.1 |
| 12.66 | 6.9865 | 0.8 |
| 12.949 | 6.831 | 1.8 |
| 13.279 | 6.6619 | 1.3 |
| 13.68 | 6.4676 | 1.2 |
| 14.45 | 6.1246 | 6.4 |
| 15.22 | 5.8165 | 1.3 |
| 15.649 | 5.6579 | 3.4 |
| 16.17 | 5.4768 | 7.9 |
| 16.65 | 5.3201 | 24.5 |
| 17.36 | 5.104 | 2.7 |
| 17.549 | 5.0494 | 4.3 |
| 18.28 | 4.8492 | 5.3 |
| 18.62 | 4.7614 | 6.4 |
| 19 | 4.667 | 3.7 |
| 19.339 | 4.586 | 1.1 |
| 19.76 | 4.4892 | 1.8 |
| 20.161 | 4.4008 | 1.7 |
| 20.46 | 4.3371 | 7.4 |
| 20.799 | 4.2672 | 2.9 |
| 21.43 | 4.143 | 4.8 |
| 21.79 | 4.0754 | 2.4 |
| 22.171 | 4.0062 | 1.7 |
| 22.45 | 3.9571 | 3.6 |
| 22.889 | 3.8821 | 1.7 |
| 23.43 | 3.7937 | 3.3 |
| 24.081 | 3.6926 | 1.6 |
| 24.46 | 3.6363 | 2 |
| 25.119 | 3.5423 | 4.4 |
| 25.998 | 3.4244 | 0.8 |
| 26.539 | 3.3559 | 0.8 |
| 26.83 | 3.3202 | 1.7 |
| 27.263 | 3.2684 | 0.9 |
| 28.191 | 3.1629 | 2.9 |

TABLE 46-continued

| Angle[°2θ] ± 0.2° | d-value[Å] | Relative intensity [%] |
|---|---|---|
| 29.309 | 3.0447 | 2 |
| 29.94 | 2.982 | 2 |
| 30.76 | 2.9043 | 0.8 |
| 33.45 | 2.6766 | 1 |
| 34.979 | 2.5631 | 0.9 |
| 35.311 | 2.5397 | 0.8 |
| 36.599 | 2.4532 | 0.7 |
| 37.441 | 2.4 | 0.7 |

48) The Hydrochloride Crystalline Form XLVIII of Compound 1

In one embodiment, the form is the hydrochloride crystalline Form XLVIII of the compound 1, which is characterized by having at least three, at least four or five characteristic peaks at the following positions in the XRPD pattern represented by angle 2θ: 6.93±0.2°, 10.51±0.2°, 10.88±0.2°, 13.63±0.2°, 14.04±0.2°, 16.77±0.2°, 21.36±0.2°, 21.83±0.2°, 24.27±0.2°.

In some preferred embodiments, the form has XRPD characteristic peaks at the positions substantially as shown in Table 47 below and/or an XRPD pattern substantially as shown in FIG. 142.

In some preferred embodiments, they also have the following characteristics:

1) In the TGA plot, there is a weight loss of 3.5±0.2% by weight before 137.2° C.; and a weight loss of 0.57±0.2% by weight between 137.2° C.-198.4° C.;
2) In the DSC curve, there is an endothermic peak at the initial temperature of 175.6±2.0° C.;
3) the TGA plot substantially as shown in FIG. 143; and/or
4) the DSC curve substantially as shown in FIG. 144.

TABLE 47

| Angle[°2θ] ± 0.2° | d-value[Å] | Relative intensity [%] |
|---|---|---|
| 6.935 | 12.736 | 49.9 |
| 8.393 | 10.5265 | 6.3 |
| 10.518 | 8.4035 | 100 |
| 10.888 | 8.1192 | 34.7 |
| 12.525 | 7.0614 | 12.5 |
| 13.638 | 6.4876 | 36.7 |
| 14.047 | 6.2994 | 48 |
| 16.773 | 5.2815 | 30.9 |
| 17.418 | 5.0873 | 17.8 |
| 17.98 | 4.9293 | 13.3 |
| 18.274 | 4.8507 | 21.6 |
| 18.934 | 4.6831 | 18.7 |
| 20.314 | 4.3679 | 23.1 |
| 20.76 | 4.2752 | 11.2 |
| 21.367 | 4.155 | 64.6 |
| 21.836 | 4.0668 | 30.2 |
| 22.618 | 3.928 | 6.3 |
| 23.025 | 3.8594 | 21.4 |
| 23.609 | 3.7653 | 19.5 |
| 24.272 | 3.6639 | 30.3 |
| 24.816 | 3.5848 | 13.4 |
| 25.798 | 3.4506 | 7.2 |
| 26.317 | 3.3836 | 18.6 |
| 26.957 | 3.3048 | 5 |
| 27.815 | 3.2047 | 7.1 |
| 28.695 | 3.1084 | 16 |
| 32.294 | 2.7697 | 9.8 |
| 33.329 | 2.6861 | 5.6 |

49) The Hydrochloride Crystalline Form XLIX of Compound 1

In one embodiment, the form is the hydrochloride crystalline Form XLIX of the compound 1, which is characterized by having at least three, at least four or five characteristic peaks at the following positions in the XRPD pattern represented by angle 2θ: 6.02±0.2°, 10.28±0.2°, 14.66±0.2°, 16.83±0.2°, 20.64±0.2°.

In some preferred embodiments, the form has XRPD characteristic peaks at the positions substantially as shown in Table 48 below and/or an XRPD pattern substantially as shown in FIG. 145.

In some preferred embodiments, they also have the following characteristics:

1) In the TGA plot, there is a weight loss of 0.12±0.02% by weight before 158.3° C.; and a weight loss of 1.0±0.2% by weight between 158.3° C.-209.3° C.;

2) In the DSC curve, there is an endothermic peak at the initial temperature of 191.7±2.0° C.;

3) the TGA plot substantially as shown in FIG. 146; and/or 4) the DSC curve substantially as shown in FIG. 147.

TABLE 48

| Angle[°2θ] ± 0.2° | d-value[Å] | Relative intensity [%] |
|---|---|---|
| 6.021 | 14.6669 | 100 |
| 9.367 | 9.4341 | 10.8 |
| 10.286 | 8.5933 | 30.4 |
| 11.311 | 7.8163 | 5.5 |
| 11.615 | 7.6126 | 4.6 |
| 11.958 | 7.3947 | 7.2 |
| 13.831 | 6.3976 | 8.3 |
| 14.667 | 6.0344 | 35.8 |
| 15.428 | 5.7385 | 11 |
| 16.167 | 5.4777 | 22 |
| 16.83 | 5.2635 | 51.5 |
| 17.691 | 5.0093 | 7.9 |
| 18.488 | 4.7952 | 27 |
| 18.816 | 4.7122 | 26.6 |
| 19.148 | 4.6314 | 19.8 |
| 20.356 | 4.3591 | 20 |
| 20.647 | 4.2983 | 44.7 |
| 21.585 | 4.1135 | 13.2 |
| 22.016 | 4.0341 | 7.3 |
| 22.558 | 3.9382 | 7.4 |
| 23.024 | 3.8596 | 23.1 |
| 23.648 | 3.7591 | 12.5 |
| 24.603 | 3.6154 | 12.1 |
| 25.324 | 3.514 | 9.8 |
| 26.944 | 3.3064 | 11 |
| 27.603 | 3.2289 | 6.8 |
| 28.363 | 3.144 | 20.5 |
| 29.515 | 3.024 | 9.7 |
| 31.691 | 2.8211 | 3.9 |

50) The Hydrochloride Crystalline Form L of Compound 1

In one embodiment, the form is the hydrochloride crystalline Form L of the compound 1, which is characterized by having at least three, at least four or five characteristic peaks at the following positions in the XRPD pattern represented by angle 2θ: 6.91±0.2°, 7.19±0.2°, 12.97±0.2°, 19.45±0.2°, 20.53±0.2°, 23.10±0.2°, 25.53±0.2°.

In some preferred embodiments, the form has XRPD characteristic peaks at the positions substantially as shown in Table 49 below and/or an XRPD pattern substantially as shown in FIG. 148.

In some preferred embodiments, they also have the following characteristics:

1) In the TGA plot, there is a weight loss of 2.5±0.2% by weight before 203.7° C.;

2) In the DSC curve, there is an endothermic peak at the initial temperature of 180.9±2.0° C.;

3) the TGA plot substantially as shown in FIG. 149; and/or 4) the DSC curve substantially as shown in FIG. 150.

TABLE 49

| Angle[°2θ] ± 0.2° | d-value[Å] | Relative intensity [%] |
|---|---|---|
| 6.915 | 12.7724 | 51.1 |
| 7.19 | 12.2843 | 46.1 |
| 8.529 | 10.359 | 21.4 |
| 10.357 | 8.5345 | 12.8 |
| 12.972 | 6.8192 | 86.7 |
| 14.03 | 6.3073 | 16.4 |
| 15.719 | 5.633 | 34.7 |
| 16.341 | 5.42 | 22.8 |
| 16.773 | 5.2813 | 36.7 |
| 16.946 | 5.2277 | 31.9 |
| 17.218 | 5.1457 | 20.6 |
| 17.745 | 4.994 | 17.8 |
| 18.504 | 4.7909 | 18.3 |
| 19.459 | 4.5579 | 100 |
| 20.535 | 4.3215 | 41.7 |
| 21.251 | 4.1775 | 39.2 |
| 21.583 | 4.1139 | 17.8 |
| 22.17 | 4.0064 | 26.7 |
| 22.763 | 3.9034 | 13.1 |
| 23.103 | 3.8466 | 63.9 |
| 23.71 | 3.7494 | 25 |
| 24.503 | 3.63 | 9.2 |
| 24.936 | 3.5678 | 34.2 |
| 25.536 | 3.4854 | 40.6 |
| 26.506 | 3.36 | 9.7 |
| 27.06 | 3.2925 | 10.8 |
| 28.094 | 3.1736 | 36.1 |
| 28.849 | 3.0922 | 18.6 |
| 29.804 | 2.9953 | 16.9 |
| 31.574 | 2.8313 | 11.7 |
| 34.474 | 2.5994 | 8.6 |

51) The Hydrochloride Crystalline Form LI of Compound 1

In one embodiment, the form is the hydrochloride crystalline Form LI of the compound 1, which is characterized by having at least three, at least four or five characteristic peaks at the following positions in the XRPD pattern represented by angle 2θ: 4.88±0.2°, 8.51±0.2°, 12.46±0.2°, 18.15±0.2°, 18.50±0.2°, 19.13±0.2°, 20.78±0.2°, 21.11±0.2°, 22.82±0.2°, 24.68±0.2°.

In some preferred embodiments, the form has XRPD characteristic peaks at the positions substantially as shown in Table 50 below and/or an XRPD pattern substantially as shown in FIG. 151.

In some preferred embodiments, they also have the following characteristics:

1) In the TGA plot, there is a weight loss of 0.40±0.2% by weight before 72.6° C.; a weight loss of 5.0±0.2% by weight between 72.6° C.-159.0° C.; and a weight loss of 1.31±0.2% by weight between 159.0° C.-199.4° C.;

2) In the DSC curve, there is an endothermic peak at the initial temperature of 183.3±2.0° C.;

3) the TGA plot substantially as shown in FIG. 152; and/or 4) the DSC curve substantially as shown in FIG. 153.

TABLE 50

| Angle[°2θ] ± 0.2° | d-value[Å] | Relative intensity [%] |
|---|---|---|
| 4.889 | 18.0594 | 87.7 |
| 7.635 | 11.57 | 15.4 |
| 8.513 | 10.378 | 45 |
| 9.936 | 8.8943 | 24.8 |
| 12.467 | 7.094 | 74.5 |
| 14.258 | 6.2068 | 22.6 |
| 14.975 | 5.911 | 11.3 |
| 15.873 | 5.5788 | 21.1 |
| 16.867 | 5.252 | 37.6 |
| 17.414 | 5.0883 | 17 |
| 18.155 | 4.8823 | 100 |

TABLE 50-continued

| Angle[°2θ] ± 0.2° | d-value[Å] | Relative intensity [%] |
|---|---|---|
| 18.506 | 4.7905 | 55.9 |
| 19.13 | 4.6356 | 60.2 |
| 19.867 | 4.4652 | 19.9 |
| 20.786 | 4.2699 | 47 |
| 21.114 | 4.2043 | 43.9 |
| 21.985 | 4.0397 | 13.6 |
| 22.829 | 3.8922 | 57.7 |
| 23.476 | 3.7864 | 25.5 |
| 24.68 | 3.6043 | 54.8 |
| 25.32 | 3.5146 | 8.8 |
| 25.864 | 3.4419 | 10.3 |
| 26.22 | 3.3959 | 21.1 |
| 26.979 | 3.3021 | 16.6 |
| 27.293 | 3.2648 | 24.6 |
| 29.216 | 3.0542 | 11.3 |
| 30.487 | 2.9297 | 9.9 |
| 32.966 | 2.7148 | 9.6 |
| 33.395 | 2.6809 | 6.8 |
| 35.084 | 2.5557 | 9 |

52) The Hydrochloride Crystalline Form LII of Compound 1

In one embodiment, the form is the hydrochloride crystalline Form LII of the compound 1, which is characterized by having at least three, at least four or five characteristic peaks at the following positions in the XRPD pattern represented by angle 2θ: 6.19±0.2°, 16.36±0.2°, 19.01±0.2°, 21.21±0.2°, 21.87±0.2°.

In some preferred embodiments, the form has XRPD characteristic peaks at the positions substantially as shown in Table 51 below and/or an XRPD pattern substantially as shown in FIG. 154.

In some preferred embodiments, they also have the following characteristics:

1) In the TGA plot, there is a weight loss of 0.01±0.002% by weight before 145.8° C.; and a weight loss of 1.92±0.2% by weight between 145.8° C.-206.0° C.;

2) In the DSC curve, there is an endothermic peak at the initial temperature of 198.1±2.0° C.;

3) the TGA plot substantially as shown in FIG. 155; and/or 4) the DSC curve substantially as shown in FIG. 156.

TABLE 51

| Angle[°2θ] ± 0.2° | d-value[Å] | Relative intensity [%] |
|---|---|---|
| 6.194 | 14.2581 | 100 |
| 10.538 | 8.3881 | 14.7 |
| 11.476 | 7.7044 | 7.5 |
| 12.274 | 7.205 | 7.7 |
| 13.44 | 6.5825 | 13.6 |
| 14.03 | 6.307 | 8.6 |
| 15.945 | 5.5537 | 11.9 |
| 16.365 | 5.412 | 56.5 |
| 19.011 | 4.6643 | 20.7 |
| 19.611 | 4.523 | 17.8 |
| 20.369 | 4.3563 | 9.1 |
| 21.213 | 4.1848 | 20.7 |
| 21.876 | 4.0596 | 23.5 |
| 22.534 | 3.9424 | 5 |
| 23.204 | 3.83 | 6.3 |
| 24.389 | 3.6466 | 7.8 |
| 24.853 | 3.5796 | 13.6 |
| 27.095 | 3.2882 | 5.6 |
| 27.934 | 3.1914 | 14.9 |
| 30.48 | 2.9304 | 7 |

53) The Hydrochloride Crystalline Form LIII of Compound 1

In one embodiment, the form is the hydrochloride crystalline Form LIII of the compound 1, which is characterized by having at least three, at least four or five characteristic peaks at the following positions in the XRPD pattern represented by angle 2θ: 8.45±0.2°, 8.78±0.2θ, 13.28±0.2°, 14.02±0.2°, 15.29±0.2°, 16.03±0.2°, 16.79±0.2°, 17.08±0.2°, 19.30±0.2°, 21.99±0.2°, 22.61±0.2°, 24.83±0.2°, 25.18±0.2θ.

In some preferred embodiments, the form has XRPD characteristic peaks at the positions substantially as shown in Table 52 below and/or an XRPD pattern substantially as shown in FIG. 157.

In some preferred embodiments, they also have the following characteristics:

1) In the TGA plot, there is a weight loss of 0.51±0.2% by weight before 65.4° C.; and a weight loss of 5.6±0.2% by weight between 65.4° C.-197.0° C.;

2) In the DSC curve, there is an endothermic peak at the initial temperature of 105.6±2.0° C.;

3) the TGA plot substantially as shown in FIG. 158; and/or 4) the DSC curve substantially as shown in FIG. 159.

TABLE 52

| Angle[°2θ] ± 0.2° | d-value[Å] | Relative intensity [%] |
|---|---|---|
| 6.407 | 13.7848 | 37.6 |
| 6.814 | 12.9624 | 30.3 |
| 8.453 | 10.4519 | 99.4 |
| 8.785 | 10.0571 | 84.3 |
| 9.953 | 8.8795 | 18.5 |
| 11.396 | 7.7583 | 36 |
| 12.698 | 6.9657 | 43.3 |
| 13.284 | 6.6593 | 51.7 |
| 14.028 | 6.3081 | 66.9 |
| 15.291 | 5.7897 | 51.7 |
| 16.033 | 5.5232 | 67.4 |
| 16.793 | 5.275 | 53.9 |
| 17.084 | 5.1859 | 100 |
| 17.572 | 5.0429 | 43.3 |
| 18.893 | 4.6932 | 32.6 |
| 19.303 | 4.5944 | 98.3 |
| 19.905 | 4.4568 | 29.8 |
| 21.993 | 4.0381 | 59.6 |
| 22.614 | 3.9287 | 82 |
| 23.473 | 3.7868 | 31.5 |
| 24.839 | 3.5815 | 57.9 |
| 25.188 | 3.5327 | 69.1 |
| 26.231 | 3.3945 | 24.2 |
| 26.919 | 3.3094 | 21.3 |
| 28.46 | 3.1335 | 46.6 |
| 32.883 | 2.7215 | 20.2 |

54) The Hydrochloride Crystalline Form LIV of Compound 1

In one embodiment, the form is the hydrochloride crystalline Form LIV of the compound 1, which is characterized by having at least three, at least four or five characteristic peaks at the following positions in the XRPD pattern represented by angle 2θ: 4.30±0.2°, 5.78±0.2°, 11.31±0.2°, 17.86±0.2°, 18.46±0.2°, 19.24±0.2°, 19.71±0.2°, 21.05±0.2°, 24.75±0.2°.

In some preferred embodiments, the form has XRPD characteristic peaks at the positions substantially as shown in Table 53 below and/or an XRPD pattern substantially as shown in FIG. 160.

In some preferred embodiments, they also have the following characteristics:
1) In the TGA plot, there is a weight loss of 1.8±0.2% by weight before 207.0° C.;
2) In the DSC curve, there are two endothermic peaks at the initial temperature of 169.6±2.0° C. and 196.7±2.0° C.;
3) the TGA plot substantially as shown in FIG. 161; and/or
4) the DSC curve substantially as shown in FIG. 162.

TABLE 53

| Angle[°2θ] ± 0.2° | d-value[Å] | Relative intensity [%] |
|---|---|---|
| 4.305 | 20.509 | 21.7 |
| 5.785 | 15.2633 | 100 |
| 10.344 | 8.5448 | 12.1 |
| 11.319 | 7.8108 | 25.5 |
| 13.831 | 6.3972 | 19.2 |
| 14.959 | 5.9174 | 14.4 |
| 15.639 | 5.6617 | 16.5 |
| 16.485 | 5.373 | 17.9 |
| 17.862 | 4.9617 | 41.5 |
| 18.468 | 4.8003 | 31.5 |
| 19.248 | 4.6075 | 23.6 |
| 19.715 | 4.4993 | 26.9 |
| 20.571 | 4.314 | 6 |
| 21.057 | 4.2156 | 23.2 |
| 21.484 | 4.1327 | 14.4 |
| 22.053 | 4.0274 | 9.4 |
| 22.672 | 3.9187 | 19 |
| 23.394 | 3.7995 | 7.1 |
| 24.757 | 3.5932 | 23.4 |
| 25.945 | 3.4314 | 11.3 |
| 26.332 | 3.3817 | 16.7 |
| 26.702 | 3.3358 | 6.3 |
| 28.188 | 3.1632 | 10.2 |
| 29.194 | 3.0564 | 9.4 |
| 31.562 | 2.8323 | 7.9 |
| 36.968 | 2.4296 | 7.7 |

55) The Hydrochloride Crystalline Form LV of Compound 1

In one embodiment, the form is the hydrochloride crystalline Form LV of the compound 1, which is characterized by having at least three, at least four or five characteristic peaks at the following positions in the XRPD pattern represented by angle 2θ: 4.90±0.2°, 14.19±0.2°, 18.66±0.2°, 19.55±0.2°, 21.77±0.2°, 25.18±0.2°.

In some preferred embodiments, the form has XRPD characteristic peaks at the positions substantially as shown in Table 54 below and/or an XRPD pattern substantially as shown in FIG. 163.

In some preferred embodiments, they also have the following characteristics:
1) In the TGA plot, there is a weight loss of 0.89±0.2% by weight before 133.9° C.; and a weight loss of 0.94±0.2% by weight between 133.9° C.-198.7° C.;
2) In the DSC curve, there is an endothermic peak at the initial temperature of 175.5±2.0° C.;
3) the TGA plot substantially as shown in FIG. 164; and/or
4) the DSC curve substantially as shown in FIG. 165.

TABLE 54

| Angle[°2θ] ± 0.2° | d-value[Å] | Relative intensity [%] |
|---|---|---|
| 4.909 | 17.9848 | 20.1 |
| 7.344 | 12.0271 | 8 |
| 8.514 | 10.3767 | 6.8 |
| 9.894 | 8.9325 | 14.4 |
| 10.223 | 8.6459 | 15.3 |
| 10.658 | 8.2934 | 13.4 |
| 11.61 | 7.6154 | 6.2 |
| 11.845 | 7.4652 | 10.6 |
| 12.505 | 7.0724 | 15.9 |
| 14.198 | 6.2328 | 100 |
| 15.117 | 5.8558 | 7.4 |
| 16.248 | 5.4508 | 4.5 |
| 17.003 | 5.2104 | 16.4 |
| 17.707 | 5.0049 | 12.3 |
| 18.152 | 4.8831 | 15.4 |
| 18.661 | 4.7511 | 66.5 |
| 19.171 | 4.6259 | 14 |
| 19.559 | 4.5349 | 28.7 |
| 19.989 | 4.4382 | 18.6 |
| 20.337 | 4.3632 | 3.1 |
| 20.761 | 4.275 | 9.7 |
| 21.038 | 4.2193 | 4 |
| 21.45 | 4.1391 | 5.5 |
| 21.776 | 4.078 | 33.5 |
| 22.044 | 4.0289 | 18.9 |
| 22.751 | 3.9054 | 12.7 |
| 23.574 | 3.7708 | 13.3 |
| 24.079 | 3.6928 | 18.8 |
| 24.699 | 3.6015 | 6.8 |
| 25.189 | 3.5326 | 27.4 |
| 25.793 | 3.4513 | 5.5 |
| 26.103 | 3.4109 | 16.7 |
| 26.744 | 3.3306 | 10.1 |
| 27.095 | 3.2882 | 15.7 |
| 27.499 | 3.2408 | 6.2 |
| 28.385 | 3.1417 | 8.7 |
| 28.942 | 3.0825 | 6.6 |
| 29.866 | 2.9892 | 8.3 |
| 30.211 | 2.9558 | 4.6 |
| 31.082 | 2.8749 | 4.7 |
| 31.807 | 2.811 | 5.8 |
| 32.868 | 2.7227 | 3.1 |
| 35.33 | 2.5384 | 3.6 |
| 37.499 | 2.3964 | 3.1 |
| 38.933 | 2.3114 | 3.9 |

In the second respect, the present invention provides a method for preparing the crystalline form or amorphous form of the compound 1 or its salt or solvate.

In one embodiment, the present invention provides a method for preparing a crystalline form of the compound 1, which comprises the following steps: mixing the compound 1 with solvent, separating the resulting solid and drying, and thereby obtaining the crystalline form of the compound 1.

In the preparation method, the compound 1 can be obtained from a variety of sources, such as commercial purchase or laboratory synthesis.

The solvents can be commonly used in laboratory, such as one or more of the water, alkane solvents, alcohol solvents, ketone solvents, ester solvents, aromatic hydrocarbon solvents, halogenated hydrocarbon solvents, nitrile solvents, ether solvents, aliphatic hydrocarbon solvents, polar aprotic solvents such as DMF, DMSO. The mass-volume ratio of the compound 1 to the solvent can be 100 mg: (0.1-1 mL).

In one embodiment, the present invention provides a method for preparing crystalline form of solvate of the compound 1, which comprises the following steps: mixing the compound 1 with the solvent corresponding to the type of solvate, separating the resulting solid and drying, and thereby obtaining the crystalline form of the solvate of the compound 1.

The solvents corresponding to the type of solvate, such as but not limited to 1,4-dioxane, ethyl acetate, toluene, chloroform, 2-methyltetrahydrofuran, methyl tert-butyl ether, acetone, N,N-dimethylformamide, acetonitrile etc.

In one embodiment, the present invention provides a method for preparing crystalline form of salt of the compound 1, which comprises the following steps: mixing the compound 1 with solvent and acid, separating the resulting solid and drying, and thereby obtaining the crystalline form of salt of the compound 1.

The solvents can be commonly used in laboratory, such as one or more of water, alkane solvents, alcohol solvents, ketone solvents, ester solvents, aromatic hydrocarbon solvents, halogenated hydrocarbon solvents, nitrile solvents, ether solvents, aliphatic hydrocarbon solvents, polar aprotic solvents such as DMF, DMSO. The acids can be pharmaceutically acceptable acids or common acids in the art, can be inorganic acids or organic acids. Further preferably, the acids can be hydrochloric acid, sulfuric acid, methanesulfonic acid, maleic acid, benzenesulfonic acid, p-toluenesulfonic acid, tartaric acid and citric acid etc.

In one embodiment, the present invention provides a method for preparing an amorphous form of the compound 1, which comprises the following steps: mixing the compound 1 with solvents and spray drying the resulting solution to obtain an amorphous form of the compound 1.

The solvents can be commonly used in laboratory, such as one or more of water, alkane solvents, alcohol solvents, ketone solvents, ester solvents, aromatic hydrocarbon solvents, halogenated hydrocarbon solvents, nitrile solvents, ether solvents, aliphatic hydrocarbon solvents, polar aprotic solvents such as DMF, DMSO. Methylene dichloride (DCM) is preferred.

In each of the above preparation methods, the preparation temperature can be conventional in the art, such as 20-50° C.

In the above preparation methods, there are no special limitations on the crystallization time, as long as the crystal can be precipitated, for example, the crystallization time can be 1-48 h.

In addition, the preparation methods of the crystalline forms or amorphous forms of compound 1 or salts or its solvates can be well known in the art, for example solvent evaporation method, suspension stirring method, heating and cooling crystallization method and mixed solvent crystallization method. The solvent evaporation method of the present invention is to volatilize the sample clarification solution at different temperatures until the solvent volatile completely. The suspension stirring method of the present invention is to stir the supersaturated solution of the sample (with the presence of insoluble solids) in different solvents for a period of time. The heating and cooling crystallization method of the present invention is to dissolve the sample in appropriate solvents under high temperature condition, and stir the filtrate out in room temperature or low temperature environment after filtration. The mixed solvent crystallization method of the present invention is to take a sample and dissolve it in appropriate solvents, add another one or more solvents, precipitate out a solid system, stir it for a short time for filtration.

In the third aspect, the present invention provides a pharmaceutical composition comprising the above-mentioned crystalline forms or amorphous forms of compound 1 or its salts or solvates, and pharmacologically acceptable excipients.

The crystalline forms or amorphous forms of compound 1 or its salts or solvates can be a therapeutically effective amount for treatment. The pharmacically acceptable excipients can be well known in the art, which in the case of solid preparations include but are not limited to: diluents, adhesives, disintegrants, lubricants, flow aids, release rate control agents, plasticizers, preservatives, antioxidants, etc.

The pharmaceutical compositions can choose the dosage forms suitable for human consumption, such as tablet, capsule, granule, powder, or pill, etc., preferably tablet, capsule, granule, disintegrating tablet, sustained release or controlled release tablet, etc.

The pharmaceutical compositions in the present invention can be prepared by various methods that are well known in the art. One or more of crystalline forms or amorphous forms of the compound 1 or its salts and solvates in a therapeutic effective amount can be mixed with one or more of pharmacically acceptable excipients to prepare dosage forms for human consumption, such as tablets, capsules, granules, etc.

The "therapeutically effective amount" is the amount of a compound in the form of the present invention that, when administered to a patient in need, is sufficient to achieve treatment of a disease state, condition, or disorder for which the compound has utility. Such a quantity would be sufficient to elicit a biological or medical response in the tissue system or patient sought by researchers or clinicians.

In the fourth aspect, the present invention provides the use of the crystalline forms or amorphous forms of above mentioned compound 1 or its salts and solvates or the use of above mentioned pharmaceutical compositions in the preparation of drugs for the prevention and/or treatment of hyperproliferative diseases.

In one embodiment, the drugs are preferably used to prevent and/or treat cancers, the cancers including but not limited to acute mononuclear leukemia, acute myelogenous leukemia, chronic myelogenous leukemia, chronic lymphocytic leukemia mixed lineage leukemia, the NUT midline carcinoma, multiple myeloma, small cell lung cancer, neuroblastoma, burkitt lymphoma, cervical cancer, esophageal cancer, ovarian cancer, colorectal cancer, prostate cancer and breast cancer.

The crystalline forms or amorphous forms of the compound 1 or its salts and solvstes have the following advantages:

The present invention for the first time discovers a variety of unreported crystalline forms or amorphous forms of the compound 1 or its salts and solvates, which can serve as an important basis for subsequent drug development, preparation development and production.

BRIEF DESCRIPTION OF THE DRAWINGS

FIG. 121 is an XRPD pattern of Compound 1 maleate crystalline Form XLI.

FIG. 122 is a TGA plot of Compound 1 maleate crystalline Form XLI.

FIG. 123 is a DSC curve of Compound 1 maleate crystalline Form XLI.

FIG. 124 is an XRPD pattern of Compound 1 maleate crystalline Form XLII.

FIG. 125 is a TGA plot of Compound 1 maleate crystalline Form XLII.

FIG. 126 is a DSC curve of Compound 1 maleate crystalline Form XLII.

FIG. 127 is an XRPD pattern of Compound 1 maleate crystalline Form XLIII.

FIG. 128 is a TGA plot of Compound 1 maleate crystalline Form XLIII.

FIG. 129 is a DSC curve of Compound 1 maleate crystalline Form XLIII.

FIG. 130 is an XRPD pattern of Compound 1 maleate crystalline Form XLIV.

FIG. 131 is a TGA plot of Compound 1 maleate crystalline Form XLIV.

FIG. 132 is a DSC curve of Compound 1 maleate crystalline Form XLIV.

Figure 1:
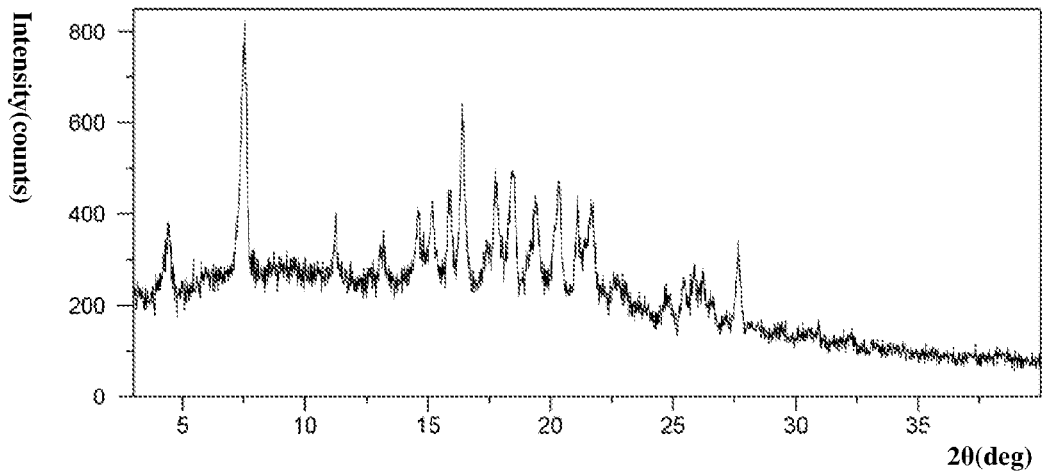
FIG. 1 is an XRPD pattern of Compound 1 crystalline Form I.
Figure 2:
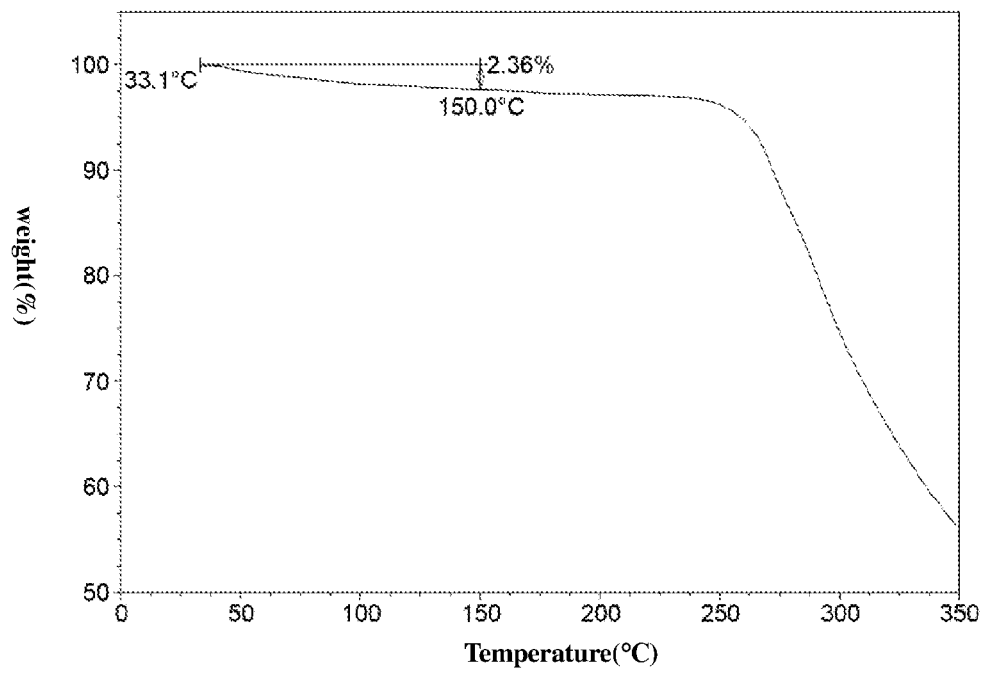
FIG. 2 is a TGA plot of Compound 1 crystalline Form I.
Figure 3:
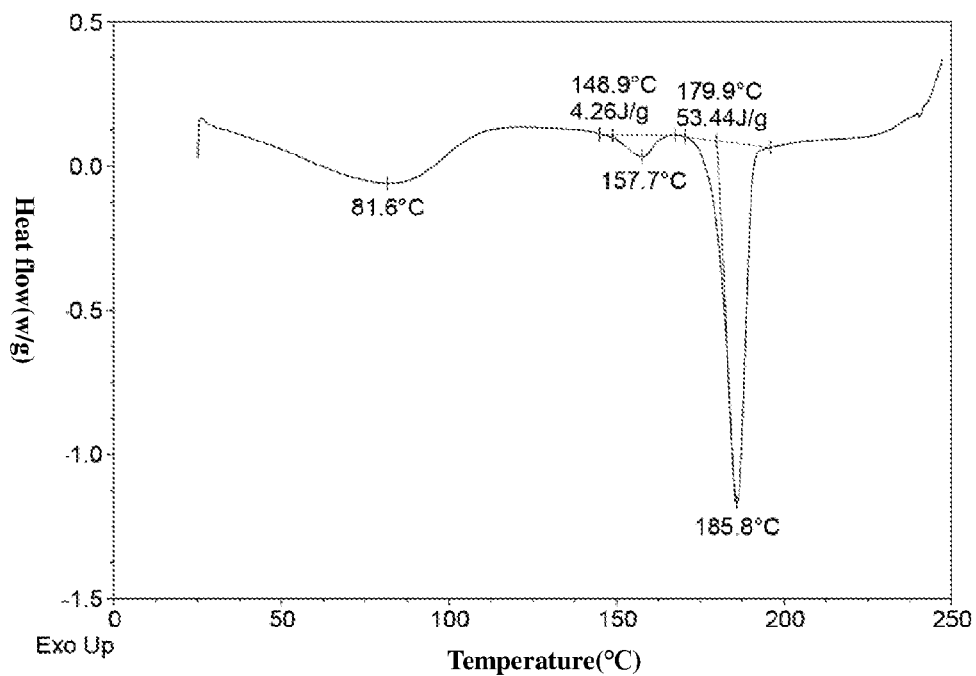
FIG. 3 is a DSC curve of Compound 1 crystalline Form I.
Figure 4:
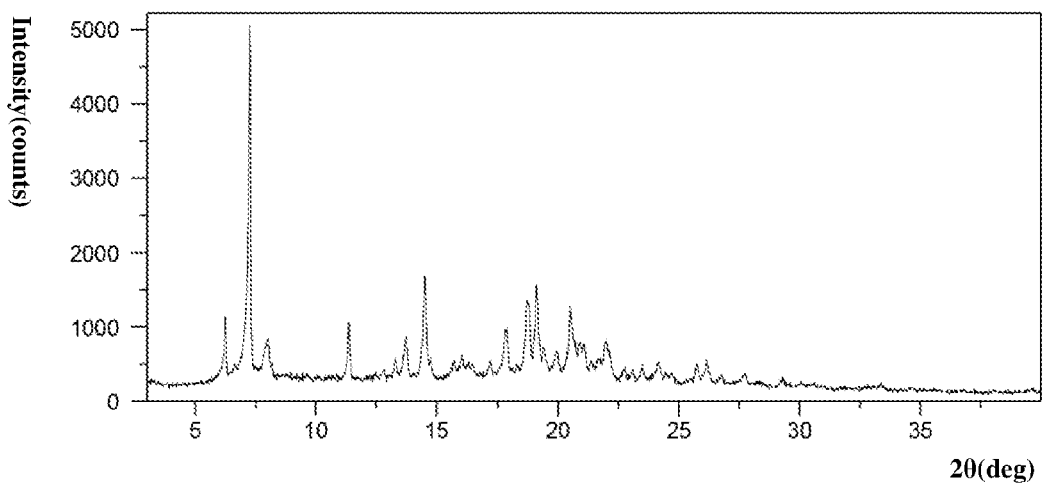
FIG. 4 is an XRPD pattern of Compound 1 crystalline Form II.
Figure 5:
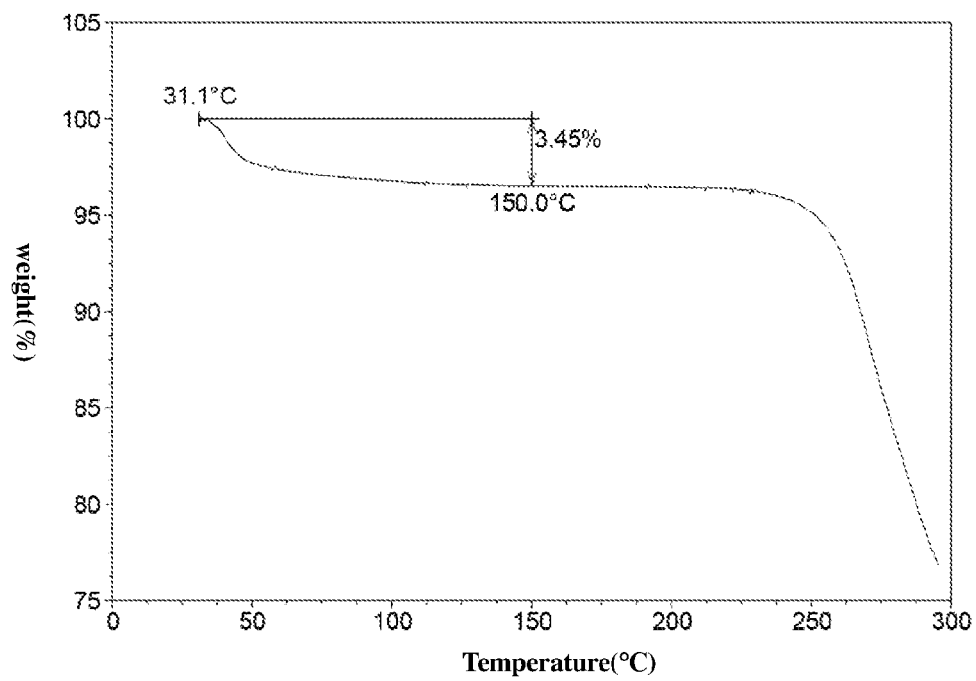
FIG. 5 is a TGA plot of Compound 1 crystalline Form II.
Figure 6:
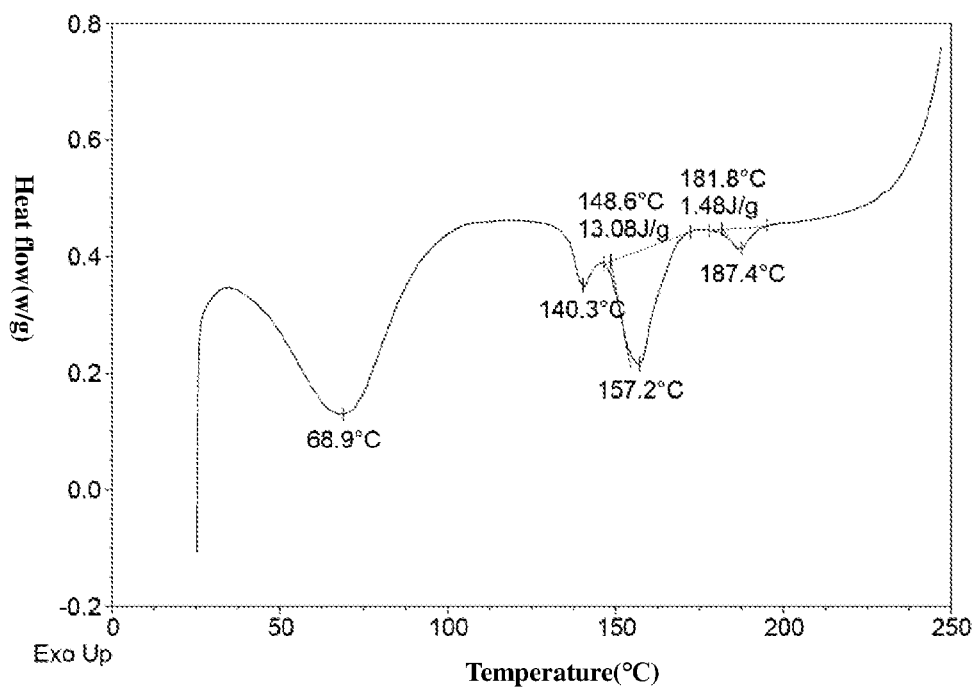
FIG. 6 is a DSC curve of Compound 1 crystalline Form II.
Figure 7:
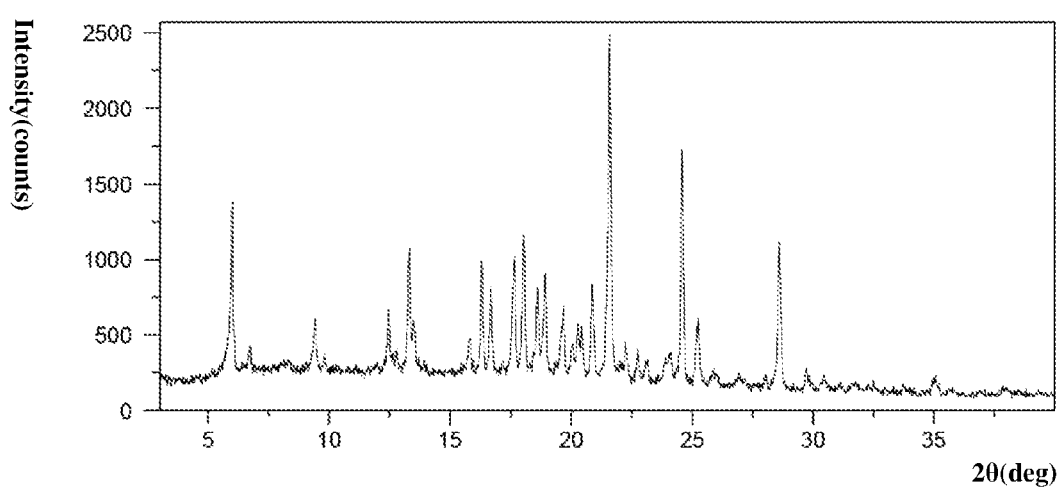
FIG. 7 is an XRPD pattern of Compound 1 crystalline Form III.
Figure 8:
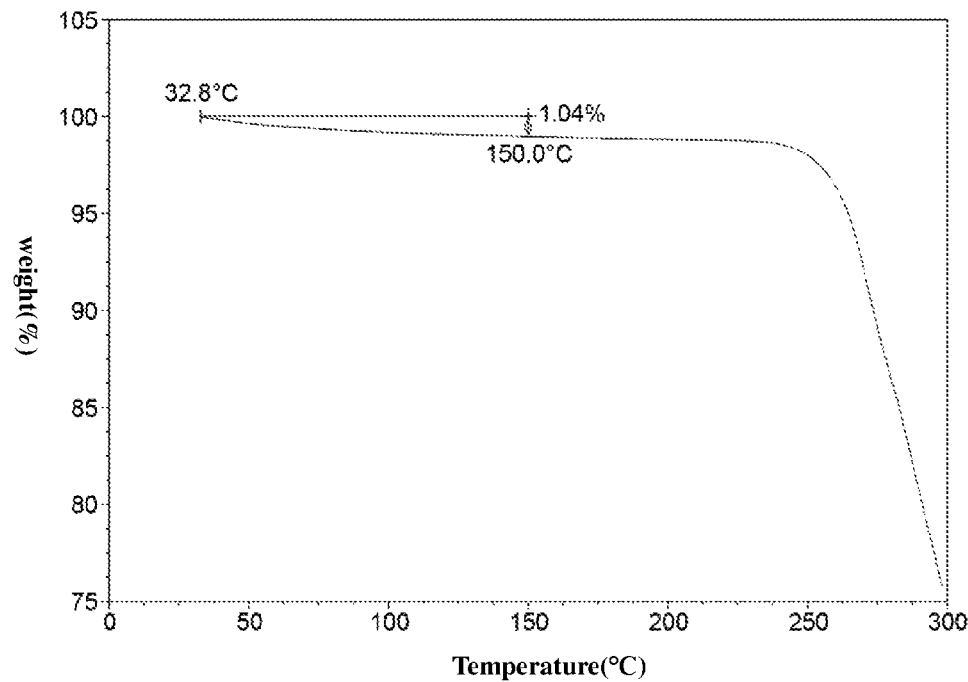
FIG. 8 is a TGA plot of Compound 1 crystalline Form III.
Figure 9:
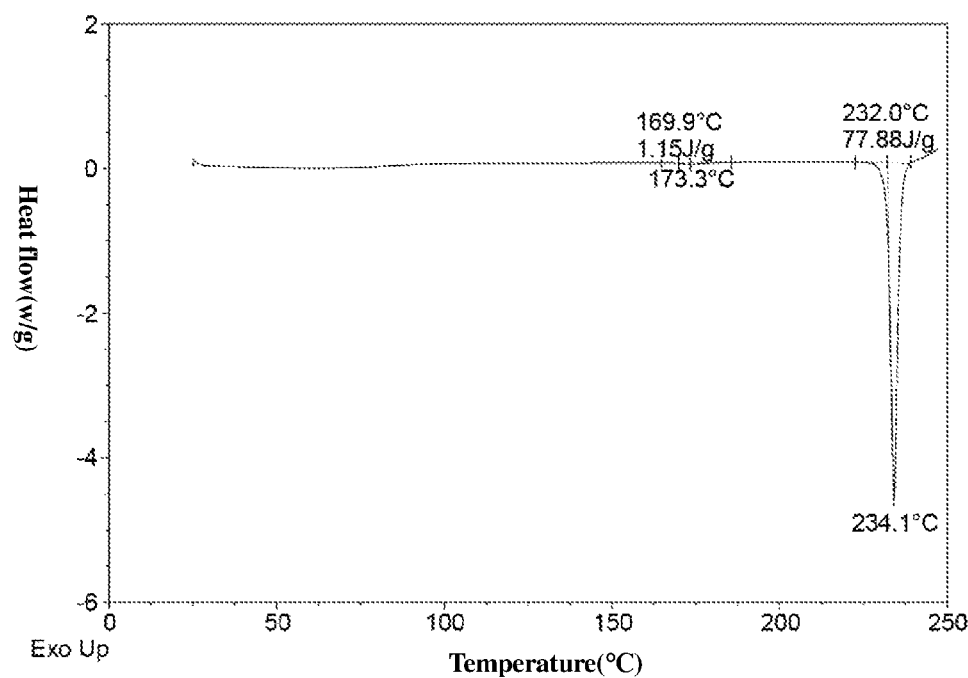
FIG. 9 is a DSC curve of Compound 1 crystalline Form III.
Figure 10:
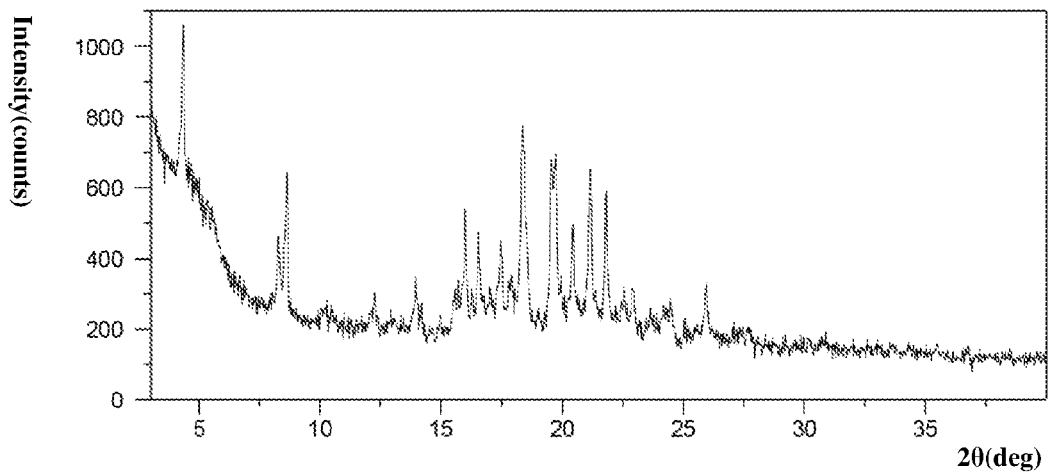
FIG. 10 is an XRPD pattern of Compound 1 1,4-dioxane solvate crystalline Form IV.
Figure 11:
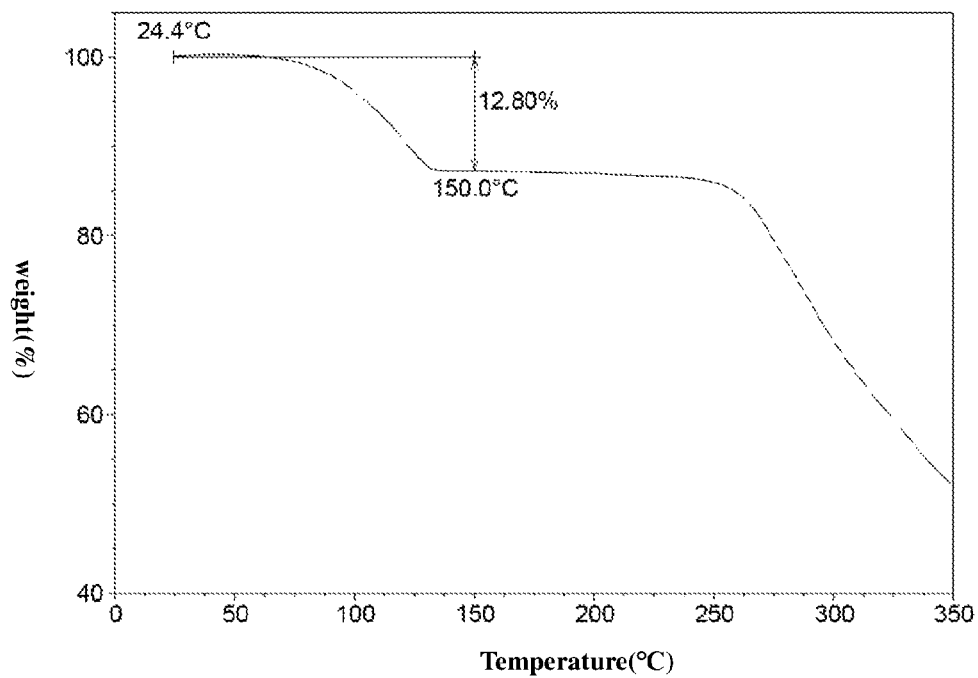
FIG. 11 is a TGA plot of Compound 1 1,4-dioxane solvate crystalline Form IV.
Figure 12:
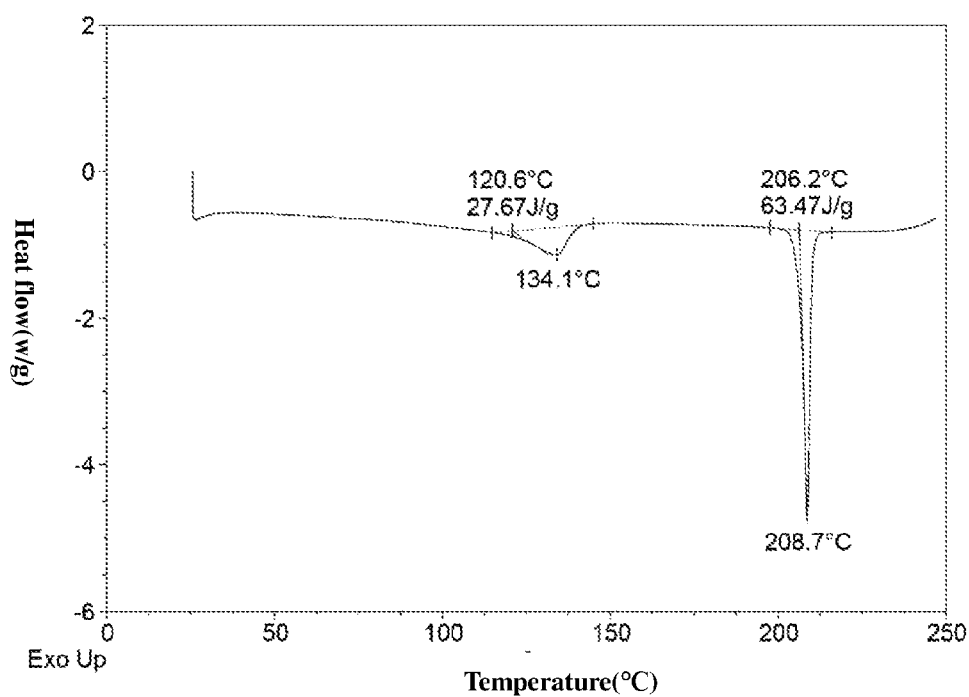
FIG. 12 is a DSC curve of Compound 1 1,4-dioxane solvate crystalline Form IV.
Figure 13:
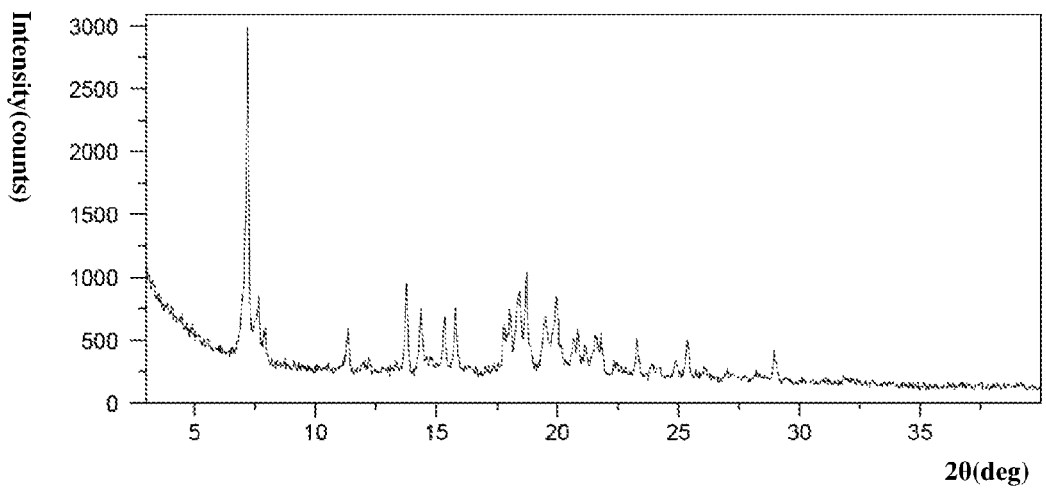
FIG. 13 is an XRPD pattern of Compound 1 ethyl acetate solvate crystalline form V.
Figure 14:
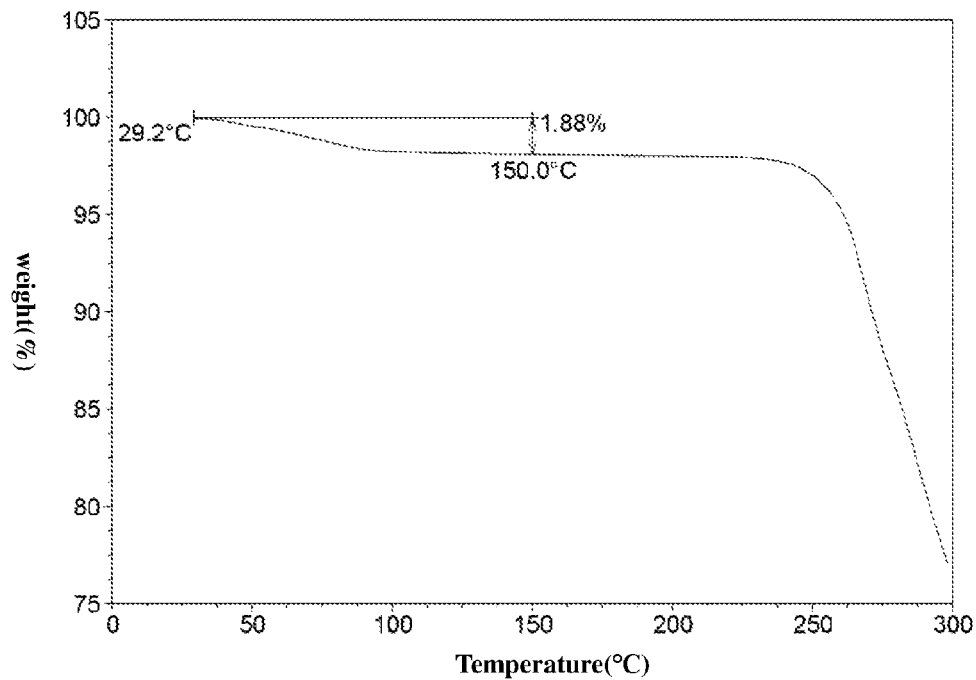
FIG. 14 is a TGA plot of Compound 1 ethyl acetate solvate crystalline form V.
Figure 15:
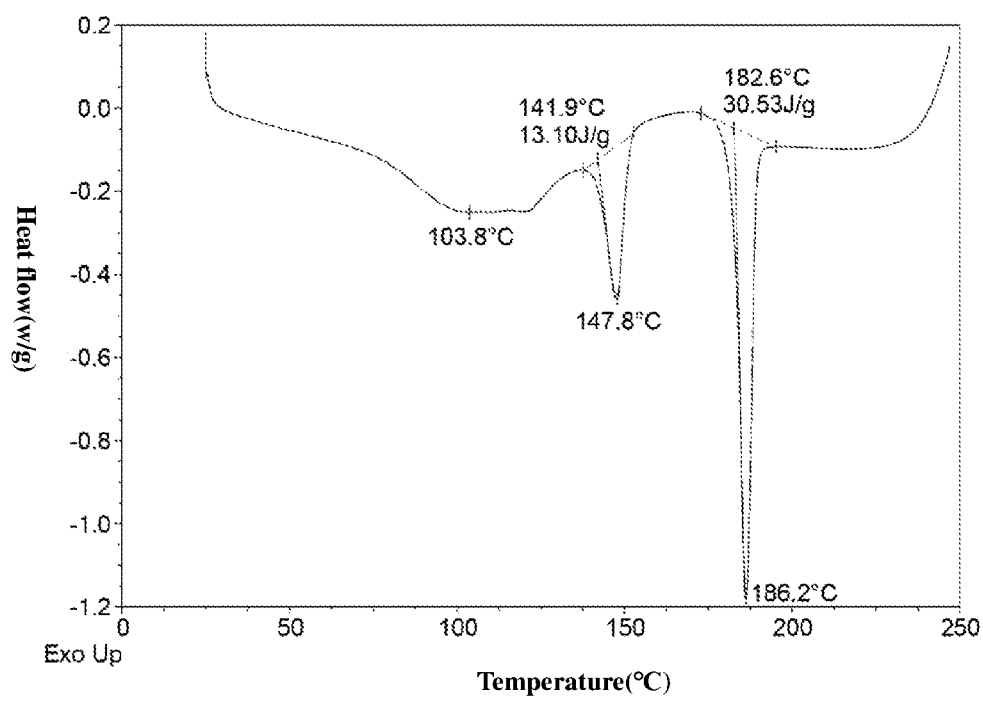
FIG. 15 is a DSC curve of Compound 1 ethyl acetate solvate crystalline form V.
Figure 16:
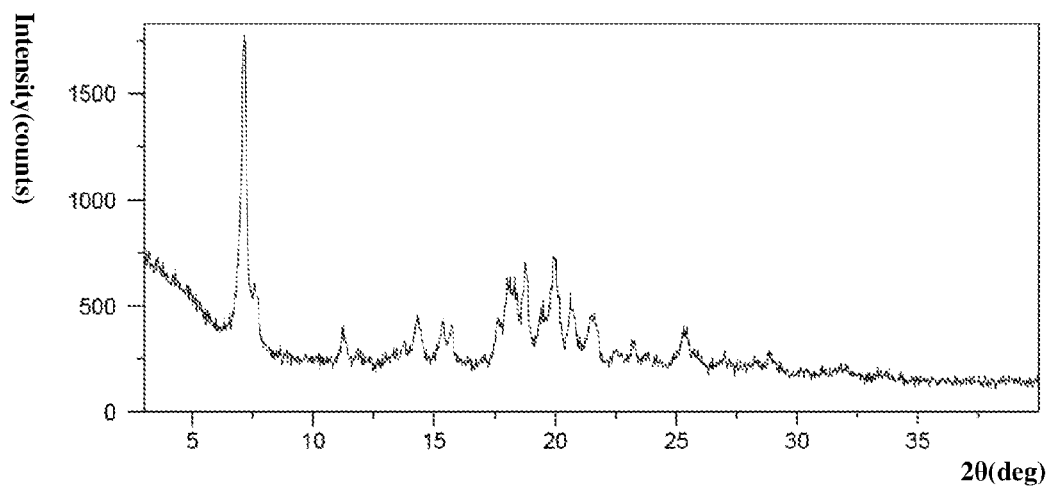
FIG. 16 is an XRPD pattern of Compound 1 methylbenzene solvate crystalline form VI.
Figure 17:
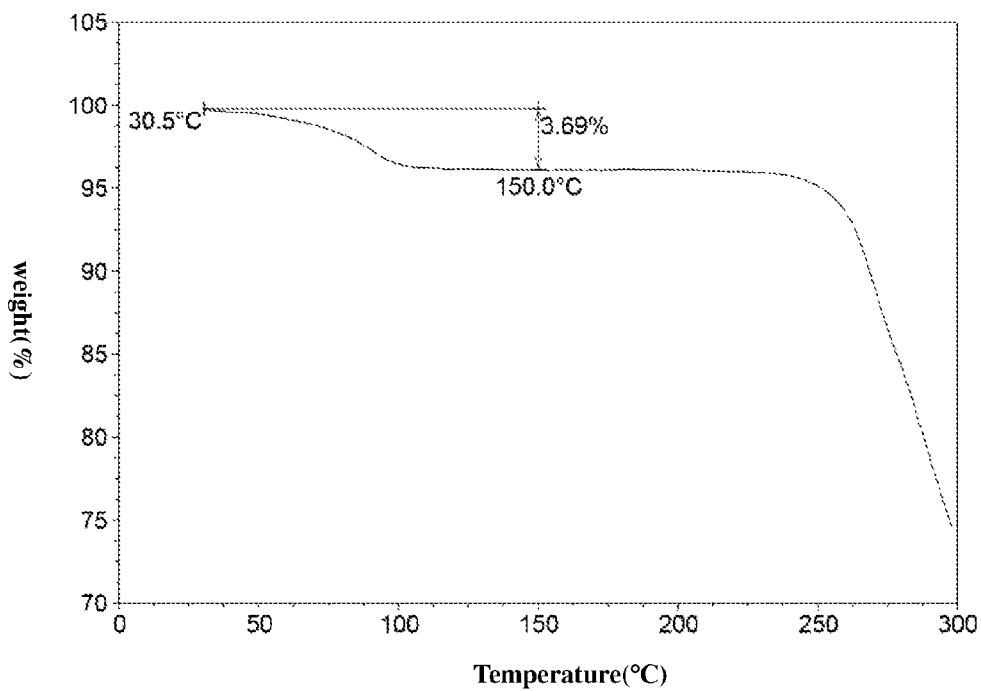
FIG. 17 is a TGA plot of Compound 1 methylbenzene solvate crystalline form VI.
Figure 18:
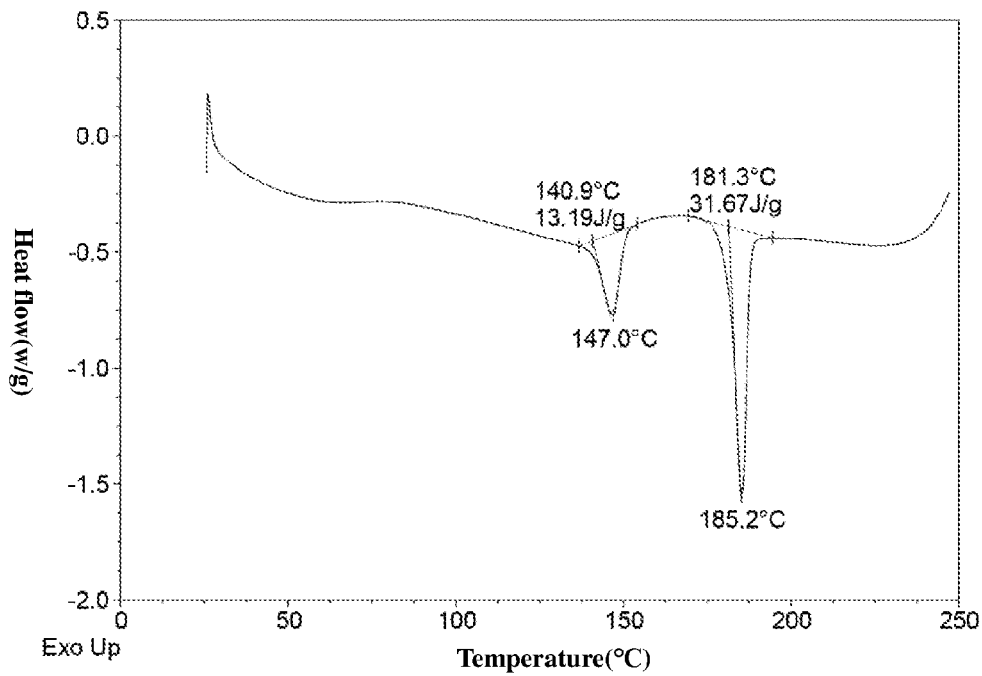
FIG. 18 is a DSC curve of Compound 1 methylbenzene solvate crystalline form VI.
Figure 19:
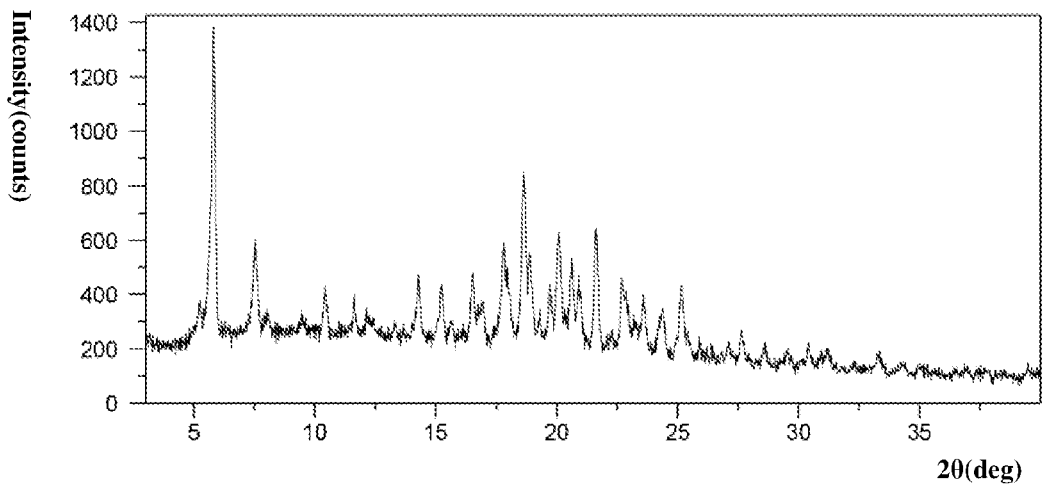
FIG. 19 is an XRPD pattern of Compound 1 crystalline Form VII.
Figure 20:
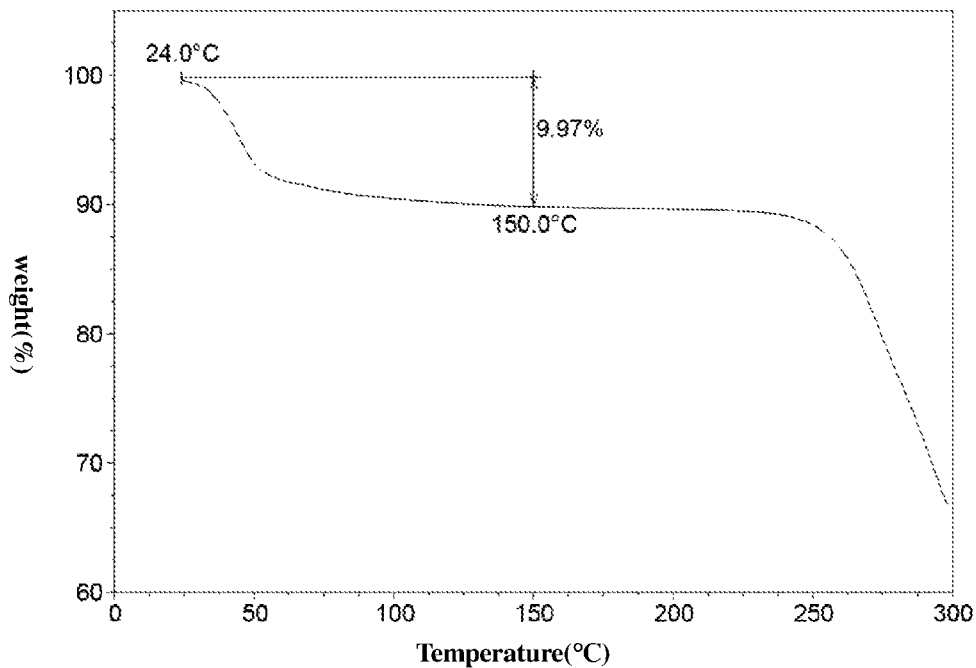
FIG. 20 is a TGA plot of Compound 1 crystalline Form VII.
Figure 21:
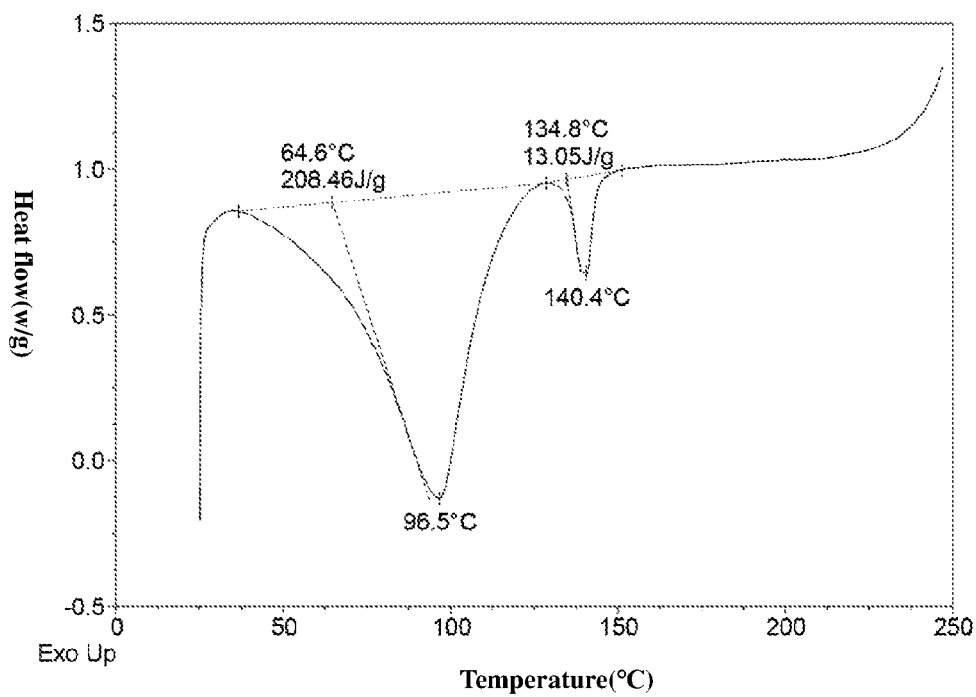
FIG. 21 is a DSC curve of Compound 1 crystalline Form VII.
Figure 22:
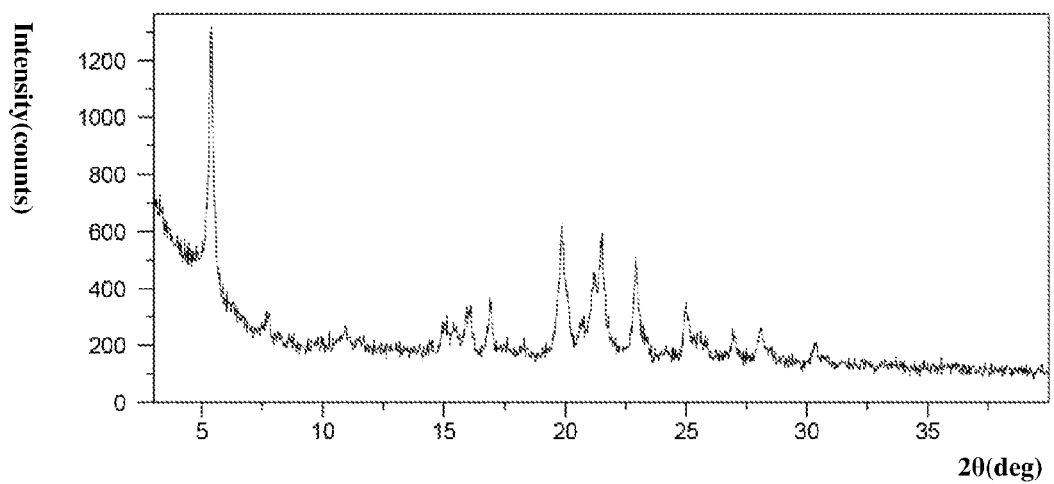
FIG. 22 is an XRPD pattern of Compound 1 chloroform solvate crystalline form VIII.
Figure 23:
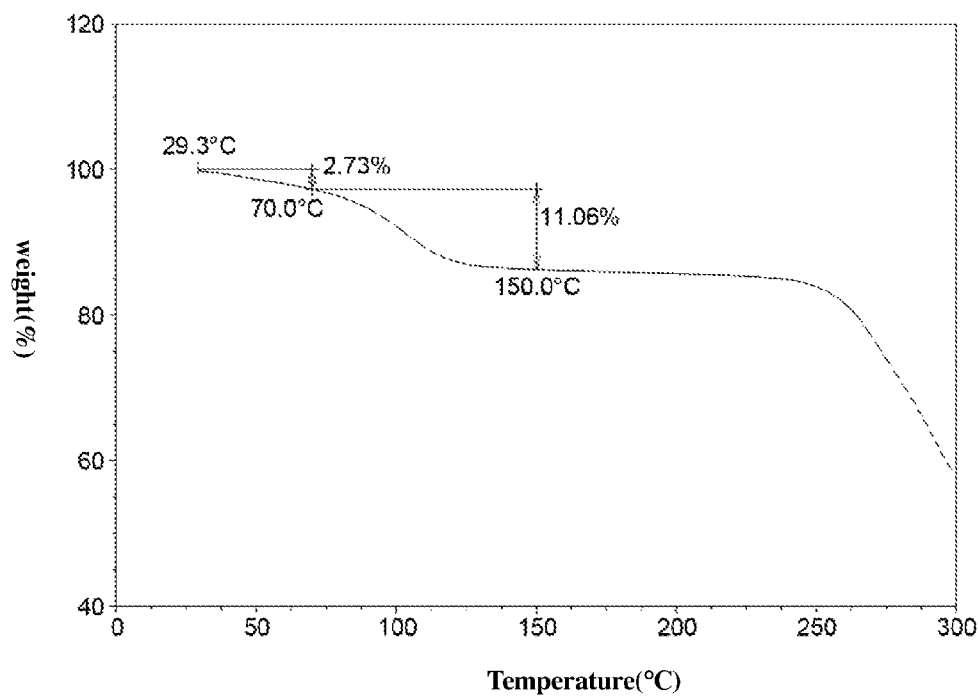
FIG. 23 is a TGA plot of Compound 1 chloroform solvate crystalline form VIII.
Figure 24:
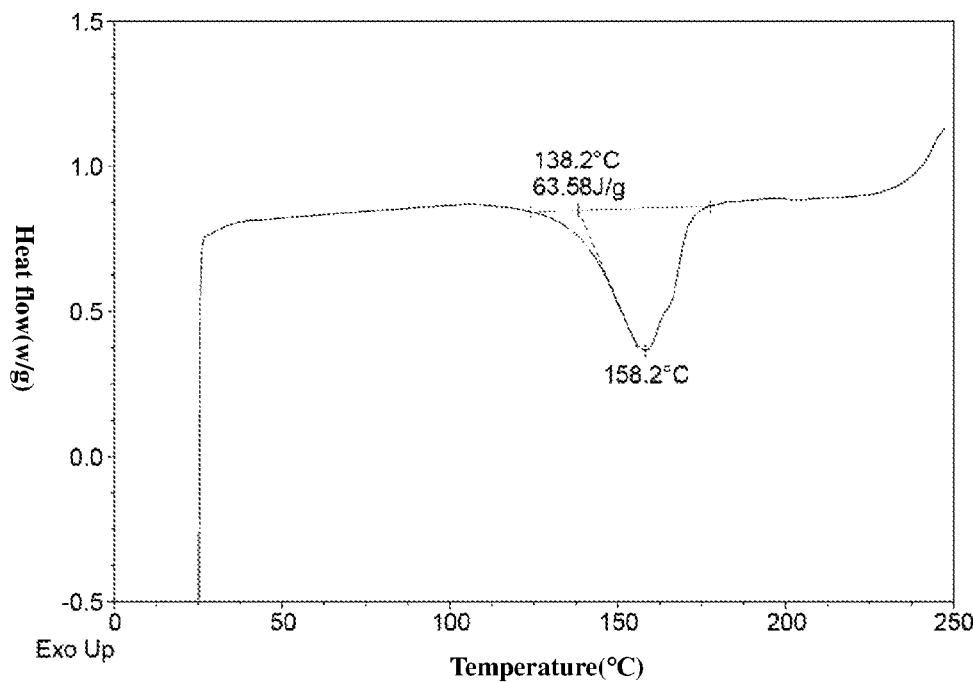
FIG. 24 is a DSC curve of Compound 1 chloroform solvate crystalline form VIII.
Figure 25:
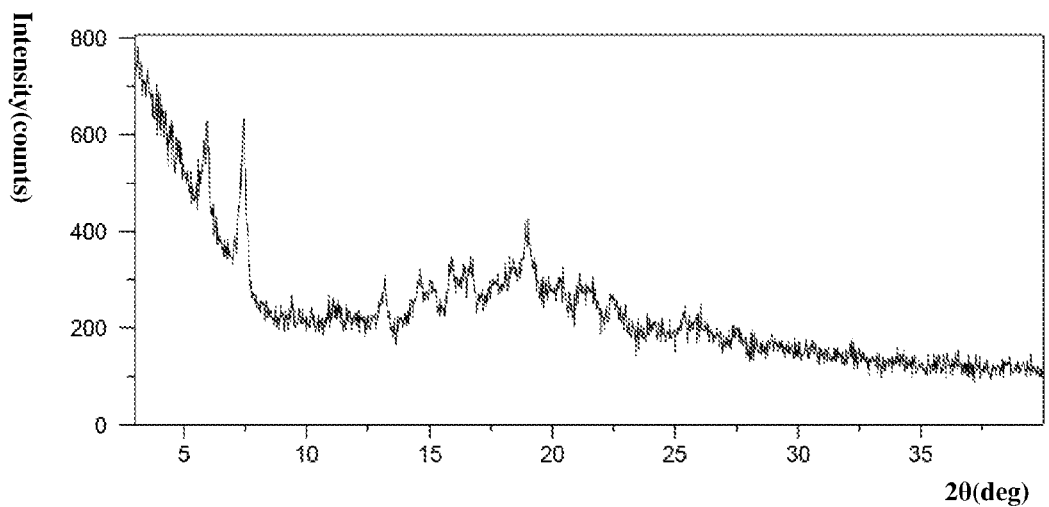
FIG. 25 is an XRPD pattern of Compound 1 methyl tert-butyl ether solvate crystalline form IX.
Figure 26:
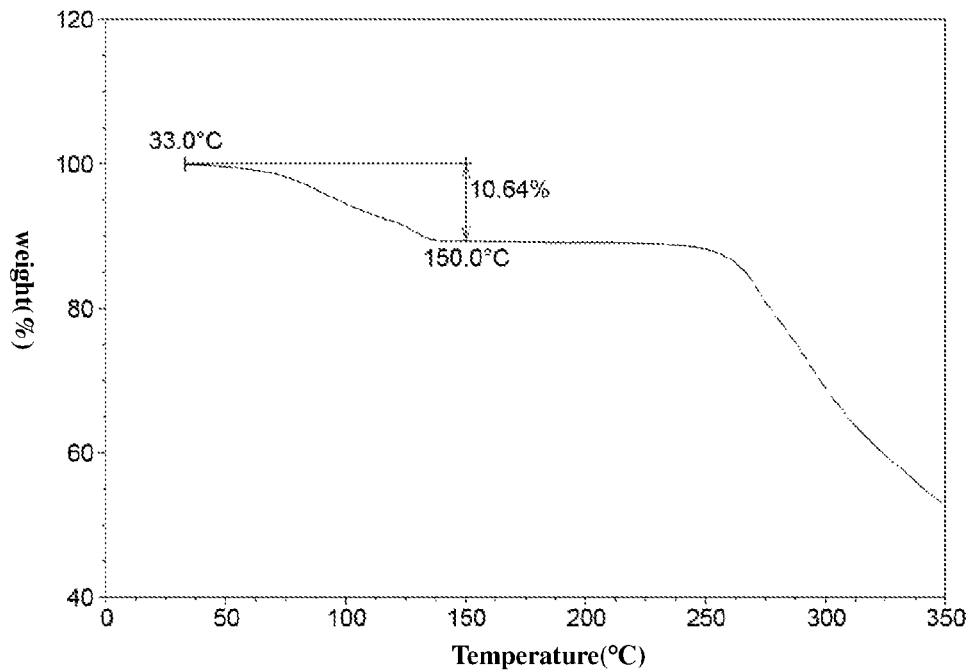
FIG. 26 is a TGA plot of Compound 1 methyl tert-butyl ether solvate crystalline form IX.
Figure 27:
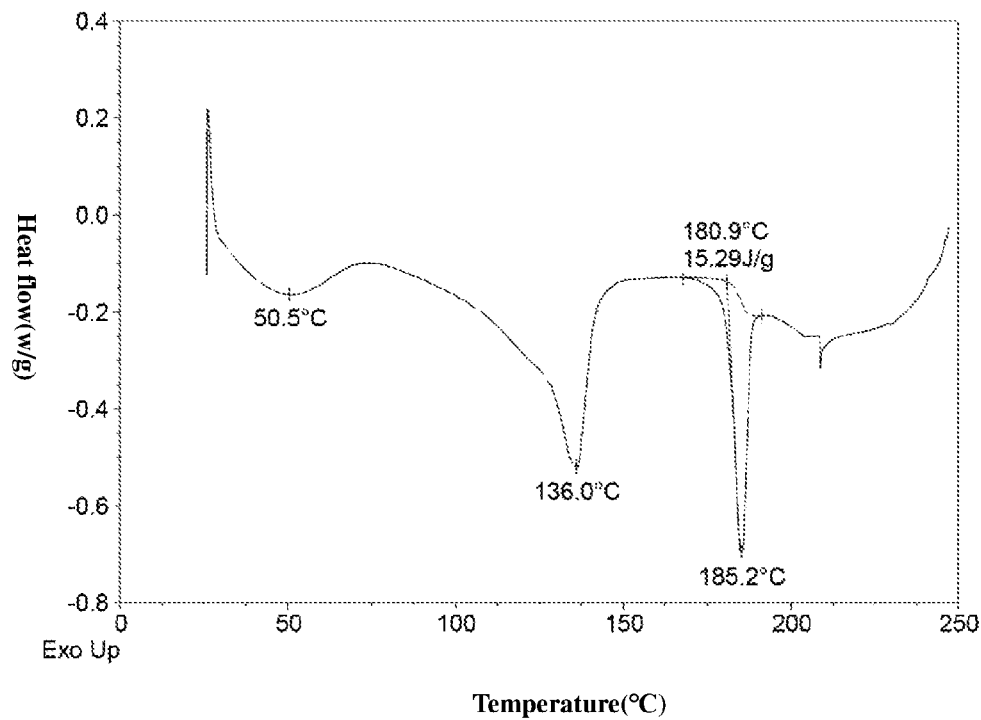
FIG. 27 is a DSC curve of Compound 1 methyl tert-butyl ether solvate crystalline form IX.
Figure 28:
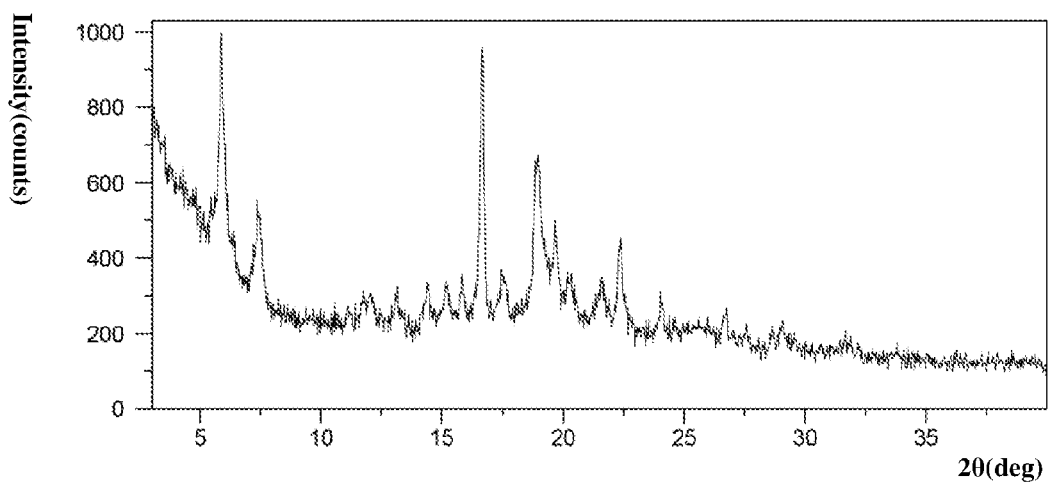
FIG. 28 is an XRPD pattern of Compound 1 2-methyltetrahydrofuran solvate crystalline form X.
Figure 29:
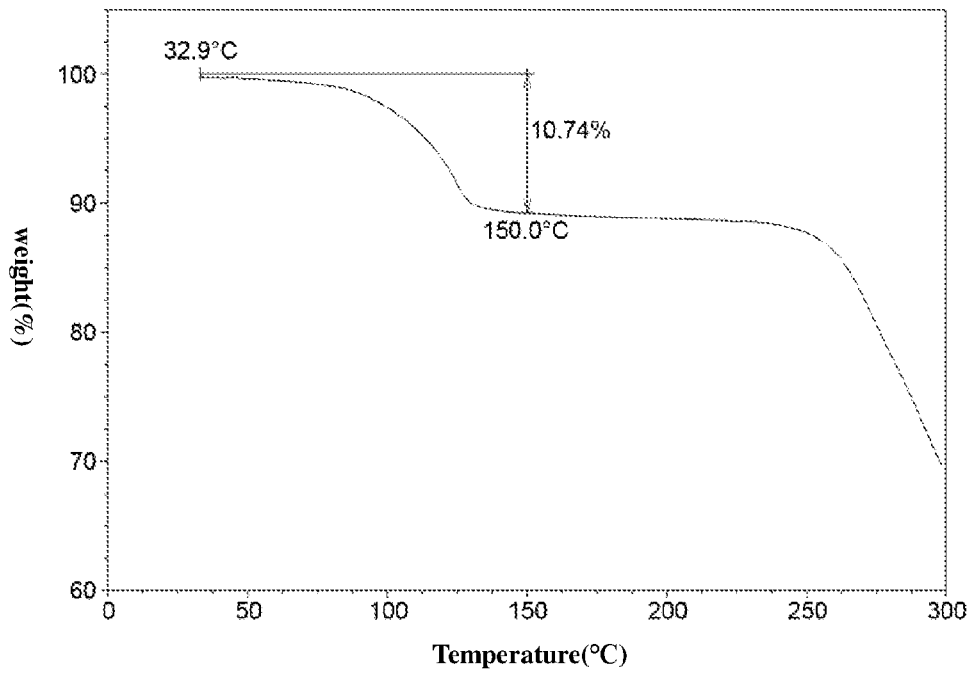
FIG. 29 is a TGA plot of Compound 1 2-methyltetrahydrofuran solvate crystalline form X.
Figure 30:
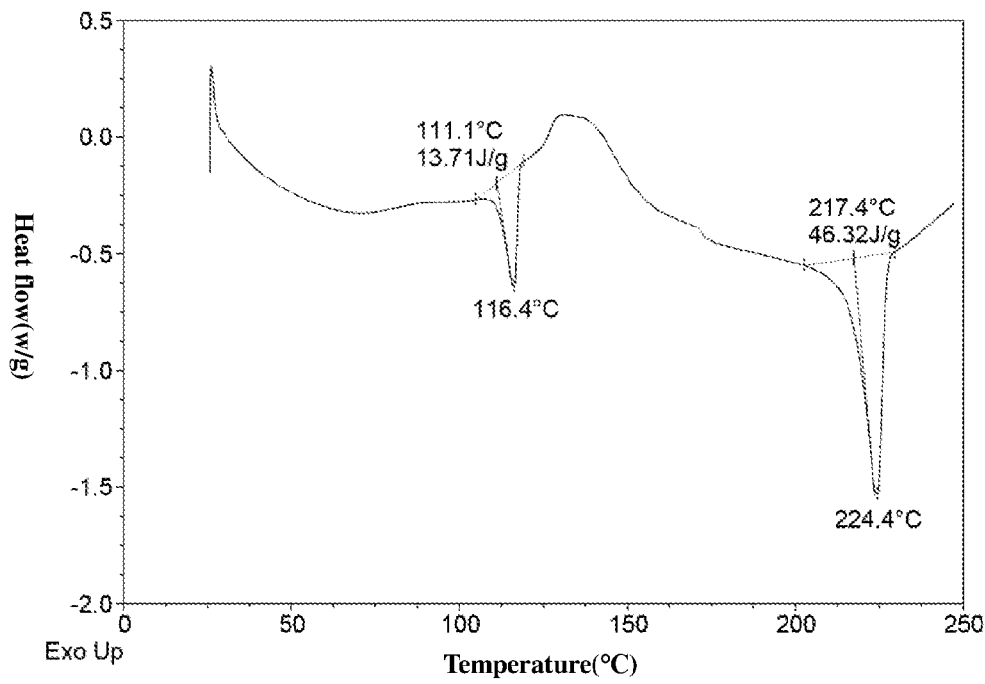
FIG. 30 is a DSC curve of Compound 1 2-methyltetrahydrofuran solvate crystalline form X.
Figure 31:
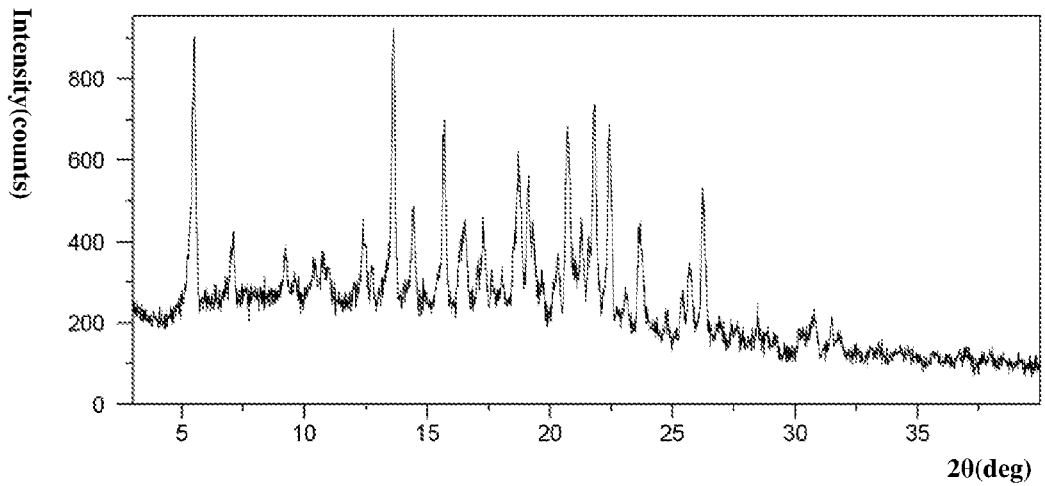
FIG. 31 is an XRPD pattern of Compound 1 crystalline Form XI.
Figure 32:
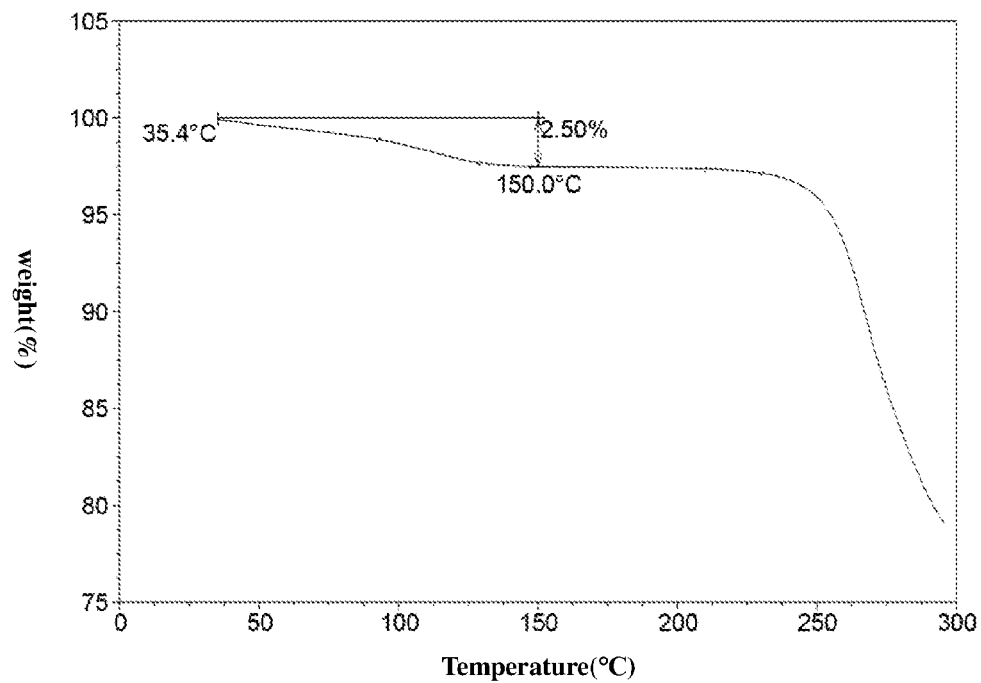
FIG. 32 is a TGA plot of Compound 1 crystalline Form XI.
Figure 33:
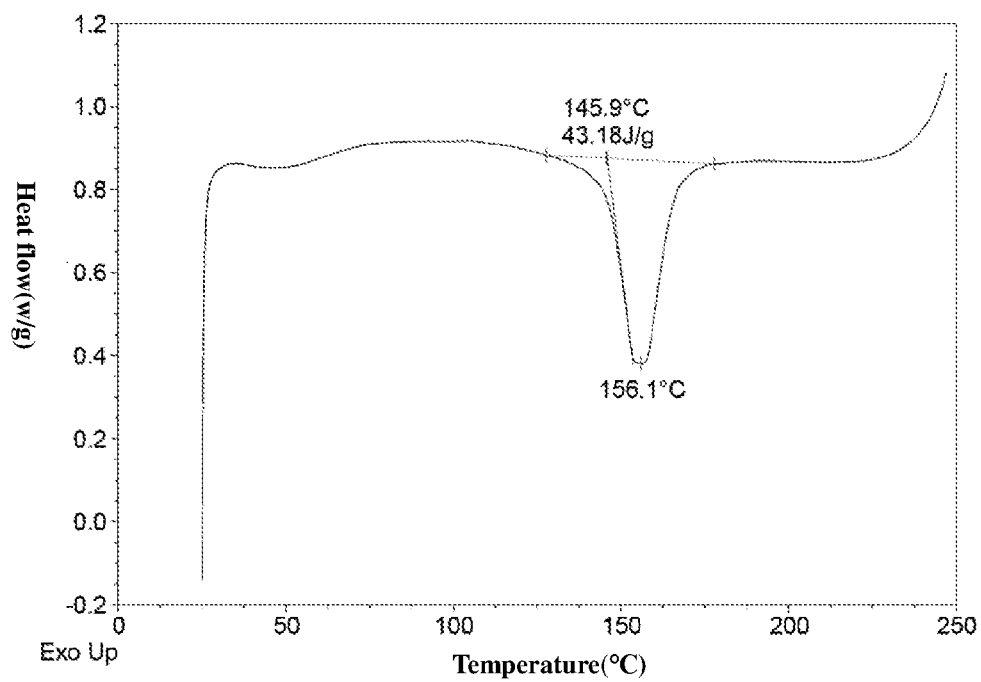
FIG. 33 is a DSC curve of Compound 1 crystalline Form XI.
Figure 34:
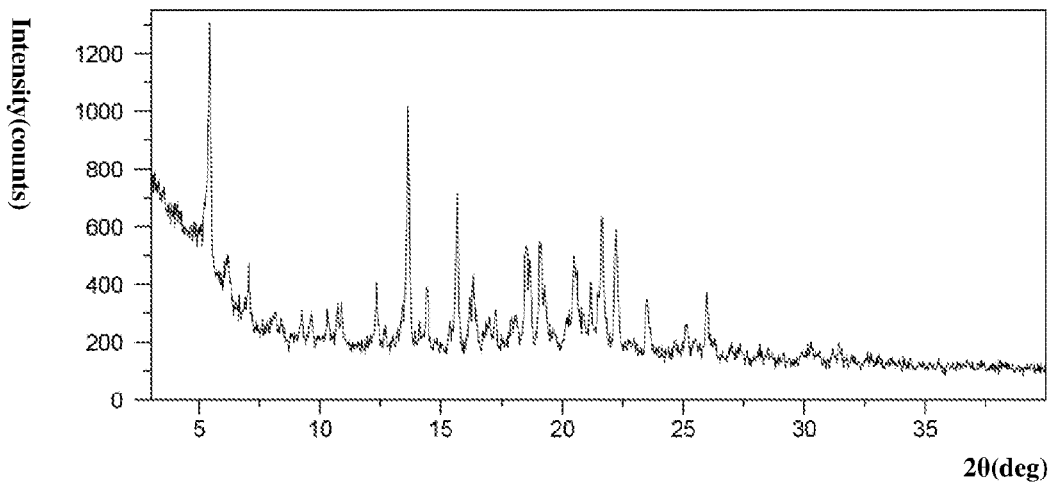
FIG. 34 is an XRPD pattern of Compound 1 acetone solvate crystalline form XII.
Figure 35:
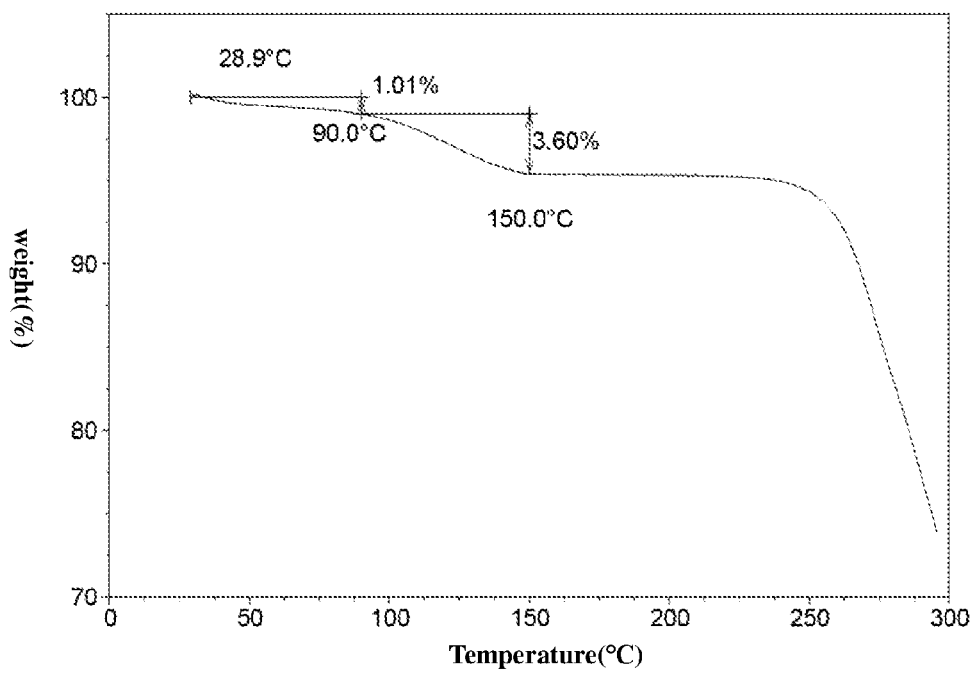
FIG. 35 is a TGA plot of Compound 1 acetone solvate crystalline form XII.
Figure 36:
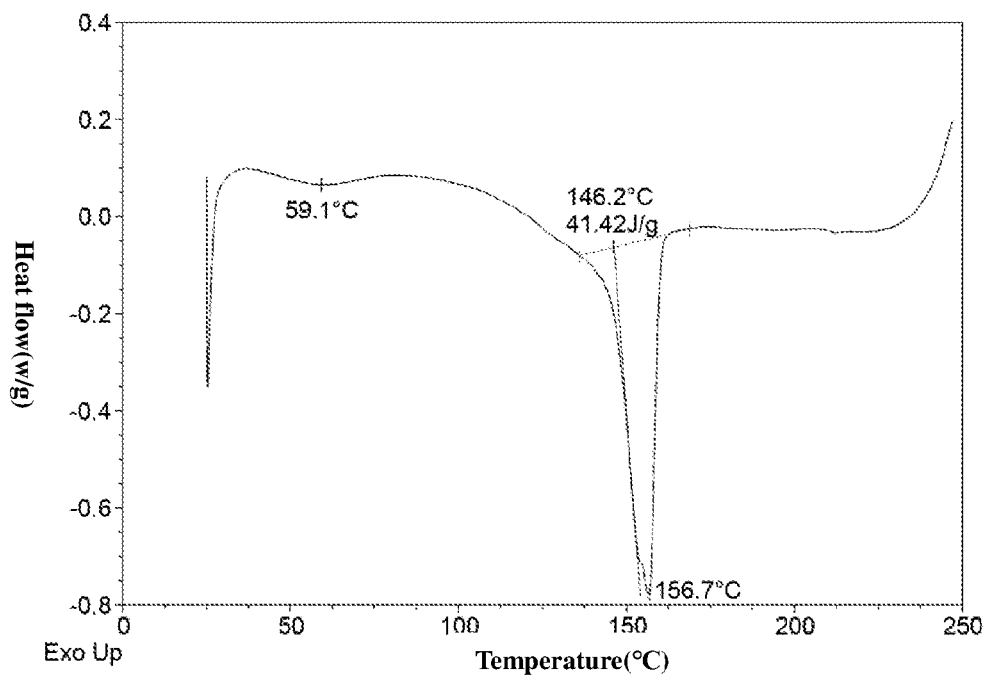
FIG. 36 is a DSC curve of Compound 1 acetone solvate crystalline form XII.
Figure 37:
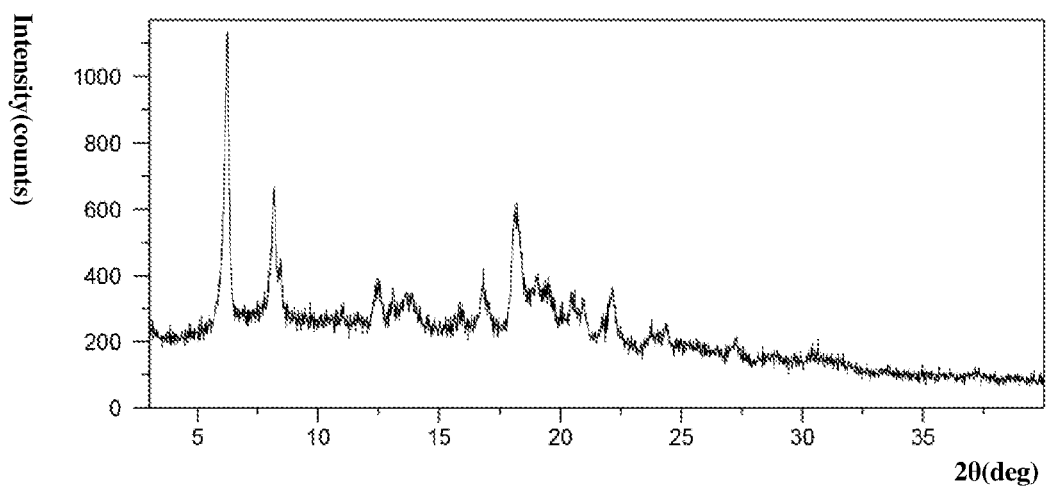
FIG. 37 is an XRPD pattern of Compound 1 crystalline Form XIII.
Figure 38:
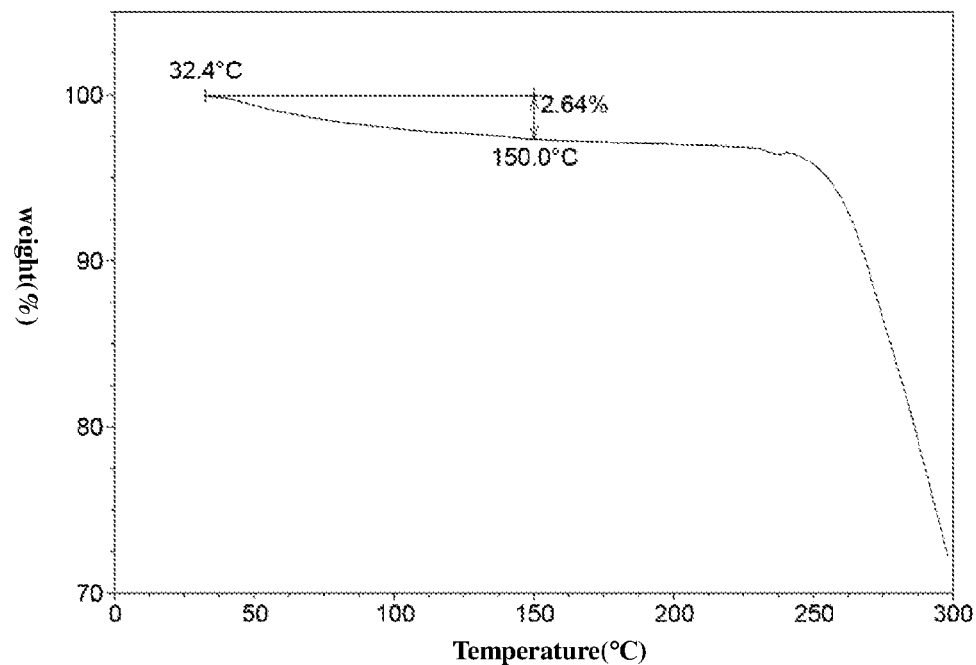
FIG. 38 is a TGA plot of Compound 1 crystalline Form XIII.
Figure 39:
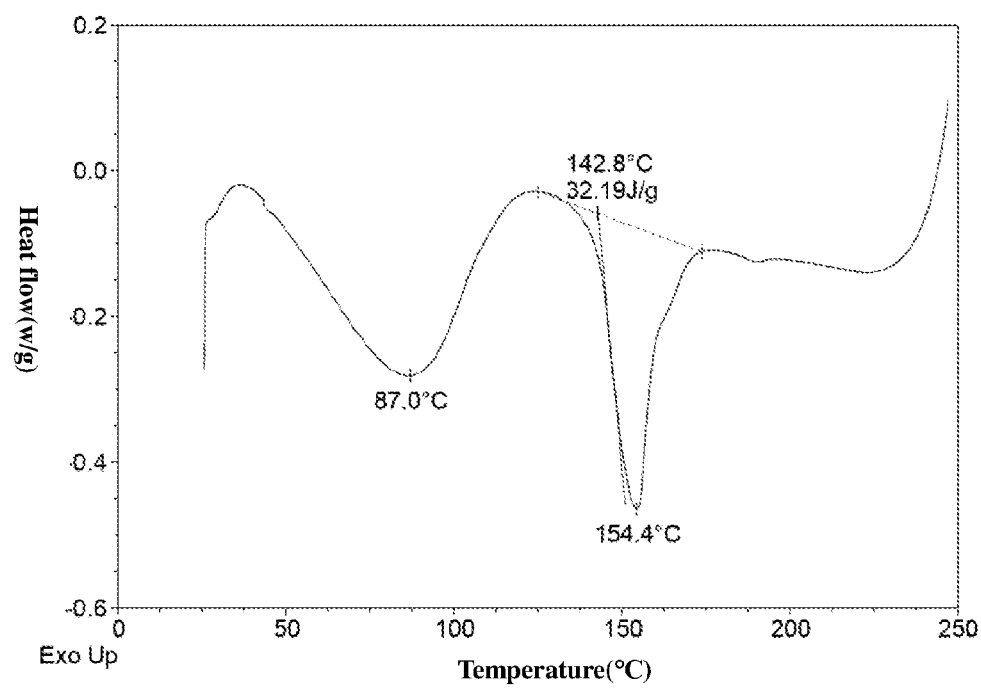
FIG. 39 is a DSC curve of Compound 1 crystalline Form XIII.
Figure 40:
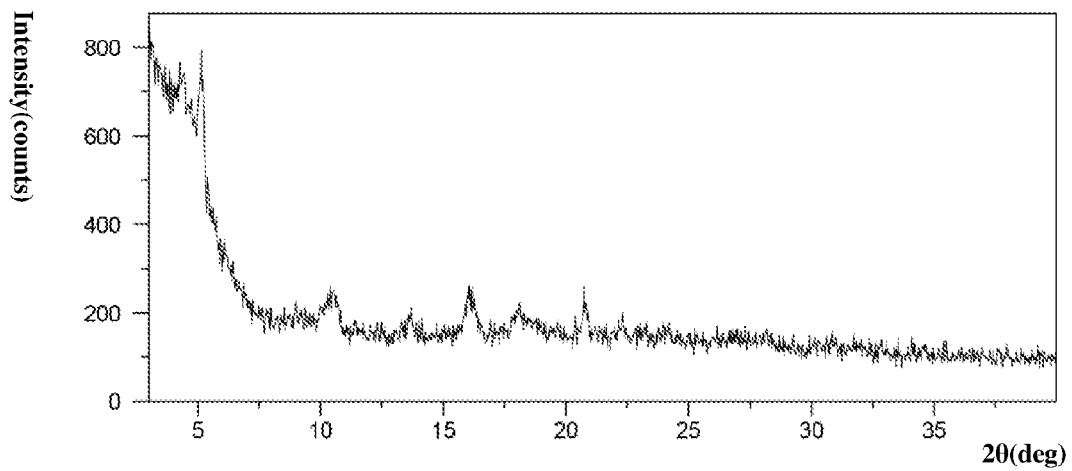
FIG. 40 is an XRPD pattern of Compound 1 crystalline Form XIV.
Figure 41:
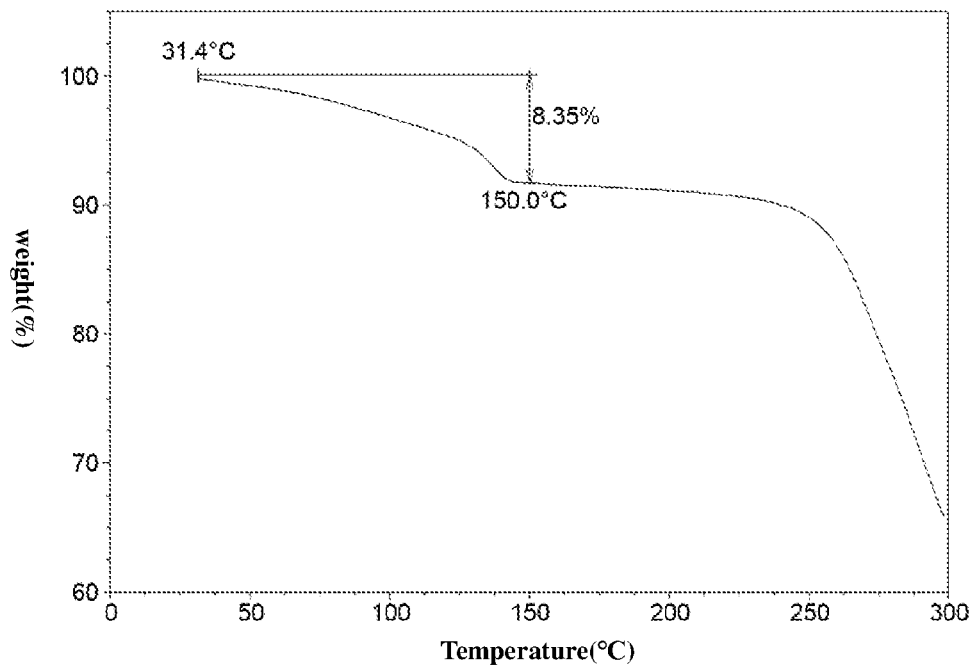
FIG. 41 is a TGA plot of Compound 1 crystalline Form XIV.
Figure 42:
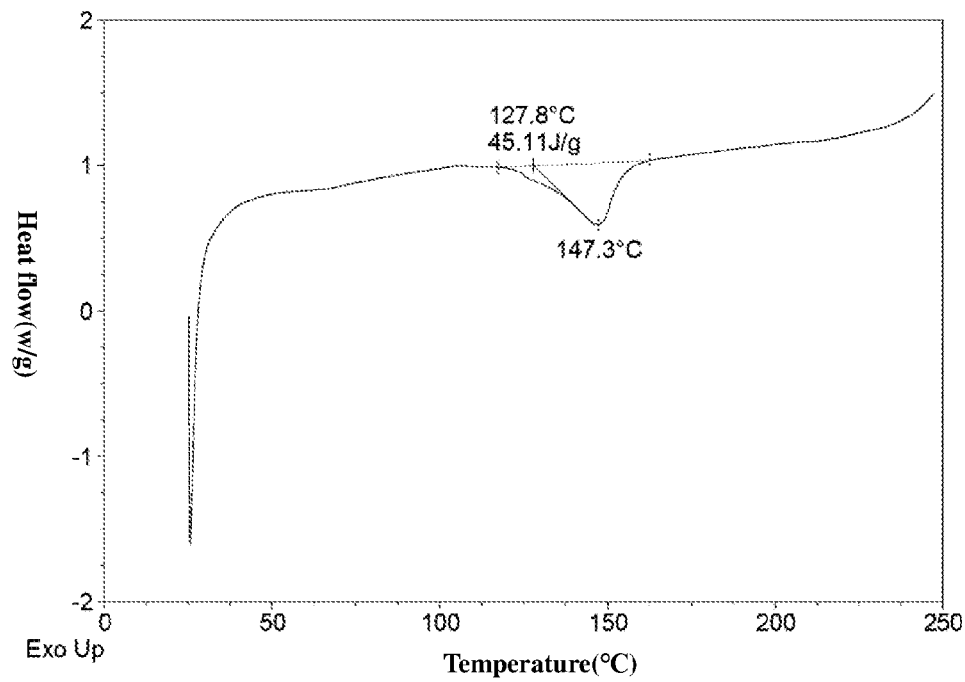
FIG. 42 is a DSC curve of Compound 1 crystalline Form XIV.
Figure 43:
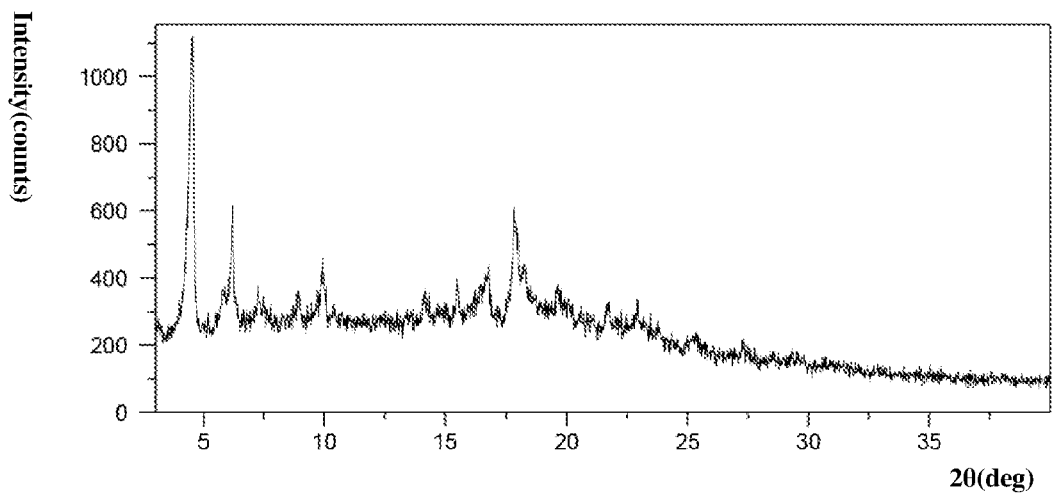
FIG. 43 is an XRPD pattern of Compound 1 crystalline Form XV.
Figure 44:
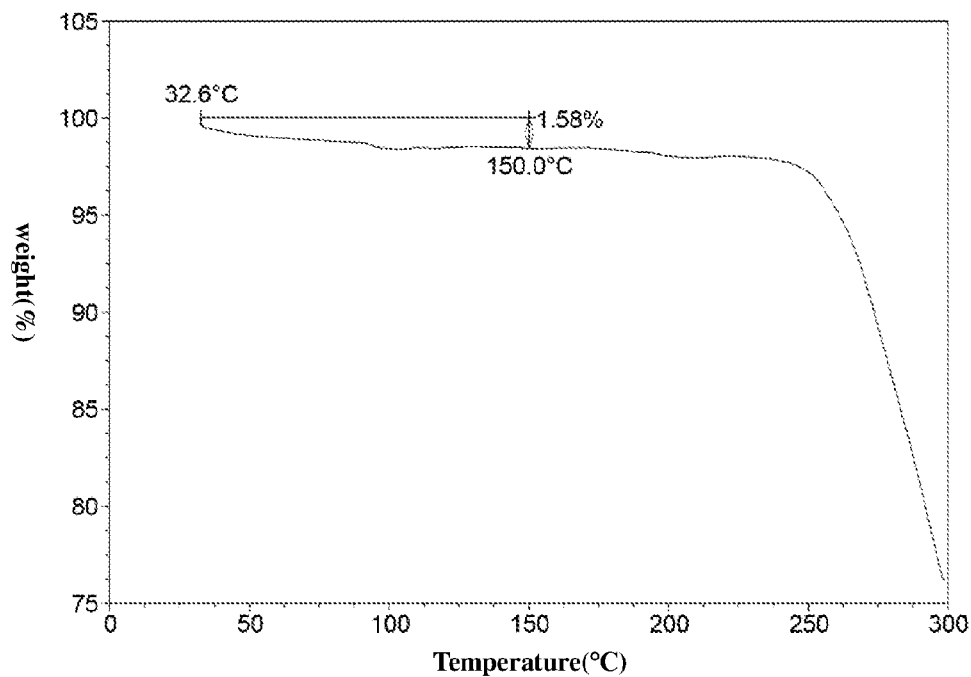
FIG. 44 is a TGA plot of Compound 1 crystalline Form XV.
Figure 45:
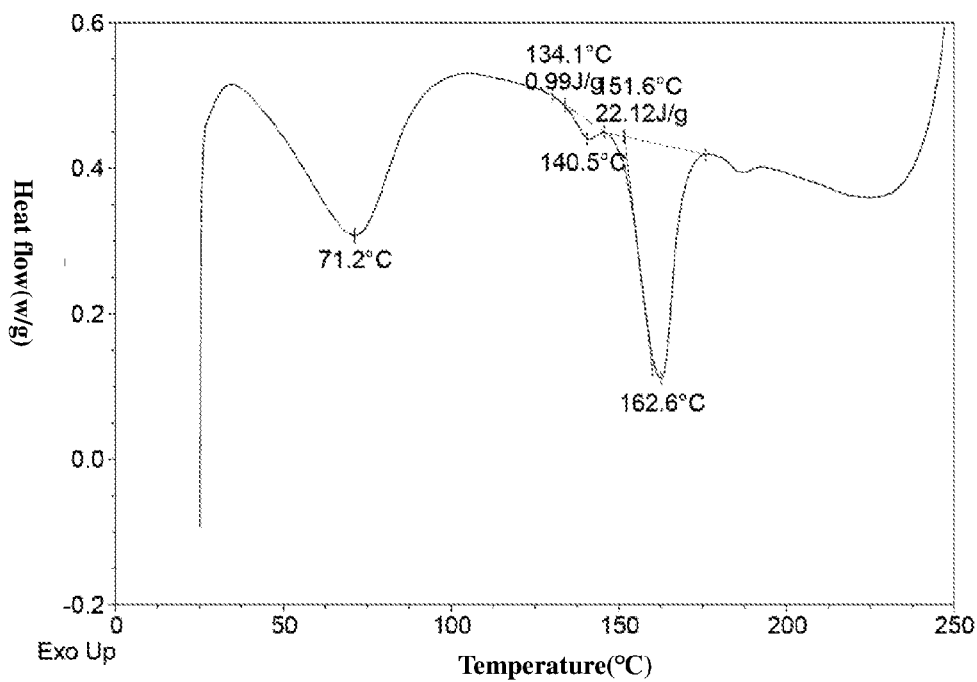
FIG. 45 is a DSC curve of Compound 1 crystalline Form XV.
Figure 46:
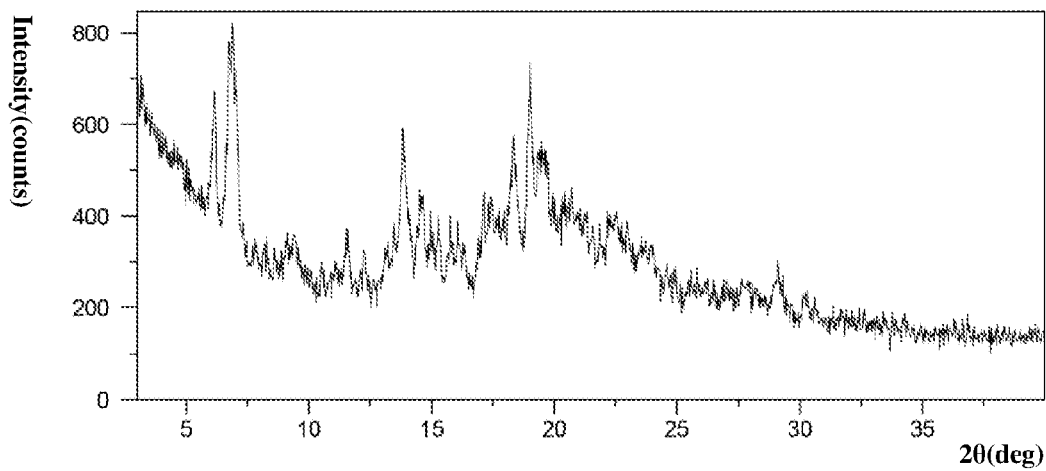
FIG. 46 is an XRPD pattern of Compound 1 N,N-dimethylformamide solvate crystalline form XVI.
Figure 47:
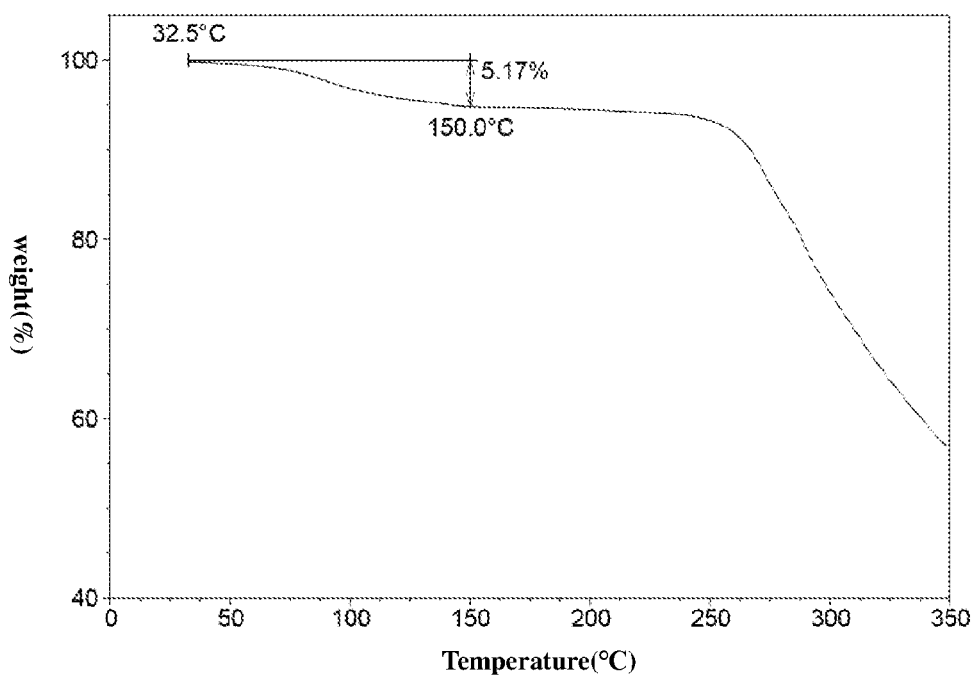
FIG. 47 is a TGA plot of Compound 1 N,N-dimethylformamide solvate crystalline form XVI.
Figure 48:
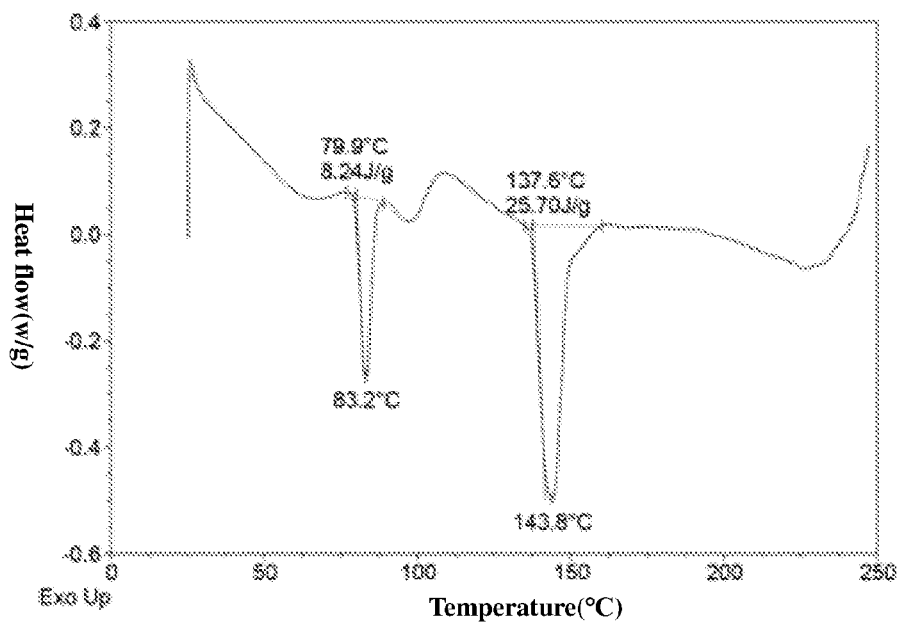
FIG. 48 is a DSC curve of Compound 1 N,N-dimethylformamide solvate crystalline form XVI.
Figure 49:
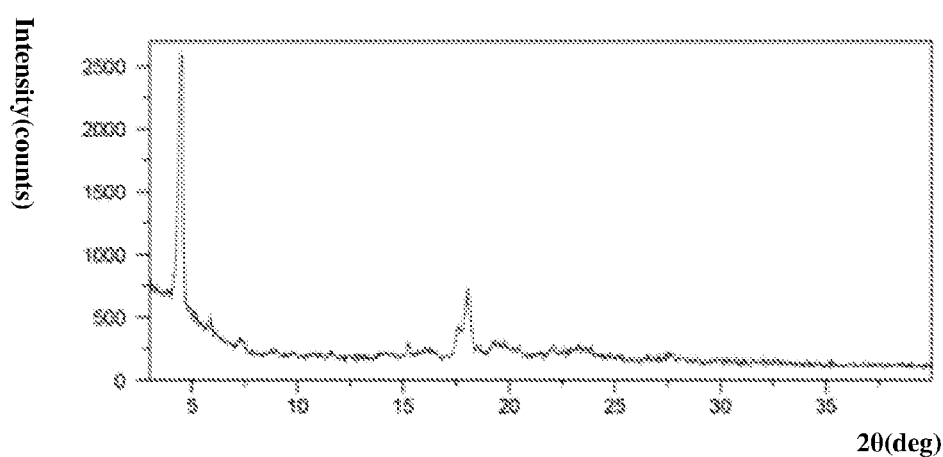
FIG. 49 is an XRPD pattern of Compound 1 crystalline Form XVII.
Figure 50:
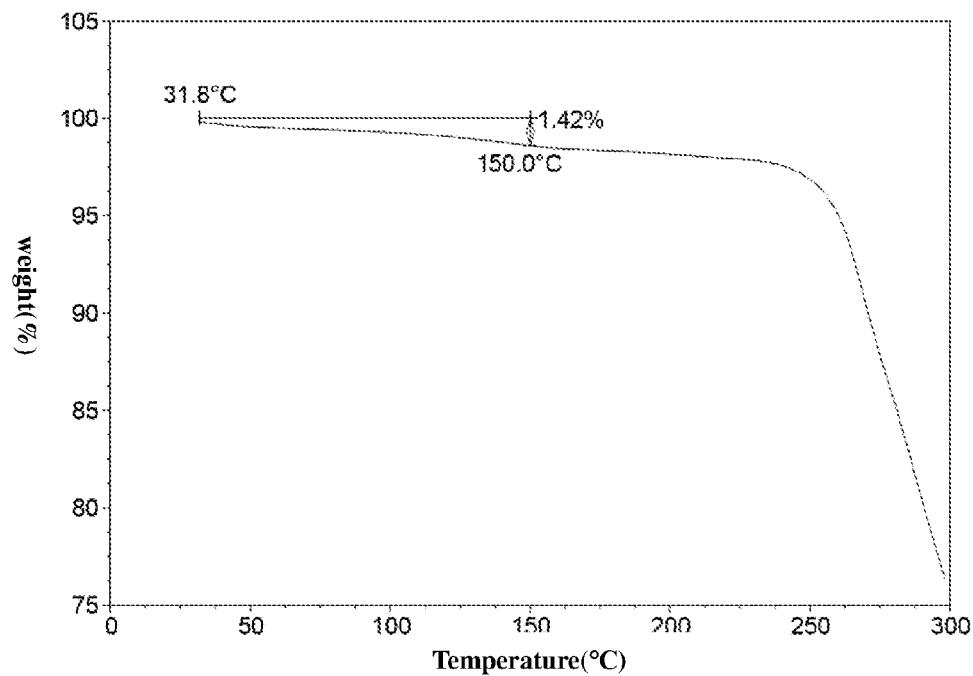
FIG. 50 is a TGA plot of Compound 1 crystalline Form XVII.
Figure 51:
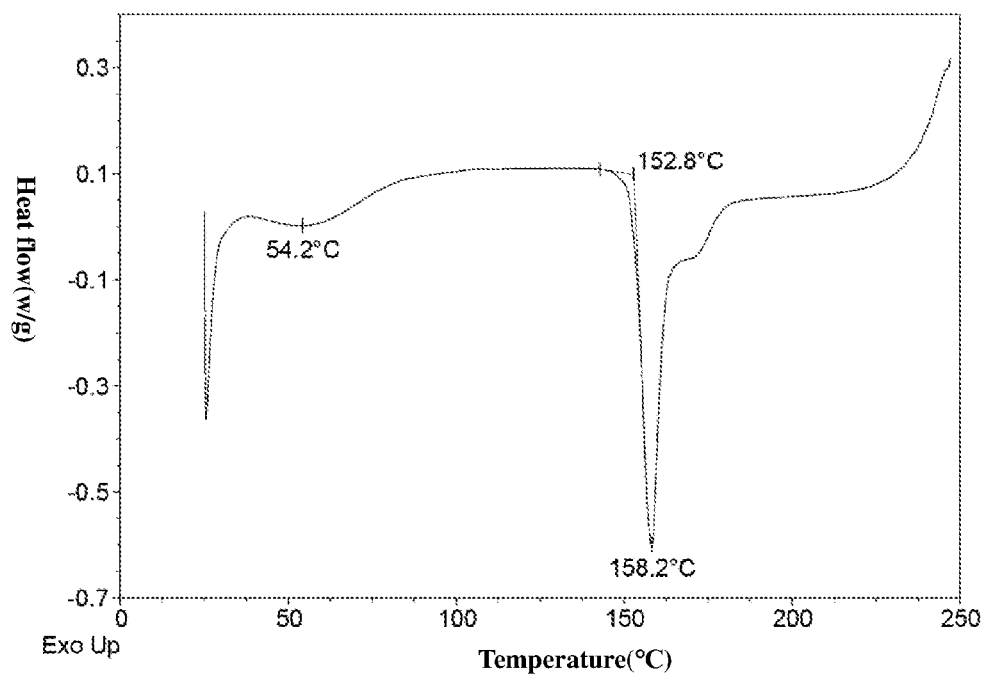
FIG. 51 is a DSC curve of Compound 1 crystalline Form XVII.
Figure 52:
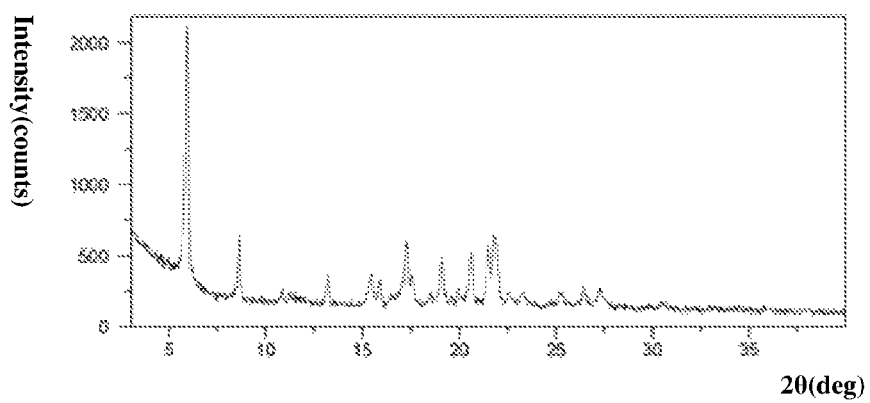
FIG. 52 is an XRPD pattern of Compound 1 crystalline Form XVIII.
Figure 53:
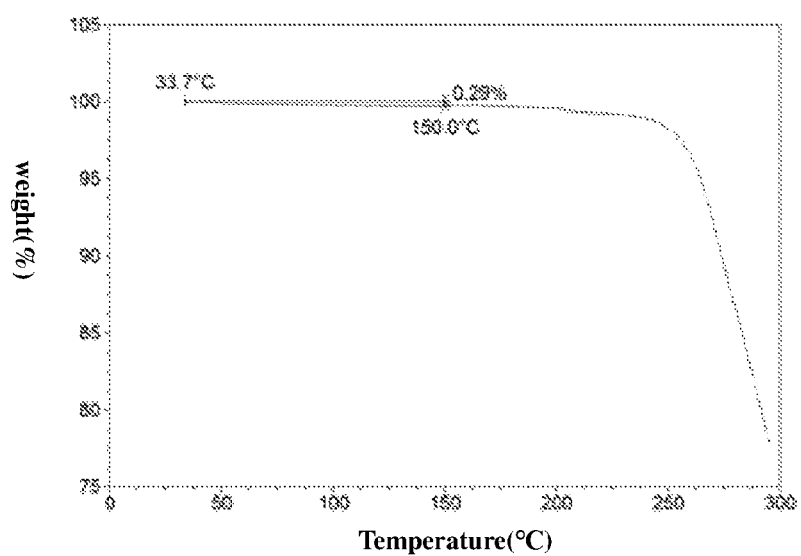
FIG. 53 is a TGA plot of Compound 1 crystalline Form XVIII
Figure 54:
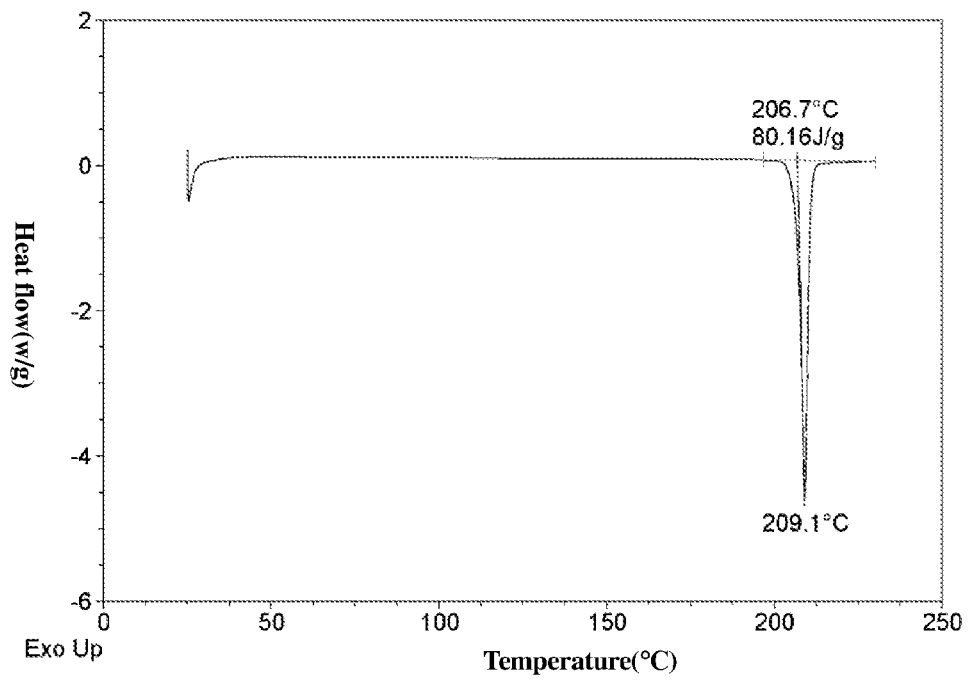
FIG. 54 is a DSC curve of Compound 1 crystalline Form XVIII.
Figure 55:
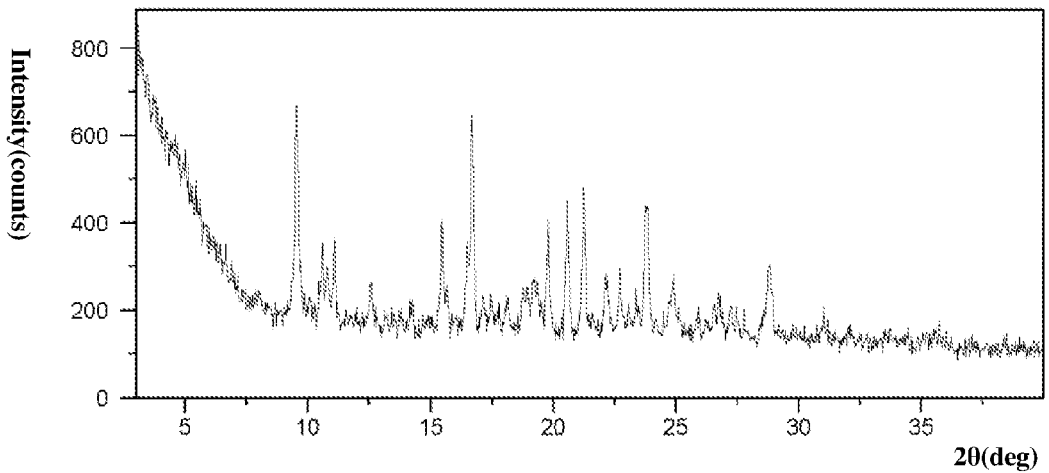
FIG. 55 is an XRPD pattern of Compound 1 hydrochloride crystalline form XIX.
Figure 56:
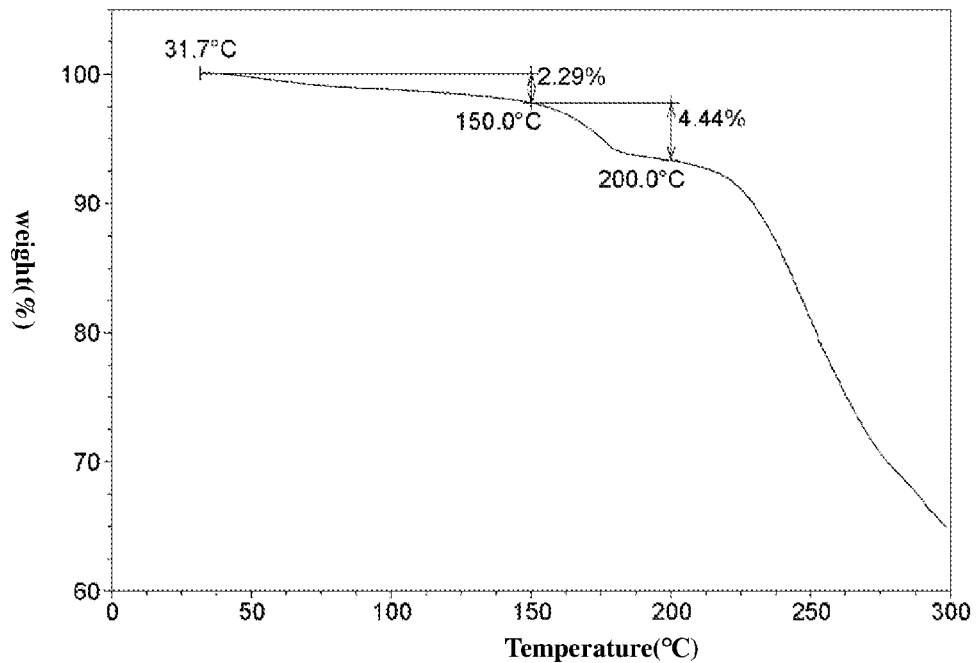
FIG. 56 is a TGA plot of Compound 1 hydrochloride crystalline form XIX.
Figure 57:
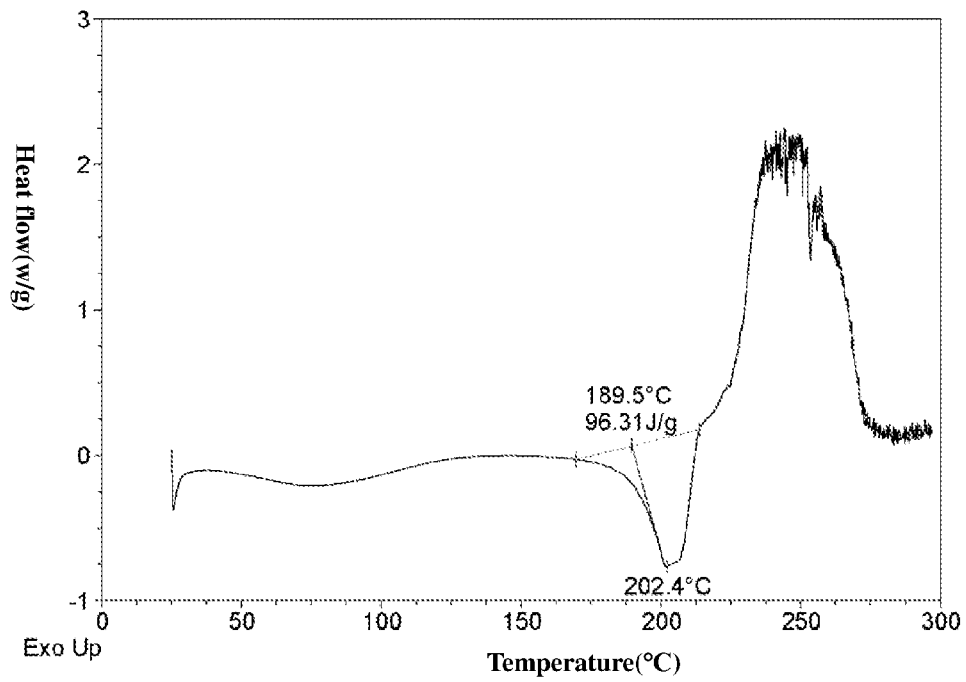
FIG. 57 is a DSC curve of Compound 1 hydrochloride crystalline form XIX.
Figure 58:
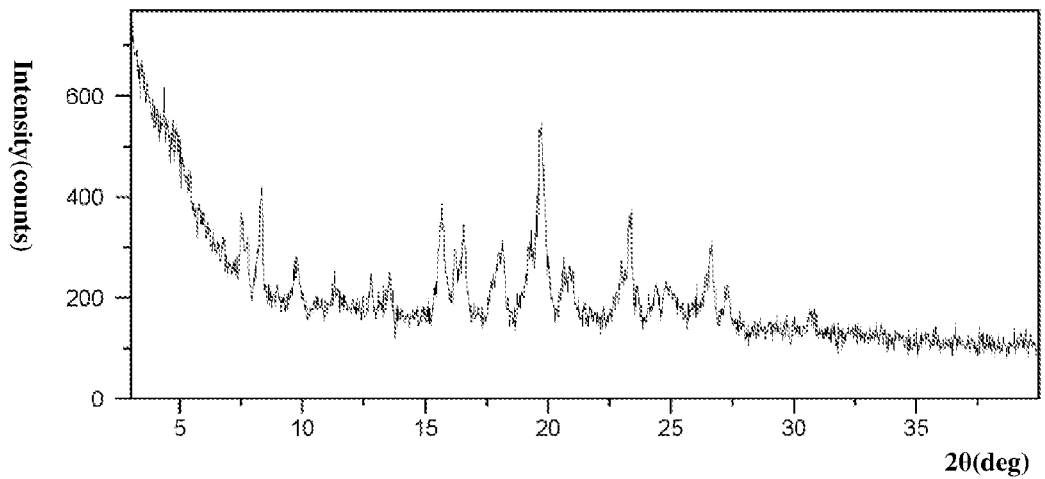
FIG. 58 is an XRPD pattern of Compound 1 sulphate crystalline form XX.
Figure 59:
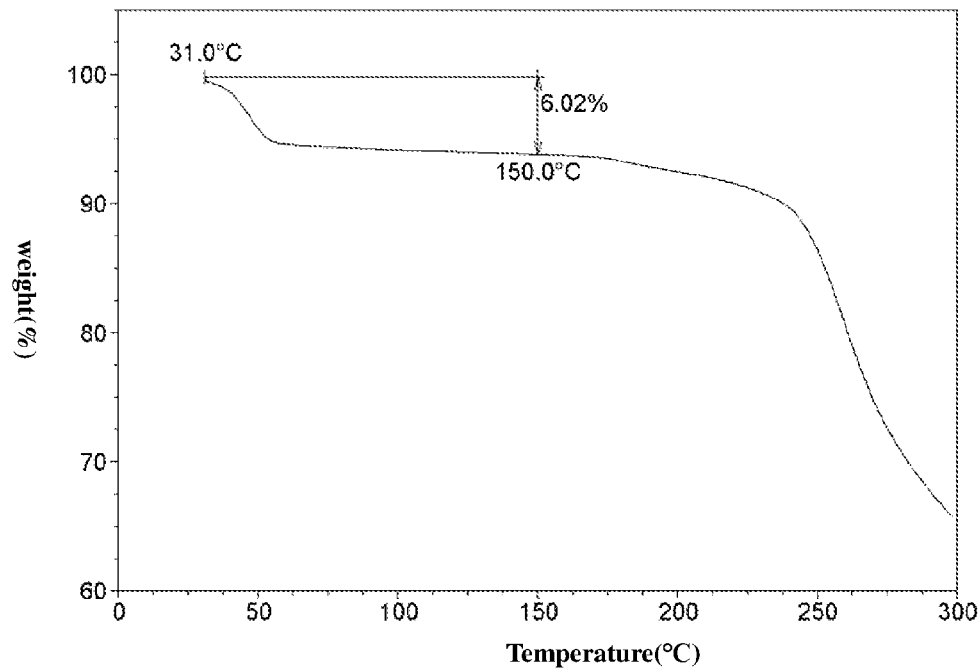
FIG. 59 is a TGA plot of Compound 1 sulphate crystalline form XX.
Figure 60:
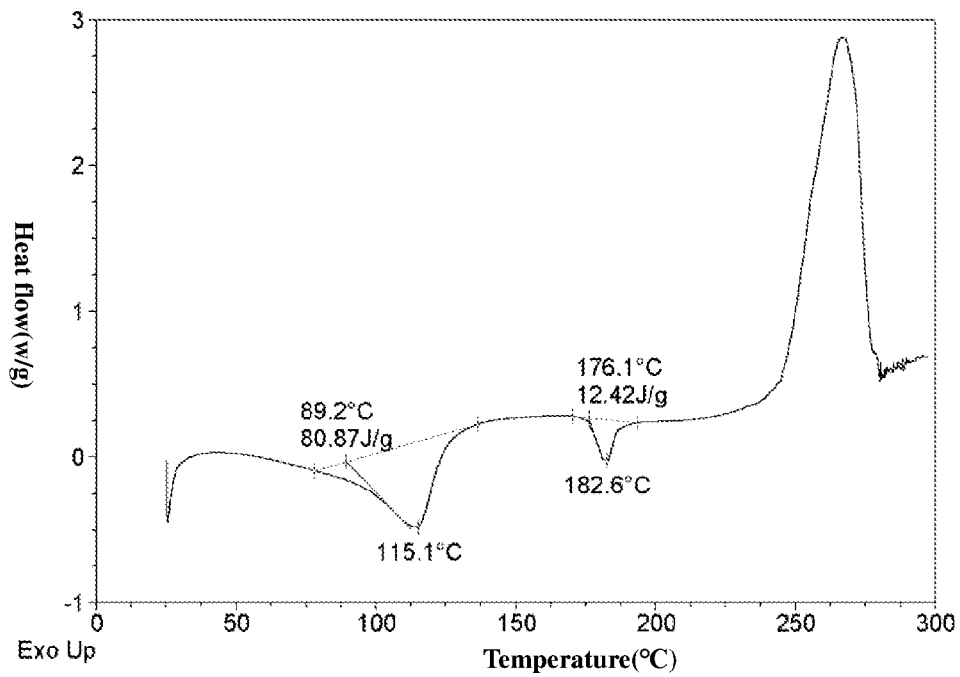
FIG. 60 is a DSC curve of Compound 1 sulphate crystalline form XX.
Figure 61:
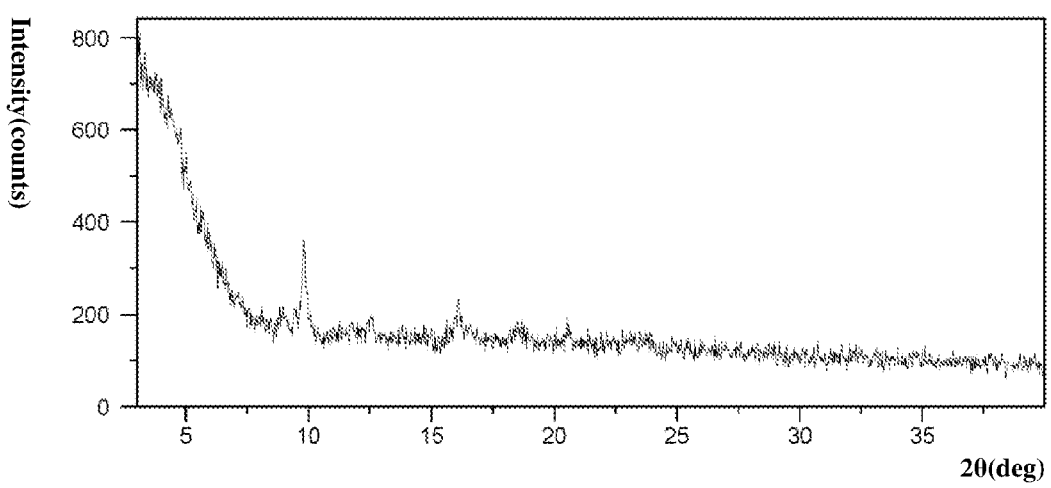
FIG. 61 is an XRPD pattern of Compound 1 mesylate crystalline form XXI.
Figure 62:
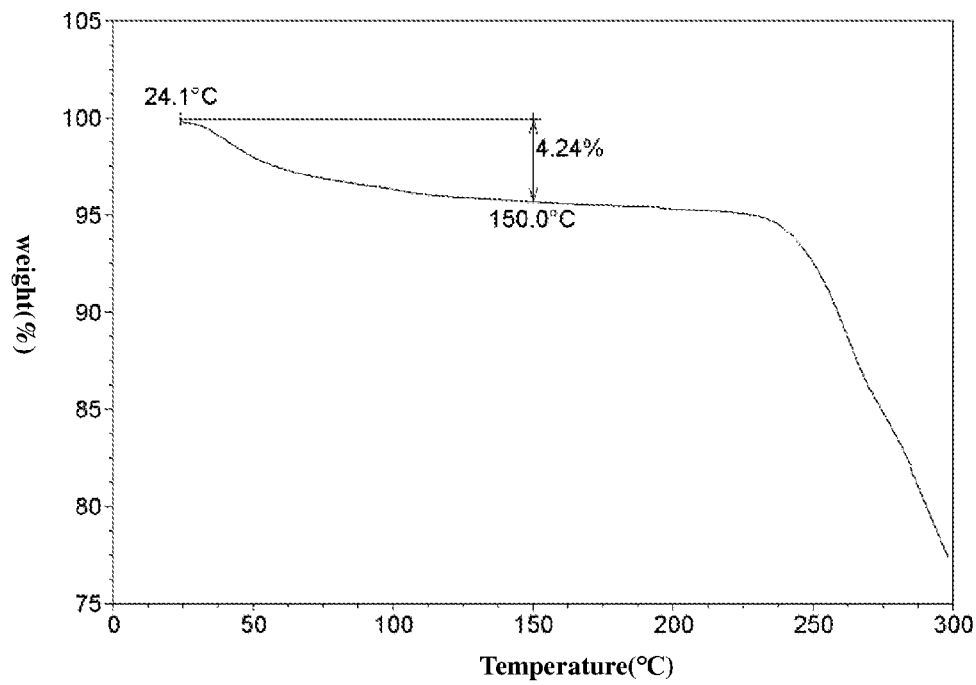
FIG. 62 is a TGA plot of Compound 1 mesylate crystalline form XXI.
Figure 63:
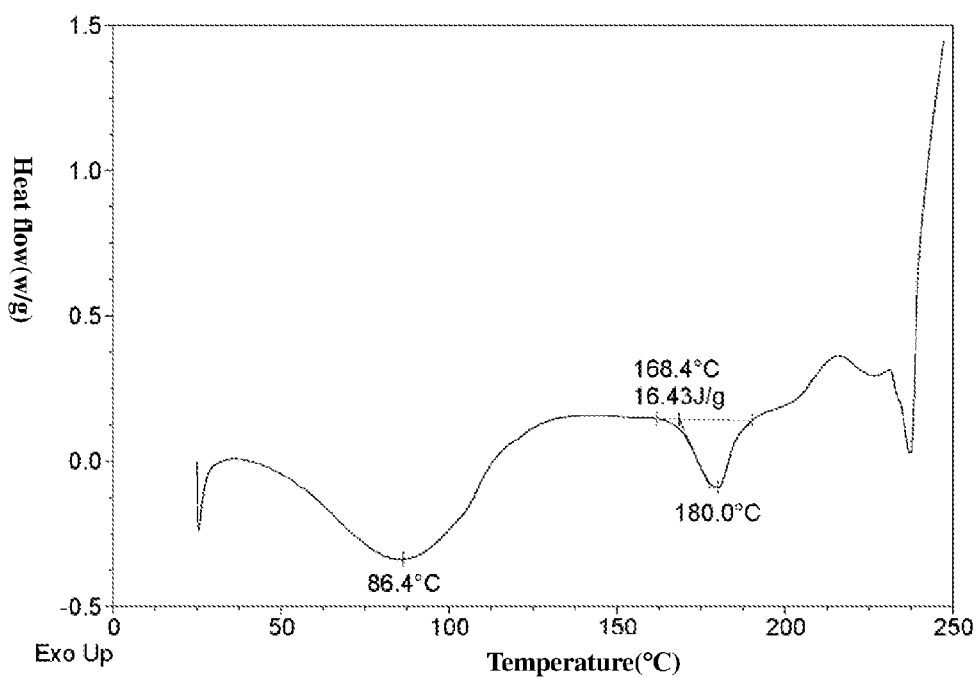
FIG. 63 is a DSC curve of Compound 1 mesylate crystalline form XXI.
Figure 64:
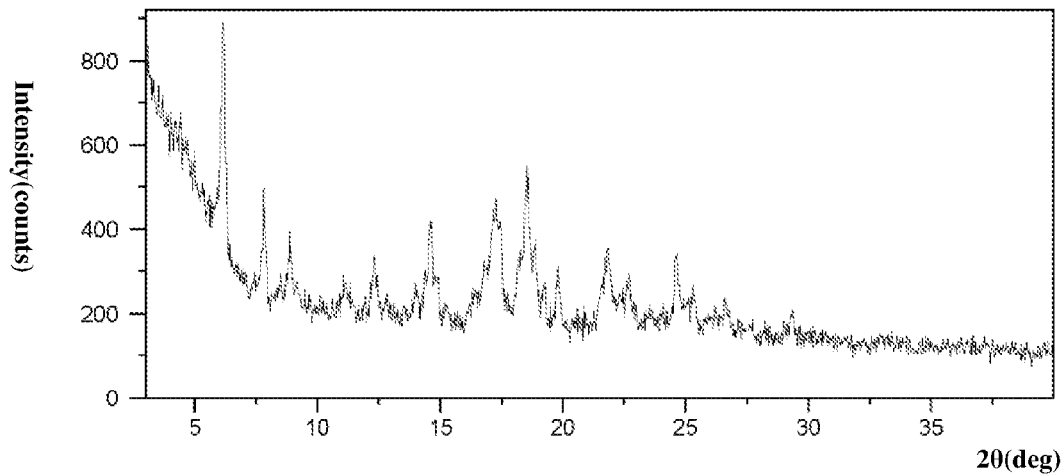
FIG. 64 is an XRPD pattern of Compound 1 mesylate crystalline form XXII.
Figure 65:
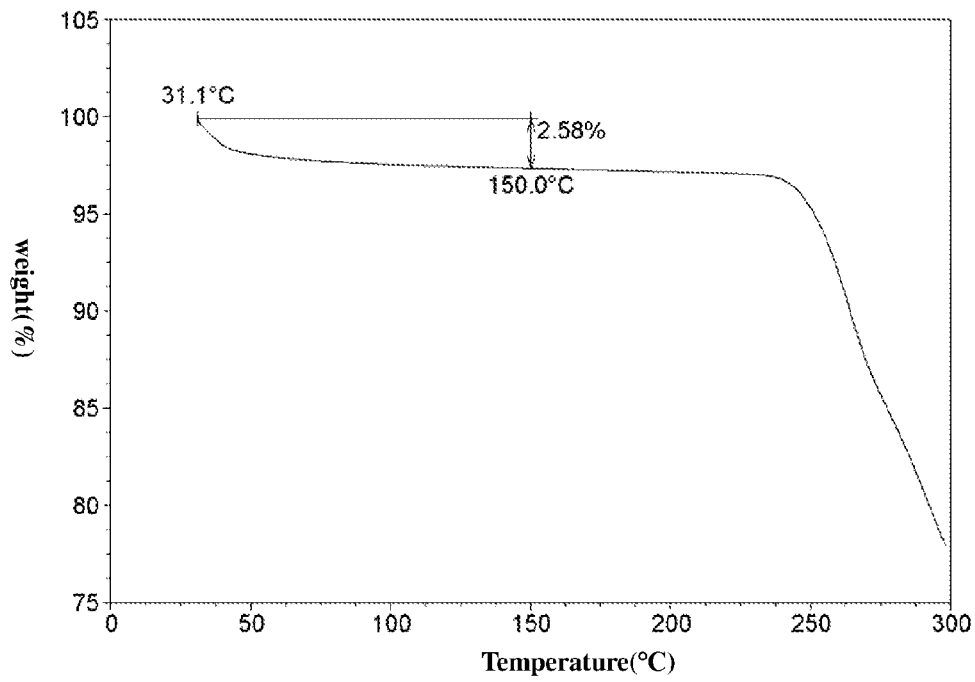
FIG. 65 is a TGA plot of Compound 1 mesylate crystalline form XXII.
Figure 66:
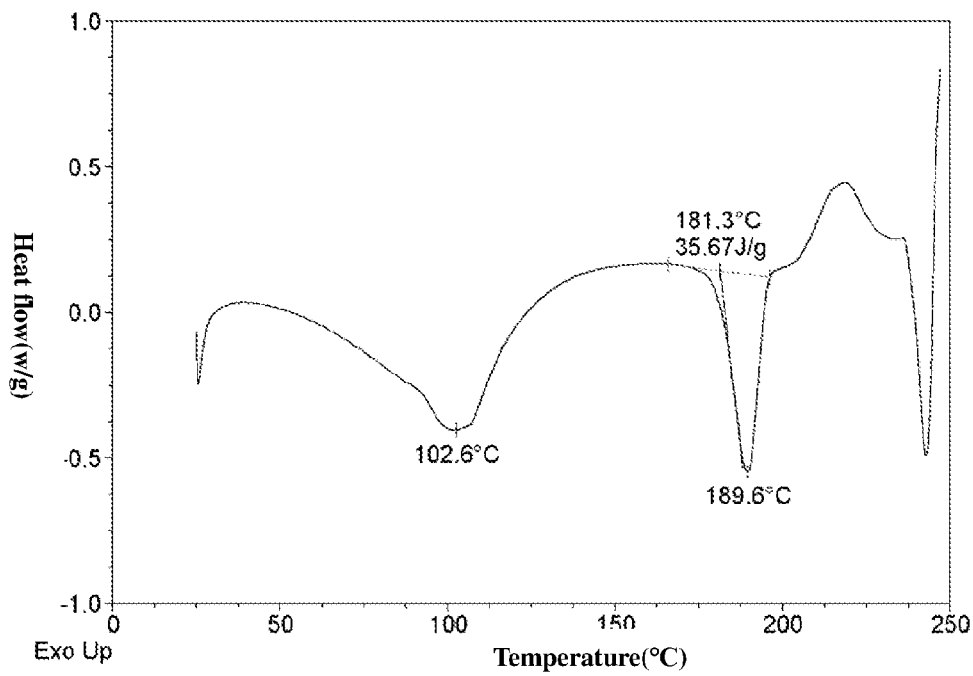
FIG. 66 is a DSC curve of Compound 1 mesylate crystalline form XXII.
Figure 67:
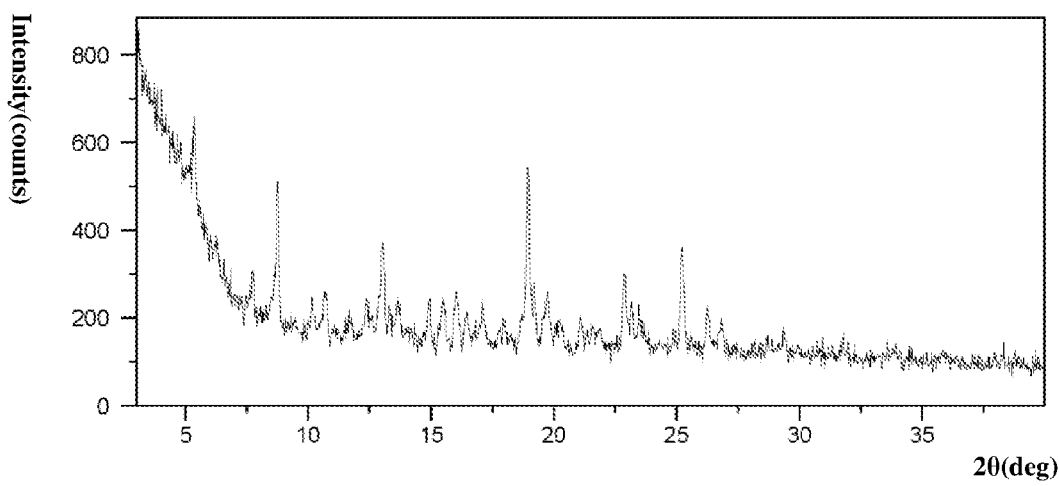
FIG. 67 is an XRPD pattern of Compound 1 maleate crystalline form XXIII.
Figure 68:
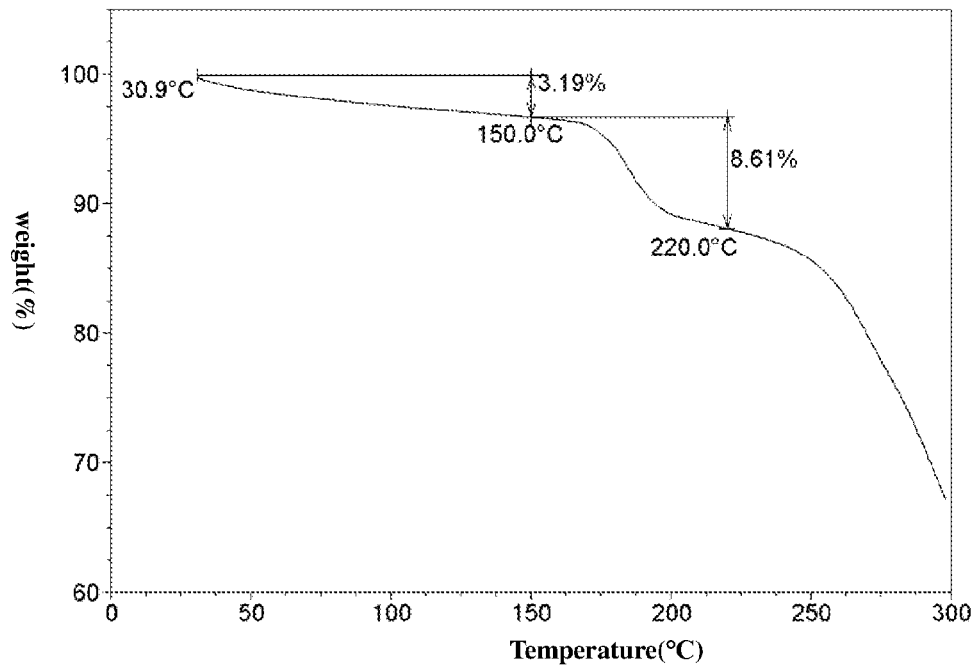
FIG. 68 is a TGA plot of Compound 1 maleate crystalline form XXIII.
Figure 69:
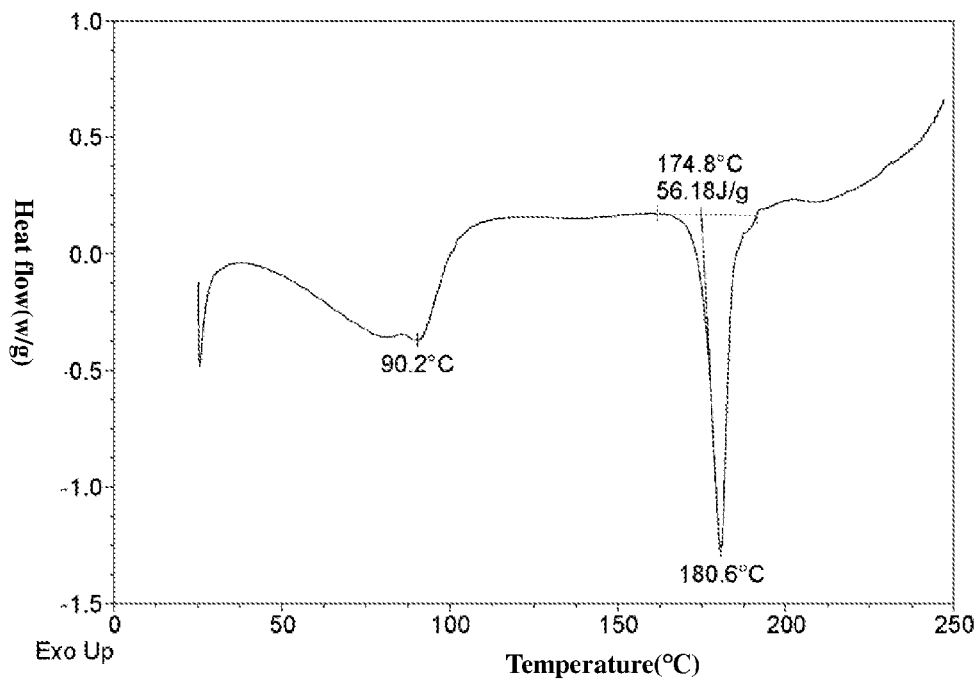
FIG. 69 is a DSC curve of Compound 1 maleate crystalline form XXIII.
Figure 70:
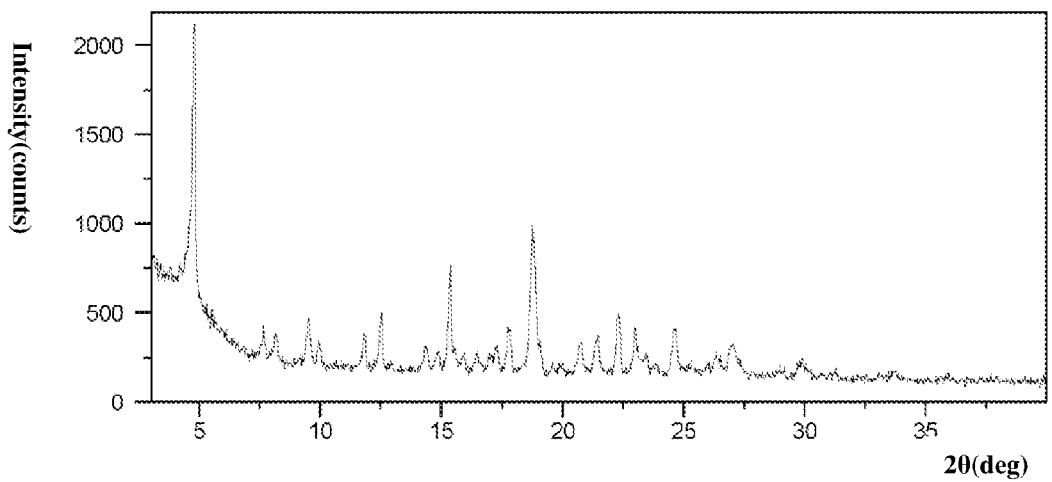
FIG. 70 is an XRPD pattern of Compound 1 maleate crystalline form XXIV.
Figure 71:
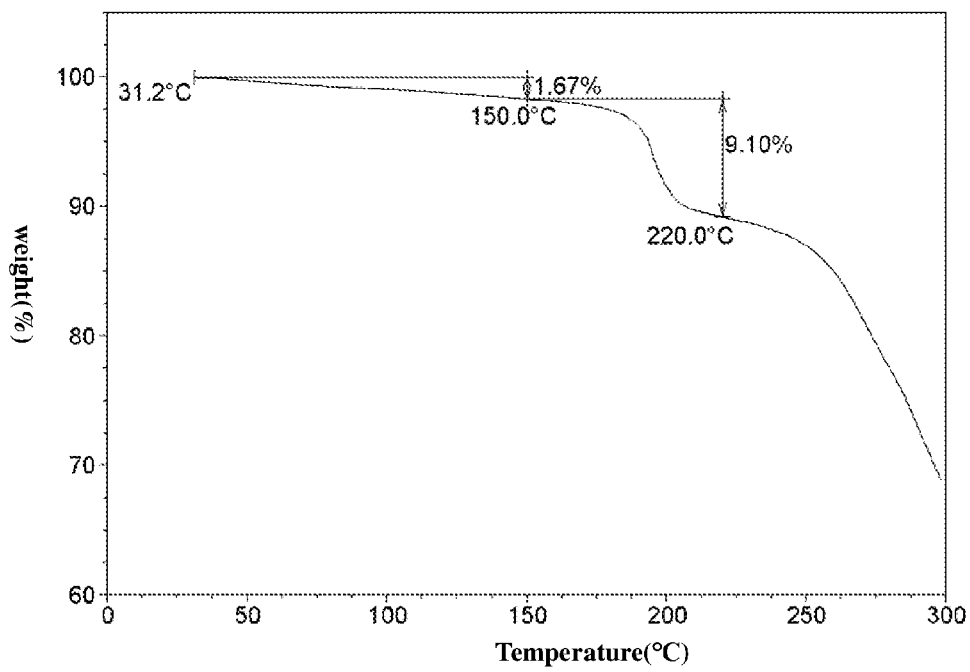
FIG. 71 is a TGA plot of Compound 1 maleate crystalline form XXIV.
Figure 72:
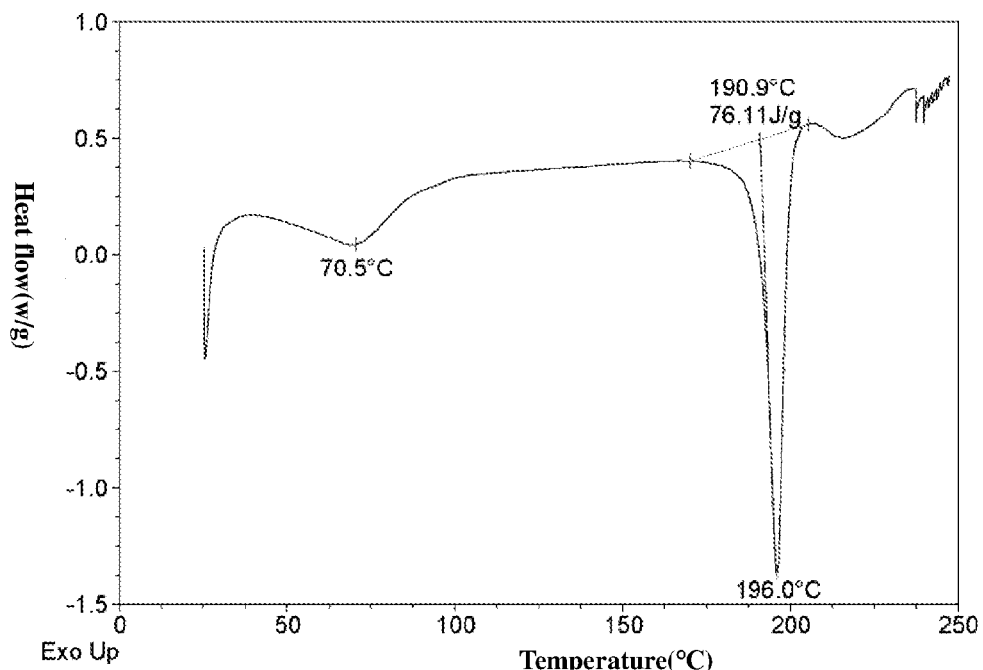
FIG. 72 is a DSC curve of Compound 1 maleate crystalline form XXIV.
Figure 73:
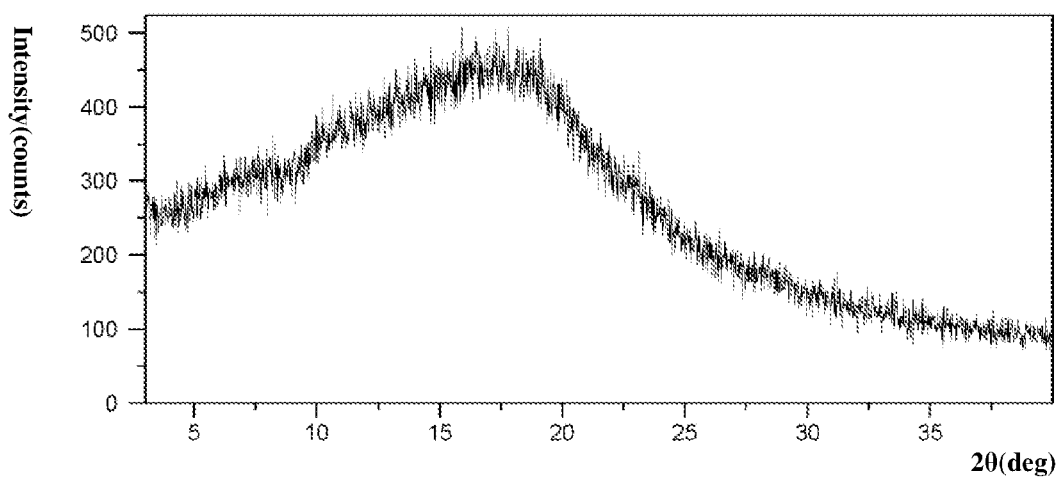
FIG. 73 is an XRPD pattern of Compound 1 amorphous form XXV.
Figure 74:
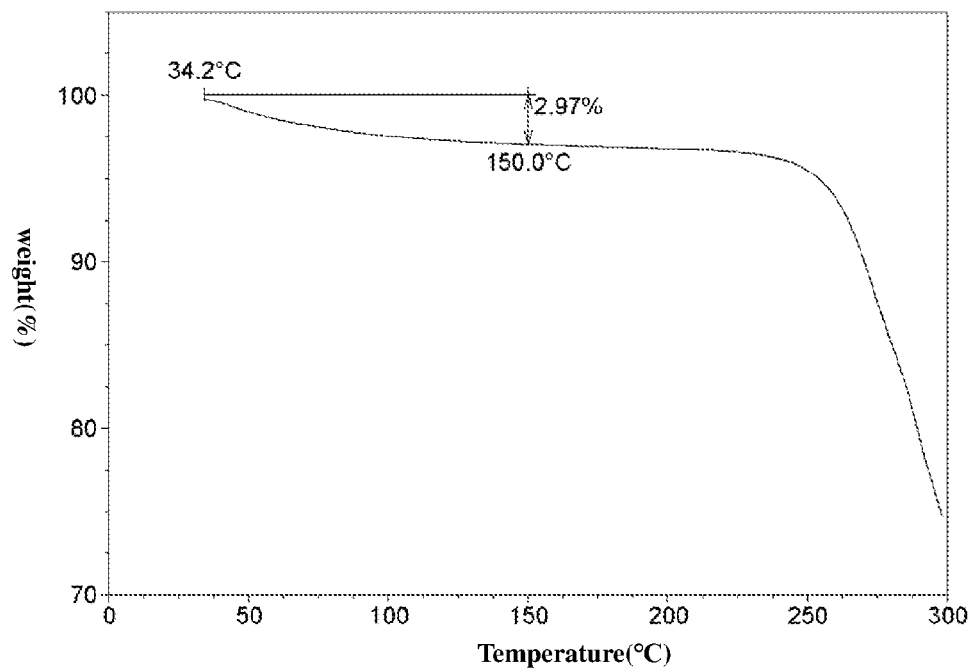
FIG. 74 is a TGA plot of Compound 1 amorphous form XXV.
Figure 75:
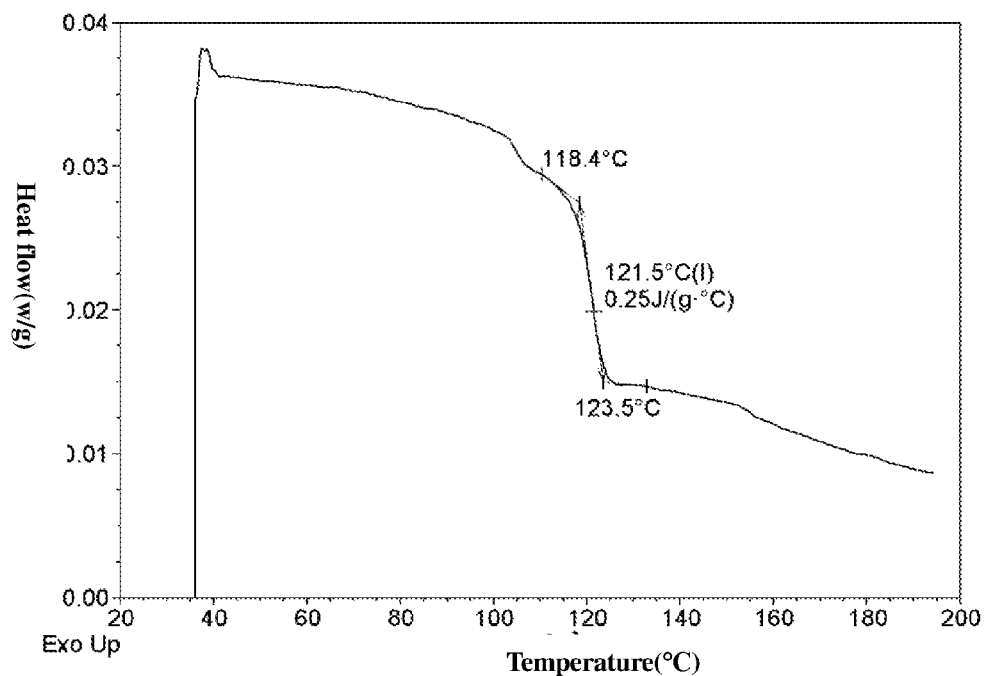
FIG. 75 is a DSC curve of Compound 1 amorphous form XXV.
Figure 76:
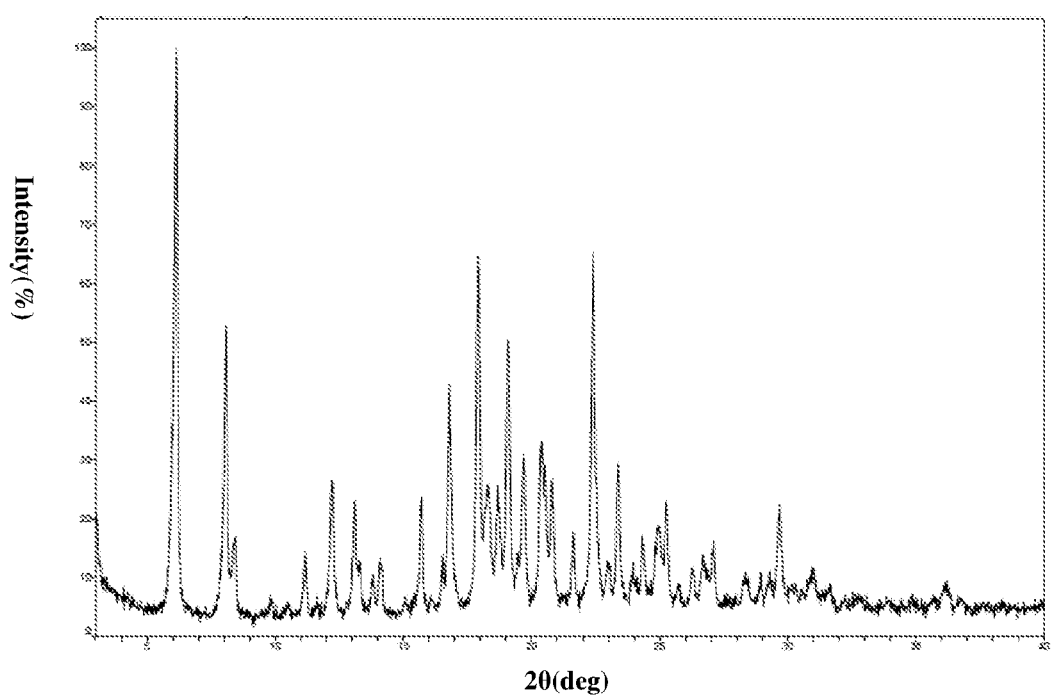
FIG. 76 is an XRPD pattern of Compound 1 acetone solvate crystalline form XXVI.
Figure 77:
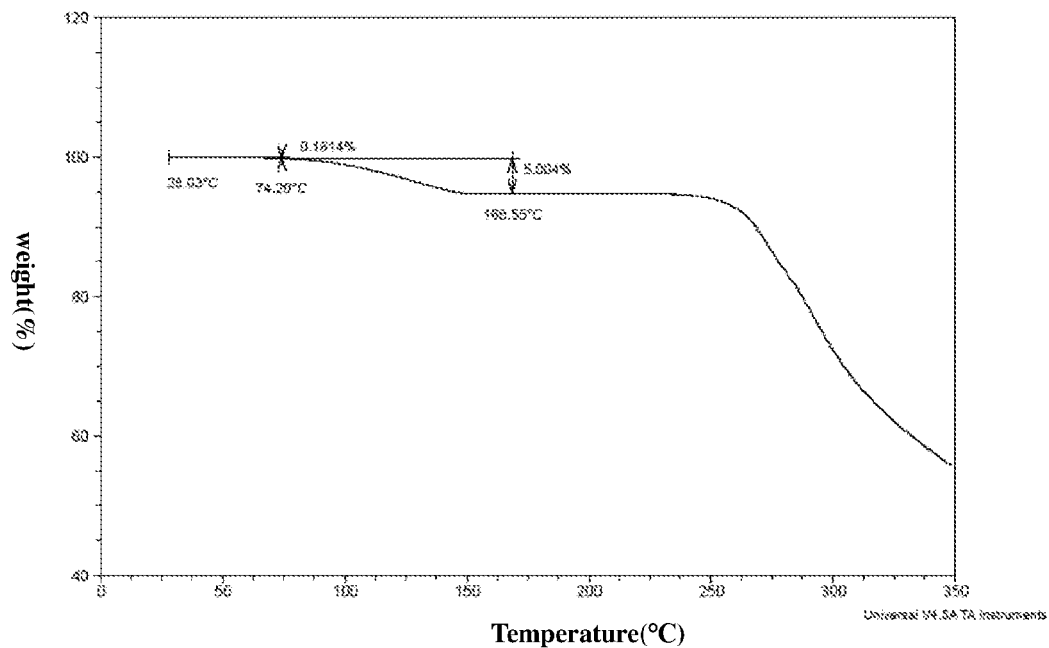
FIG. 77 is a TGA plot of Compound 1 acetone solvate crystalline form XXVI.
Figure 78:
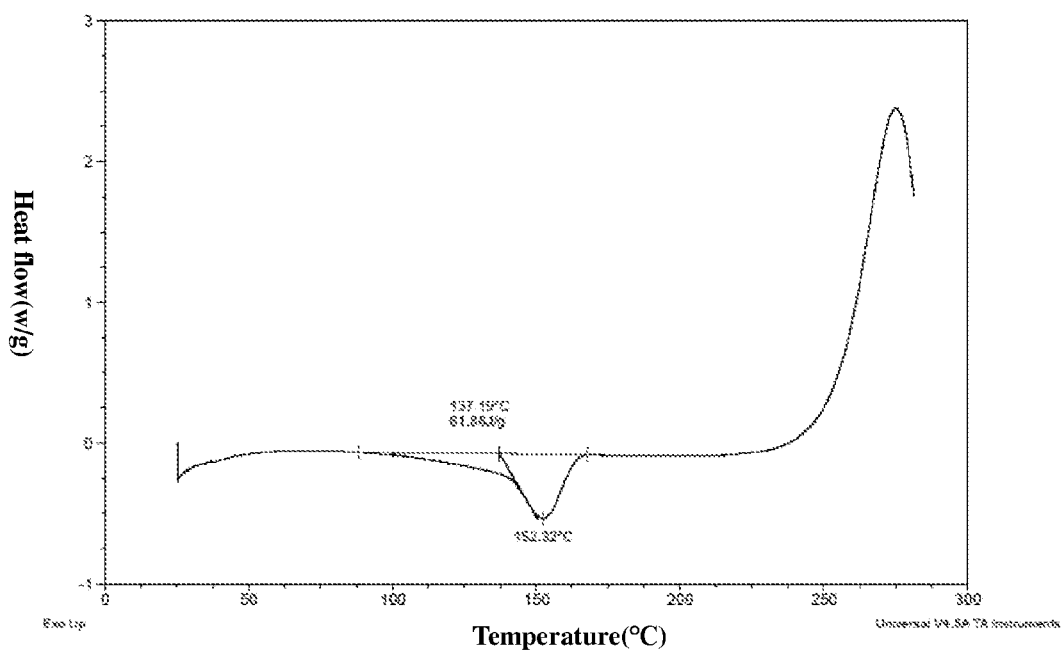
FIG. 78 is a DSC curve of Compound 1 acetone solvate crystalline form XXVI.
Figure 79:
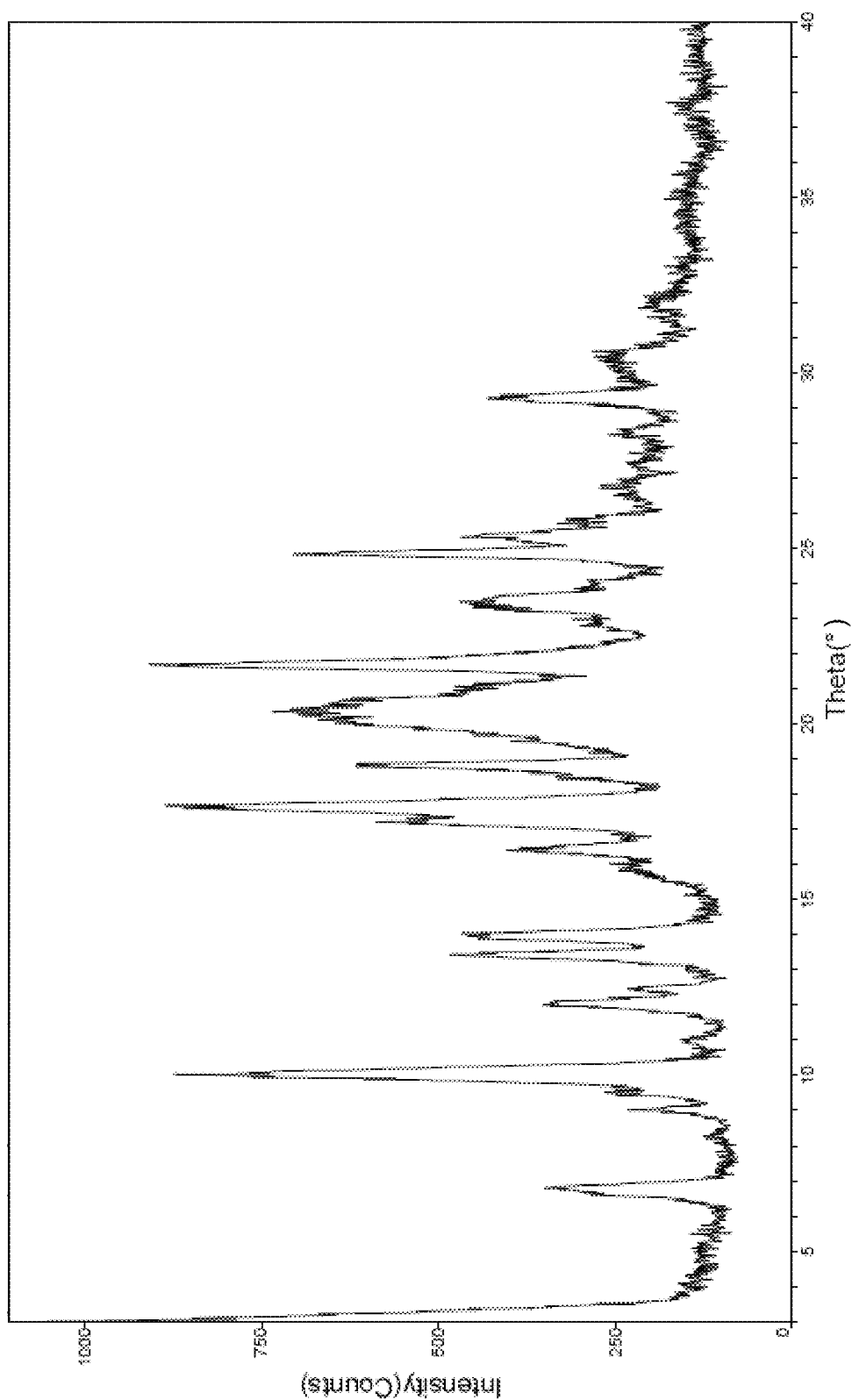
FIG. 79 is an XRPD pattern of Compound 1 benzene sulfonate crystalline Form XXVII.
Figure 80:
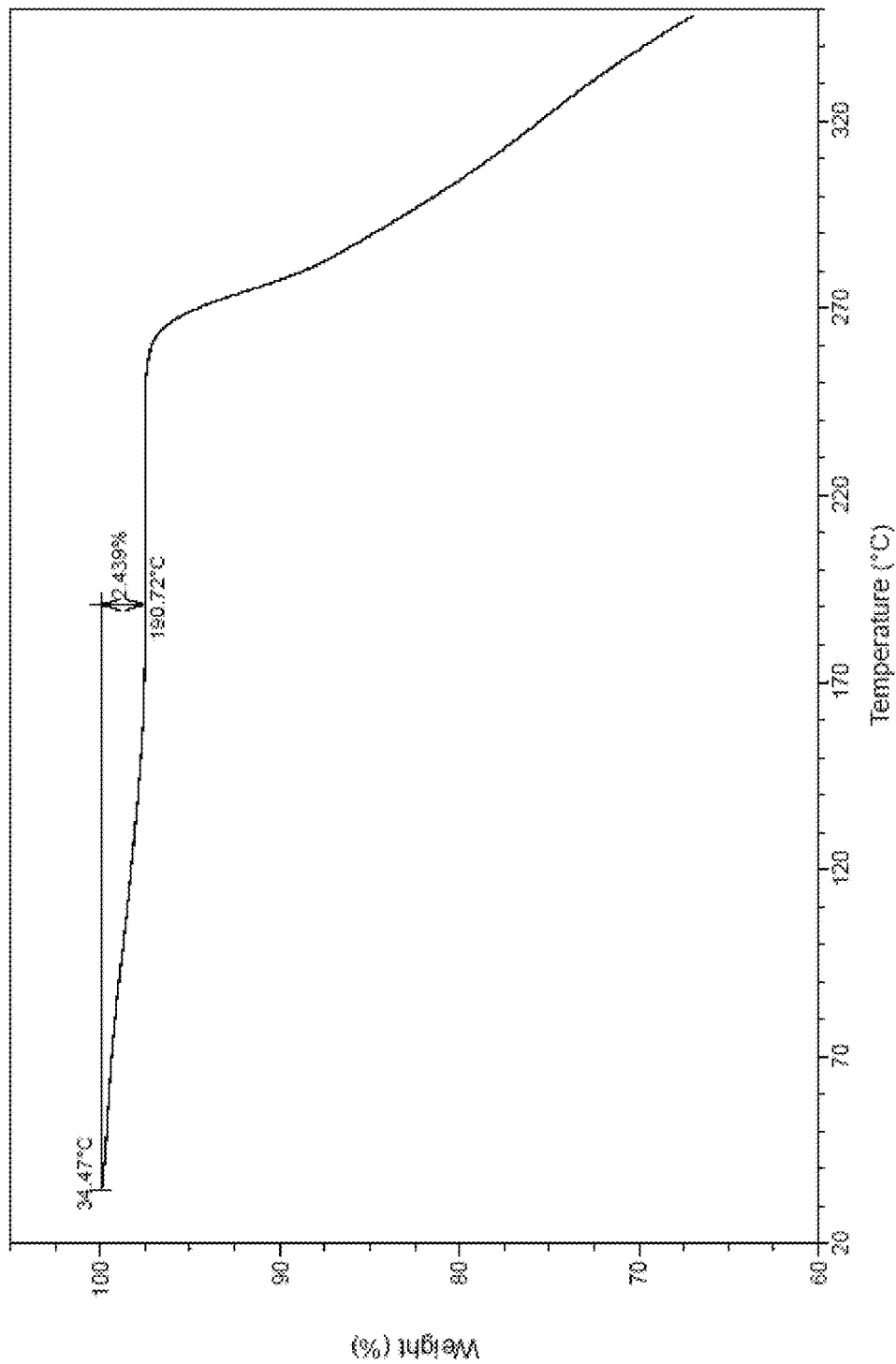
FIG. 80 is a TGA plot of Compound 1 benzene sulfonate crystalline Form XXVII.
Figure 81:
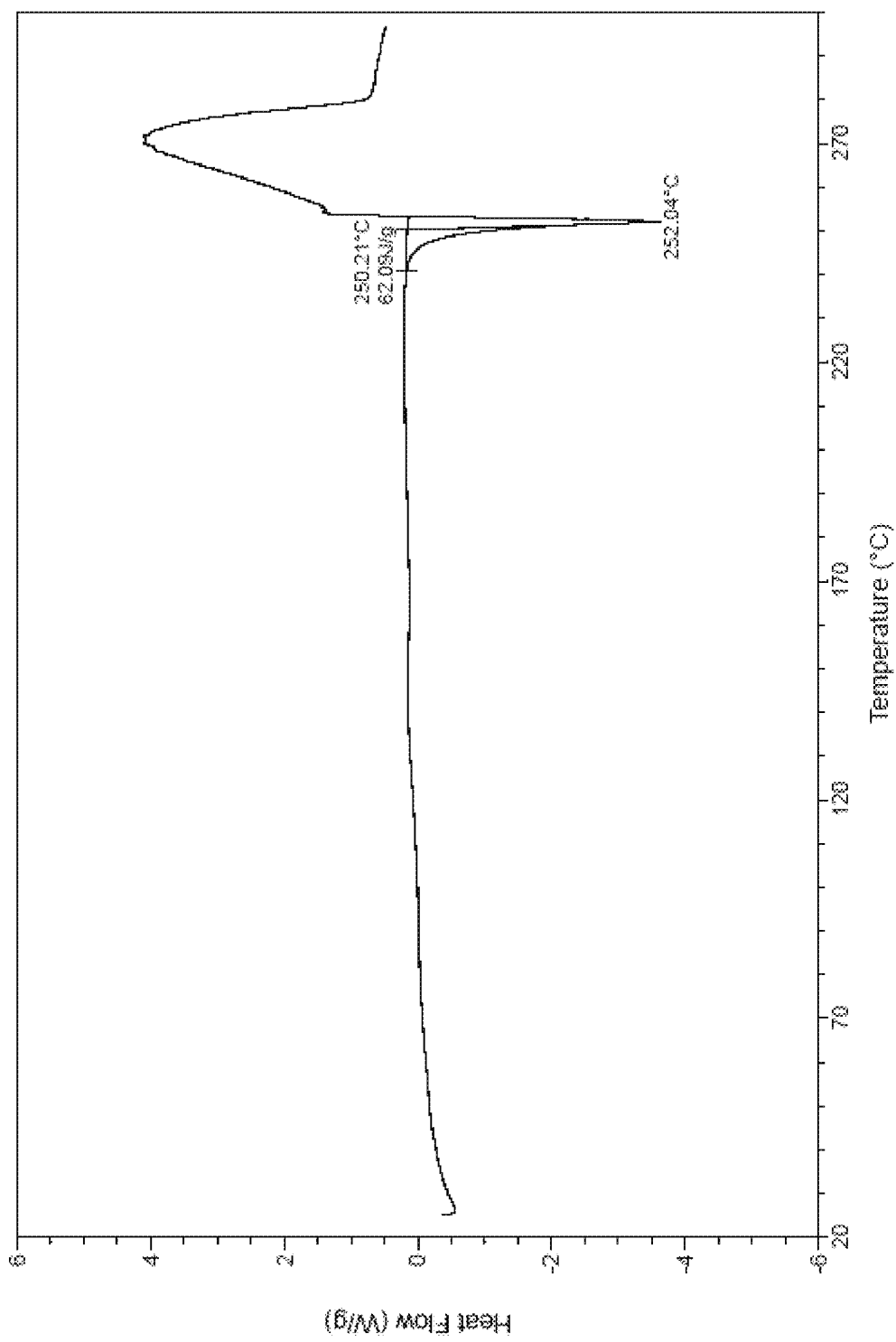
FIG. 81 is a DSC curve of Compound 1 benzene sulfonate crystalline Form XXVII.
Figure 82:
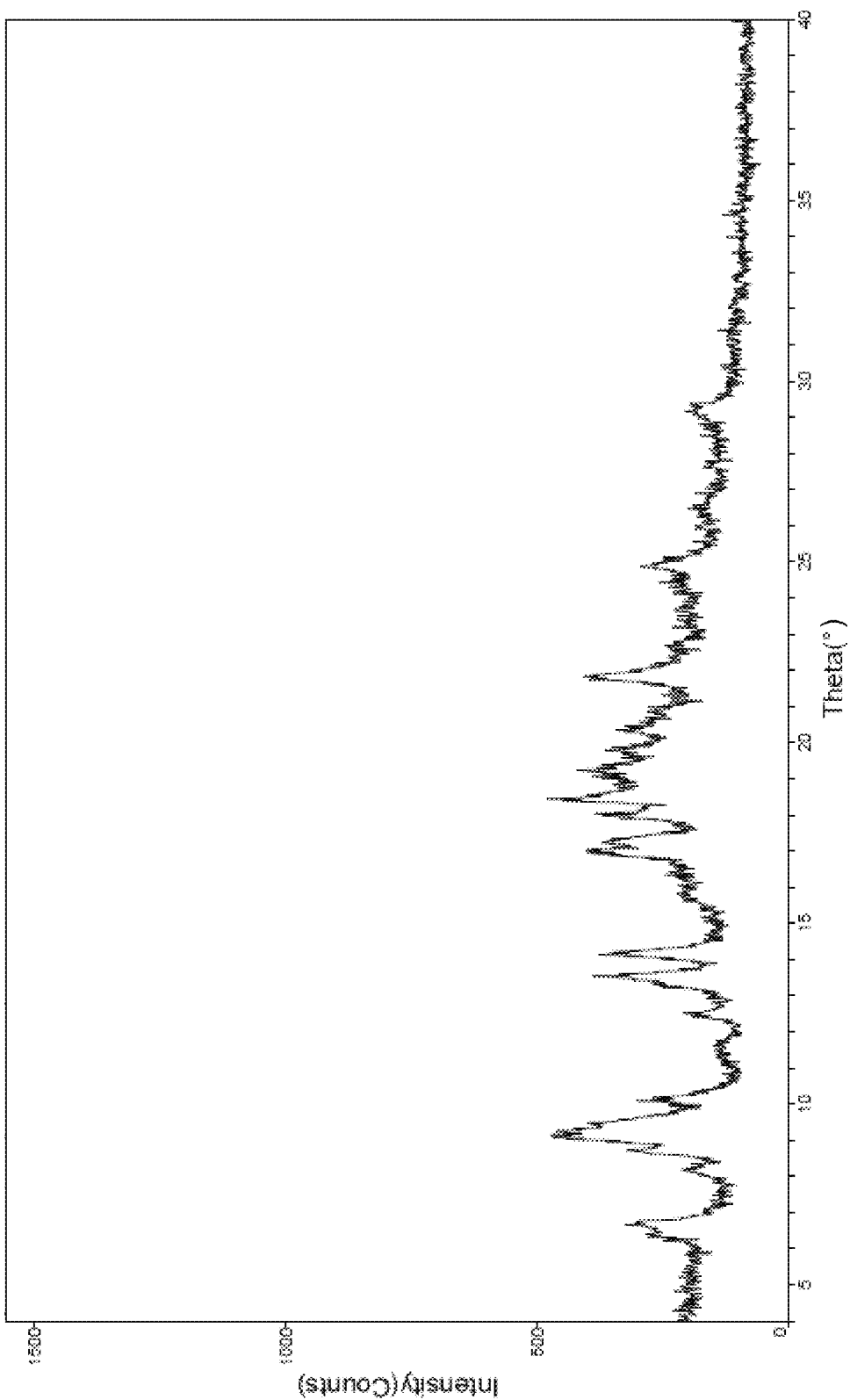
FIG. 82 is an XRPD pattern of Compound 1 p-toluenesulfonate crystalline Form XXVIII.
Figure 83:
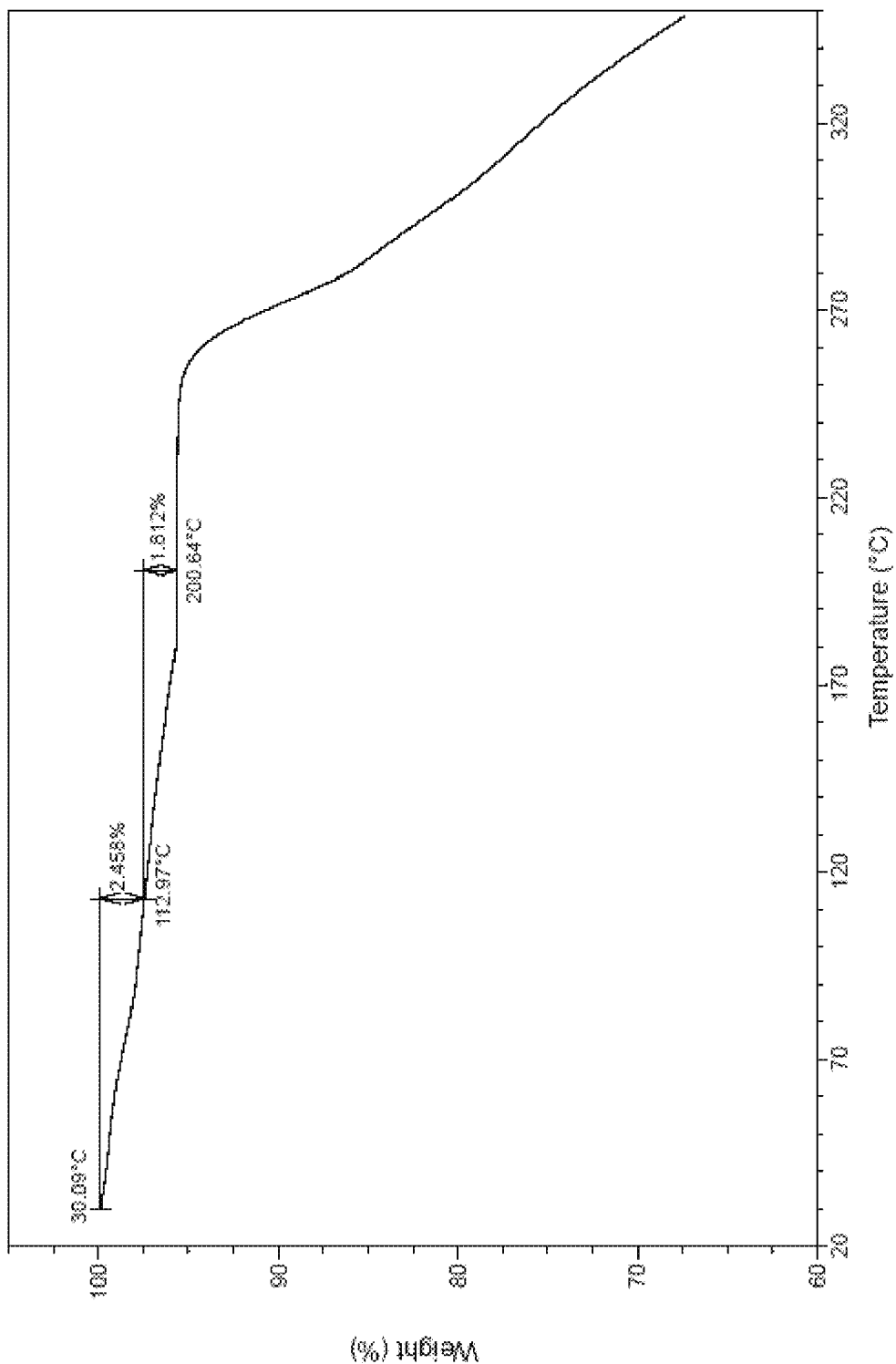
FIG. 83 is a TGA plot of Compound 1 p-toluenesulfonate crystalline Form XXVIII.
Figure 84:
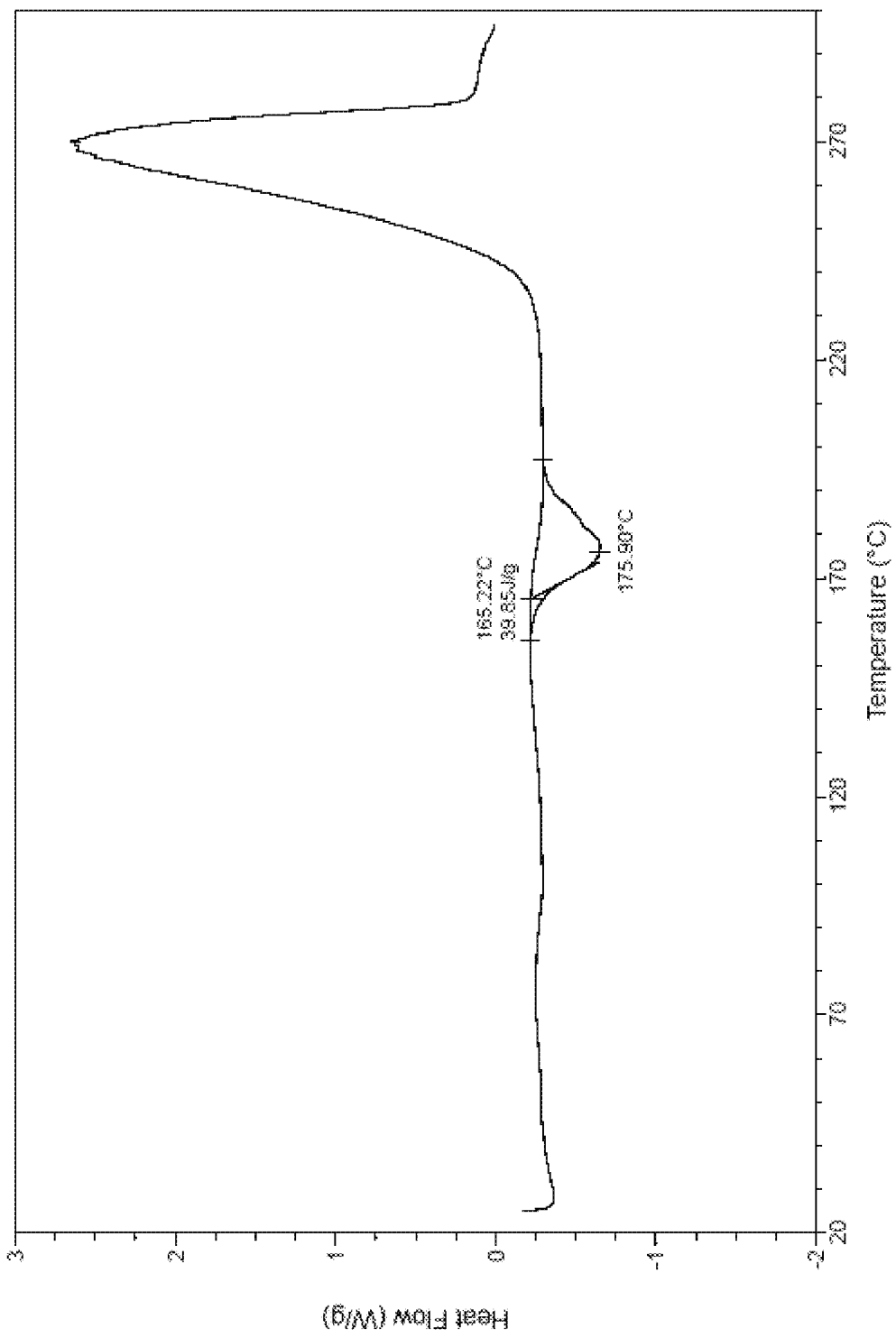
FIG. 84 is a DSC curve of Compound 1 p-toluenesulfonate crystalline Form XXVIII.
Figure 85:
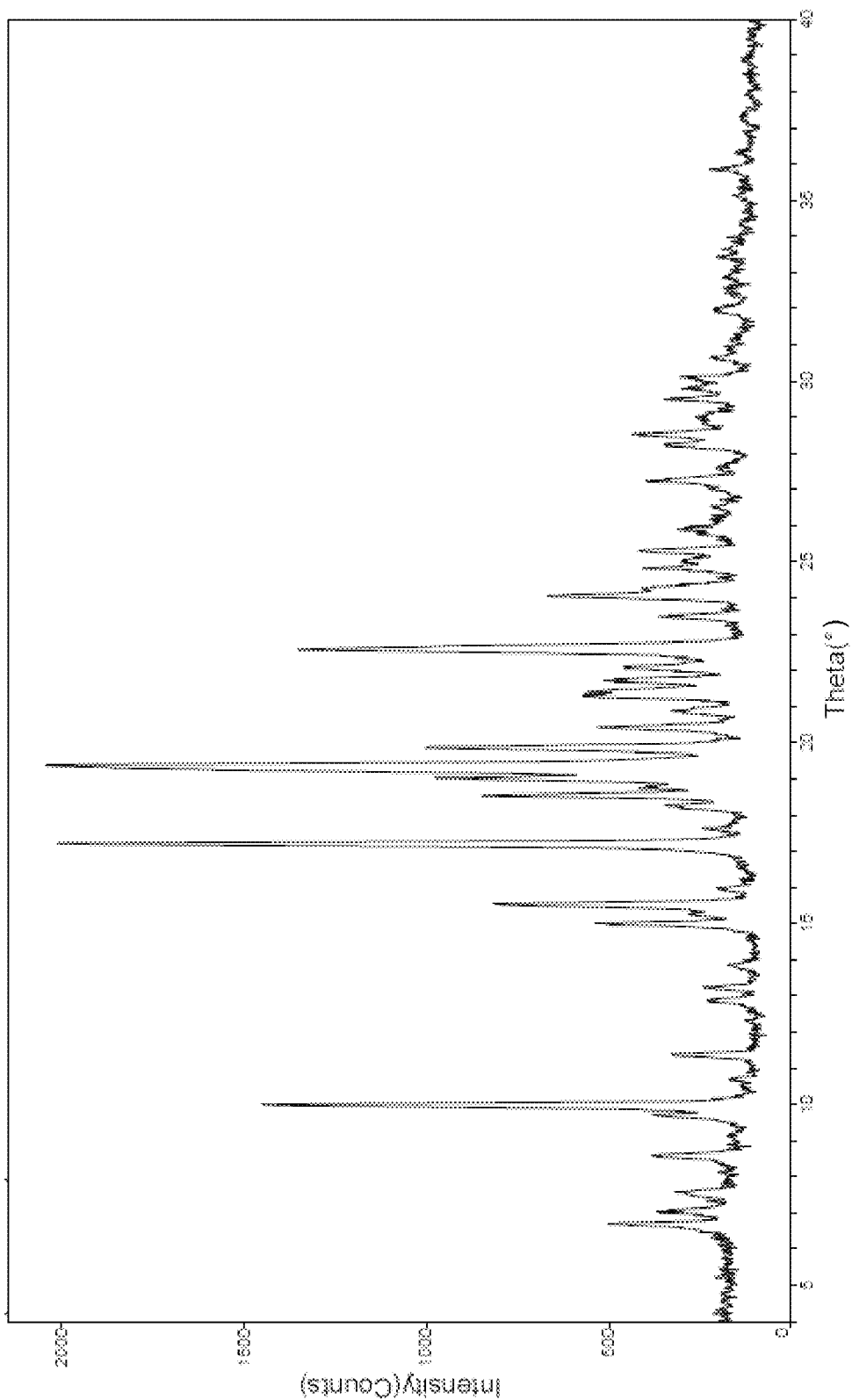
FIG. 85 is an XRPD pattern of Compound 1 p-toluenesulfonate crystalline Form XXIX.
Figure 86:
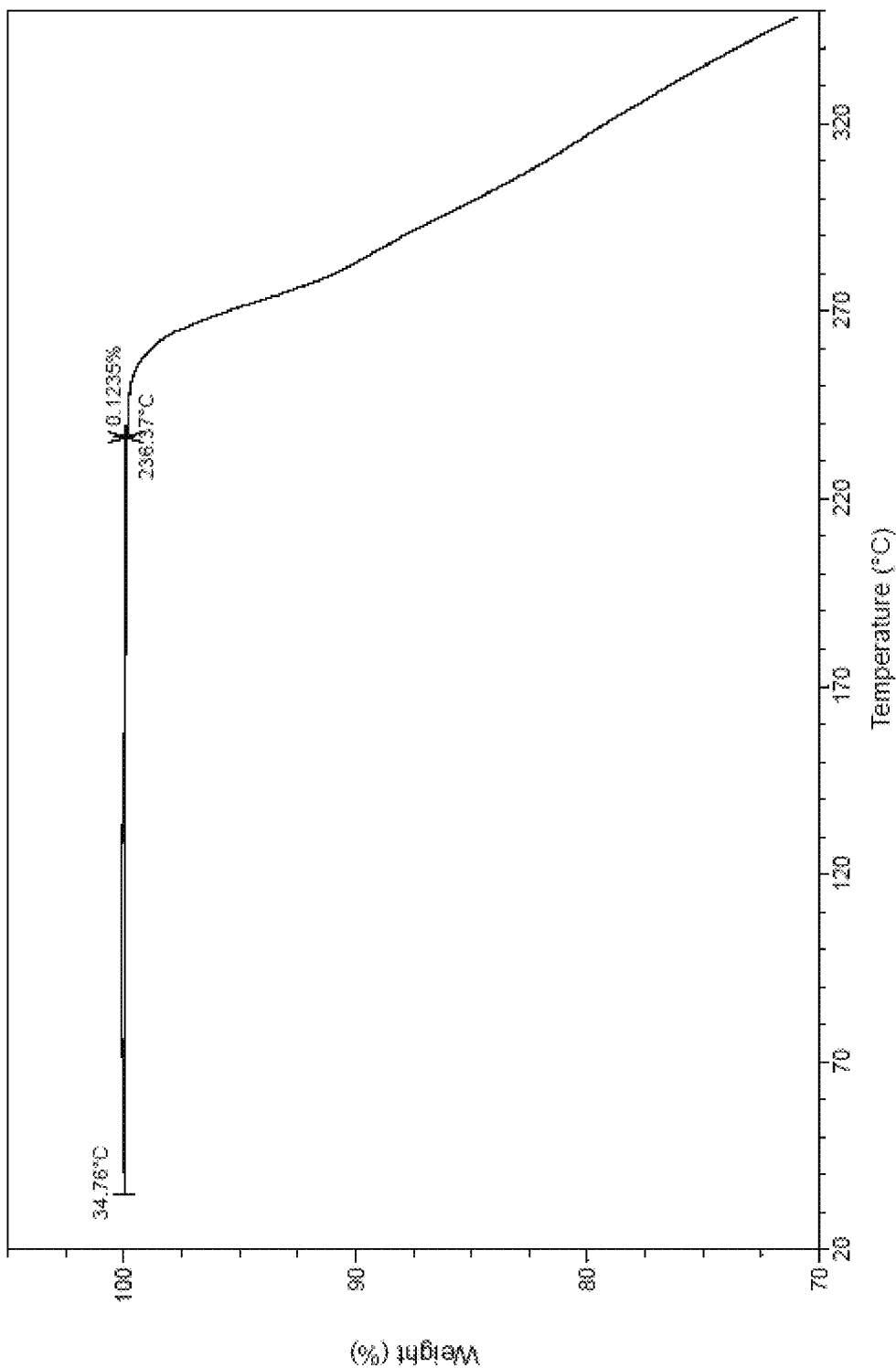
FIG. 86 is a TGA plot of Compound 1 p-toluenesulfonate crystalline Form XXIX.
Figure 87:
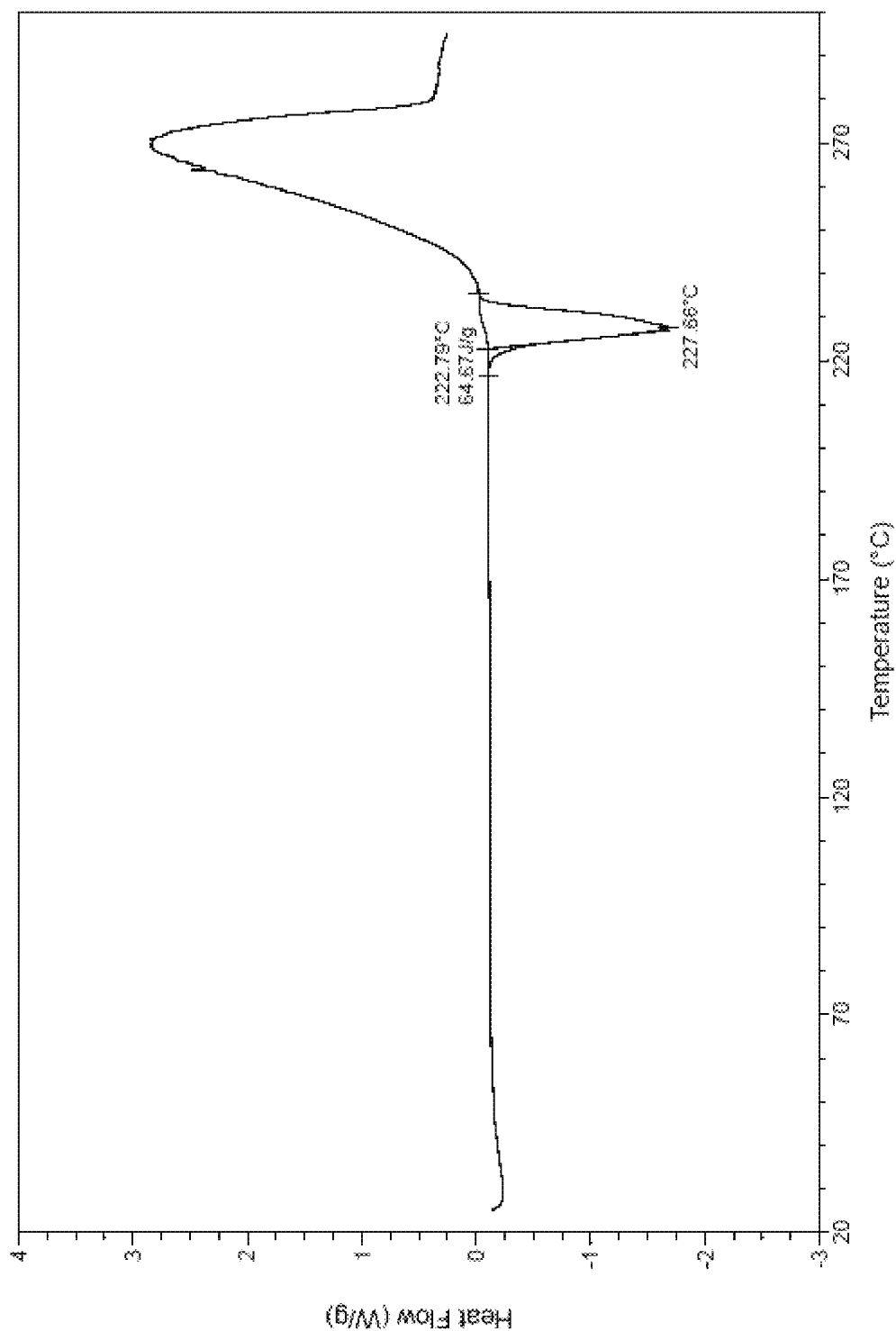
FIG. 87 is a DSC curve of Compound 1 p-toluenesulfonate crystalline Form XXIX.
Figure 88:
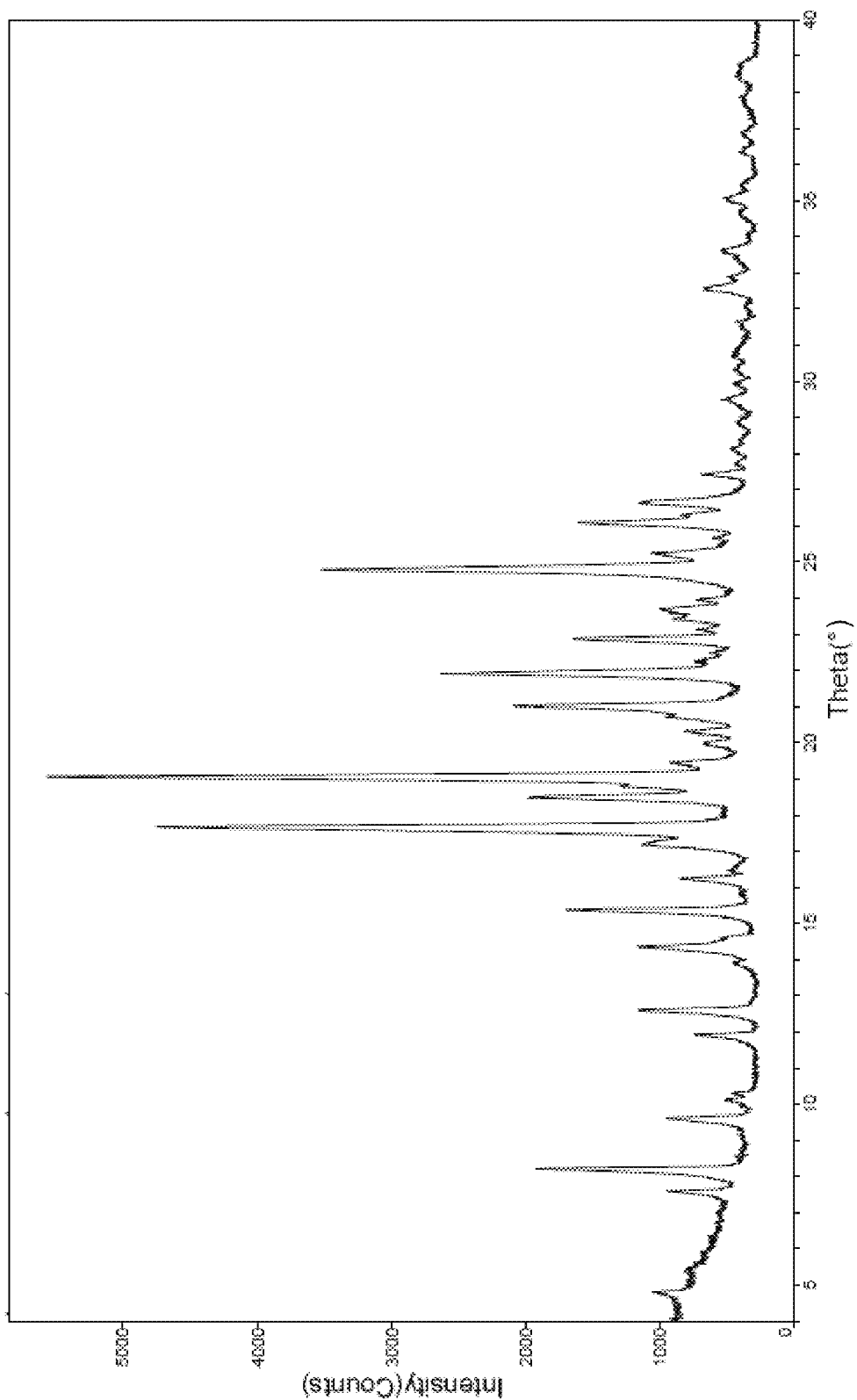
FIG. 88 is an XRPD pattern of Compound 1 sulphate crystalline Form XXX.
Figure 89:
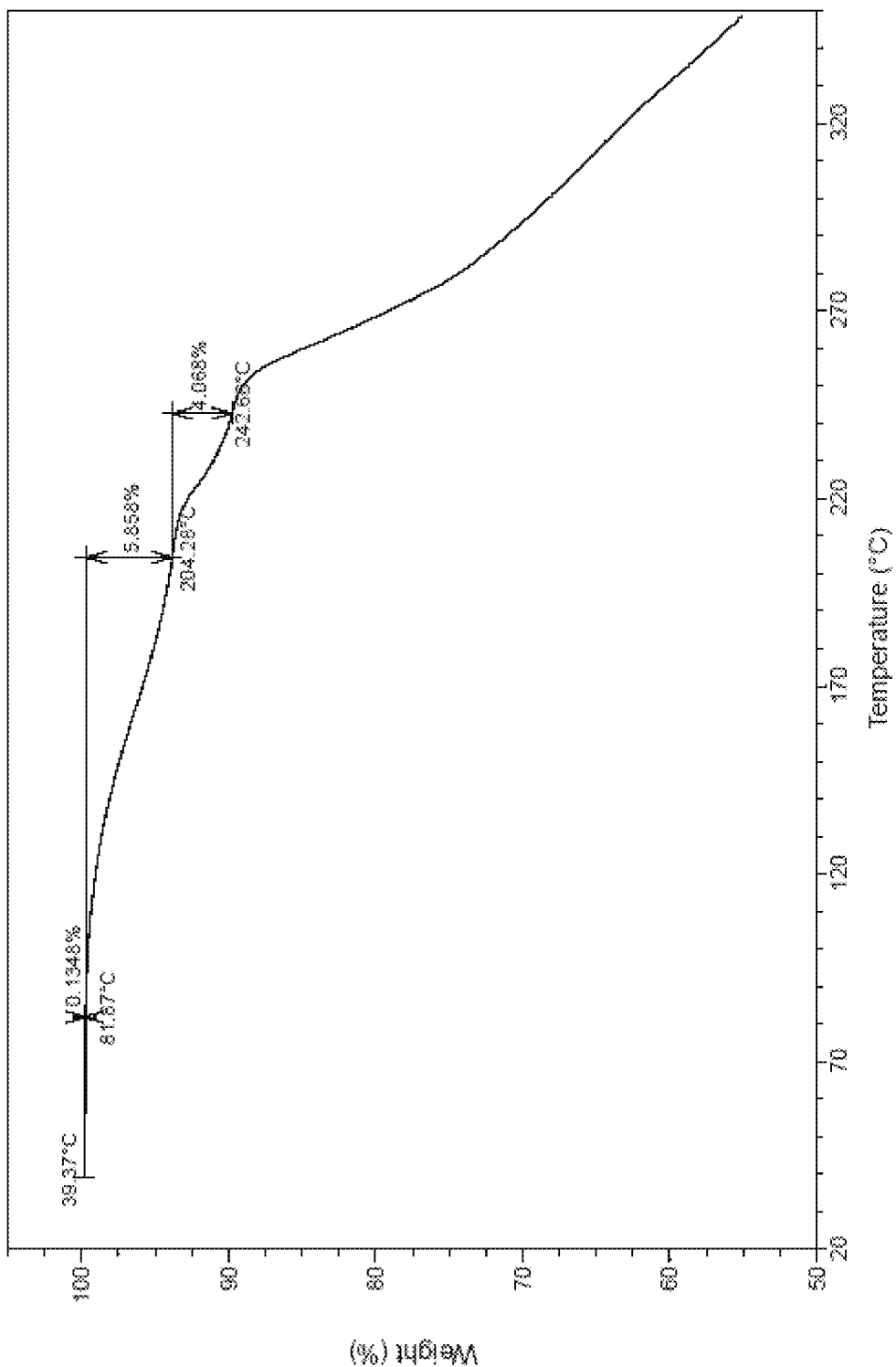
FIG. 89 is a TGA plot of Compound 1 sulphate crystalline Form XXX.
Figure 90:
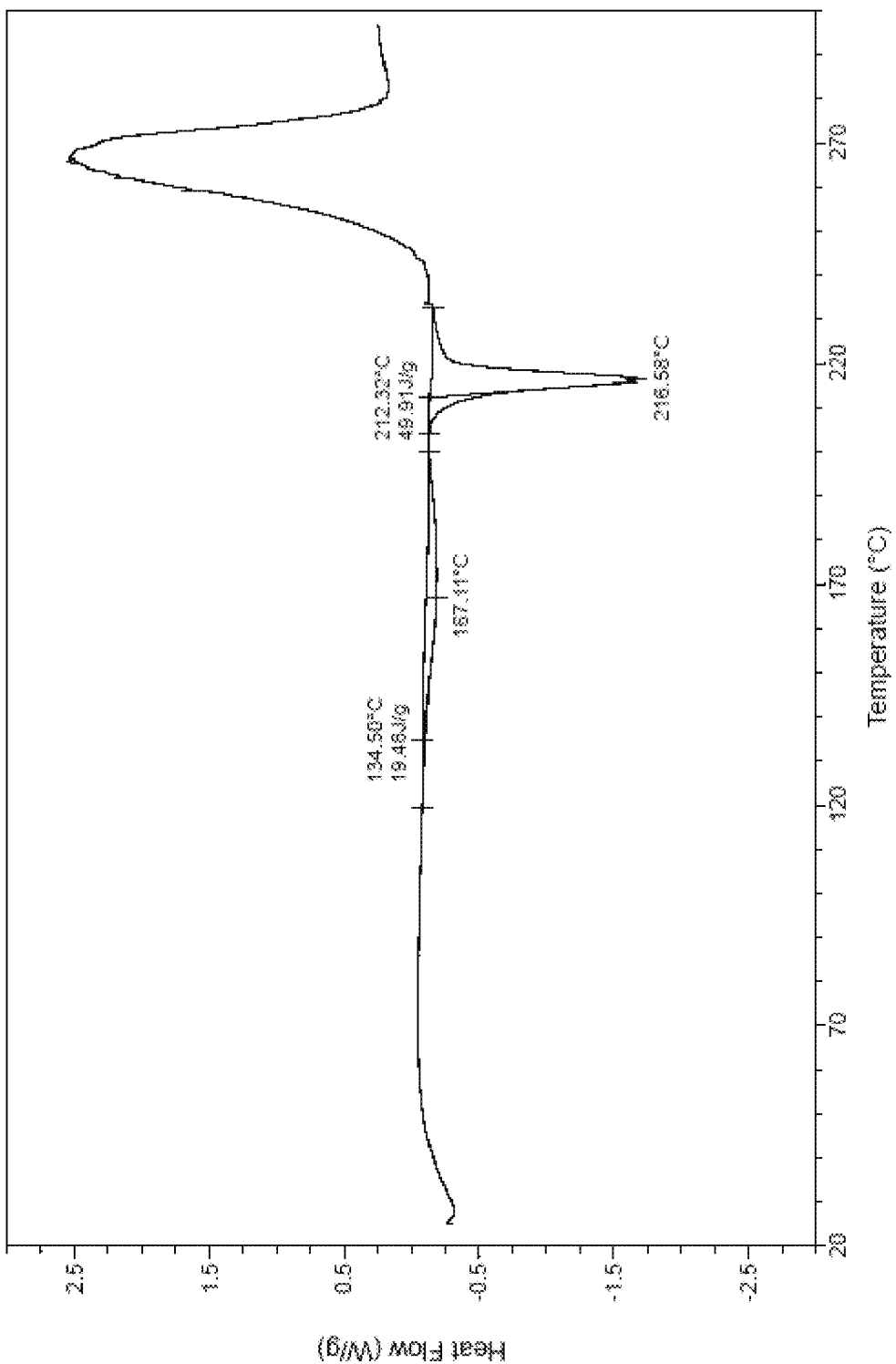
FIG. 90 is a DSC curve of Compound 1 sulphate crystalline Form XXX.
Figure 91:
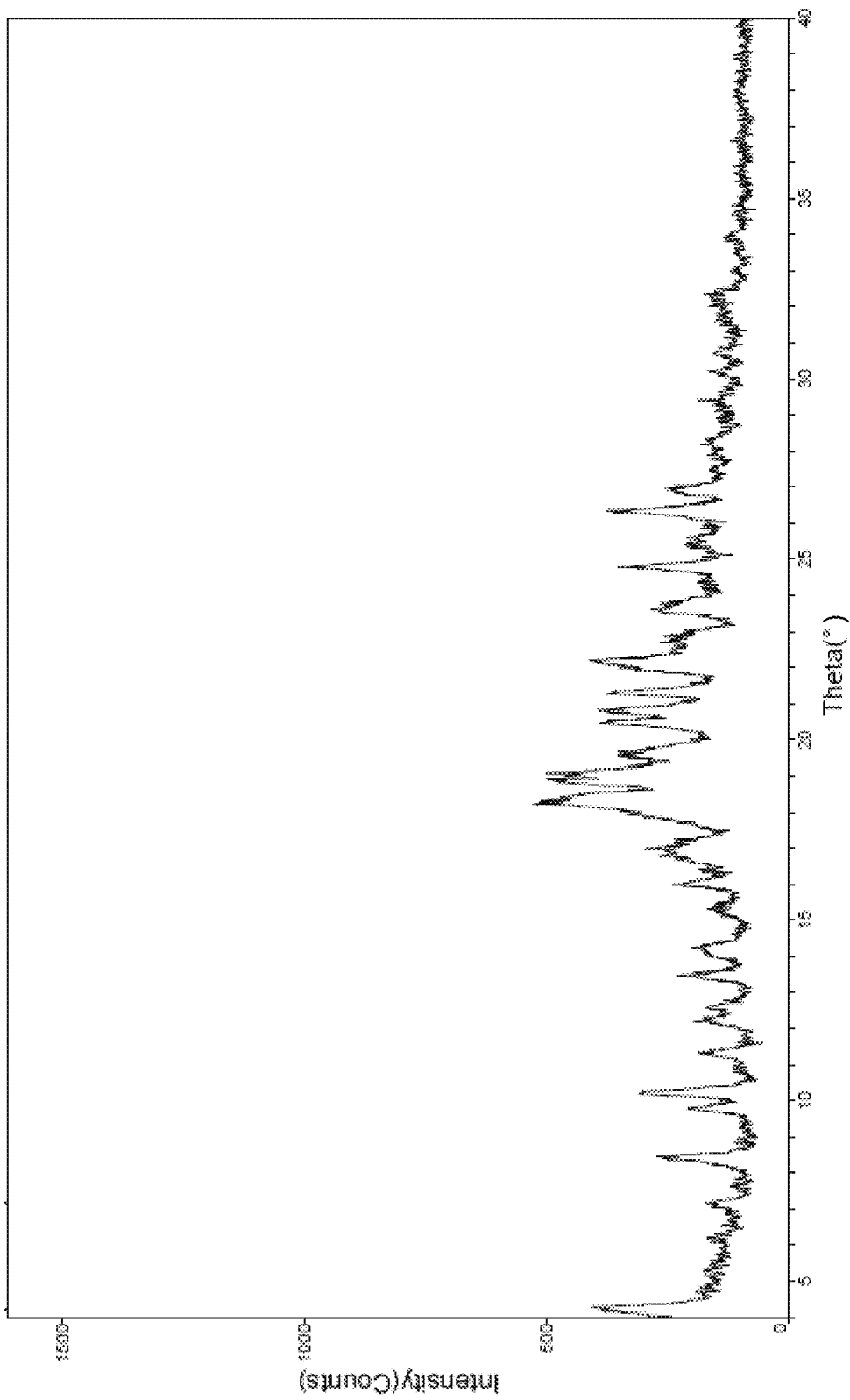
FIG. 91 is an XRPD pattern of Compound 1 sulphate crystalline Form XXXI.
Figure 92:
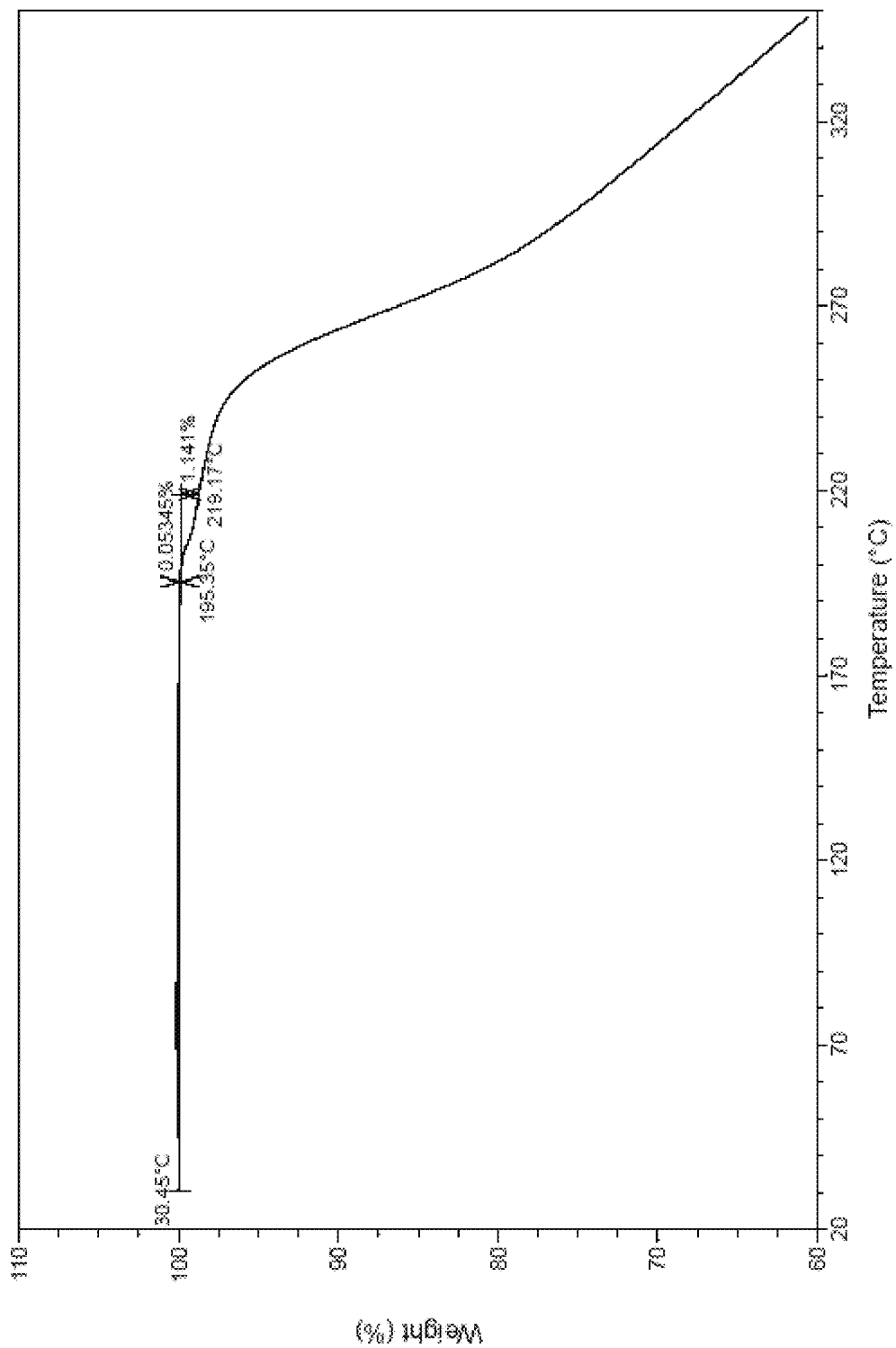
FIG. 92 is a TGA plot of Compound 1 sulphate crystalline Form XXXI.
Figure 93:
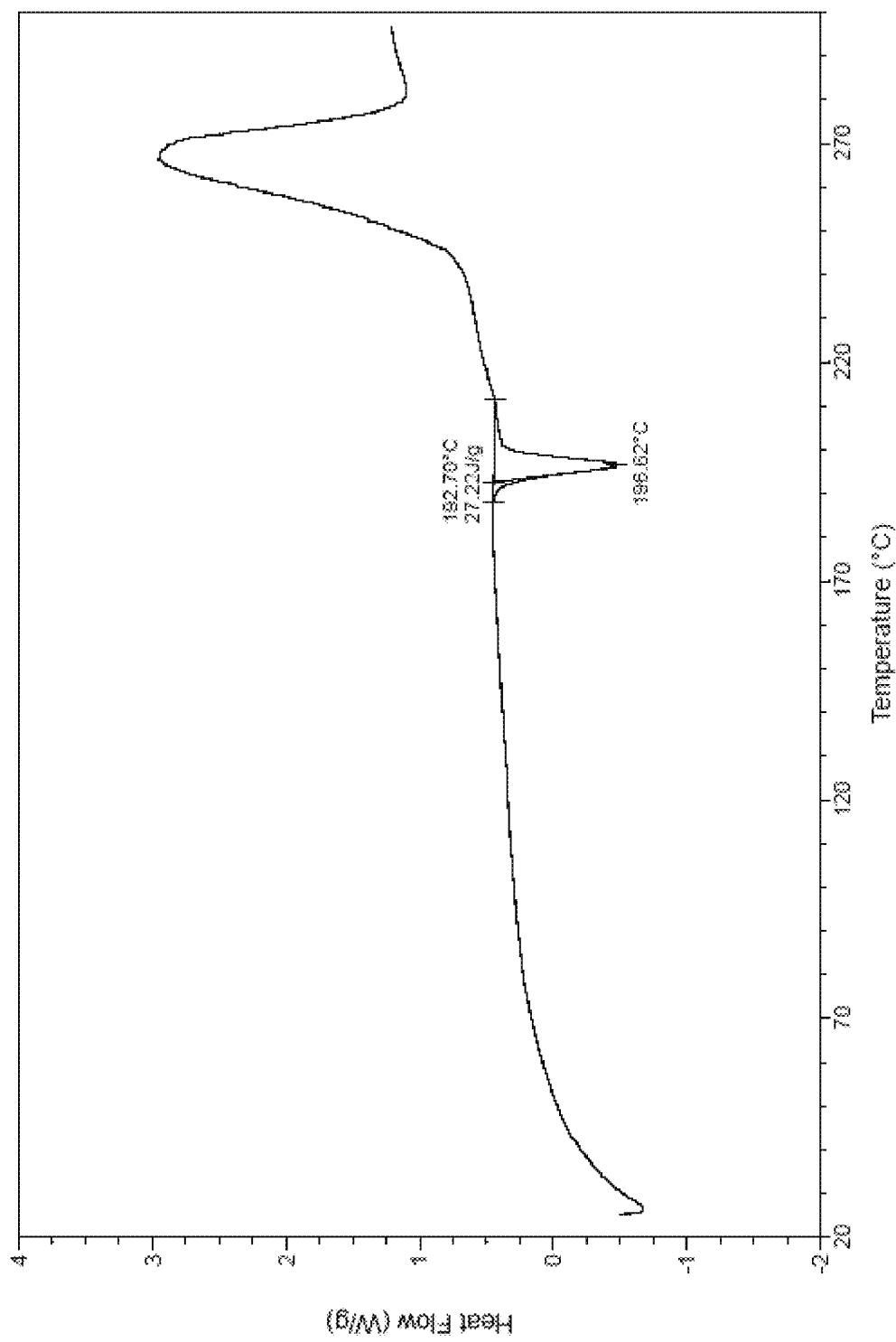
FIG. 93 is a DSC curve of Compound 1 sulphate crystalline Form XXXI.
Figure 94:
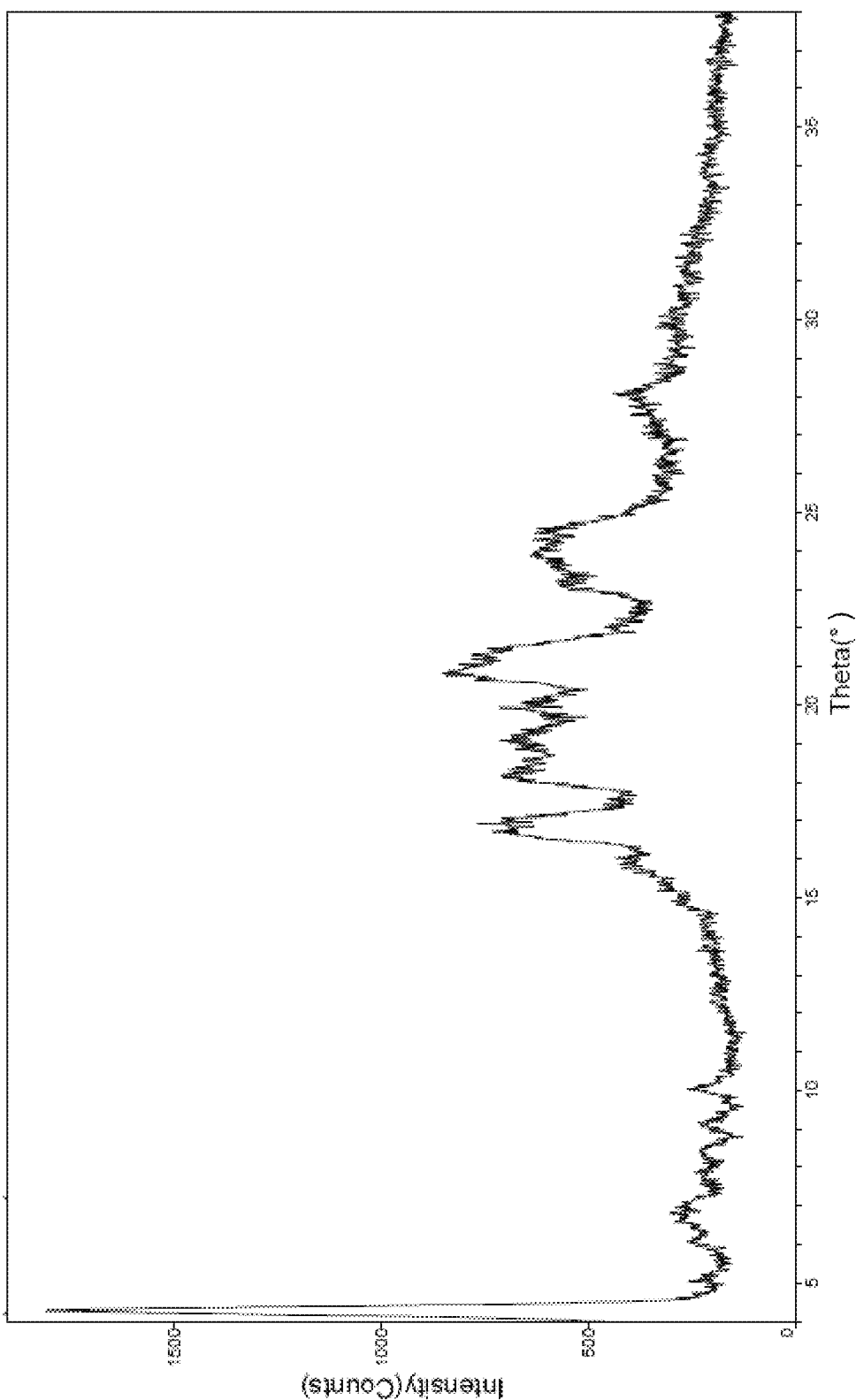
FIG. 94 is an XRPD pattern of Compound 1 sulphate crystalline Form XXXII.
Figure 95:
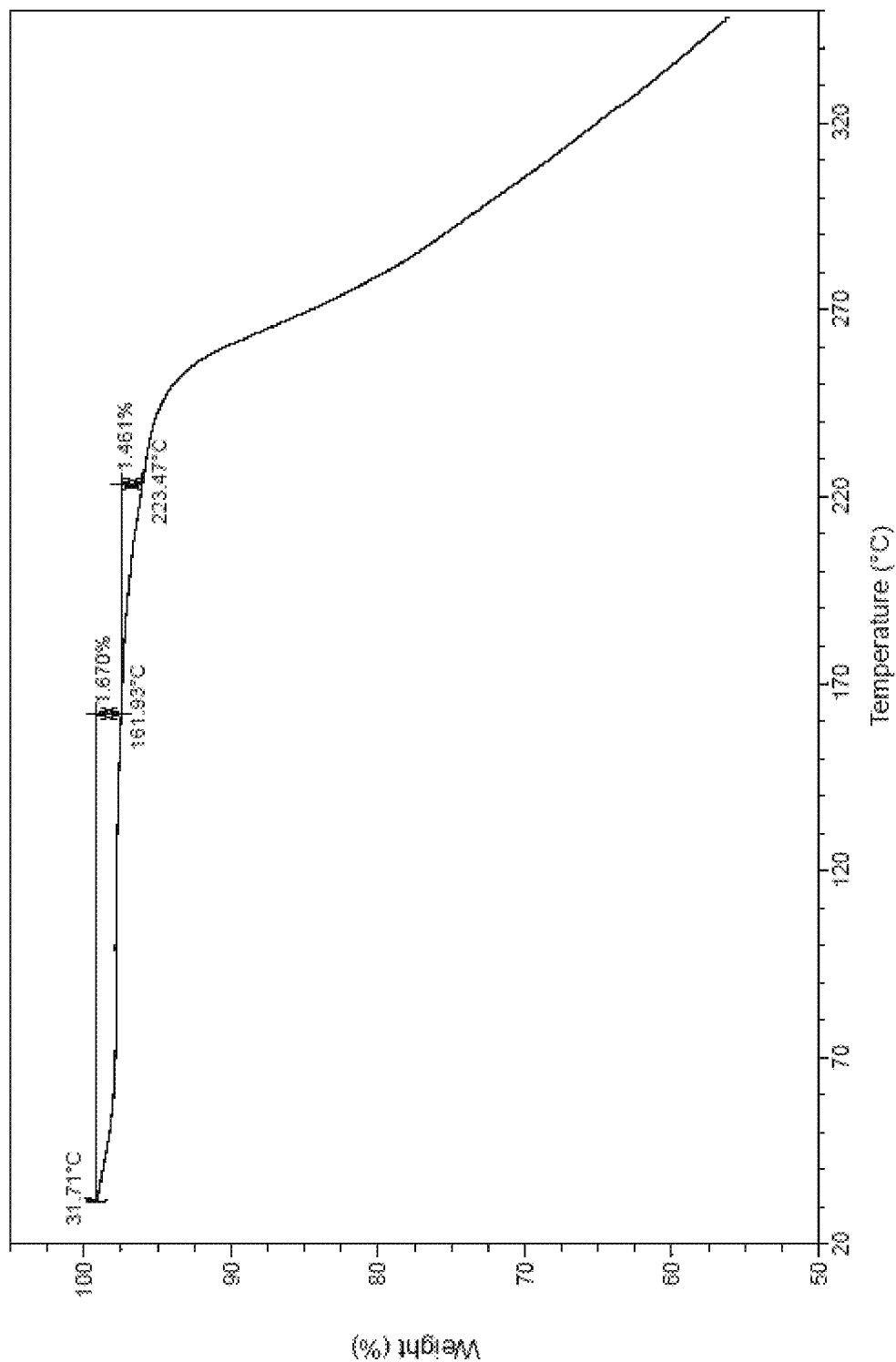
FIG. 95 is a TGA plot of Compound 1 sulphate crystalline Form XXXII.
Figure 96:
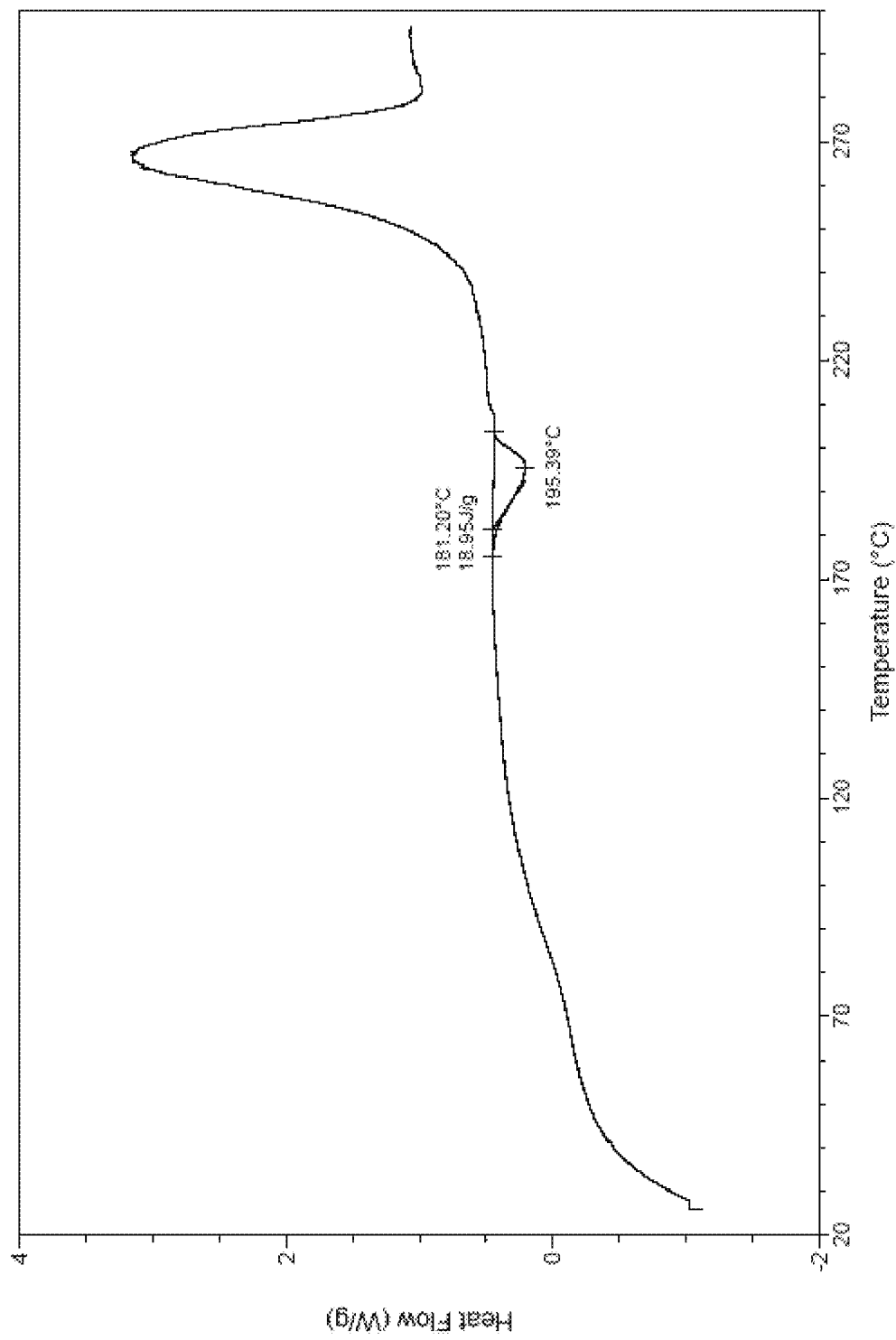
FIG. 96 is a DSC curve of Compound 1 sulphate crystalline Form XXXII.
Figure 97:
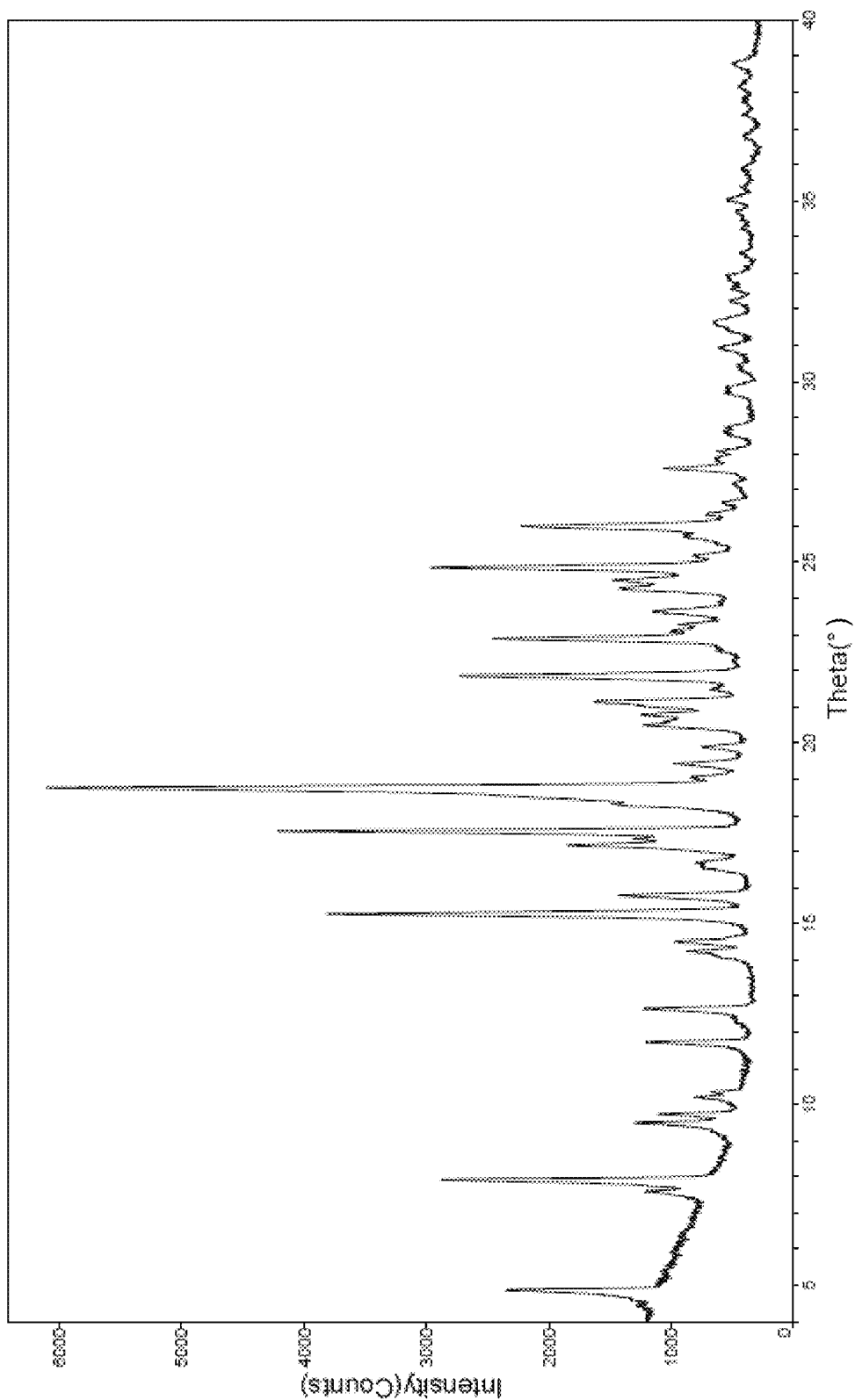
FIG. 97 is an XRPD pattern of Compound 1 mesylate crystalline Form XXXIII.
Figure 98:
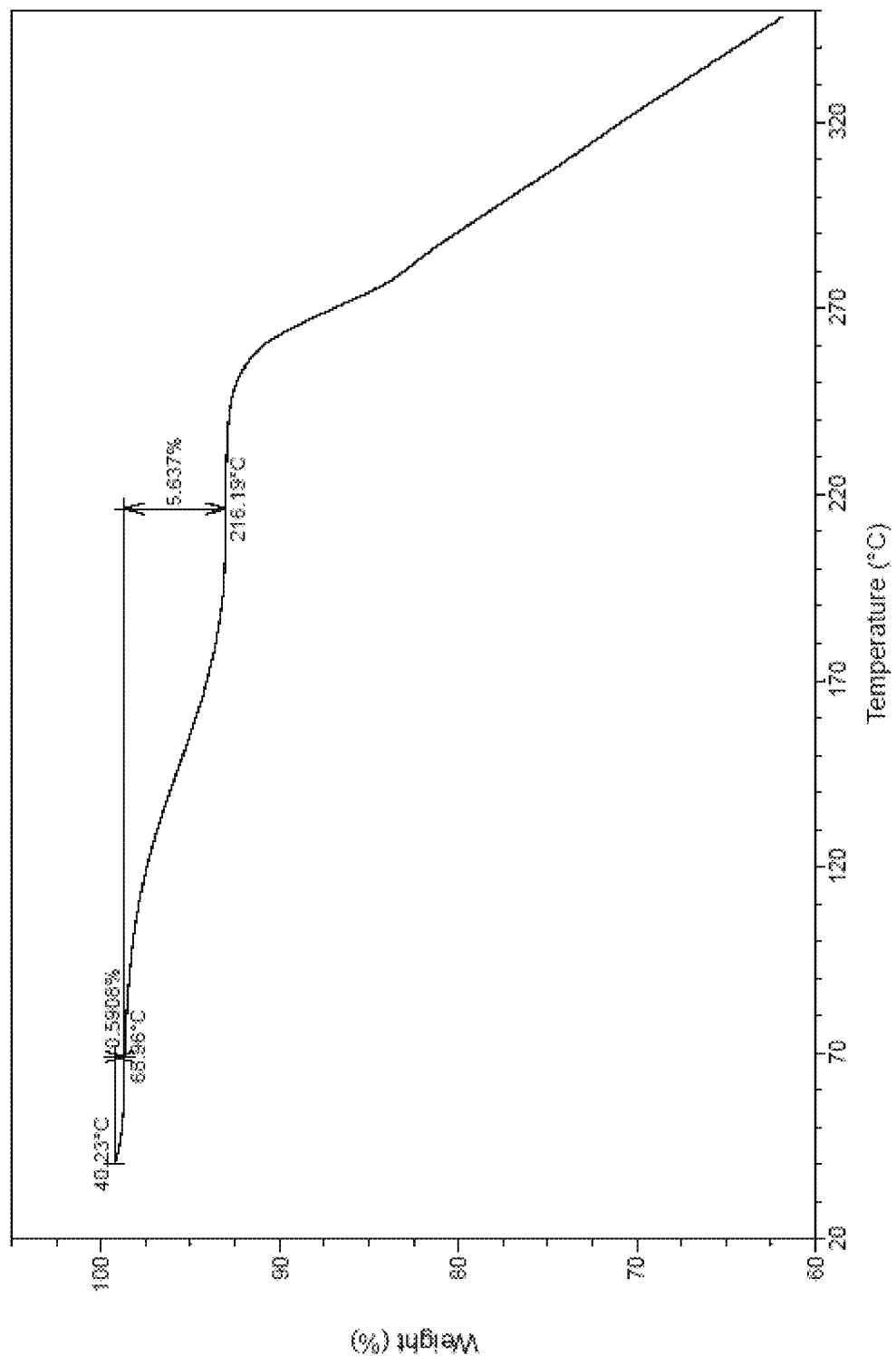
FIG. 98 is a TGA plot of Compound 1 mesylate crystalline Form XXXIII.
Figure 99:
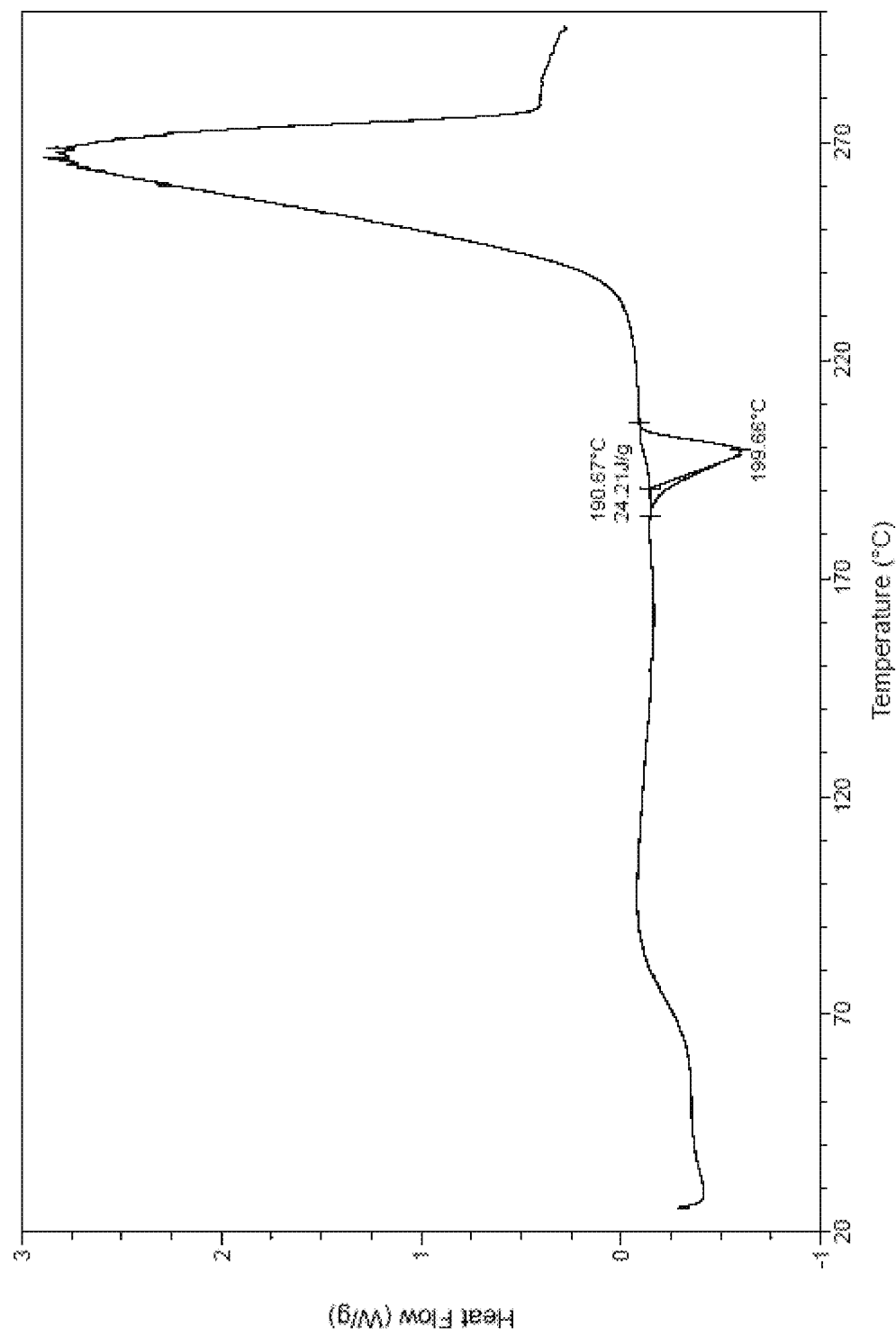
FIG. 99 is a DSC curve of Compound 1 mesylate crystalline Form XXXIII.
Figure 100:
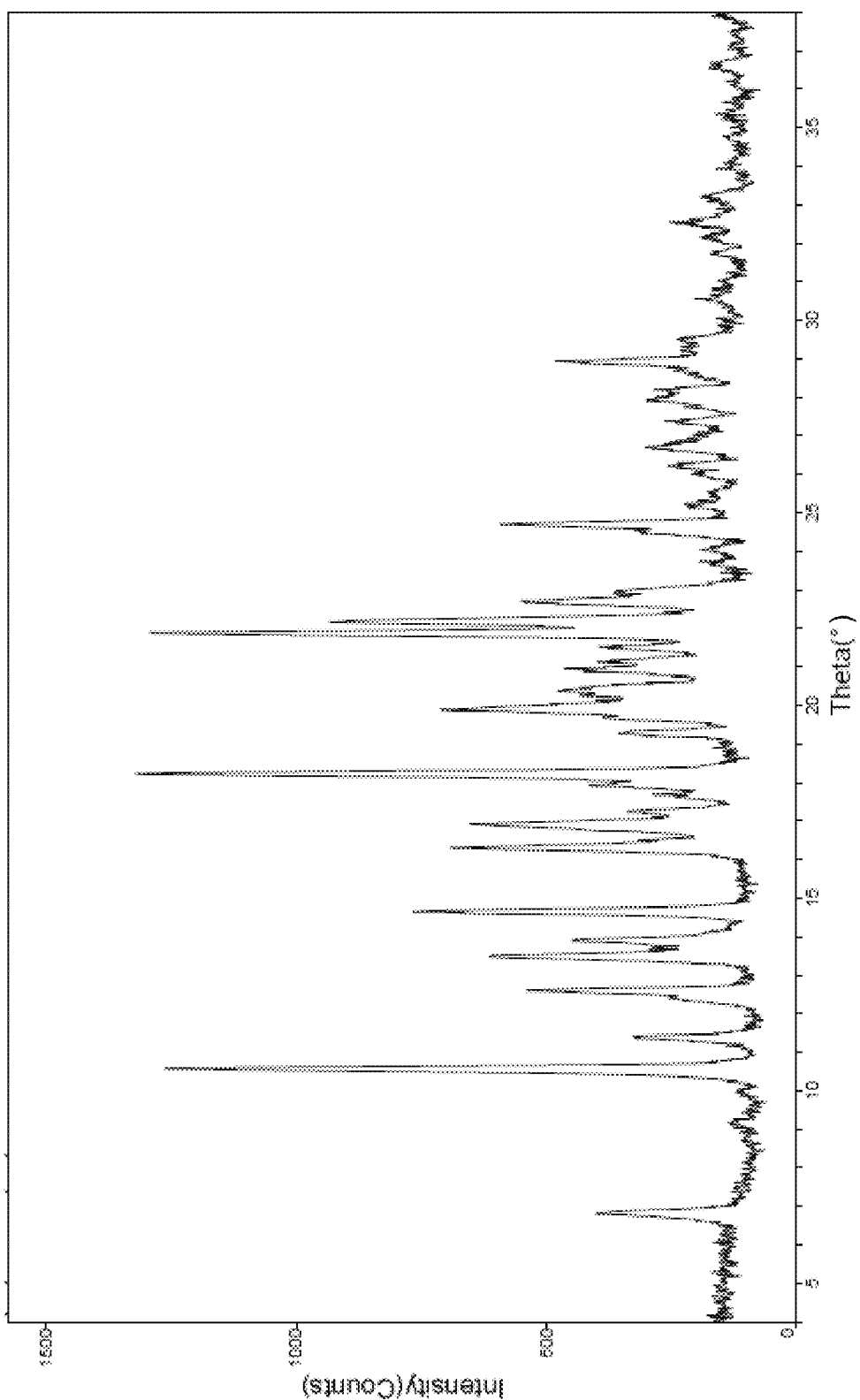
FIG. 100 is an XRPD pattern of Compound 1 mesylate crystalline Form XXXIV.
Figure 101:
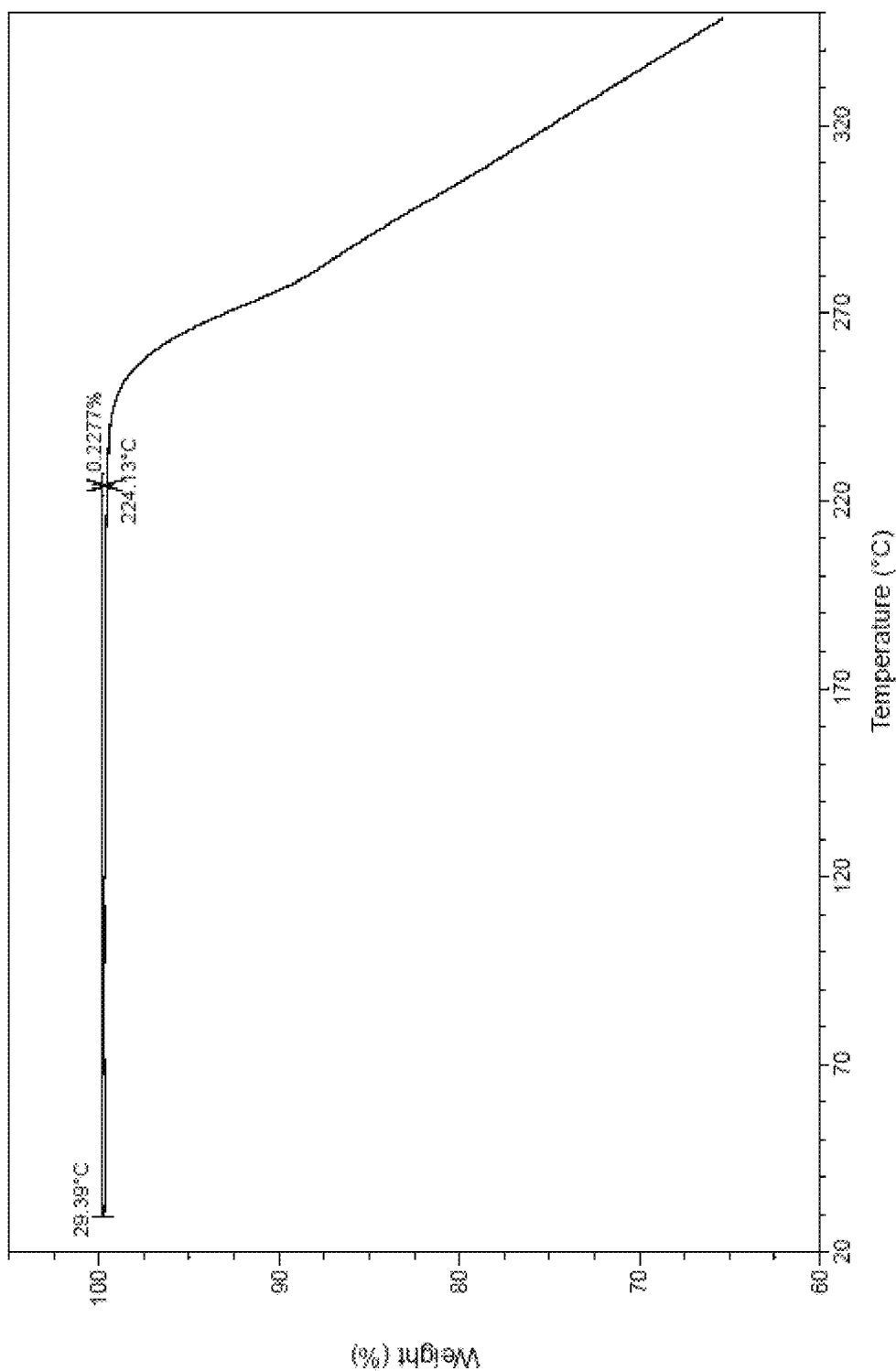
FIG. 101 is a TGA plot of Compound 1 mesylate crystalline Form XXXIV.
Figure 102:
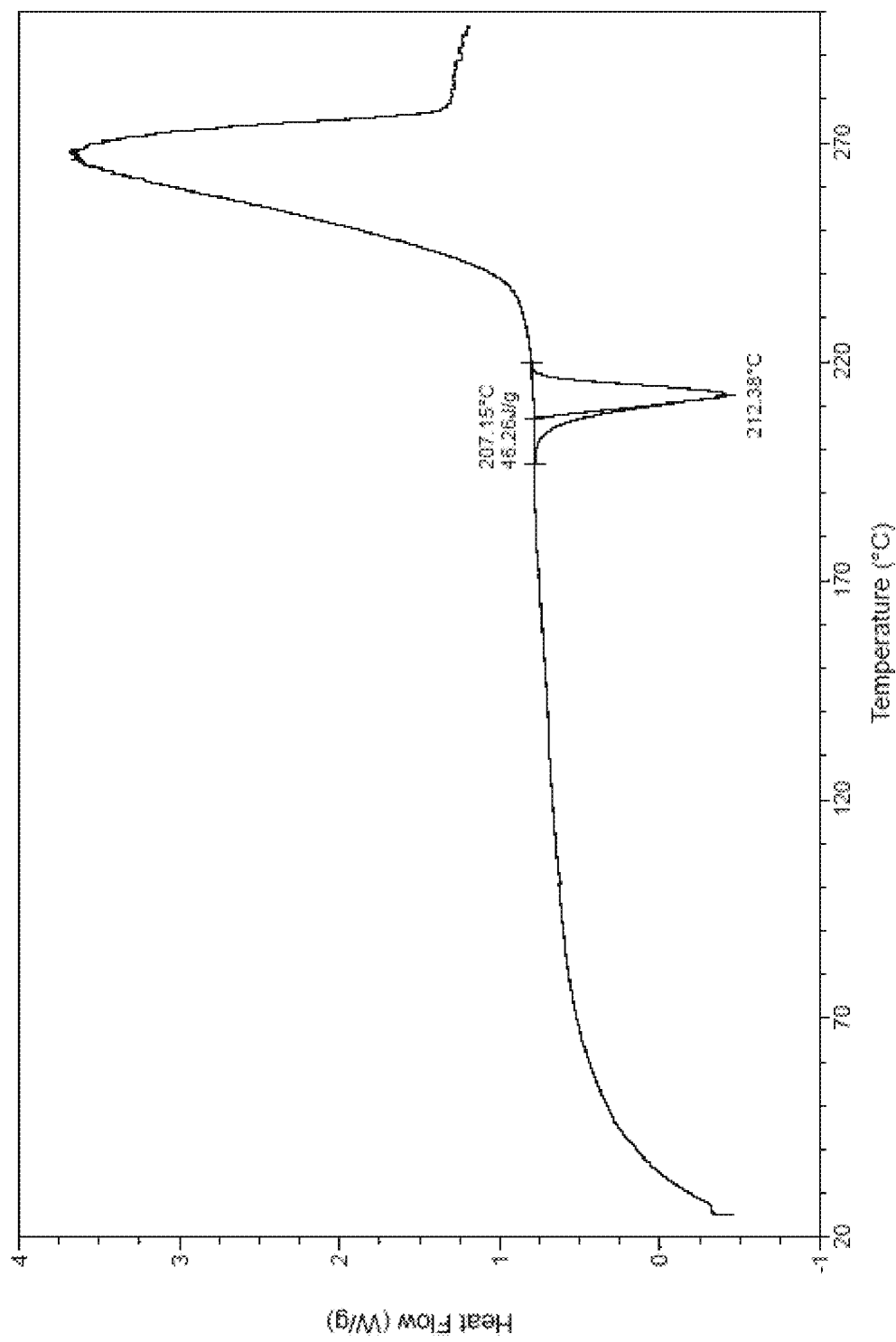
FIG. 102 is a DSC curve of Compound 1 mesylate crystalline Form XXXIV.
Figure 103:
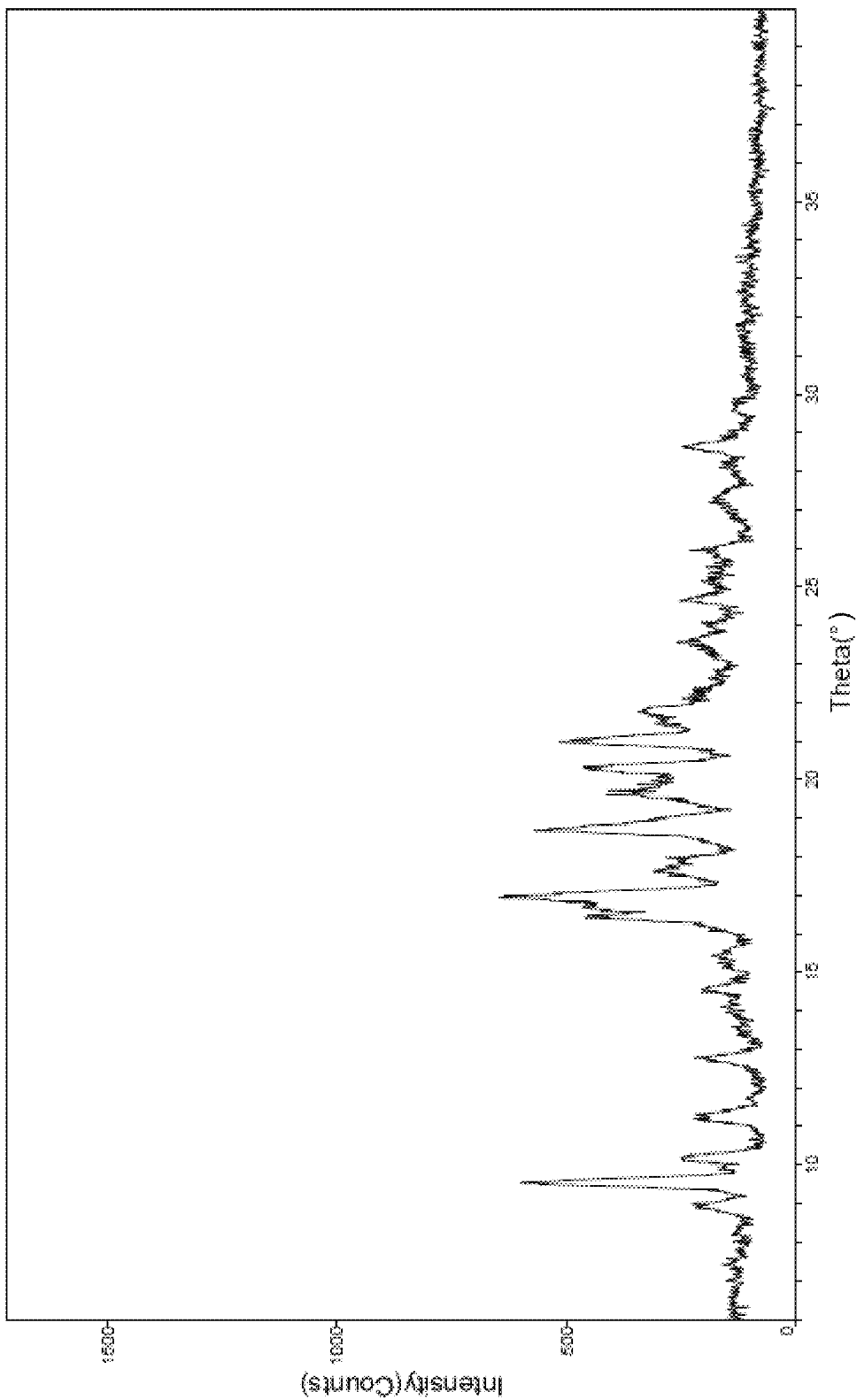
FIG. 103 is an XRPD pattern of Compound 1 mesylate crystalline Form XXXV.
Figure 104:
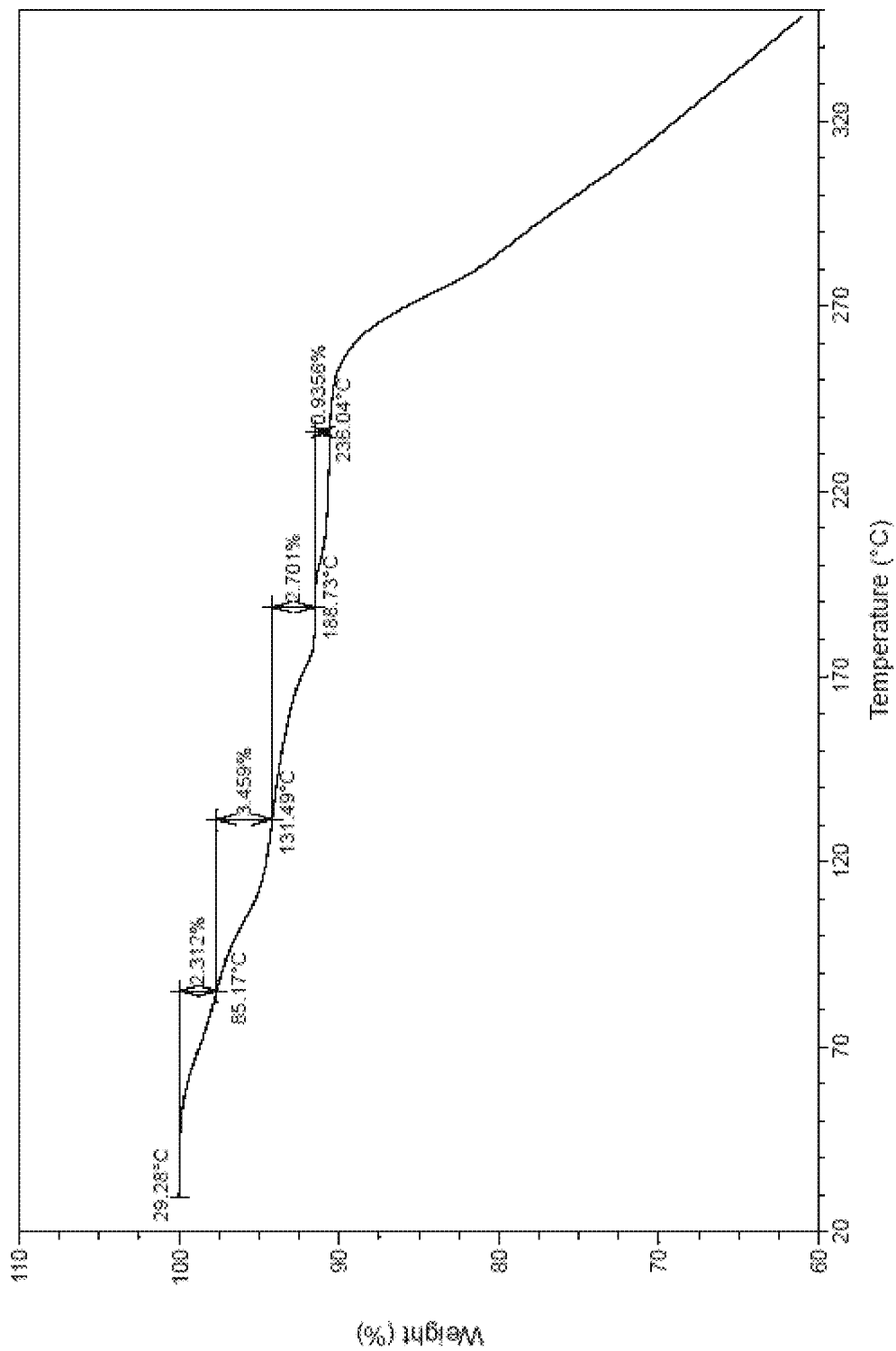
FIG. 104 is a TGA plot of Compound 1 mesylate crystalline Form XXXV.
Figure 105:
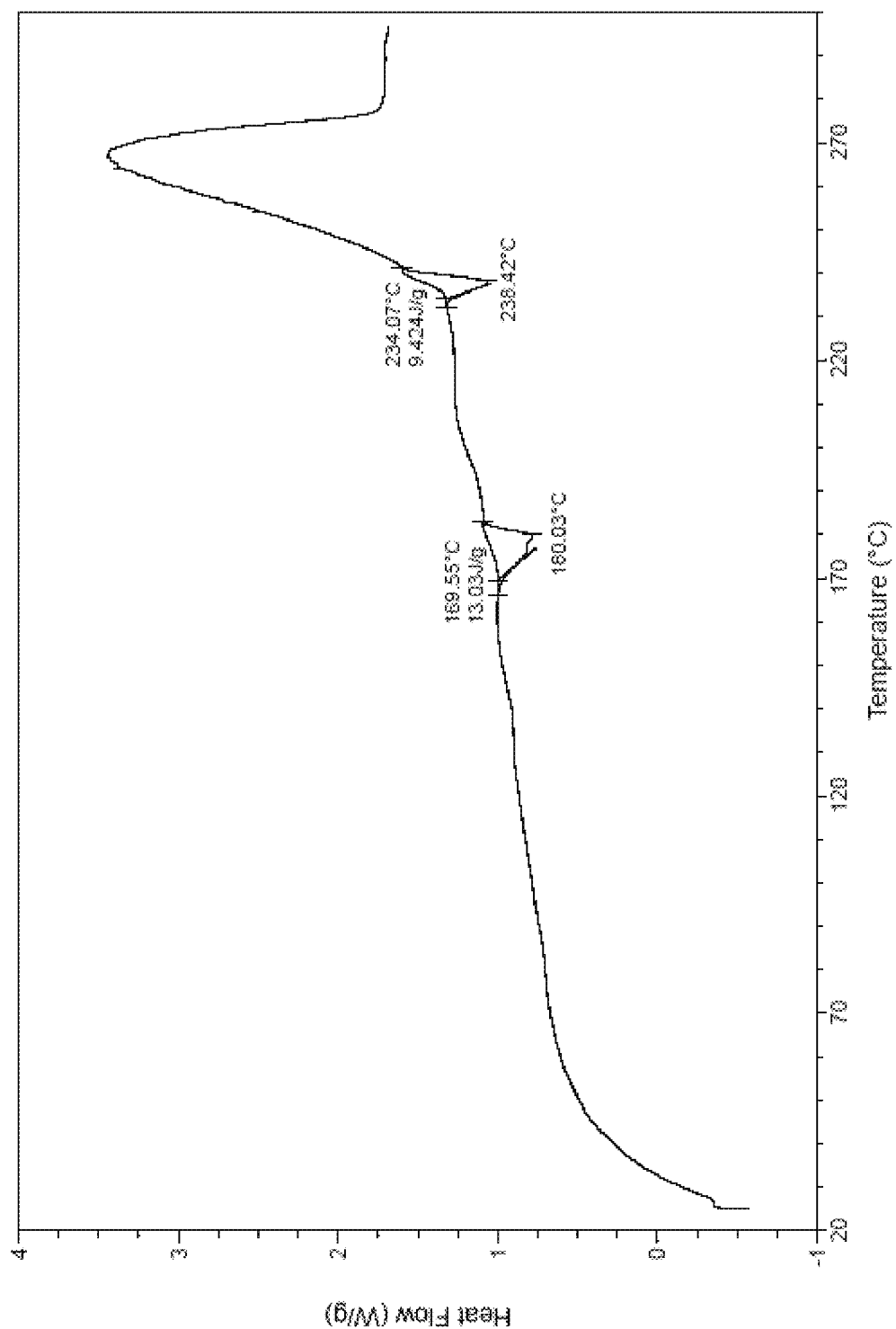
FIG. 105 is a DSC curve of Compound 1 mesylate crystalline Form XXXV.
Figure 106:
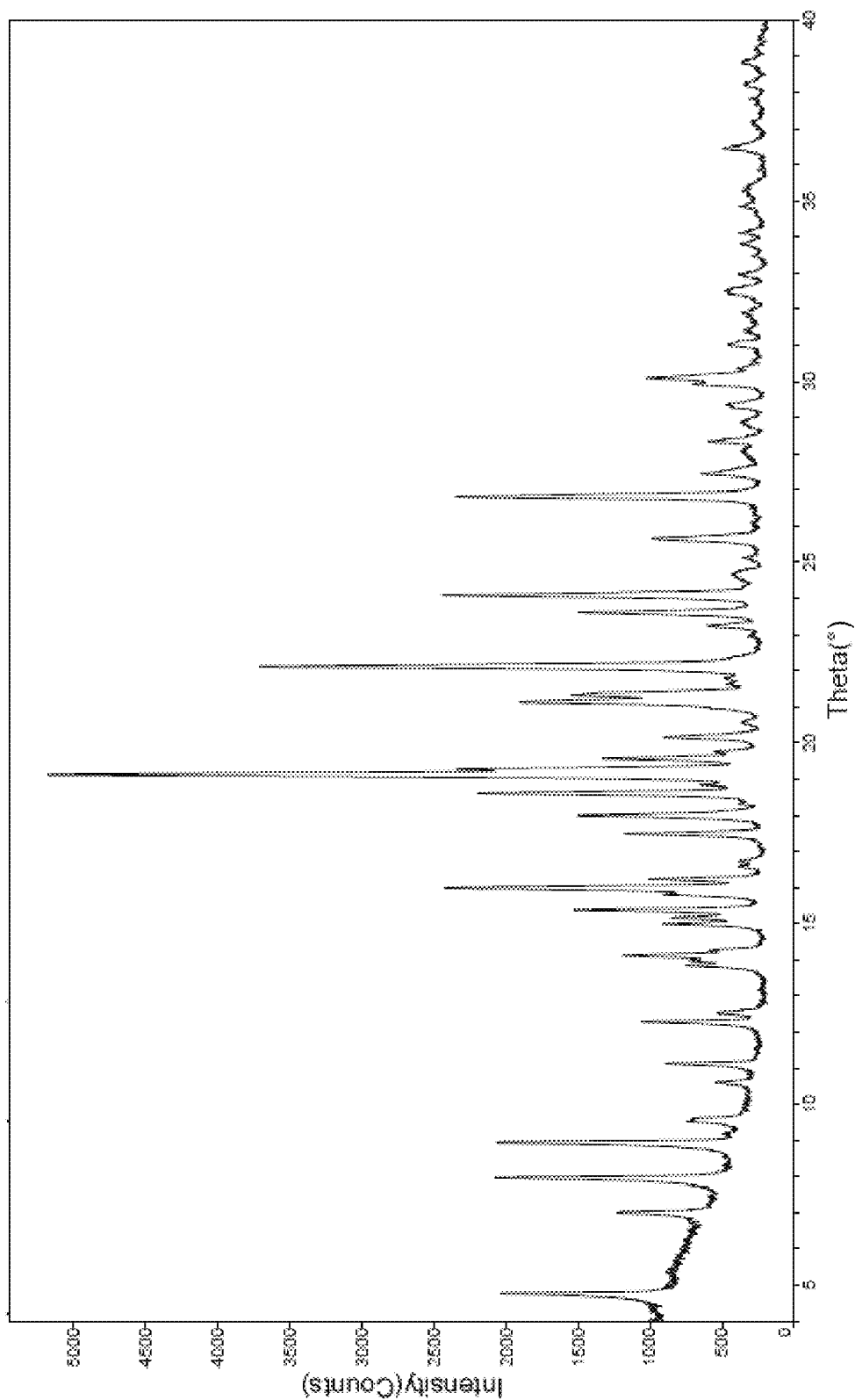
FIG. 106 is an XRPD pattern of Compound 1 citrate crystalline Form XXXVI.
Figure 107:
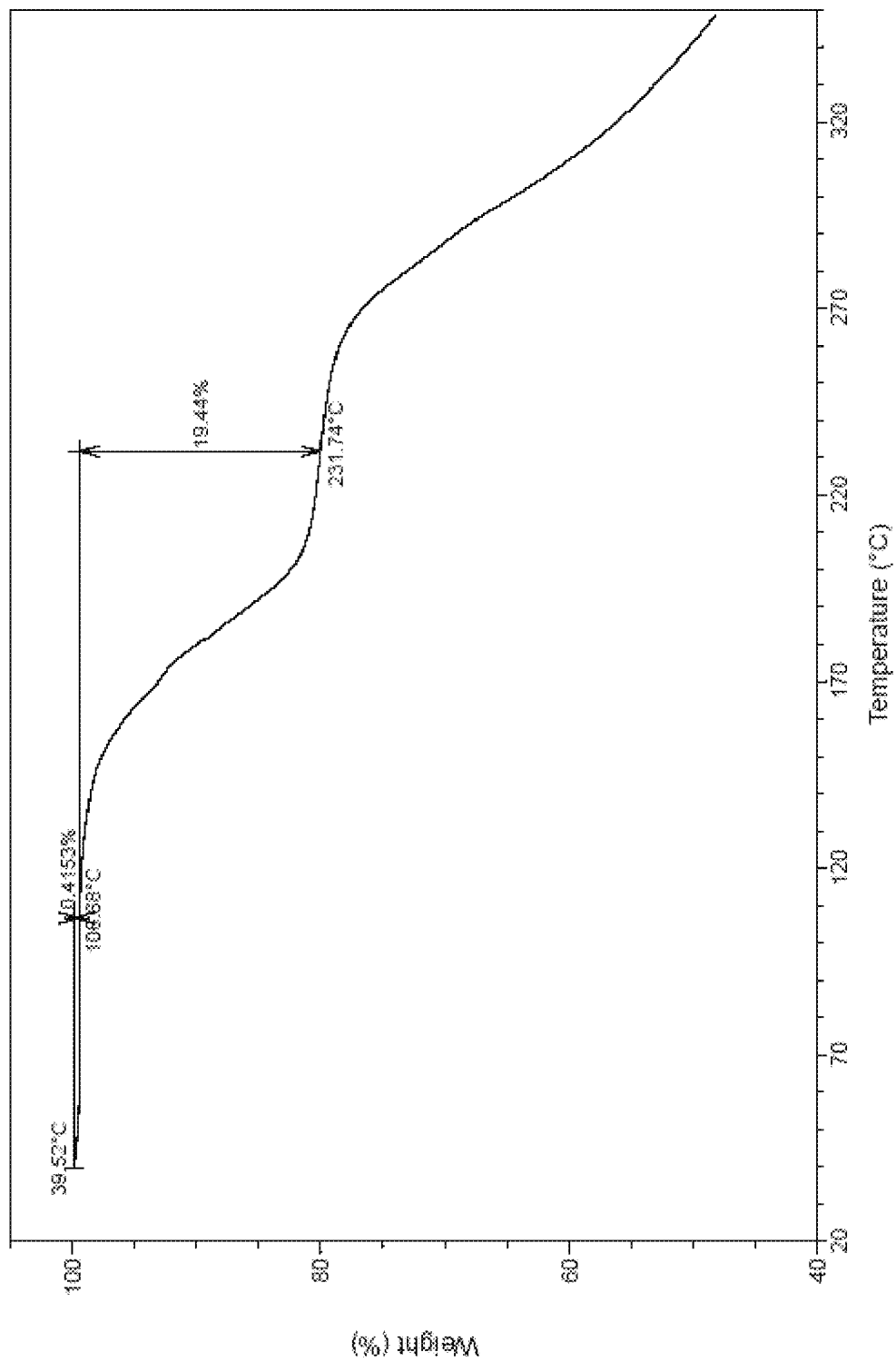
FIG. 107 is a TGA plot of Compound 1 citrate crystalline Form XXXVI.
Figure 108:
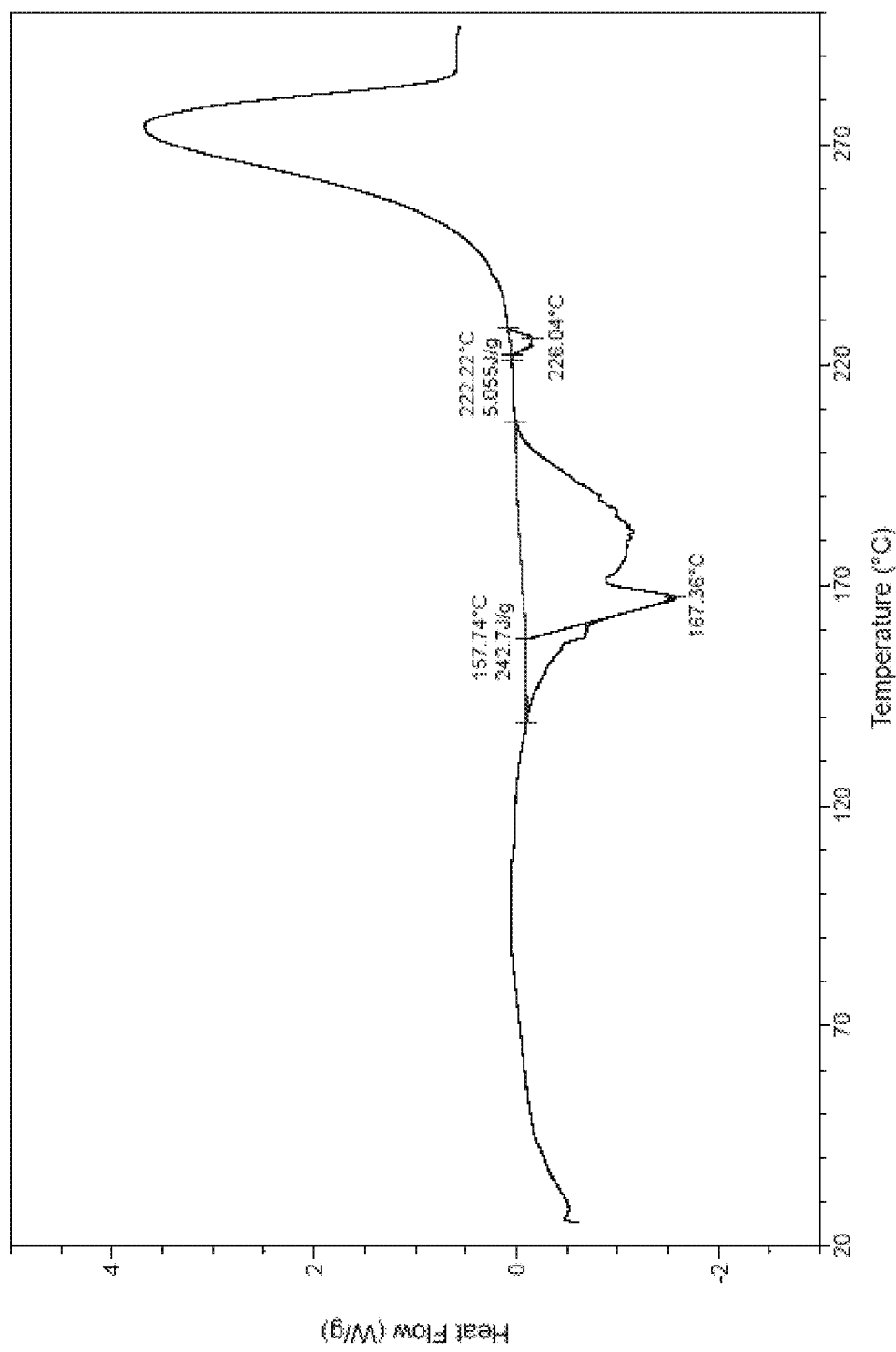
FIG. 108 is a DSC curve of Compound 1 citrate crystalline Form XXXVI.
Figure 109:
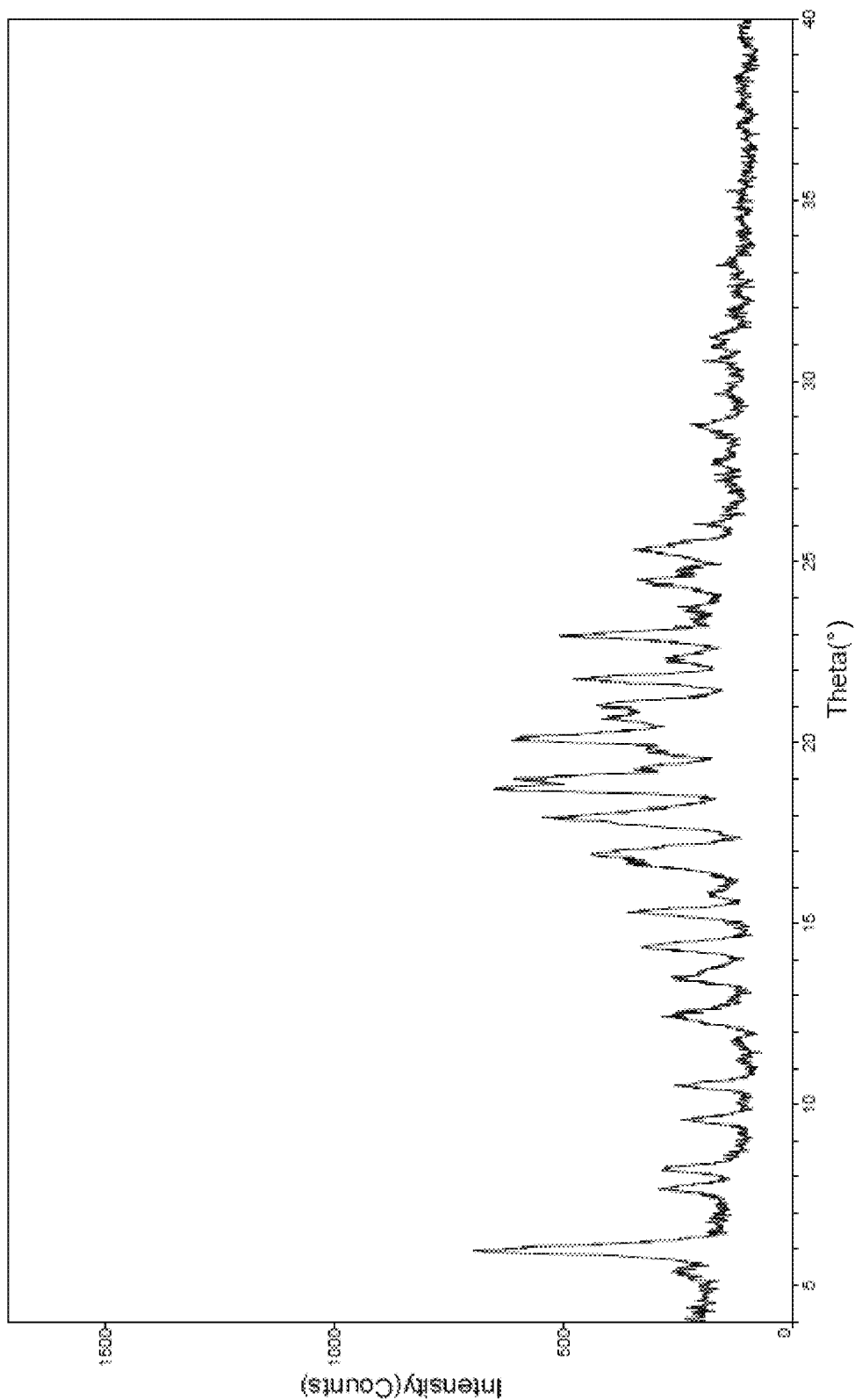
FIG. 109 is an XRPD pattern of Compound 1 citrate crystalline Form XXXVII.
Figure 110:
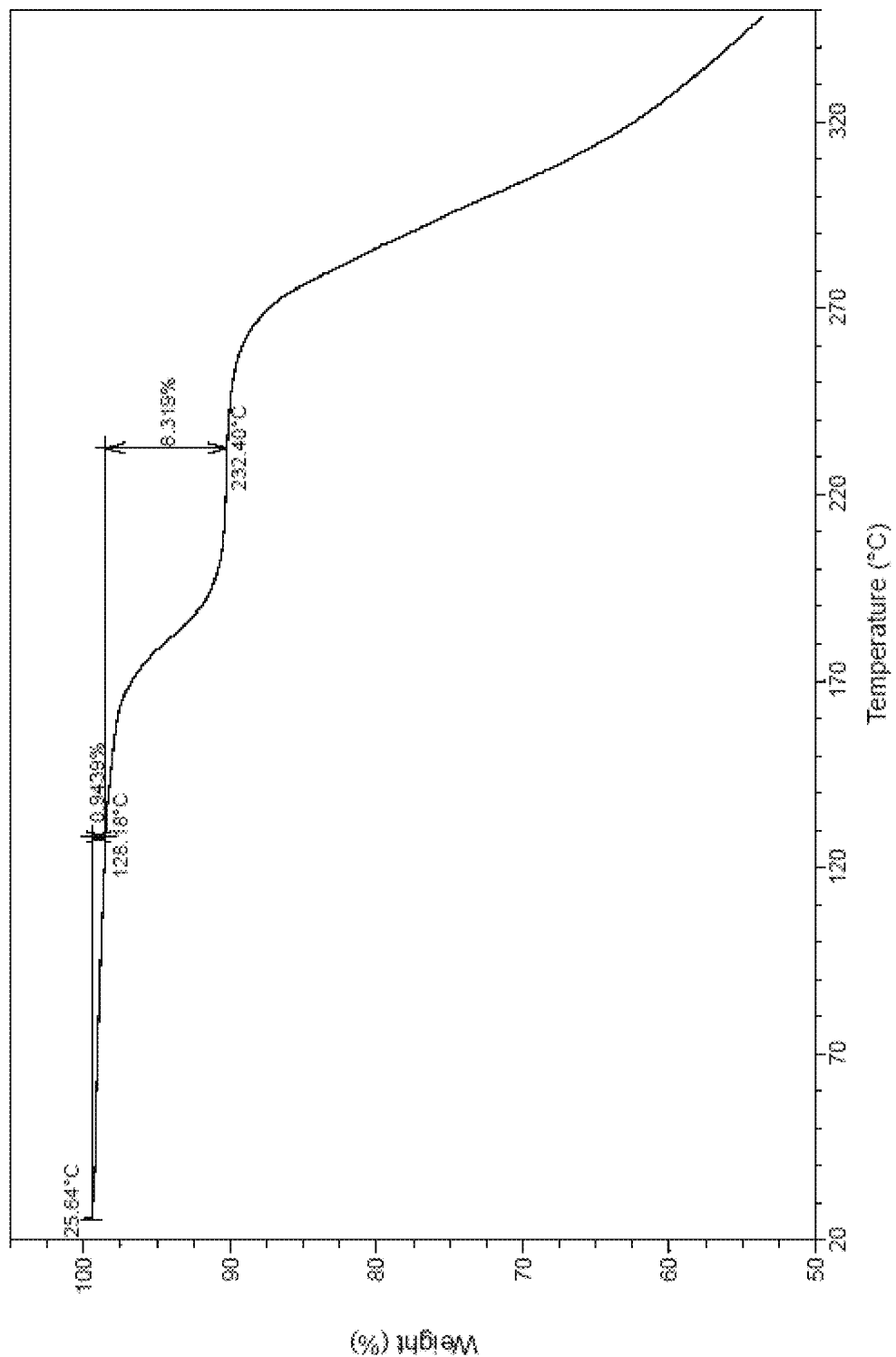
FIG. 110 is a TGA plot of Compound 1 citrate crystalline Form XXXVII.
Figure 111:
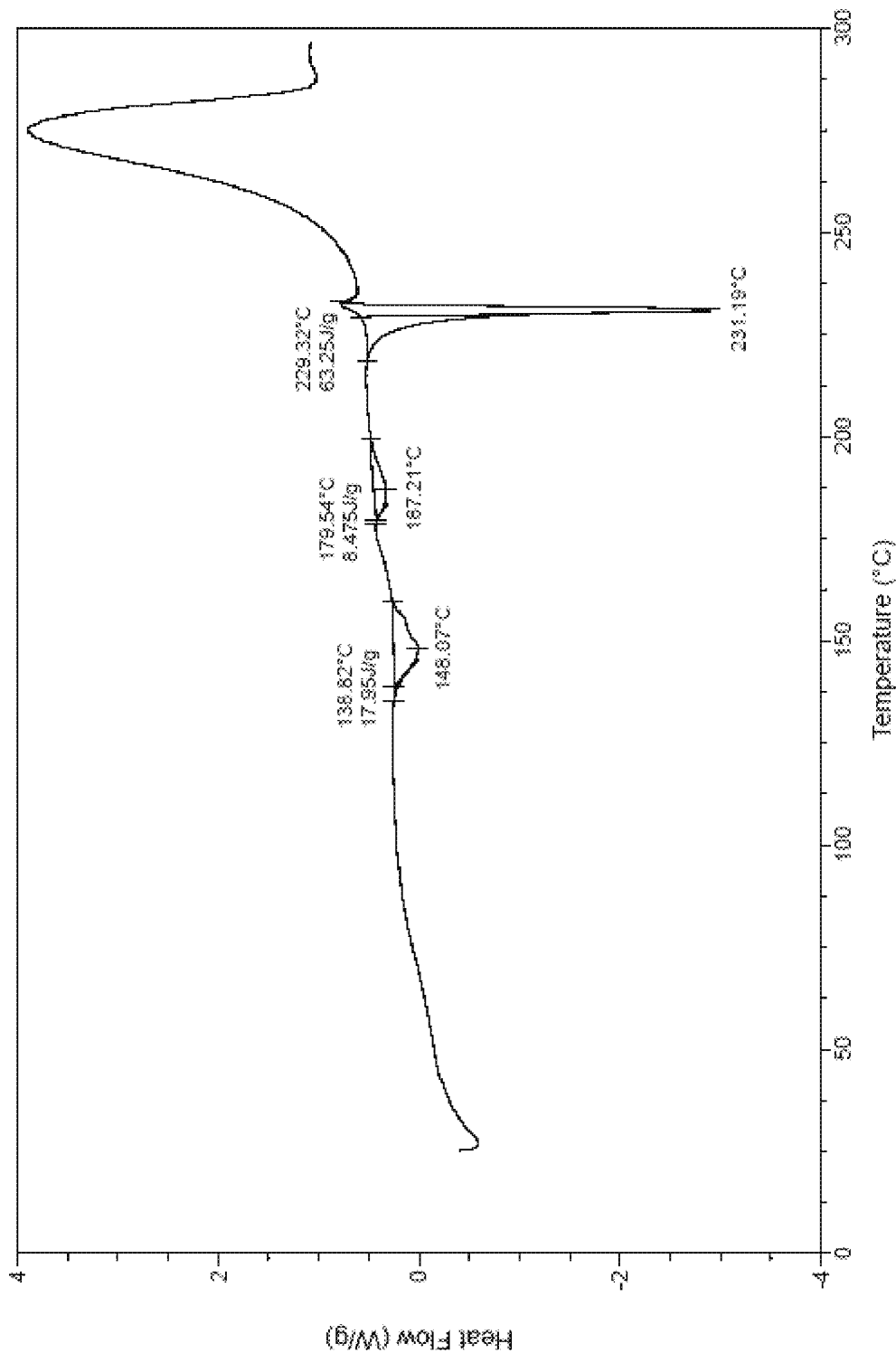
FIG. 111 is a DSC curve of Compound 1 citrate crystalline Form XXXVII.
Figure 112:
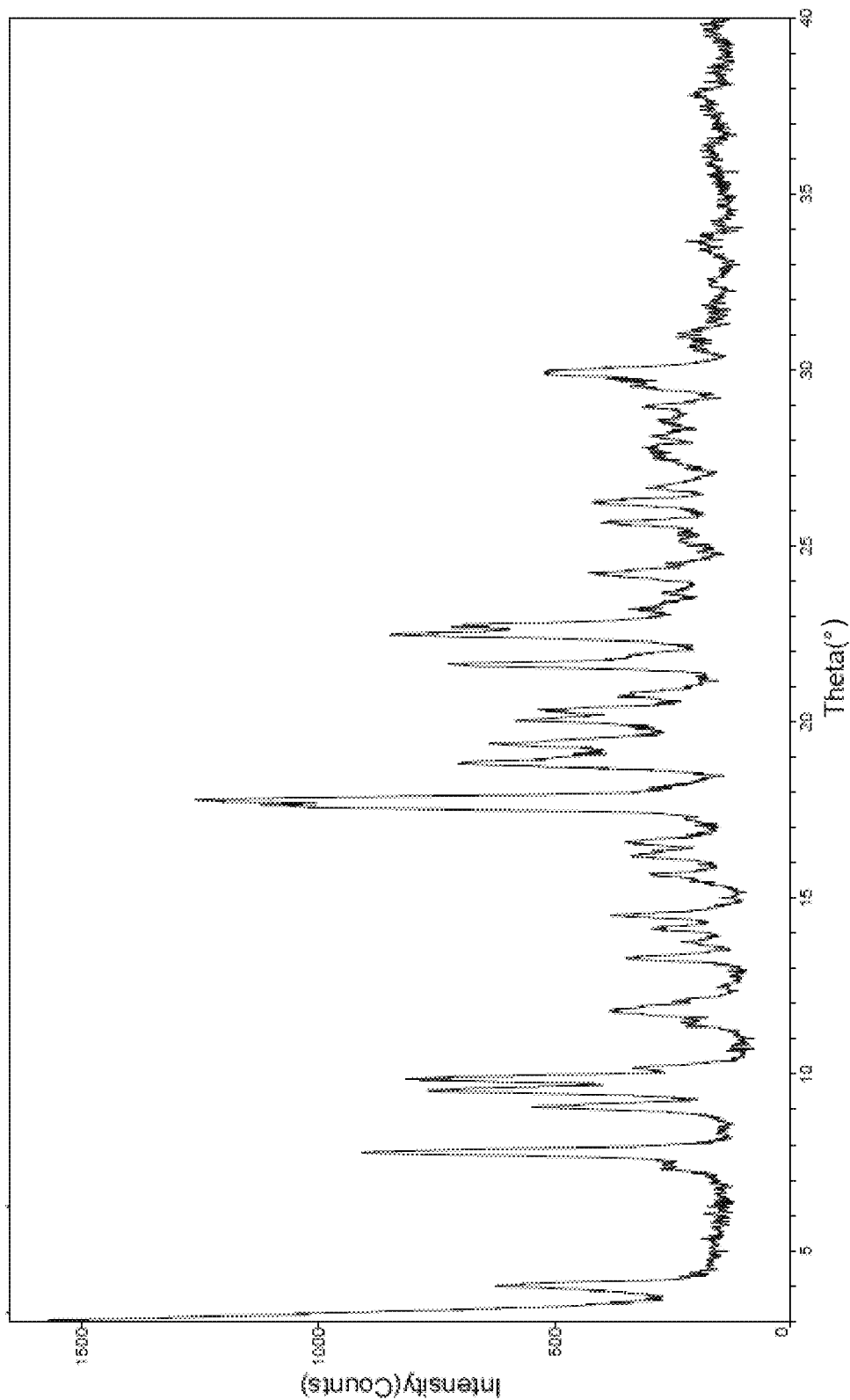
FIG. 112 is an XRPD pattern of Compound 1 citrate crystalline Form XXXVIII.
Figure 113:
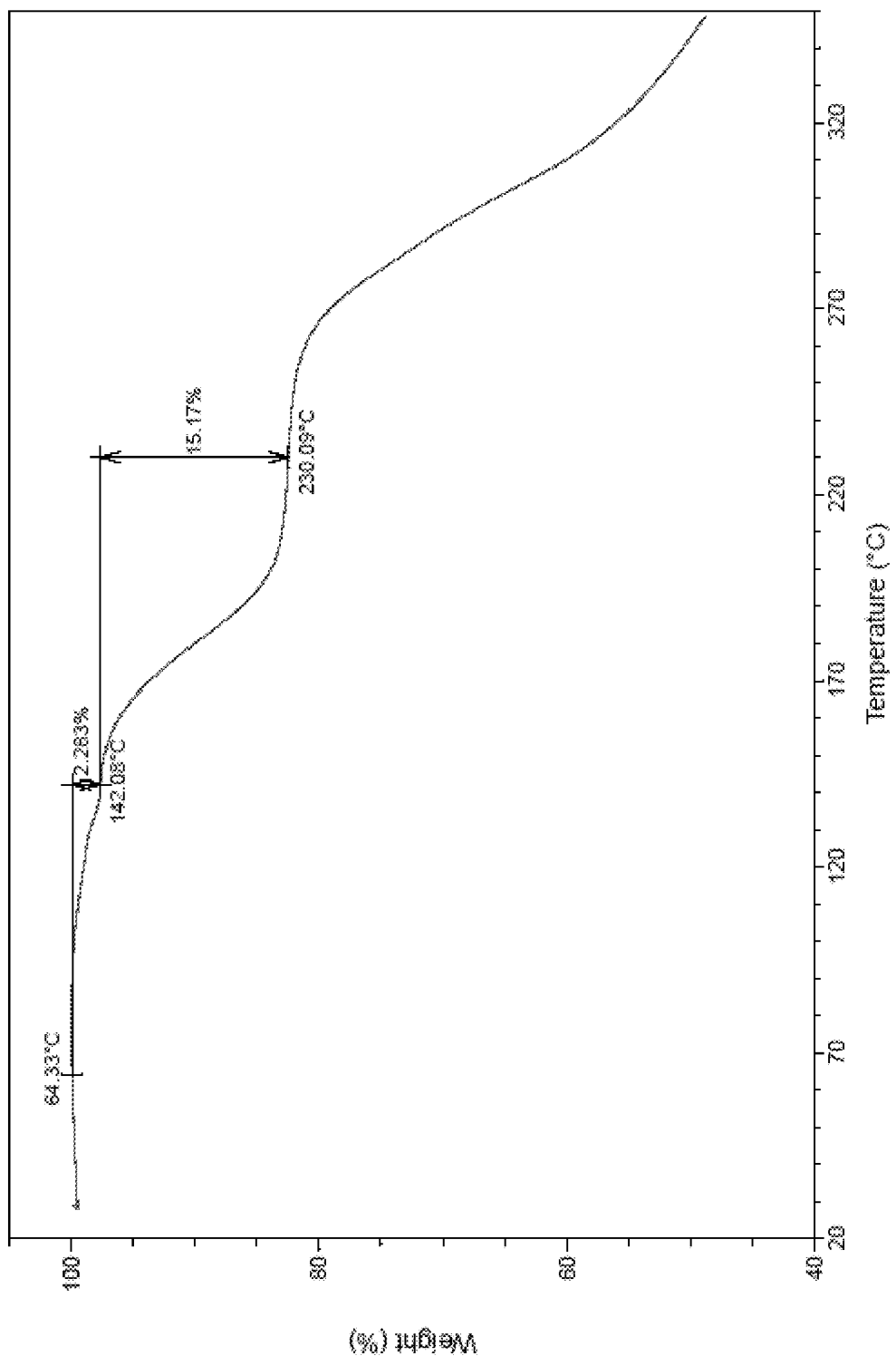
FIG. 113 is a TGA plot of Compound 1 citrate crystalline Form XXXVIII.
Figure 114:
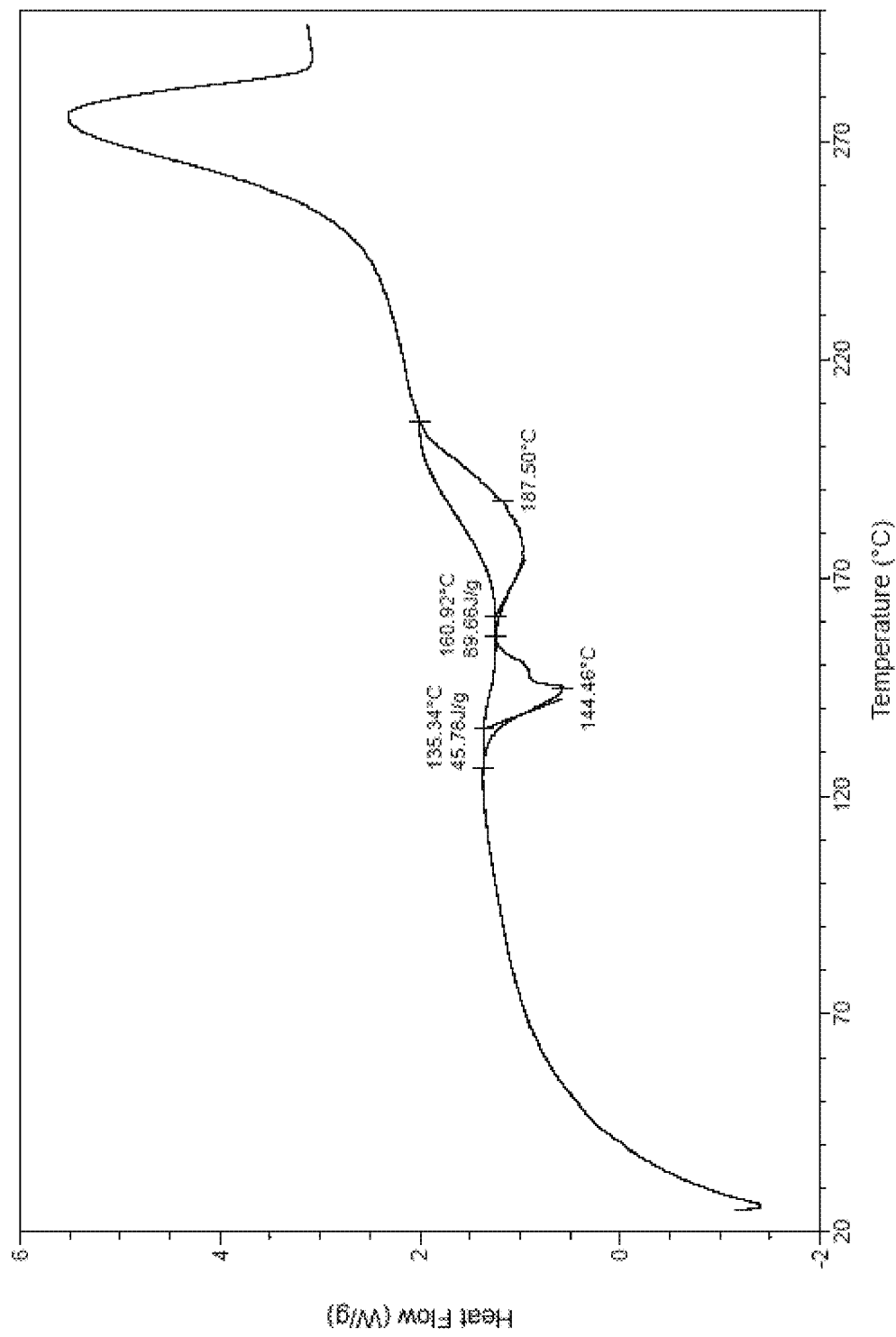
FIG. 114 is a DSC curve of Compound 1 citrate crystalline Form XXXVIII.
Figure 115:
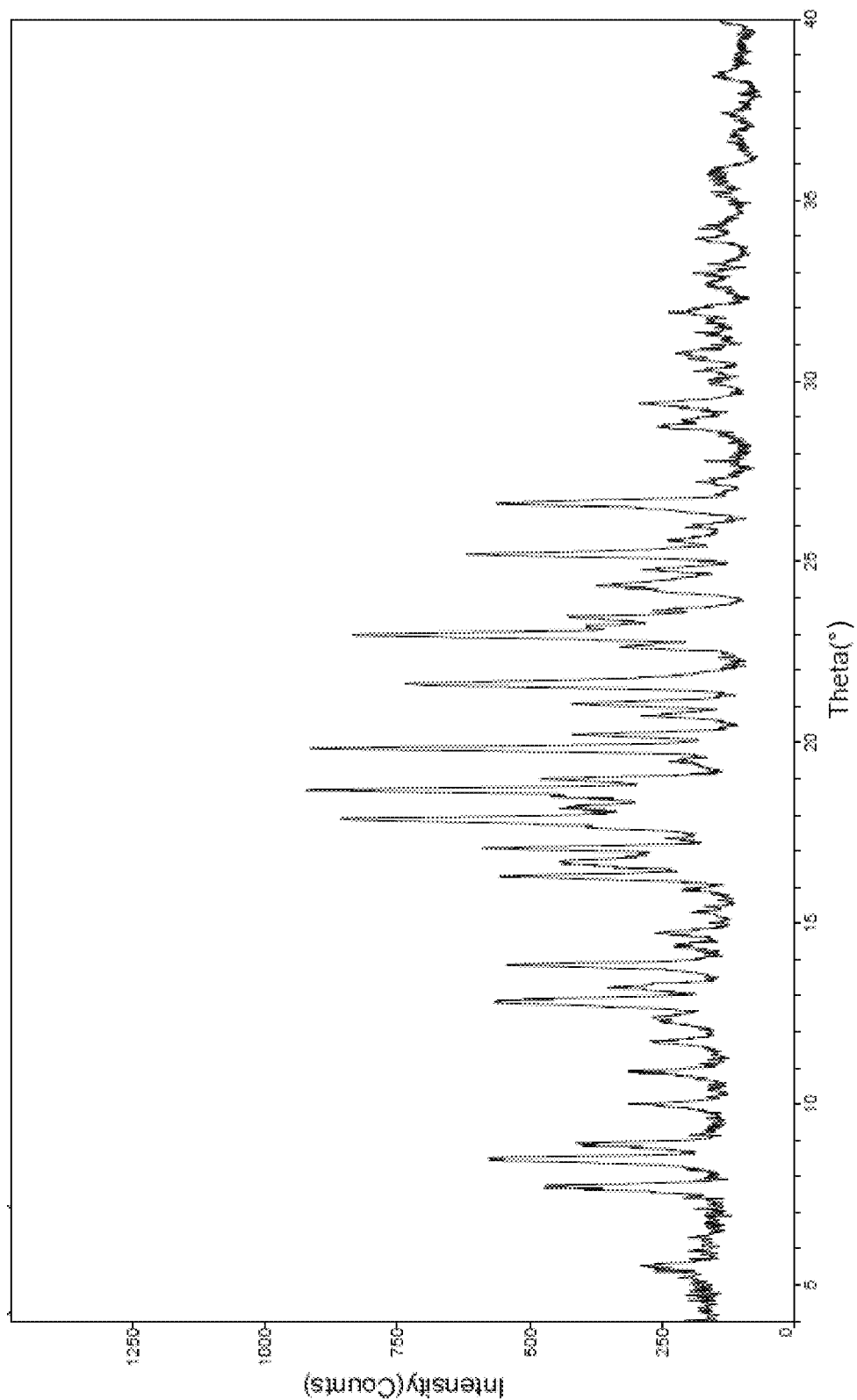
FIG. 115 is an XRPD pattern of Compound 1 citrate crystalline Form XXXIX.
Figure 116:
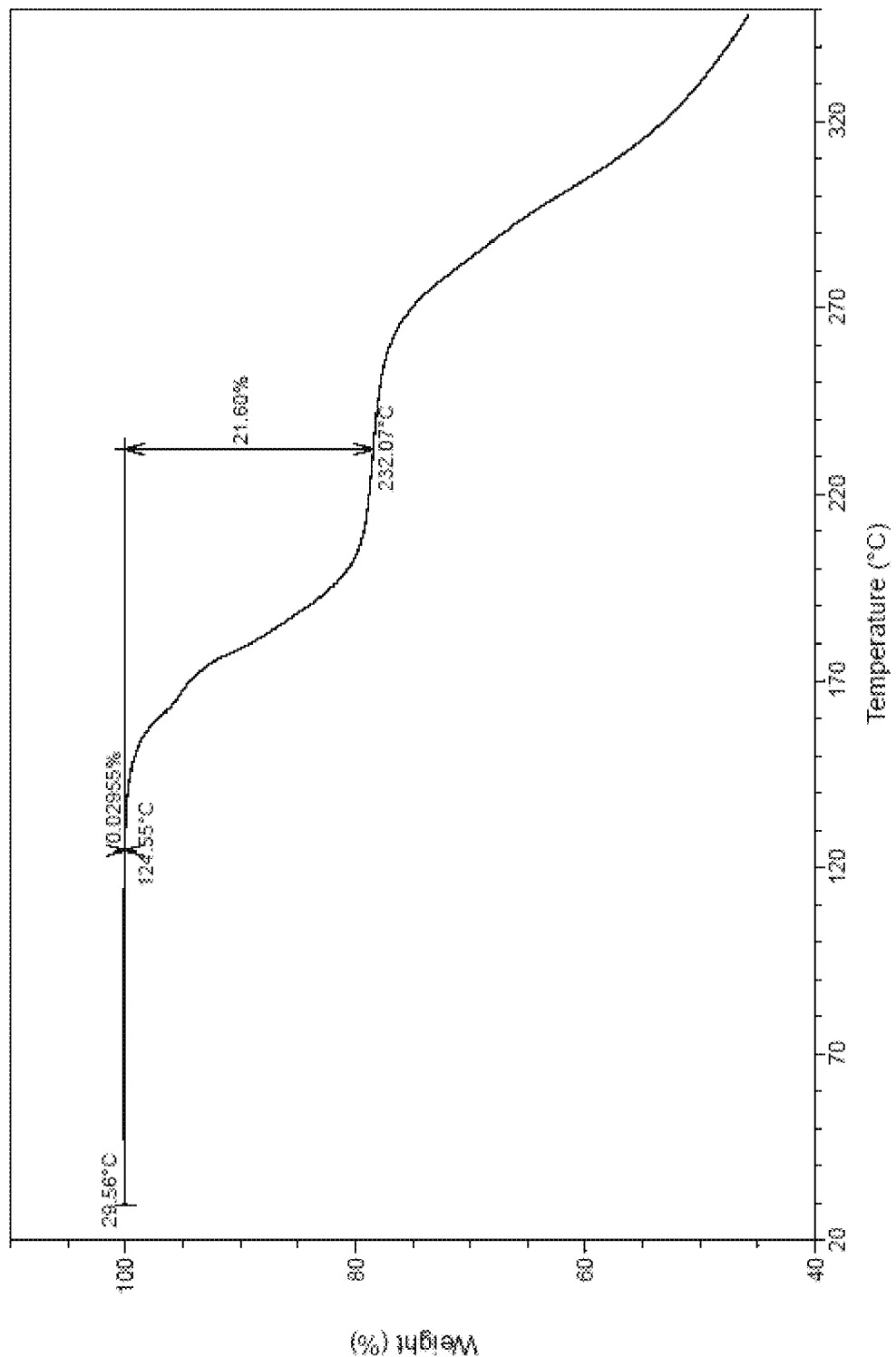
FIG. 116 is a TGA plot of Compound 1 citrate crystalline Form XXXIX.
Figure 117:
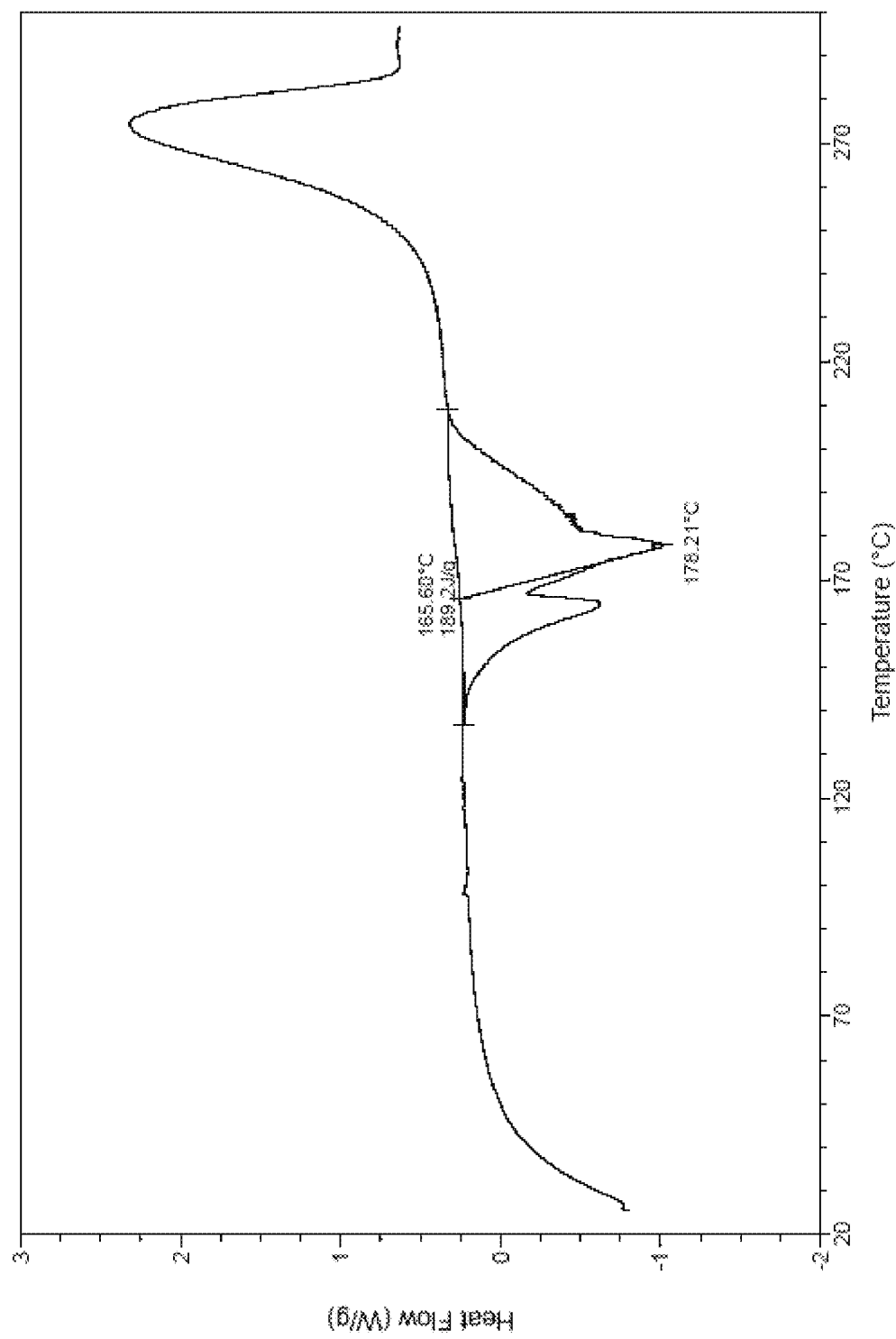
FIG. 117 is a DSC curve of Compound 1 citrate crystalline Form XXXIX.
Figure 118:
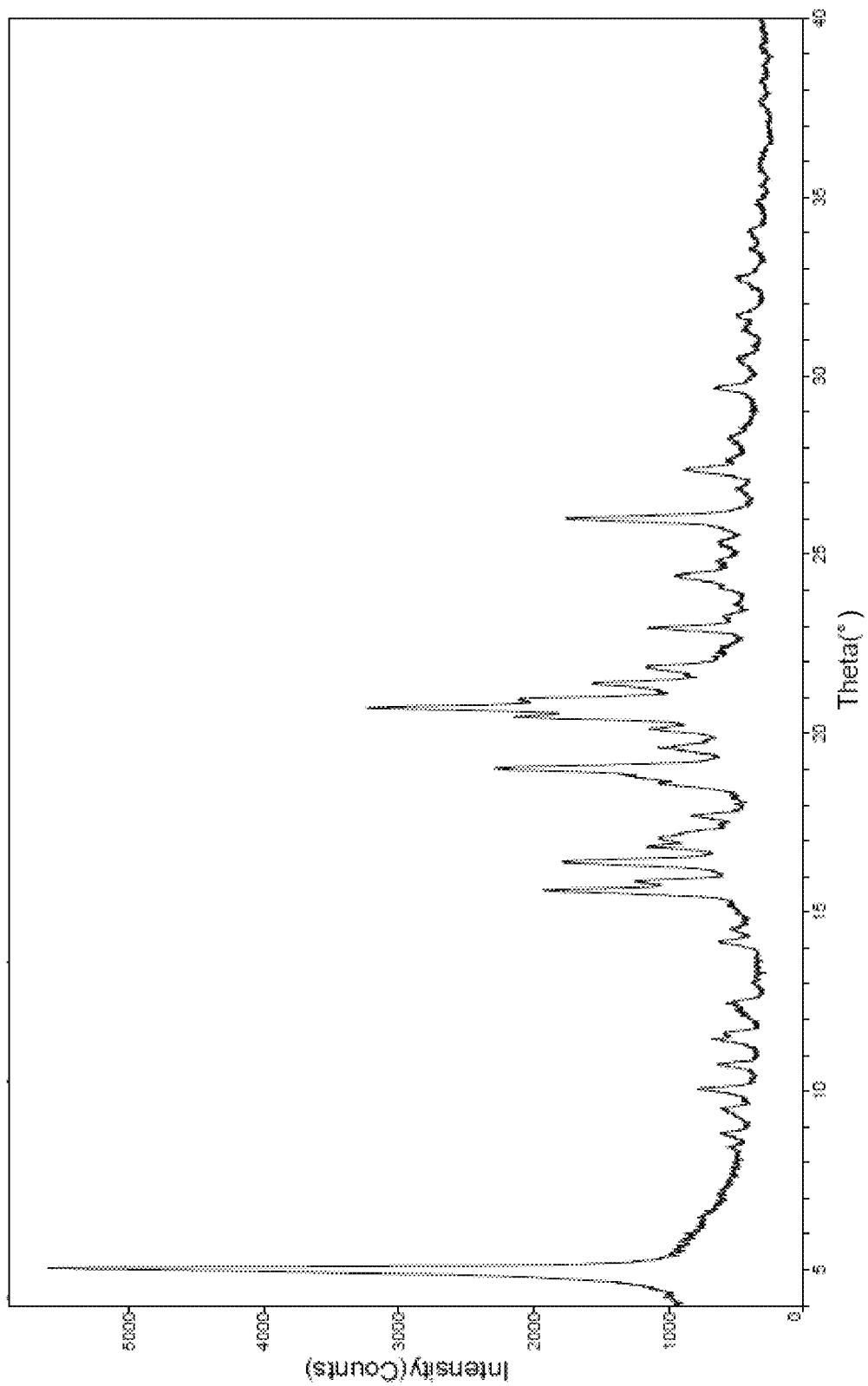
FIG. 118 is an XRPD pattern of Compound 1 maleate crystalline Form XL.
Figure 119:
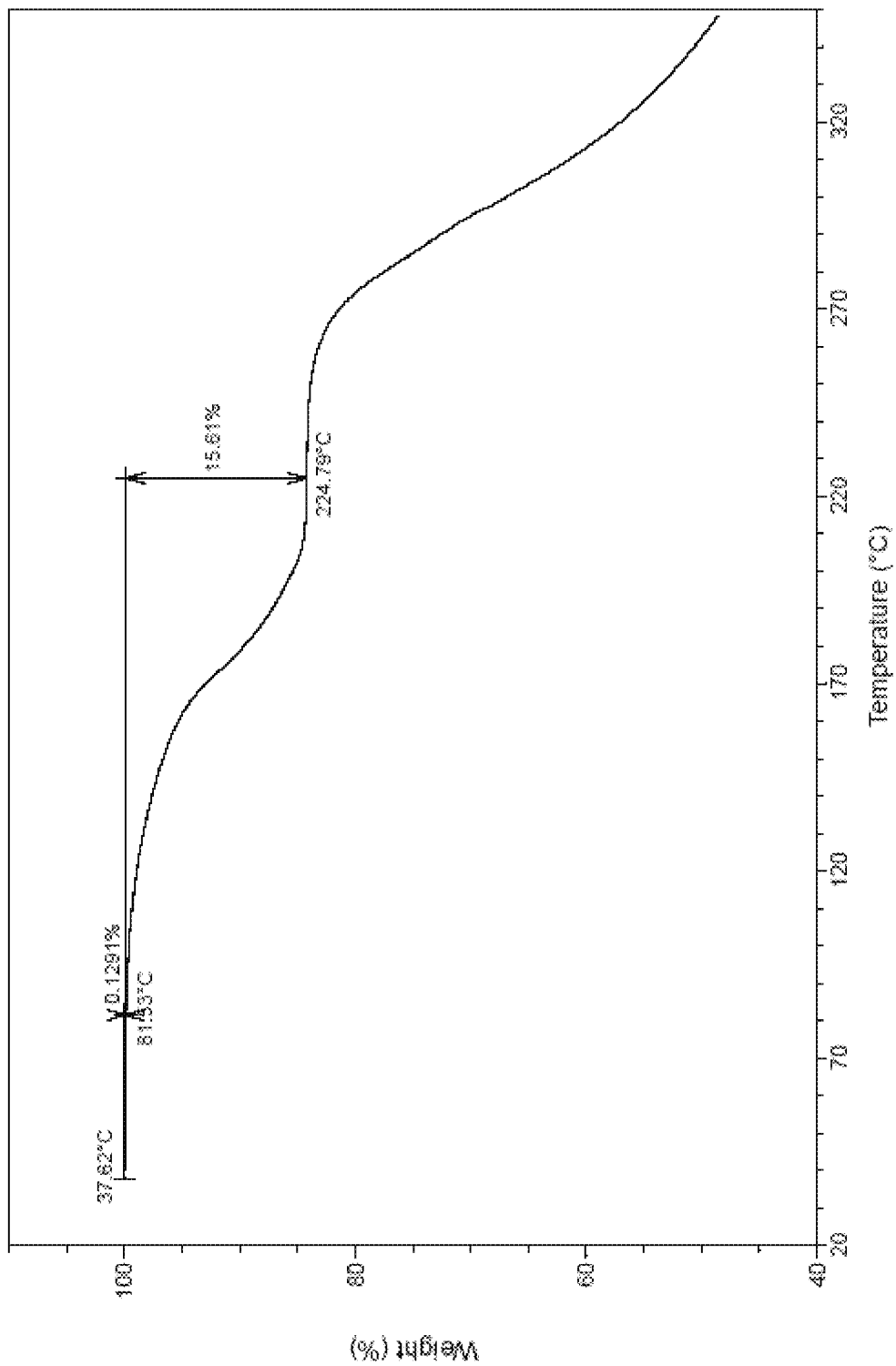
FIG. 119 is a TGA plot of Compound 1 maleate crystalline Form XL.
Figure 120:
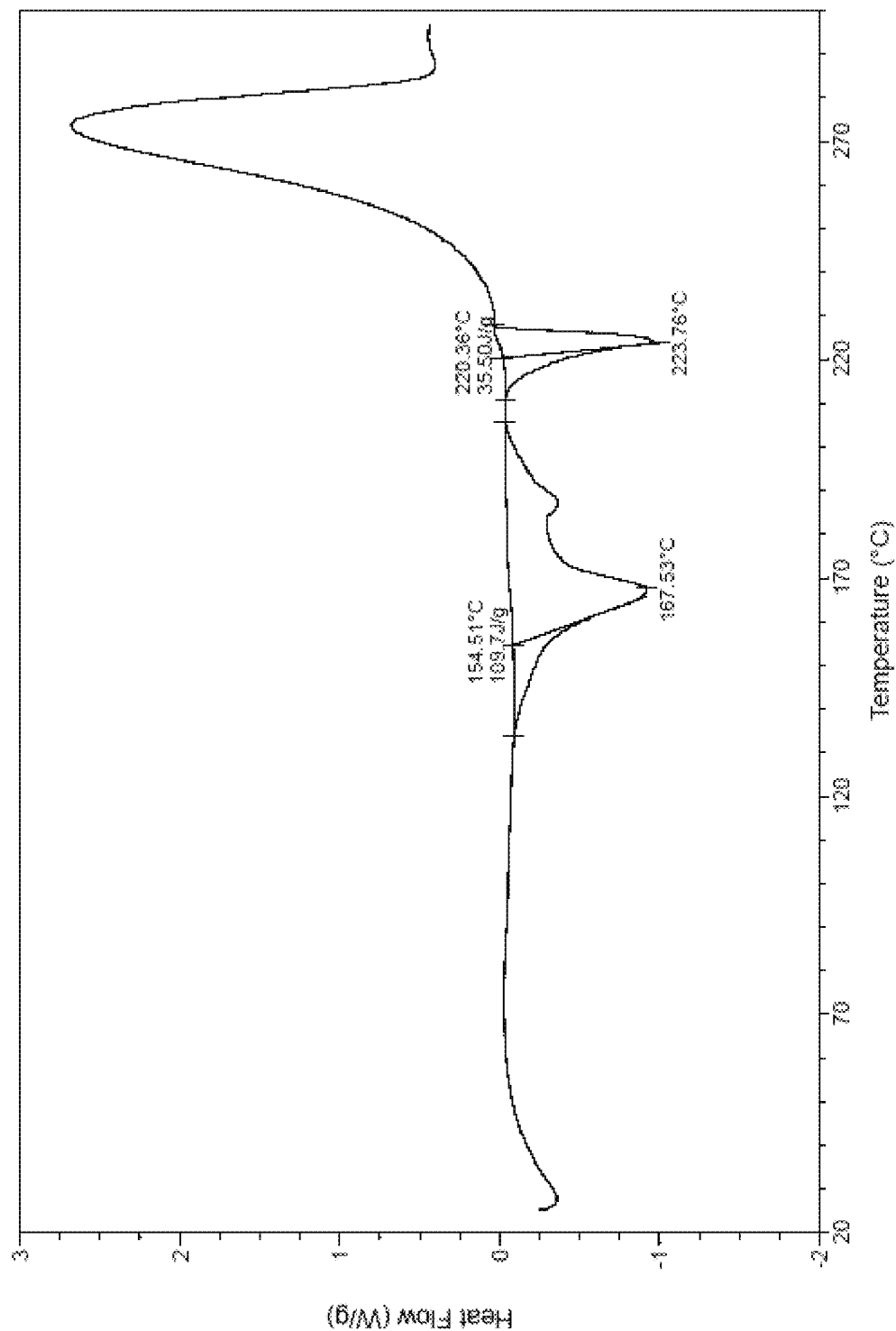
FIG. 120 is a DSC curve of Compound 1 maleate crystalline Form XL.
Figure 121:
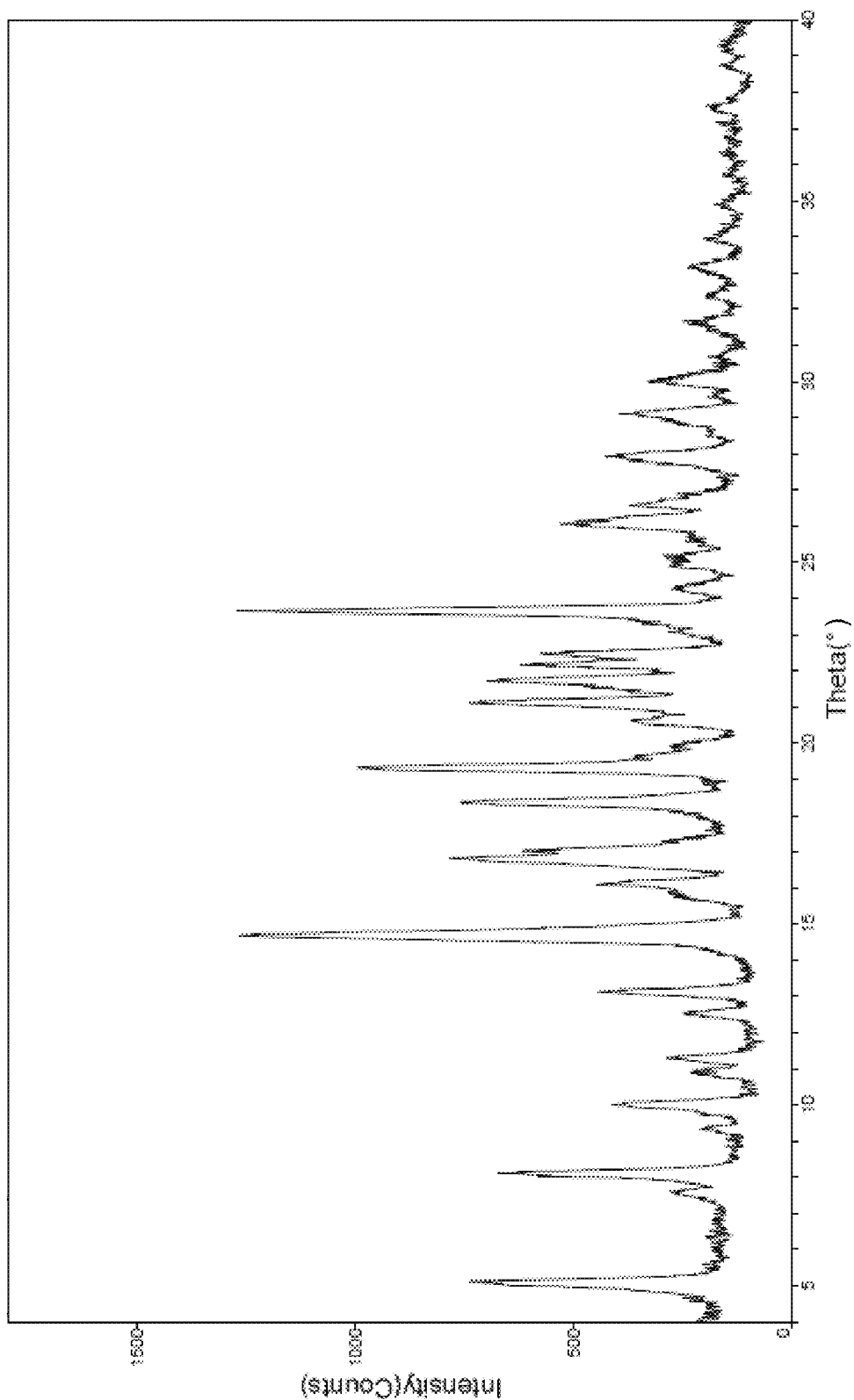
Figure 122:
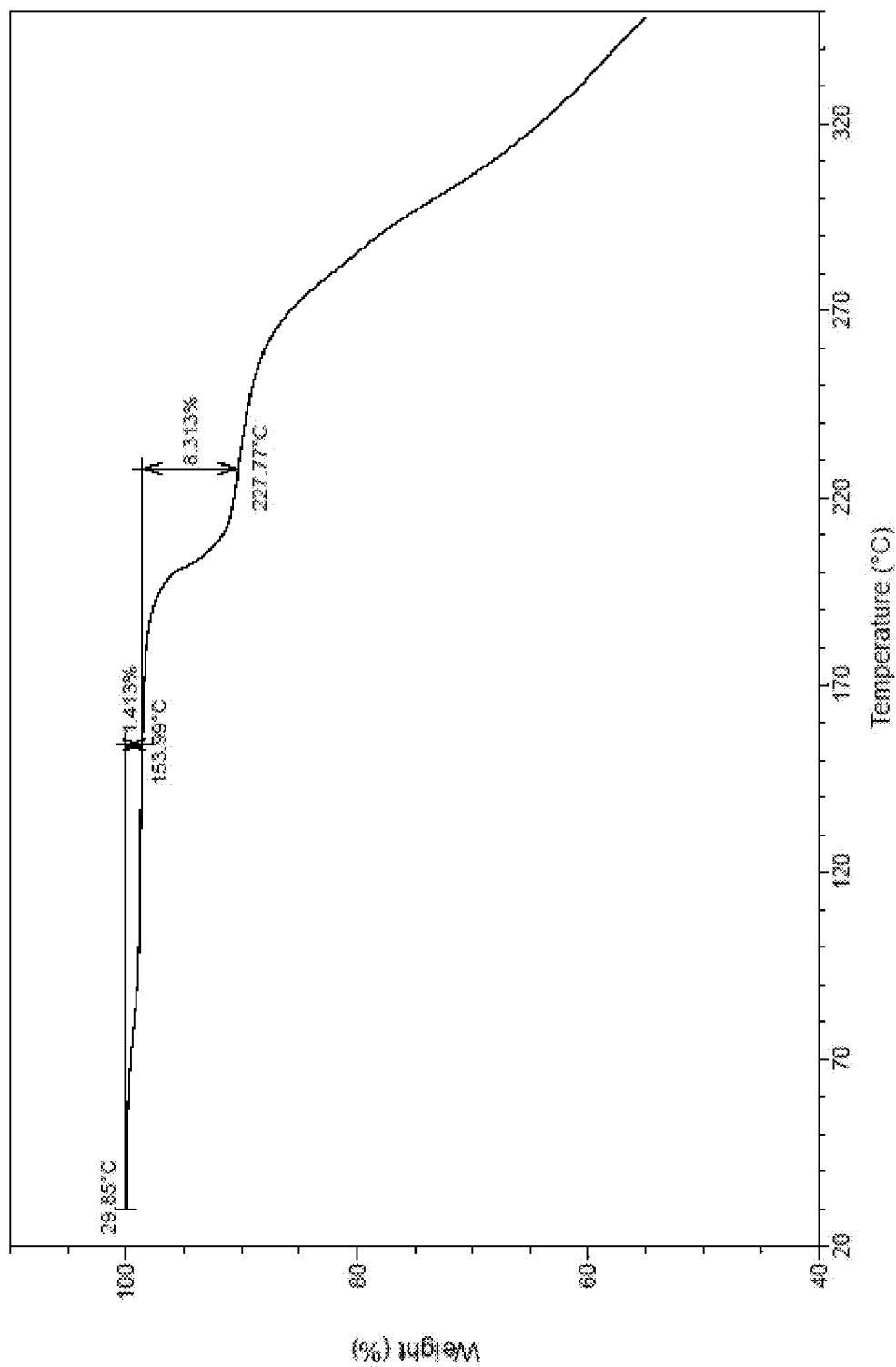
Figure 123:
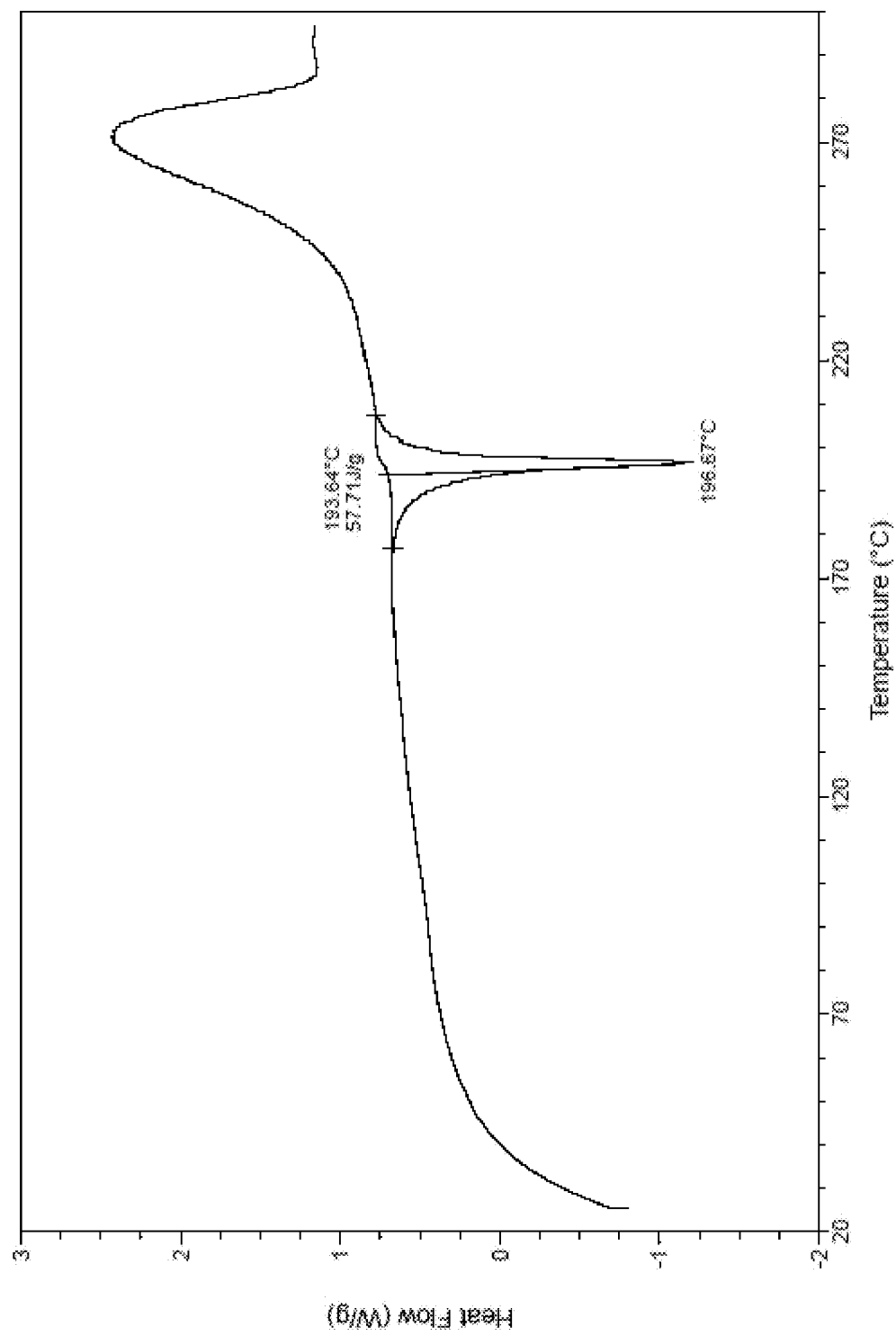
Figure 124:
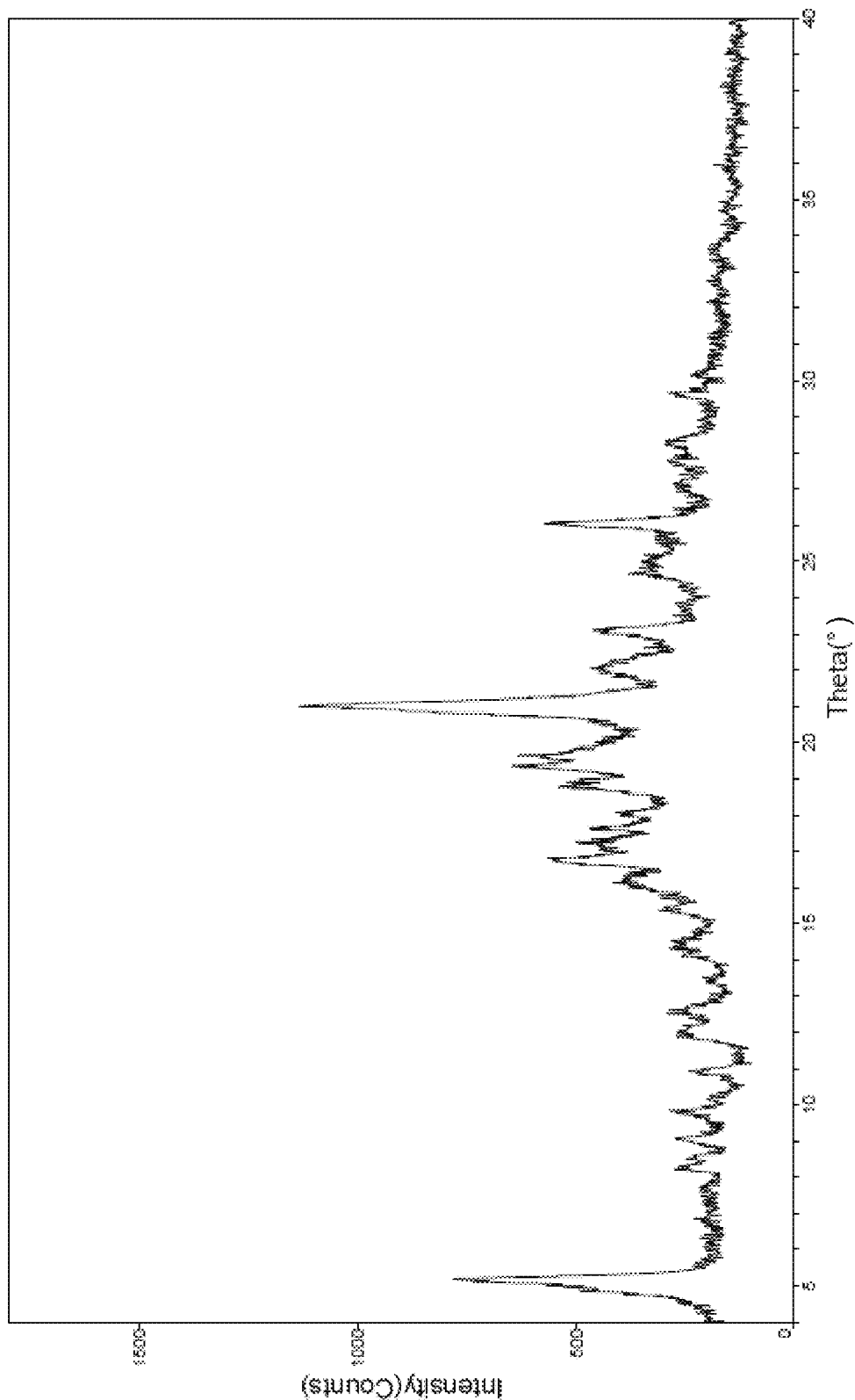
Figure 125:
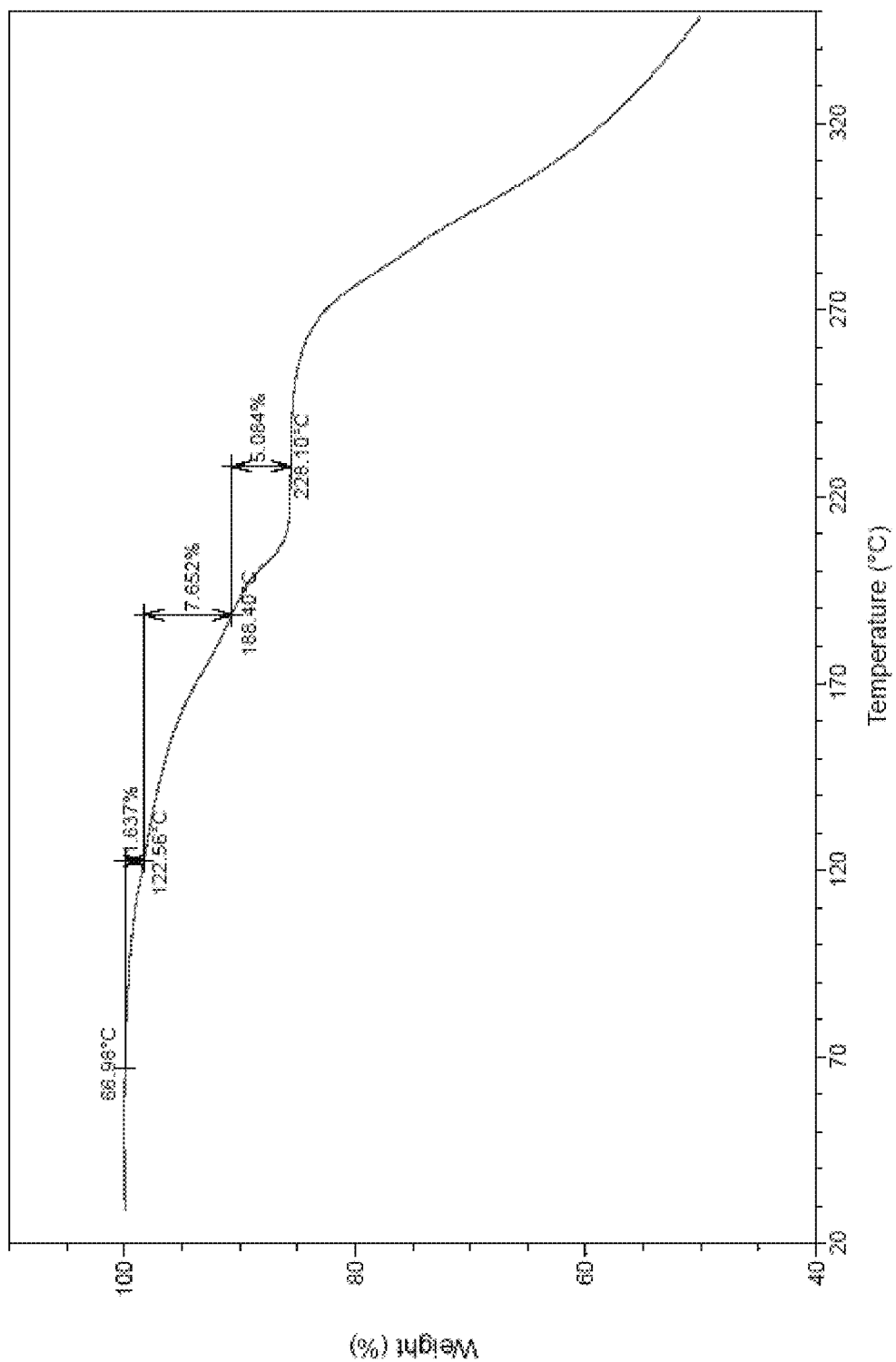
Figure 126:
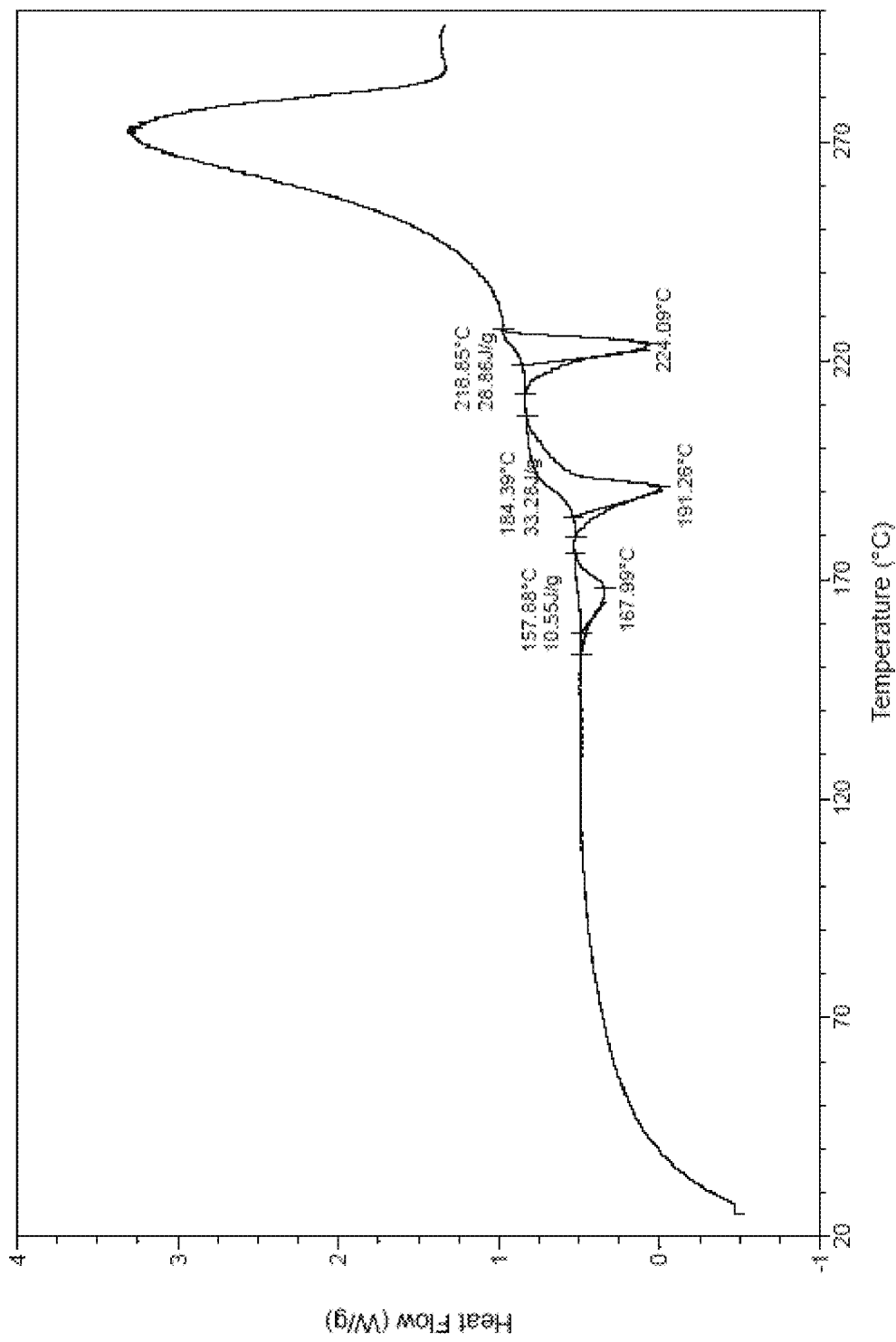
Figure 127:
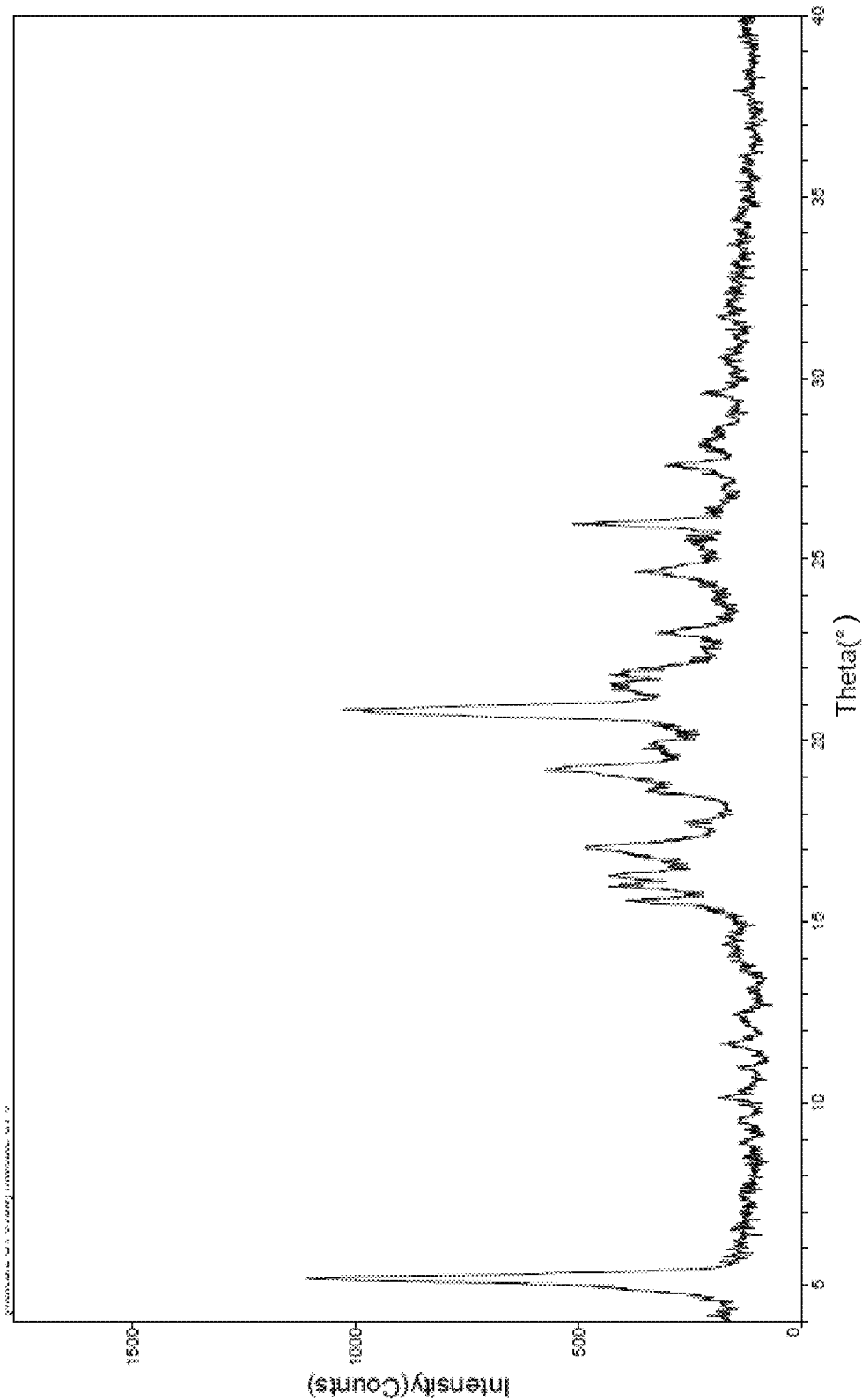
Figure 128:
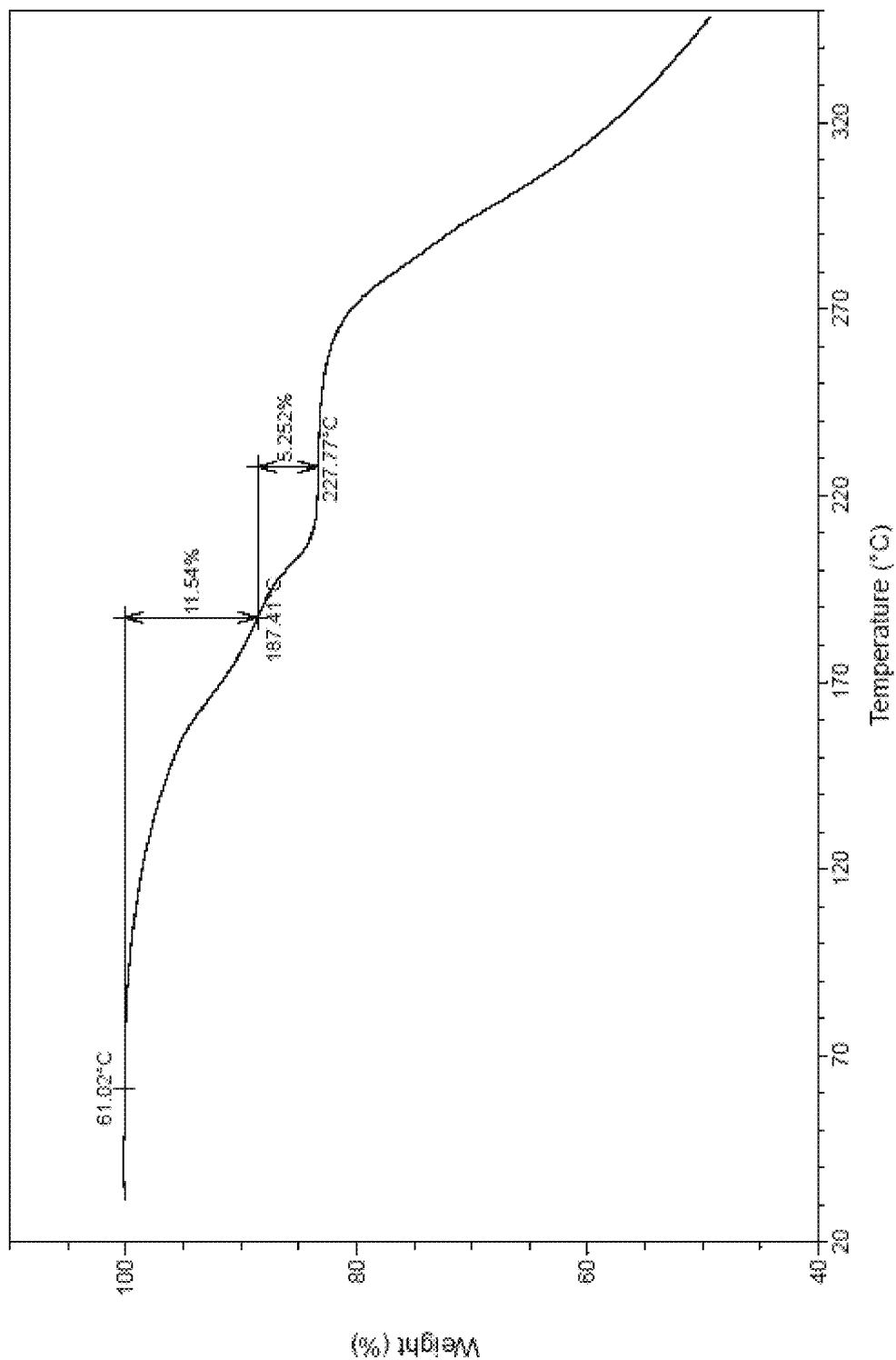
Figure 129:
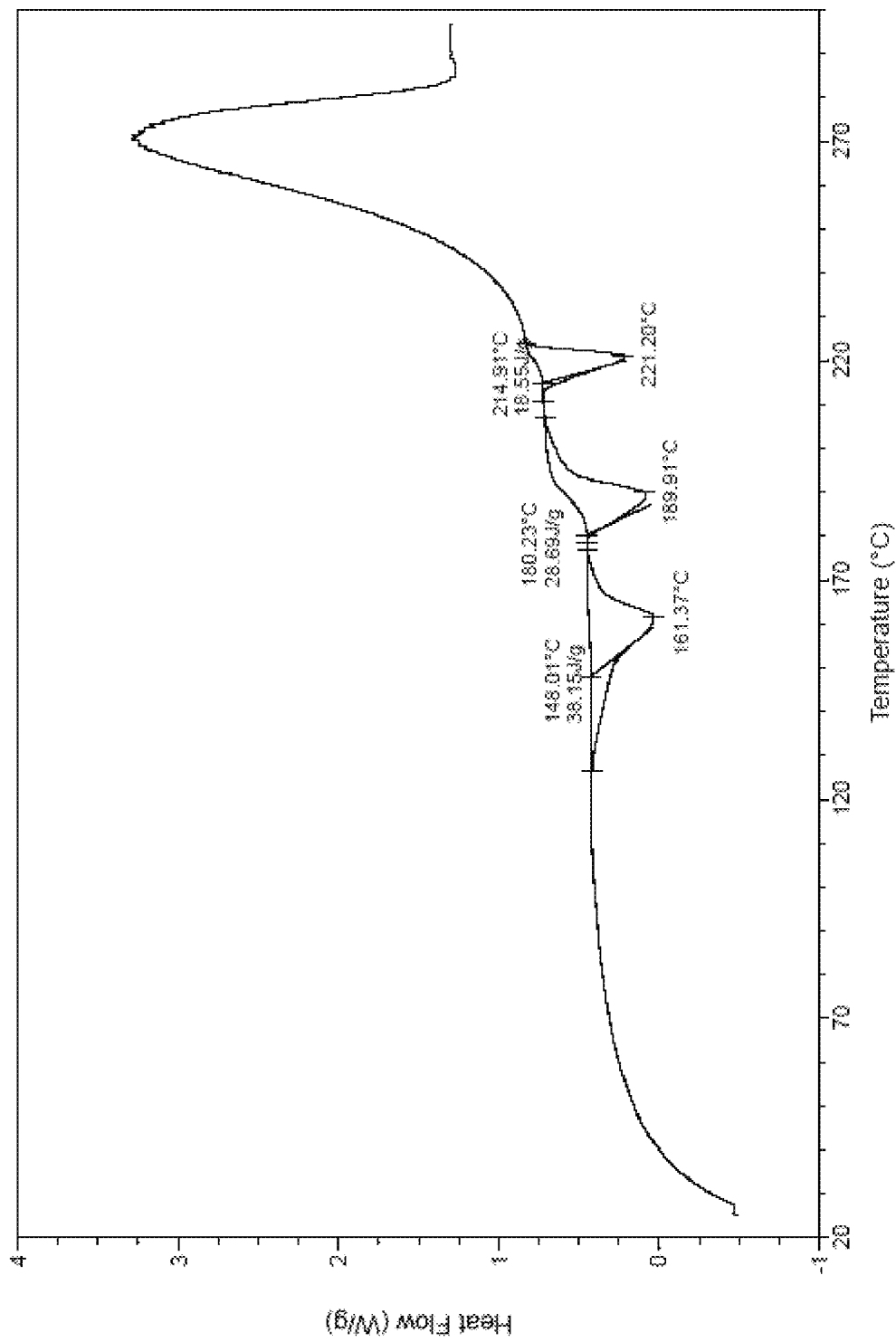
Figure 130:
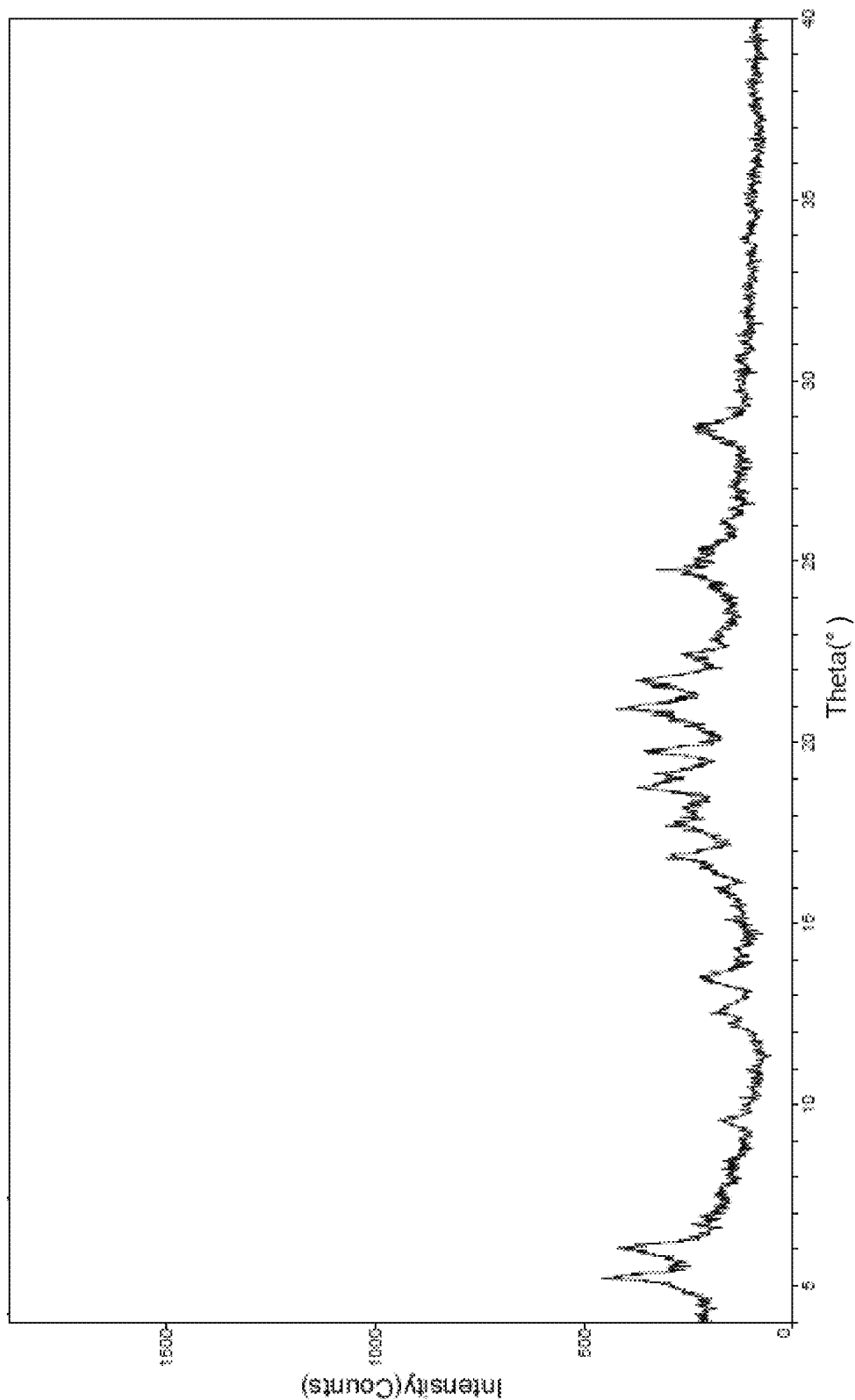
Figure 131:
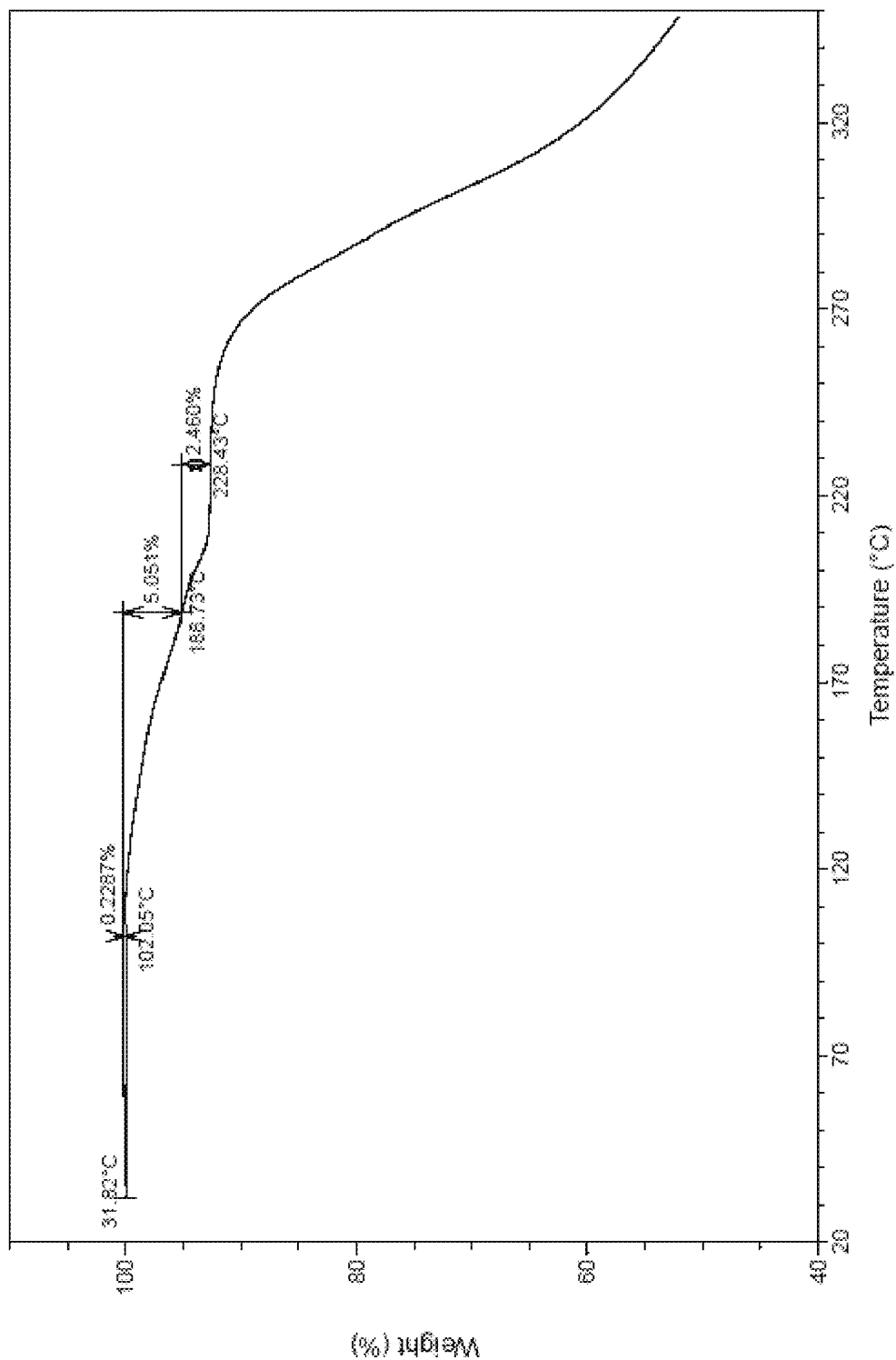
Figure 132:
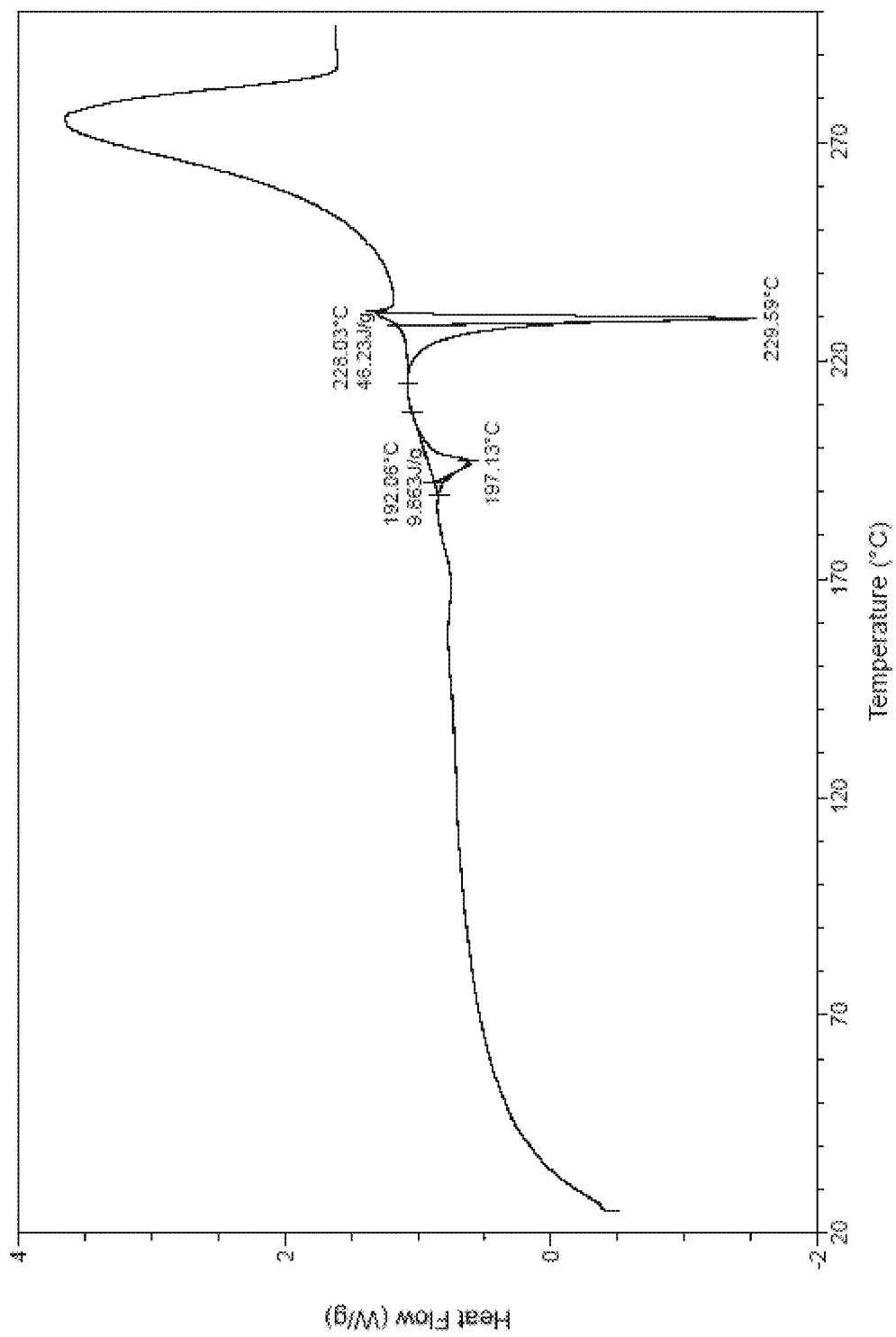
Figure 133:
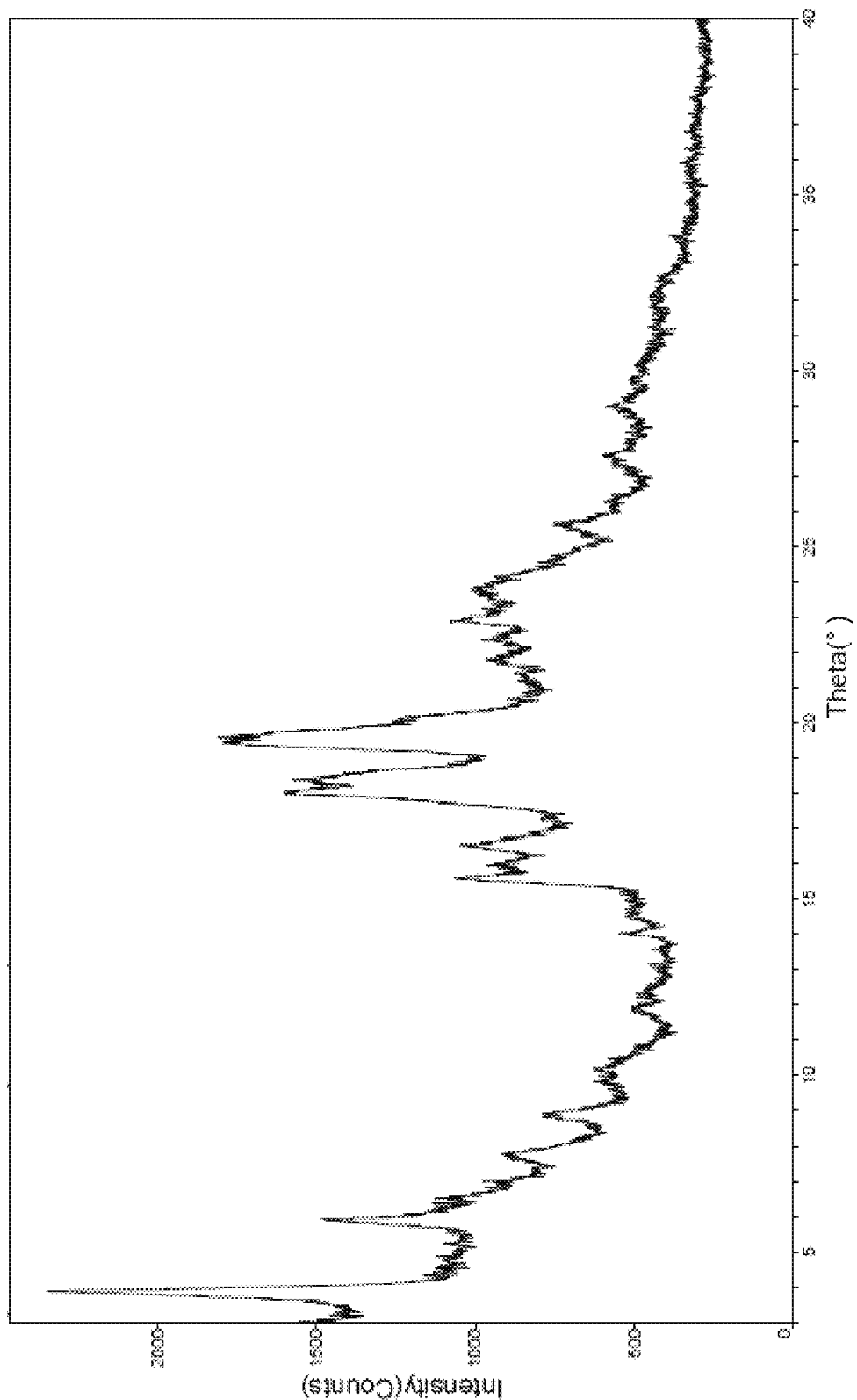

FIG. 133 is an XRPD pattern of Compound 1 tartrate crystalline Form XLV.

Figure 134:
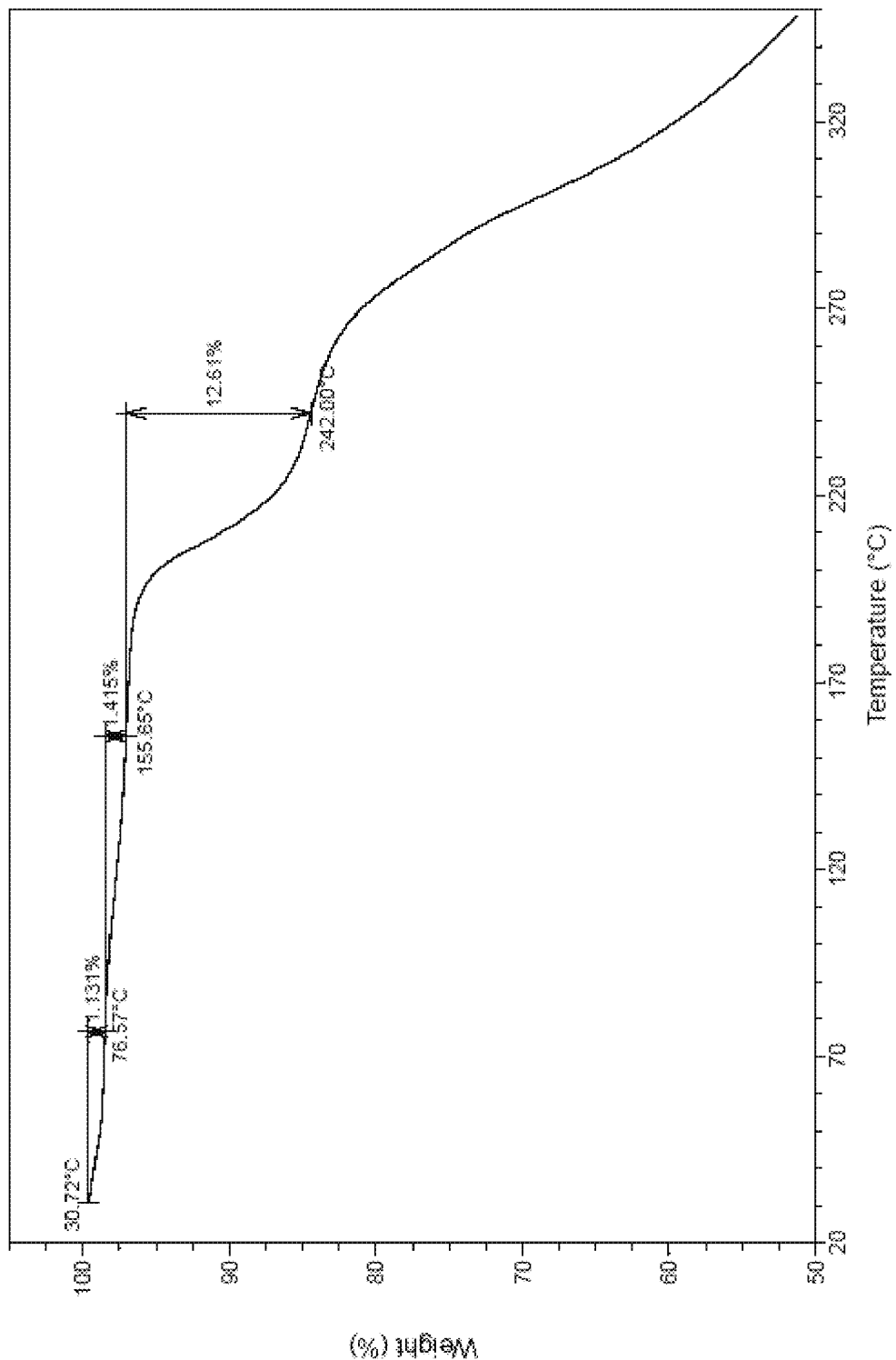

FIG. 134 is a TGA plot of Compound 1 tartrate crystalline Form XLV.

Figure 135:
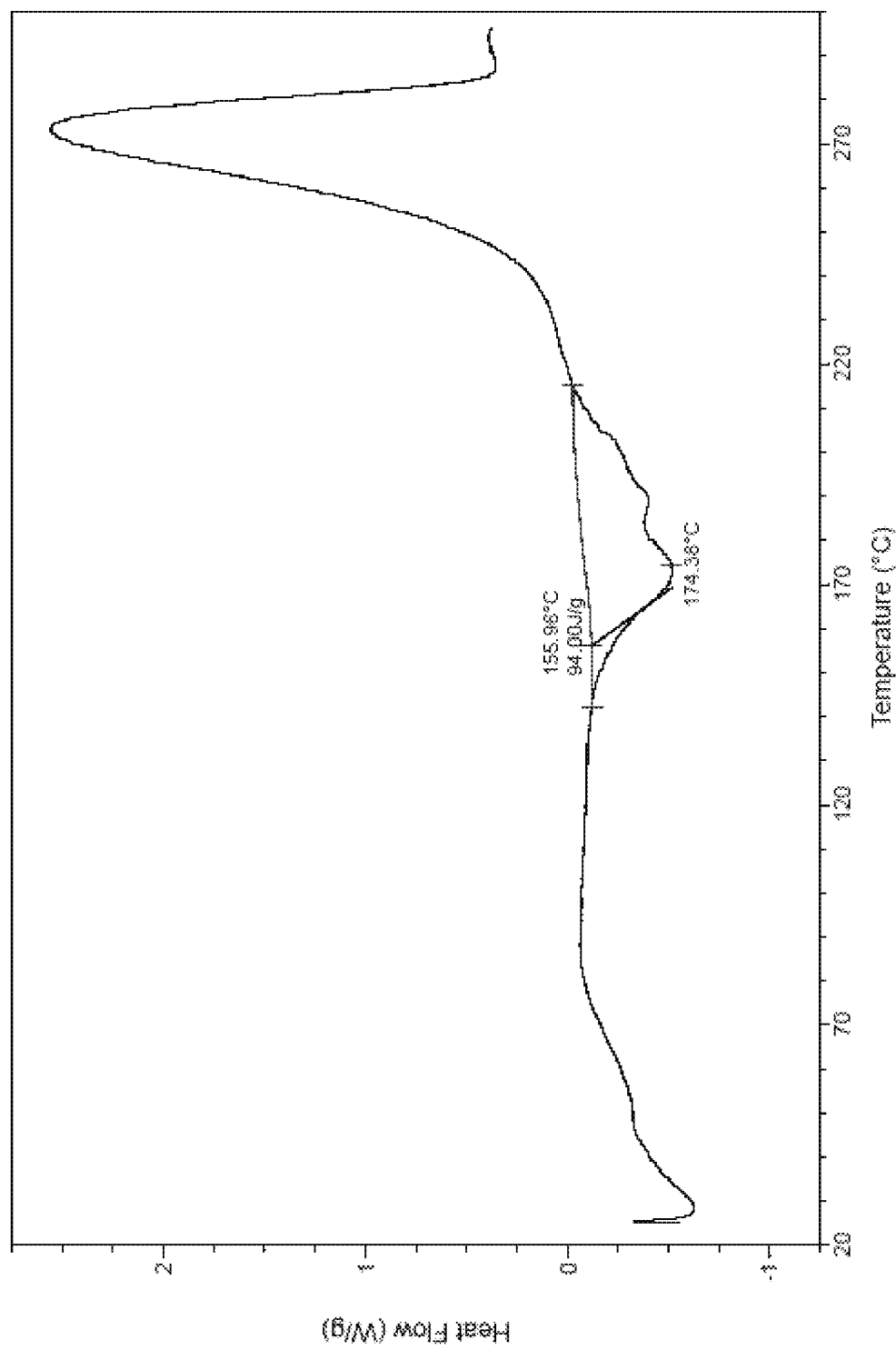

FIG. 135 is a DSC curve of Compound 1 tartrate crystalline Form XLV.

Figure 136:
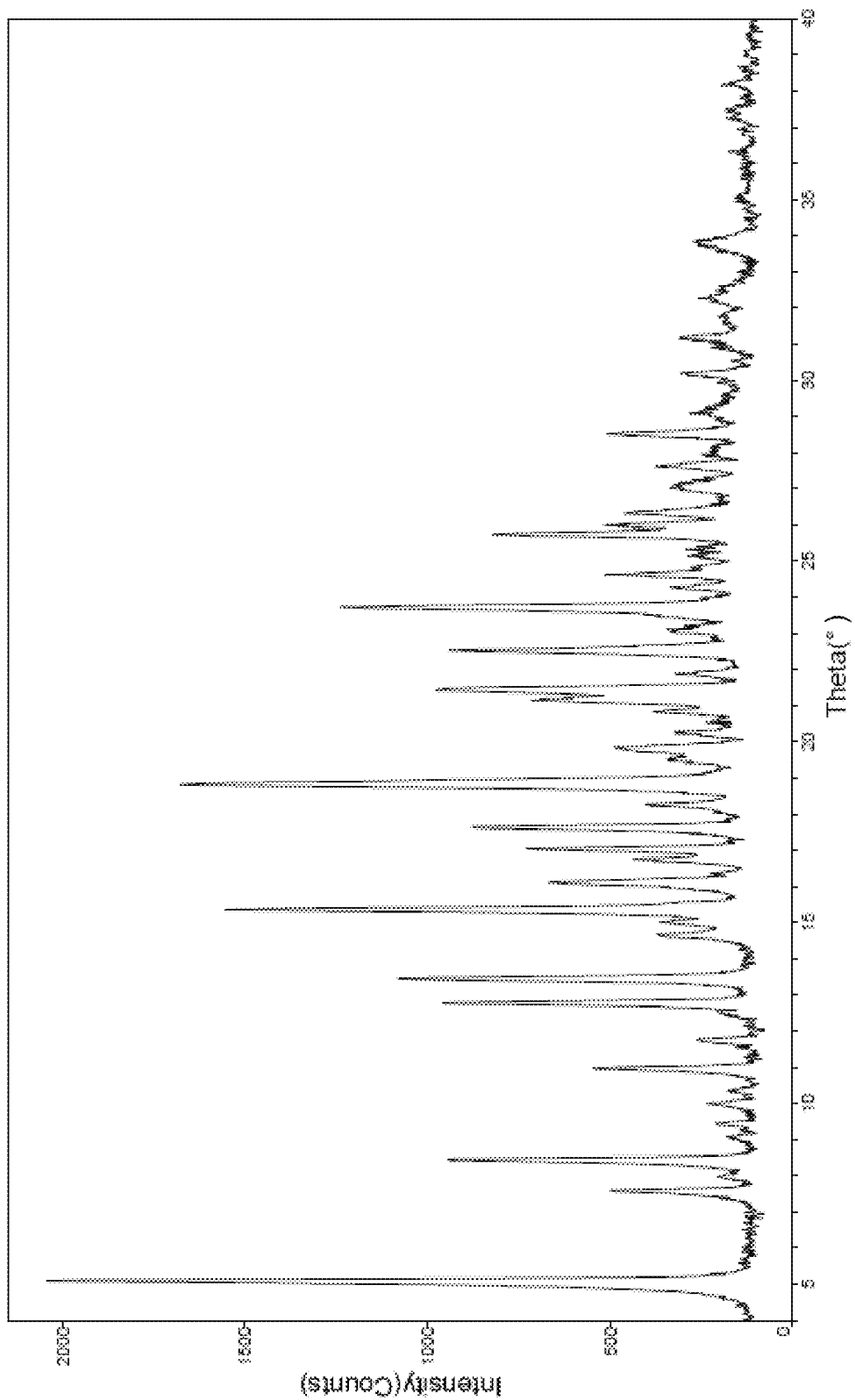

FIG. 136 is an XRPD pattern of Compound 1 hydrochloride crystalline Form XLVI.

Figure 137:
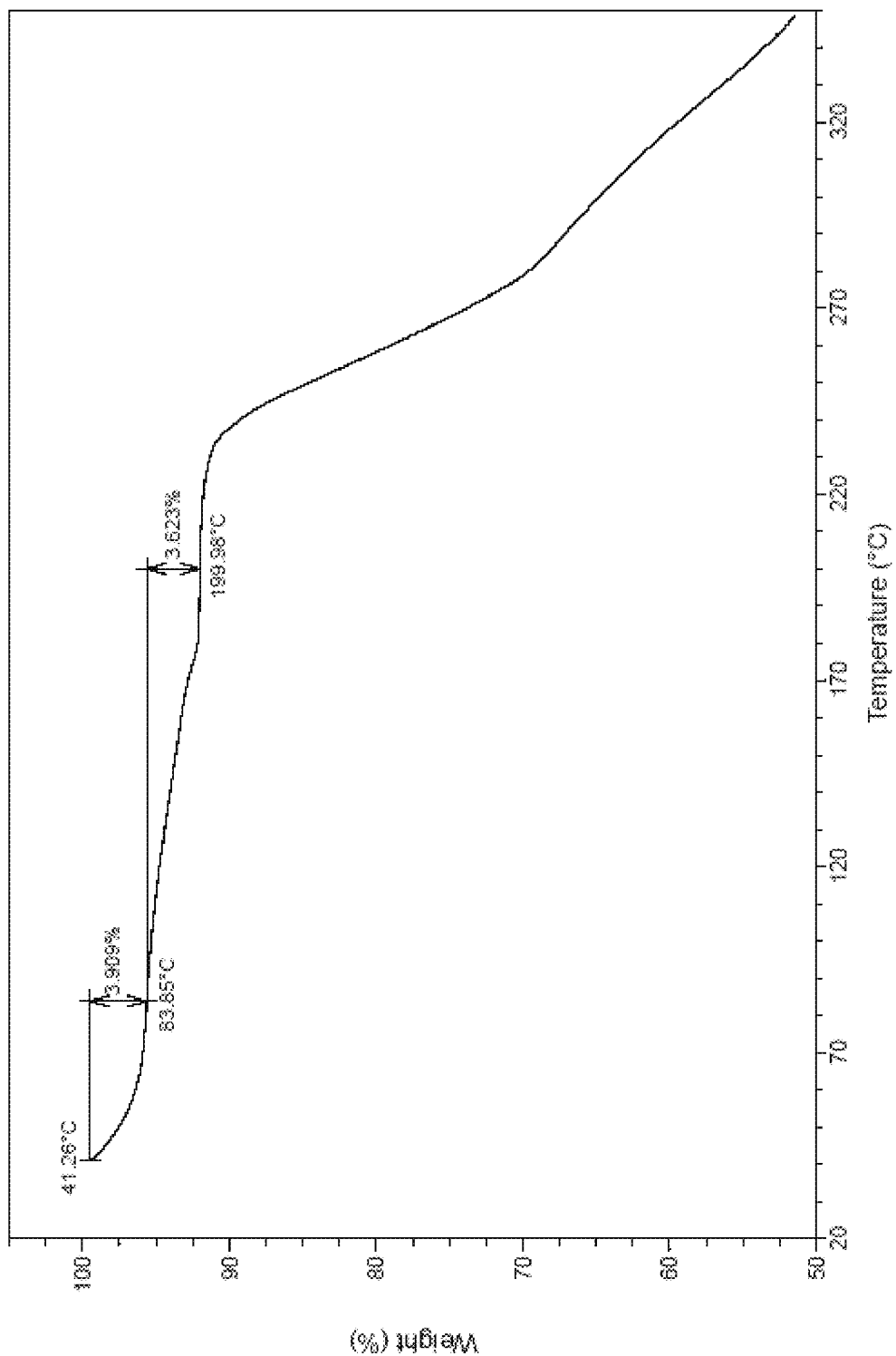

FIG. 137 is a TGA plot of Compound 1 hydrochloride crystalline Form XLVI.

Figure 138:
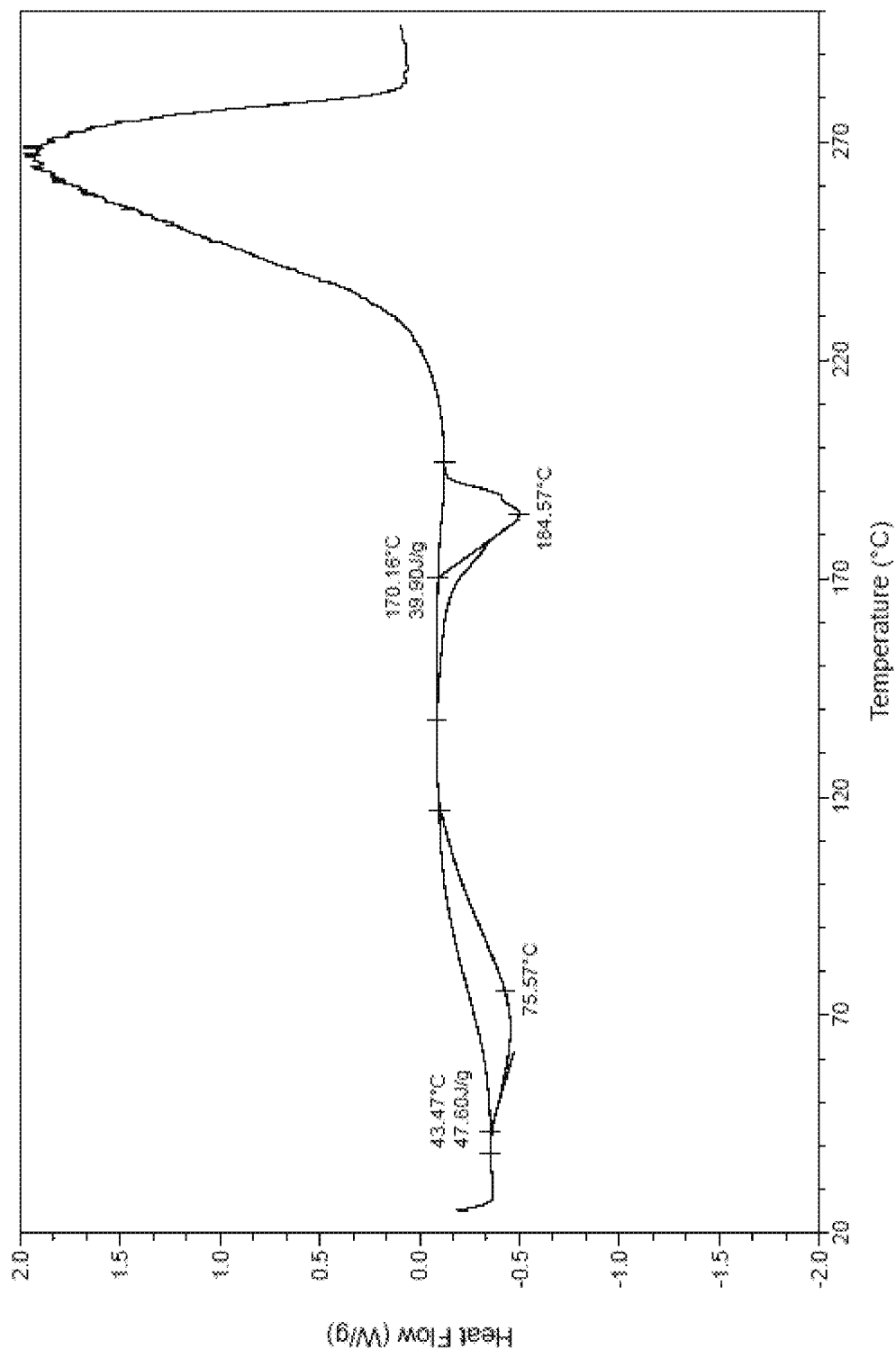

FIG. 138 is a DSC curve of Compound 1 hydrochloride crystalline Form XLVI.

Figure 139:
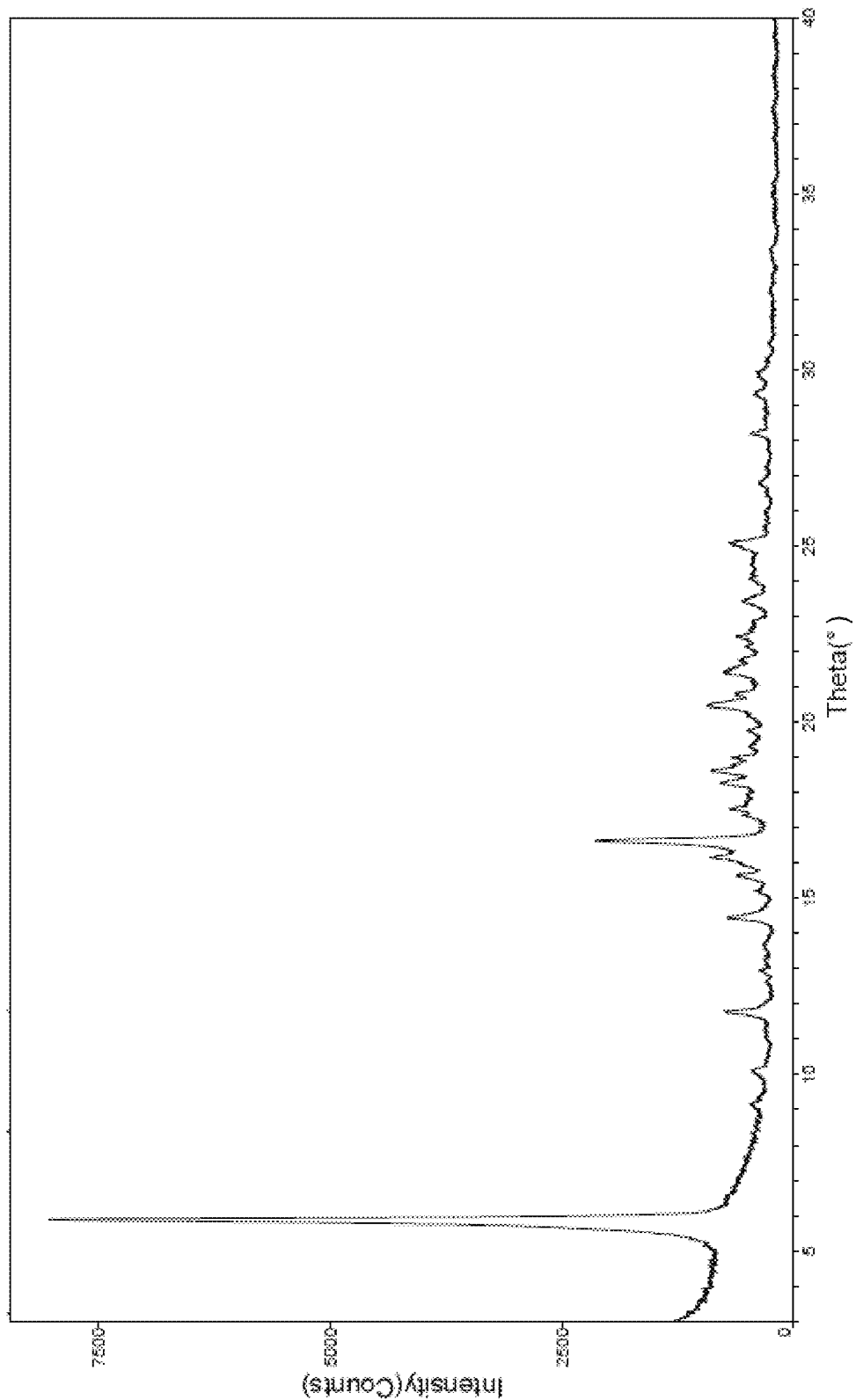

FIG. 139 is an XRPD pattern of Compound 1 hydrochloride crystalline Form XLVII.

Figure 140:
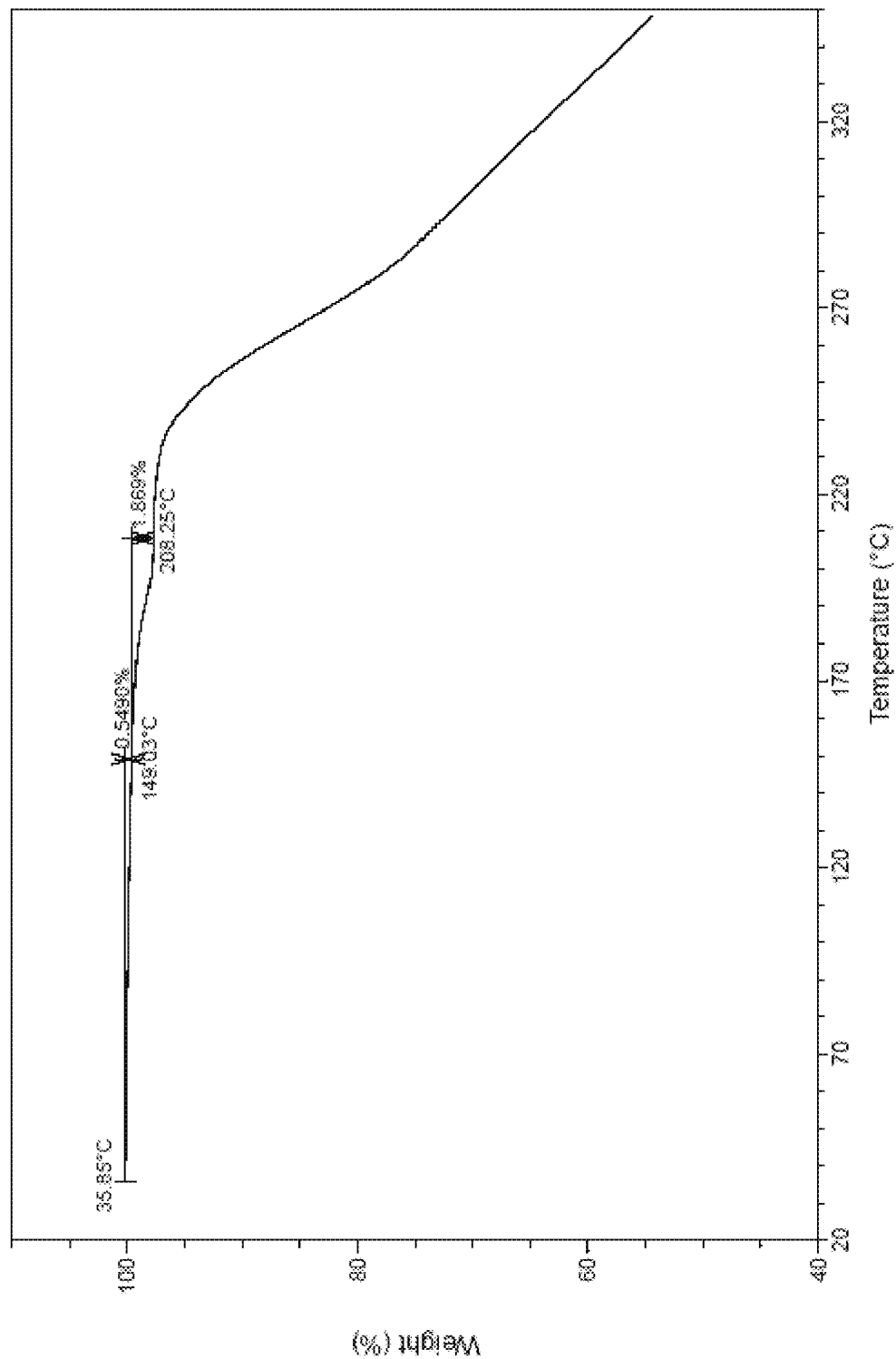

FIG. 140 is a TGA plot of Compound 1 hydrochloride crystalline Form XLVII.

Figure 141:
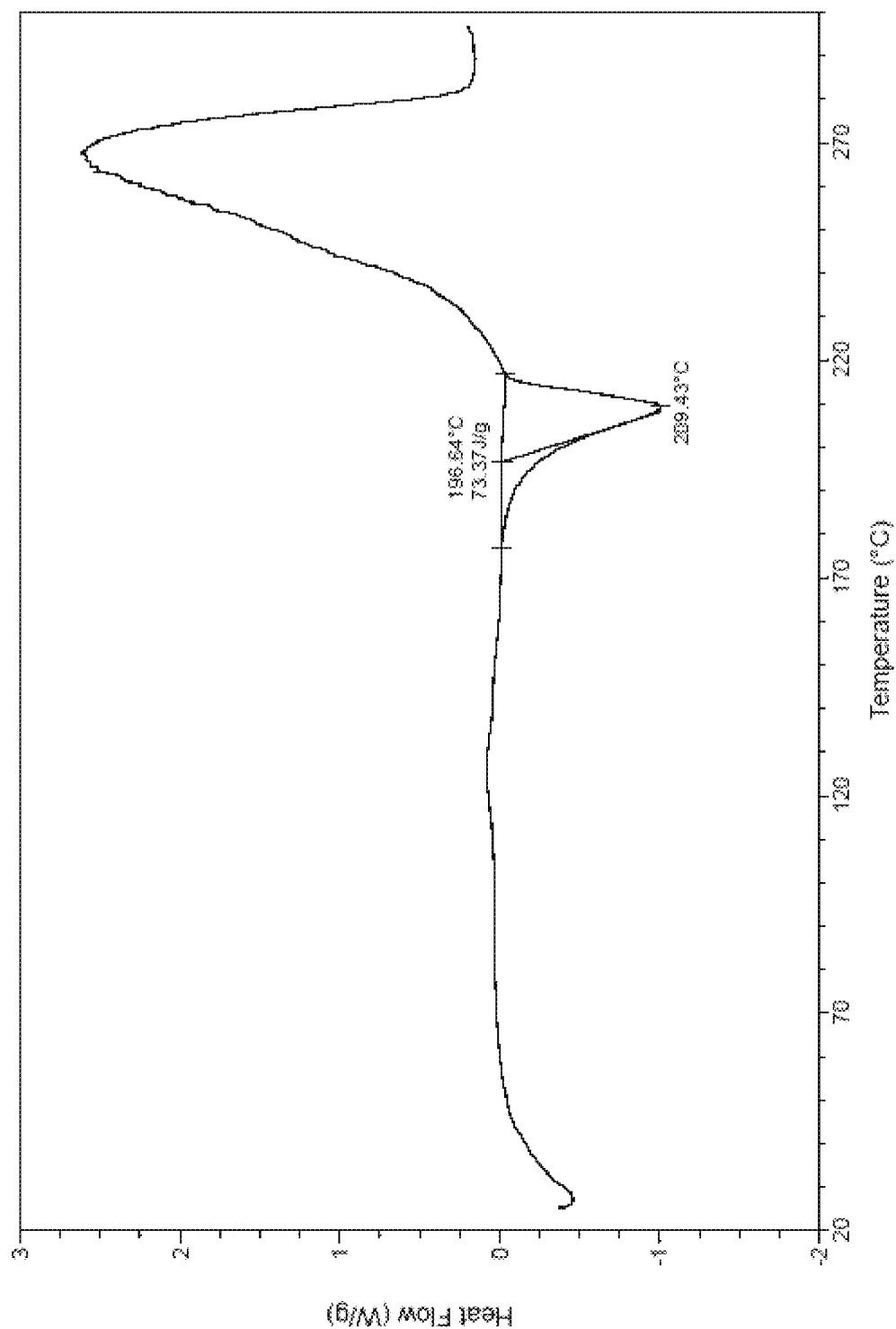

FIG. 141 is a DSC curve of Compound 1 hydrochloride crystalline Form XLVII.

Figure 142:
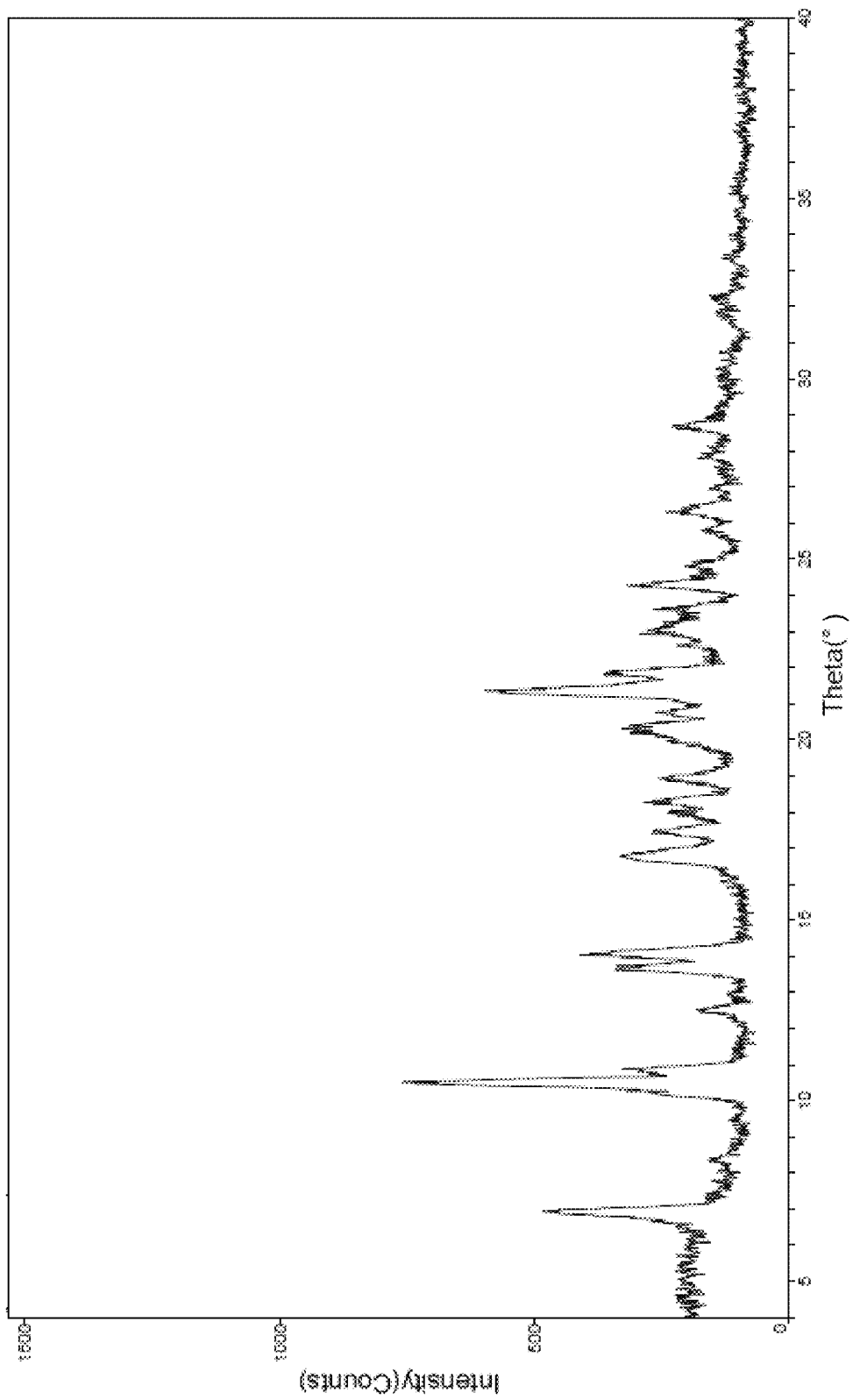

FIG. 142 is an XRPD pattern of Compound 1 hydrochloride crystalline Form XLVIII.

Figure 143:
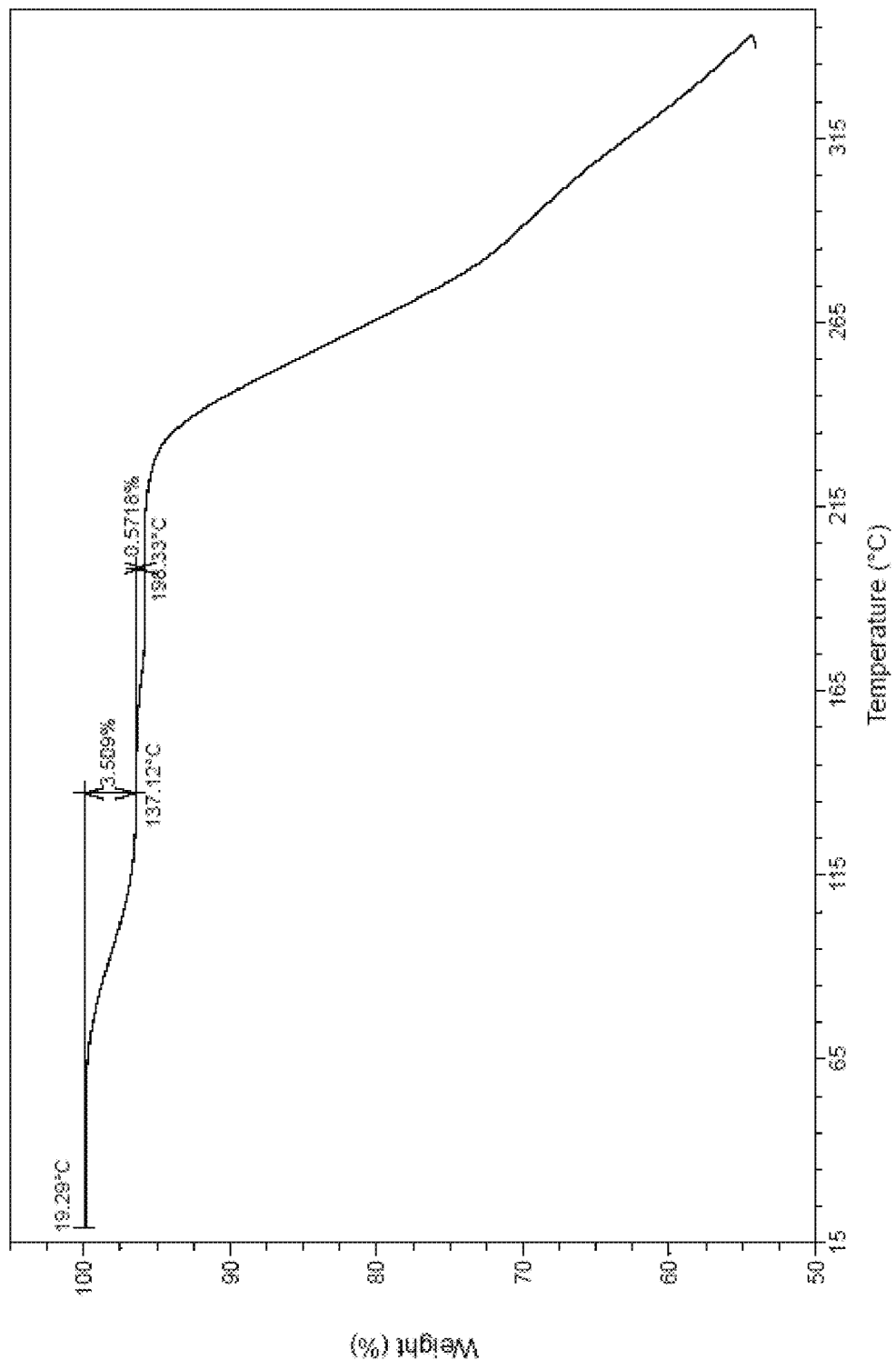

FIG. 143 is a TGA plot of Compound 1 hydrochloride crystalline Form XLVIII.

Figure 144:
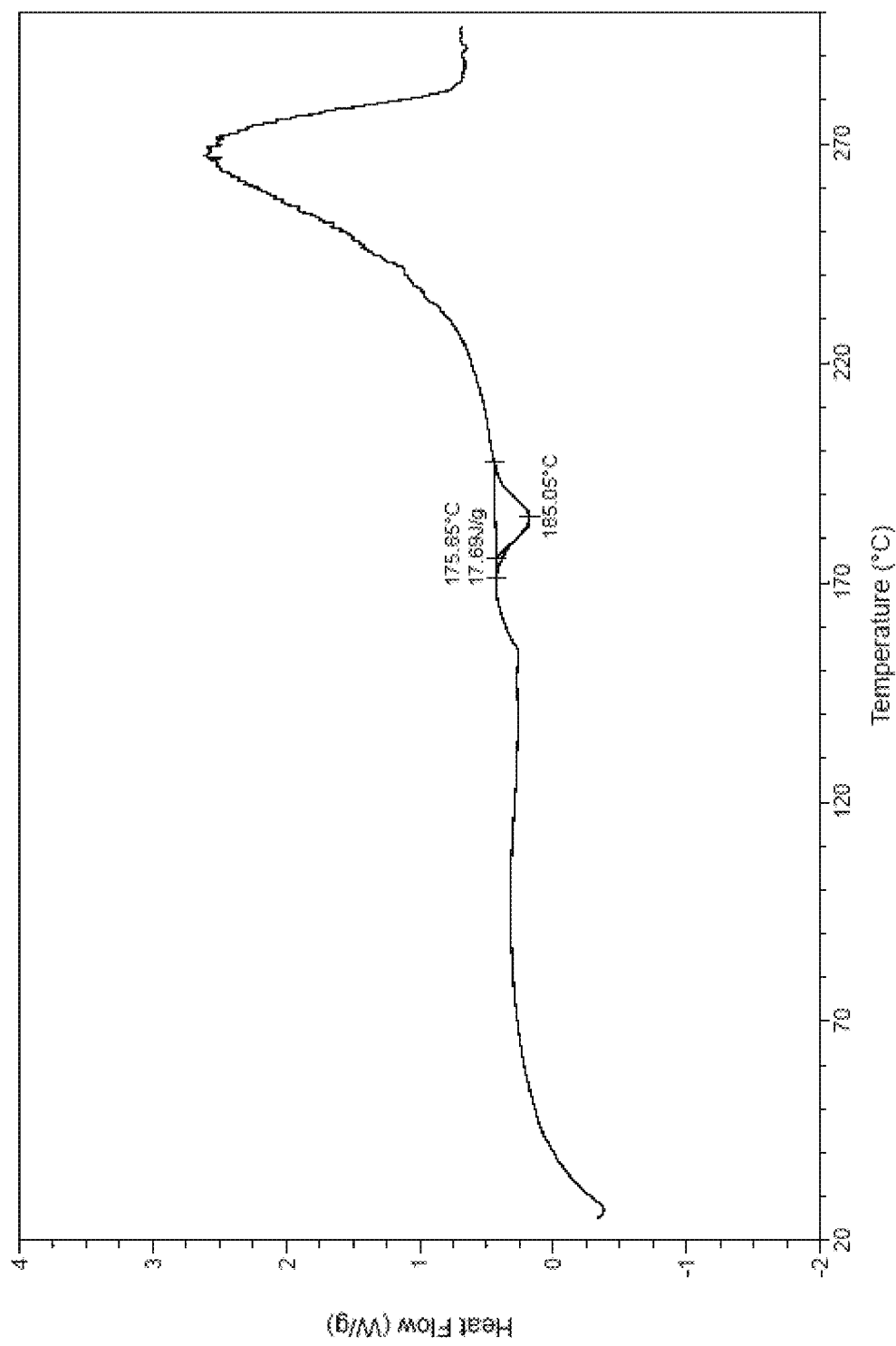

FIG. 144 is a DSC curve of Compound 1 hydrochloride crystalline Form XLVIII.

Figure 145:
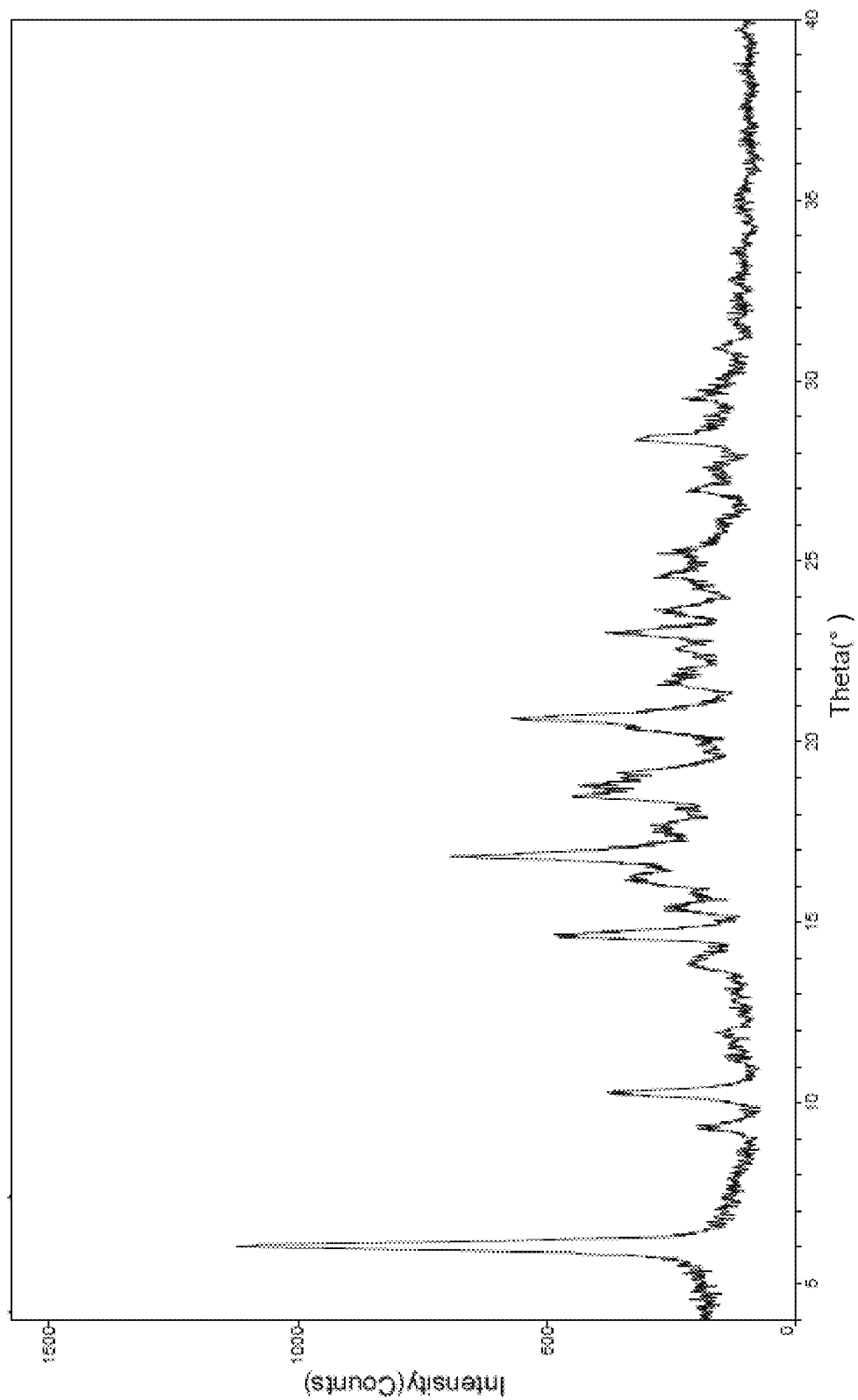

FIG. 145 is an XRPD pattern of Compound 1 hydrochloride crystalline Form XLIX.

Figure 146:
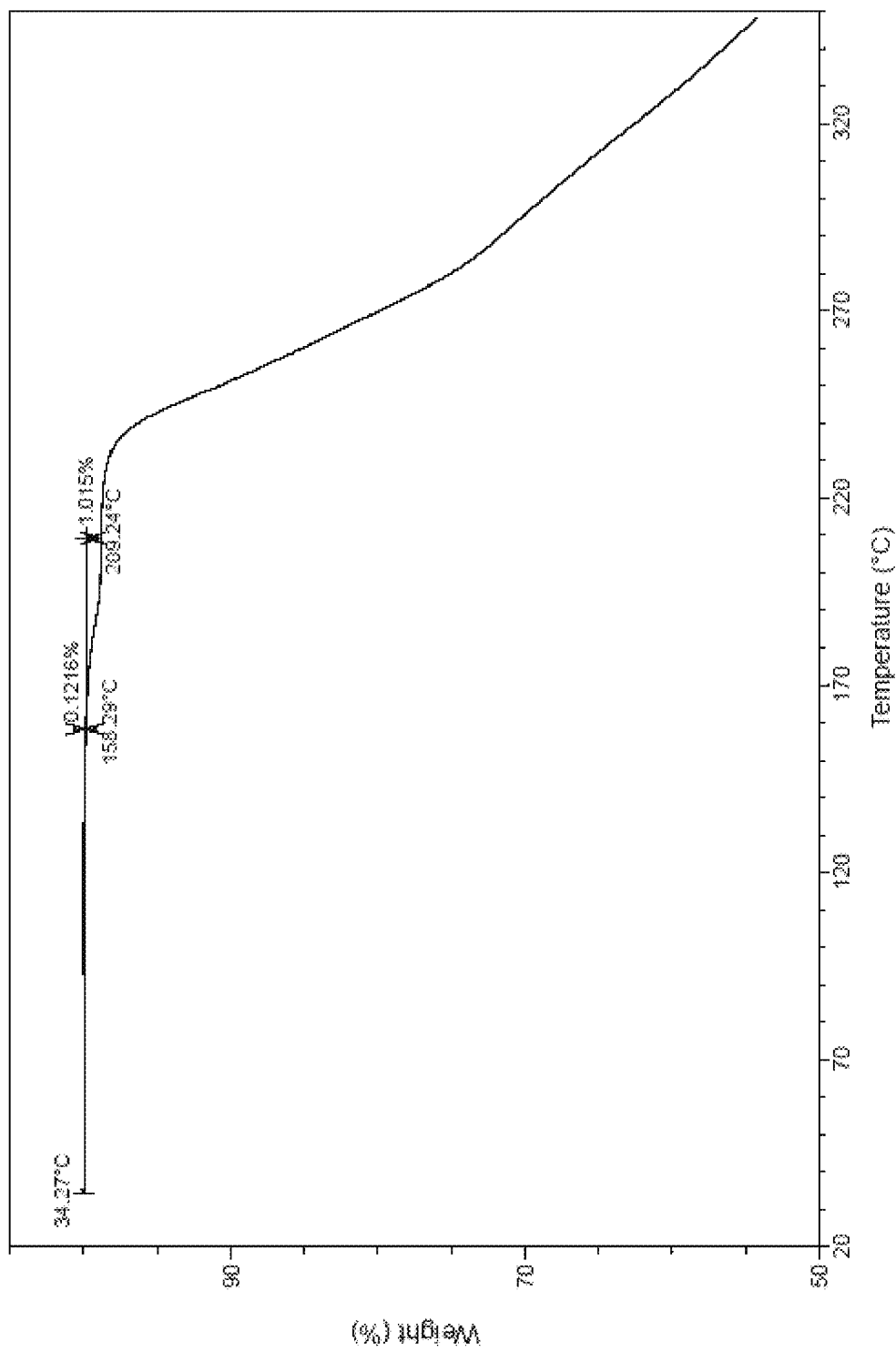

FIG. 146 is a TGA plot of Compound 1 hydrochloride crystalline Form XLIX.

Figure 147:
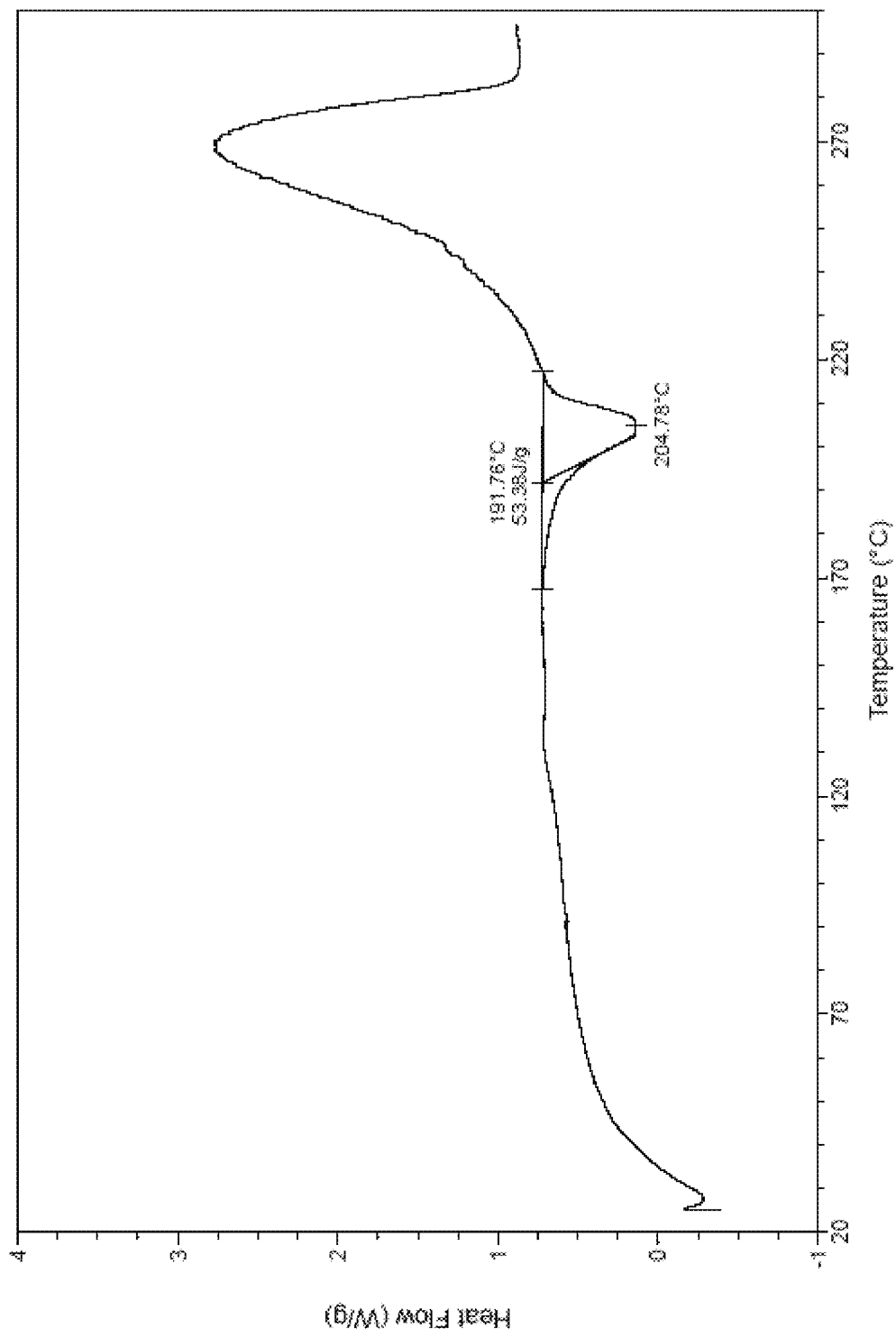

FIG. 147 is a DSC curve of Compound 1 hydrochloride crystalline Form XLIX.

Figure 148:
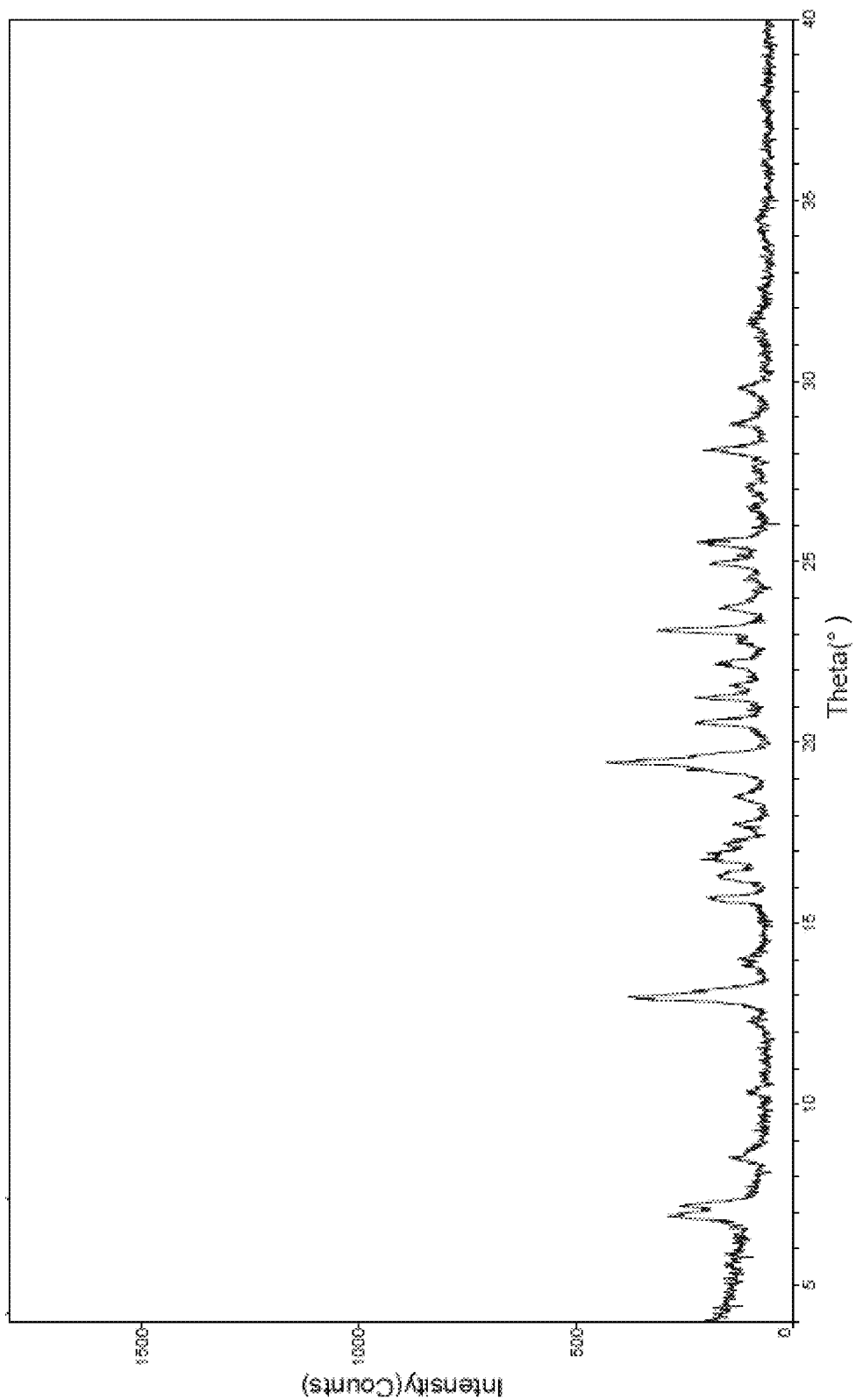

FIG. 148 is an XRPD pattern of Compound 1 hydrochloride crystalline Form L.

Figure 149:
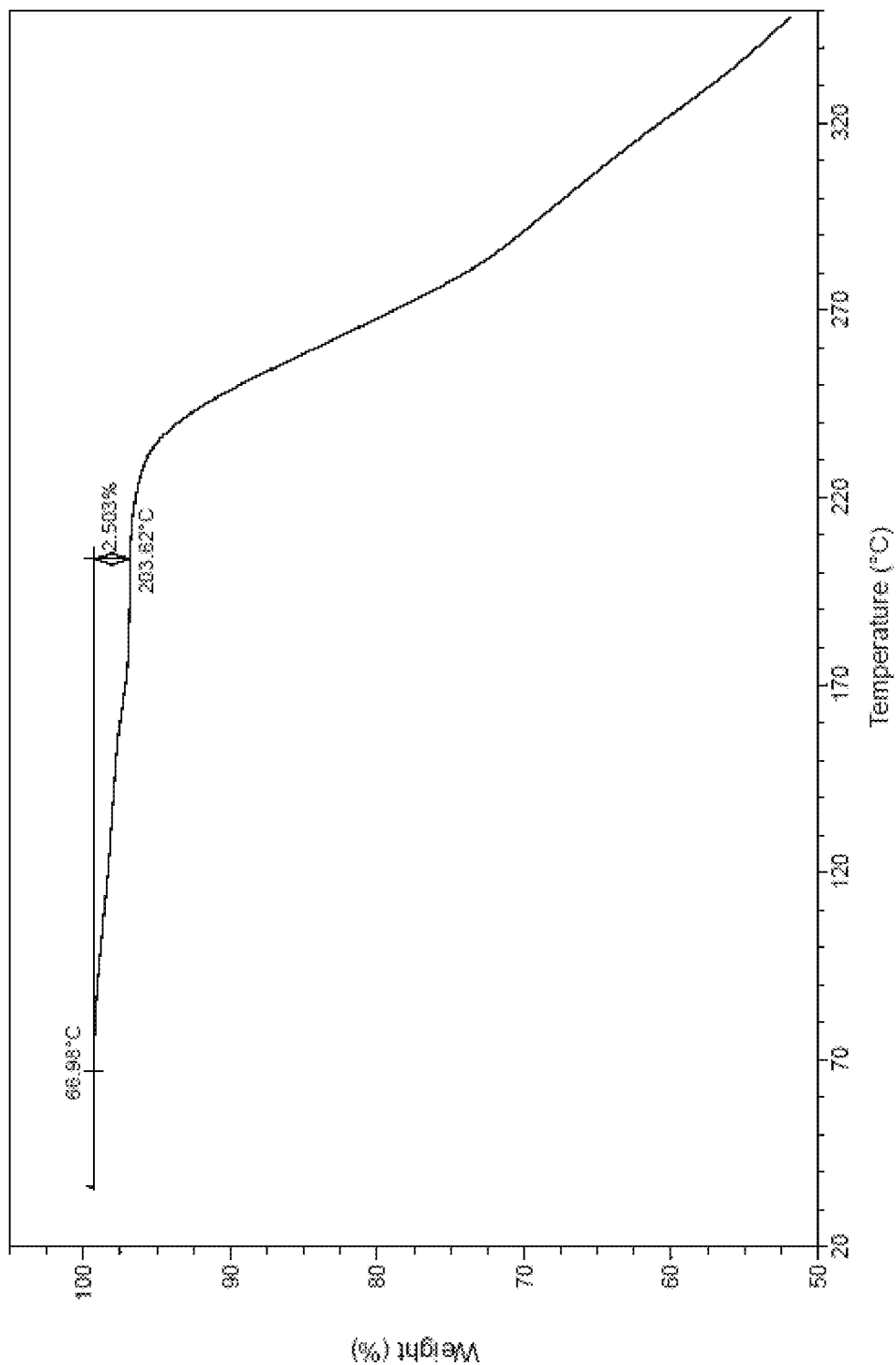

FIG. 149 is a TGA plot of Compound 1 hydrochloride crystalline Form L.

Figure 150:
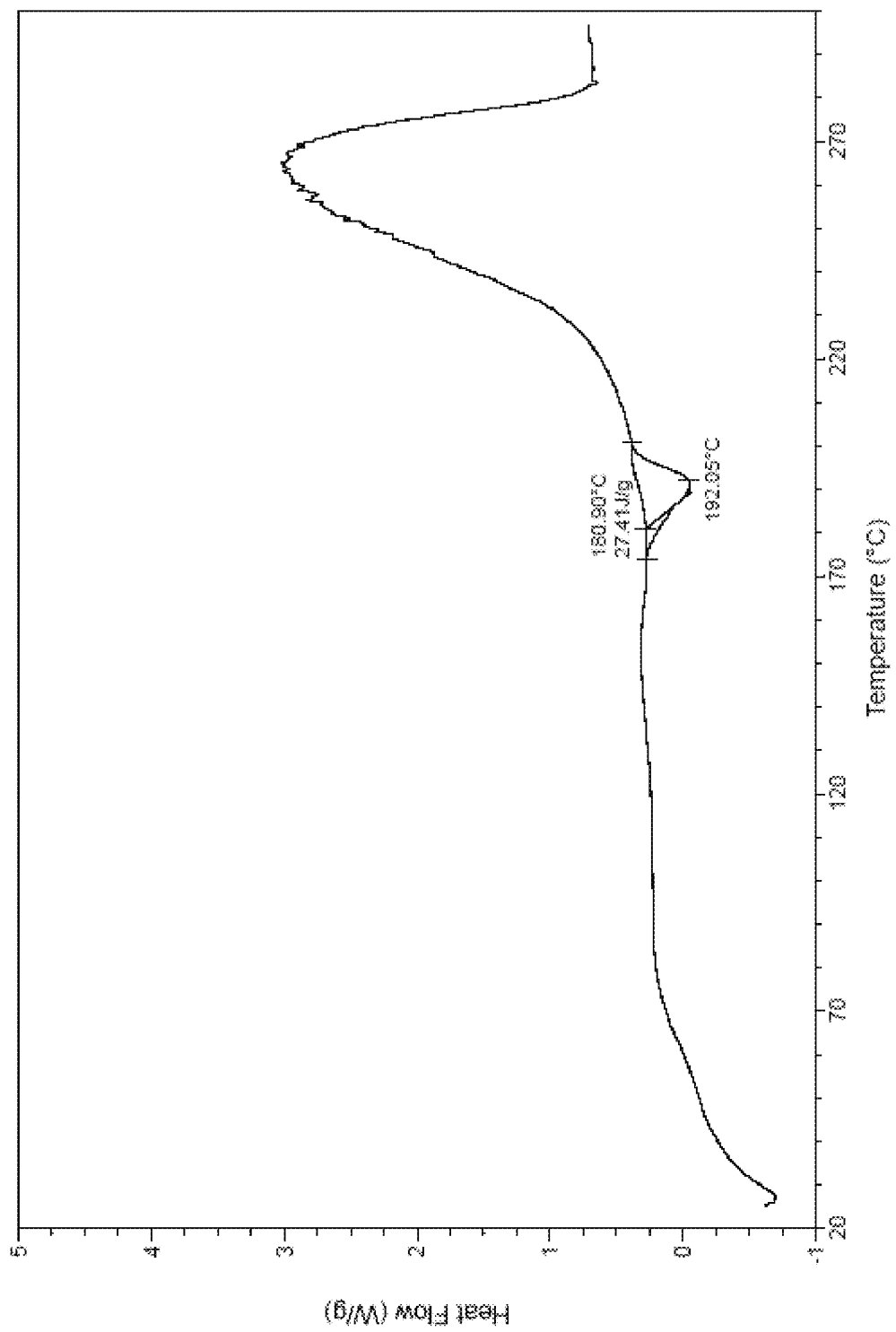

FIG. 150 is a DSC curve of Compound 1 hydrochloride crystalline Form L.

Figure 151:
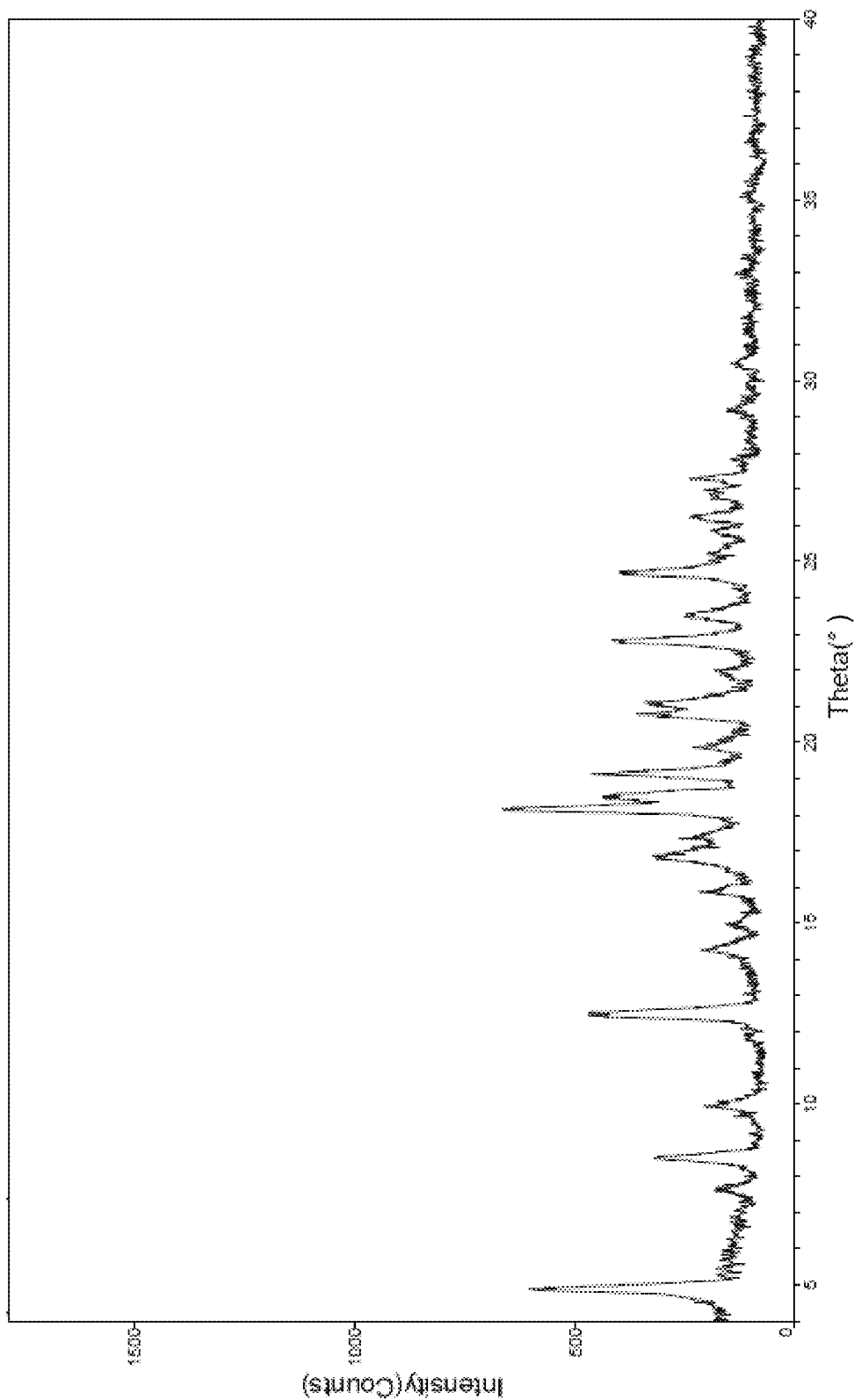

FIG. 151 is an XRPD pattern of Compound 1 hydrochloride crystalline Form LI.

Figure 152:
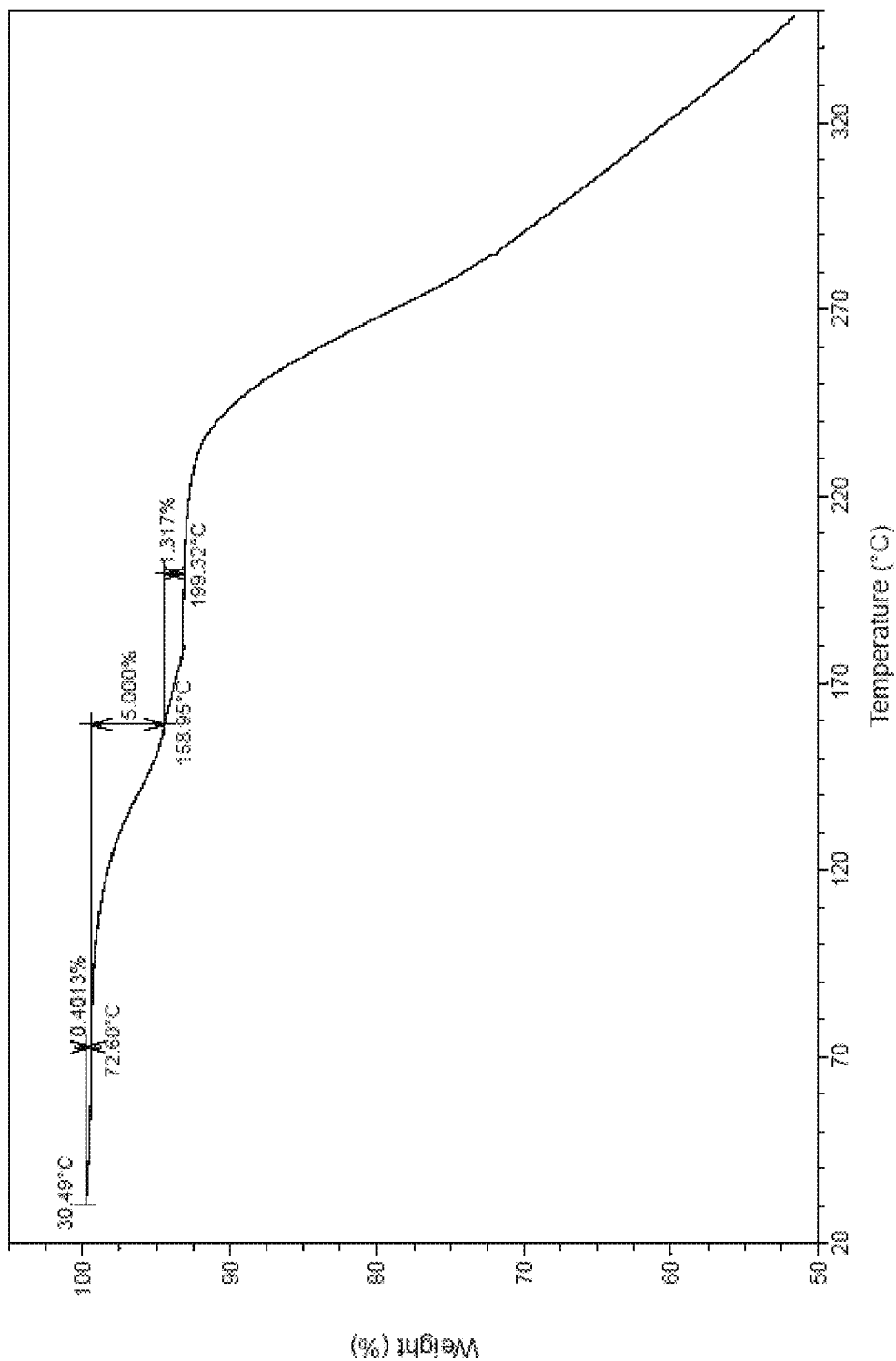

FIG. 152 is a TGA plot of Compound 1 hydrochloride crystalline Form LI.

Figure 153:
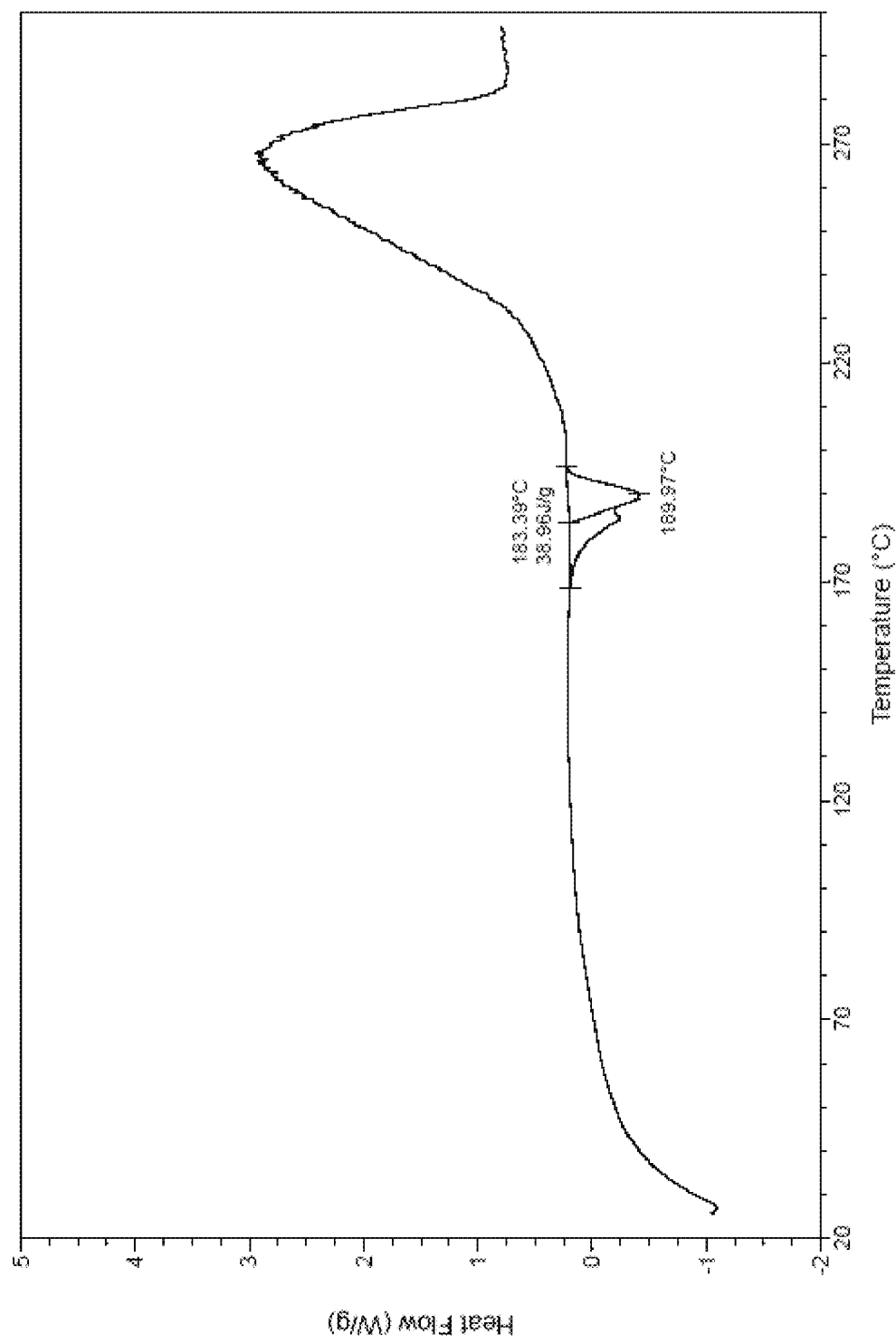

FIG. 153 is a DSC curve of Compound 1 hydrochloride crystalline Form LI.

Figure 154:
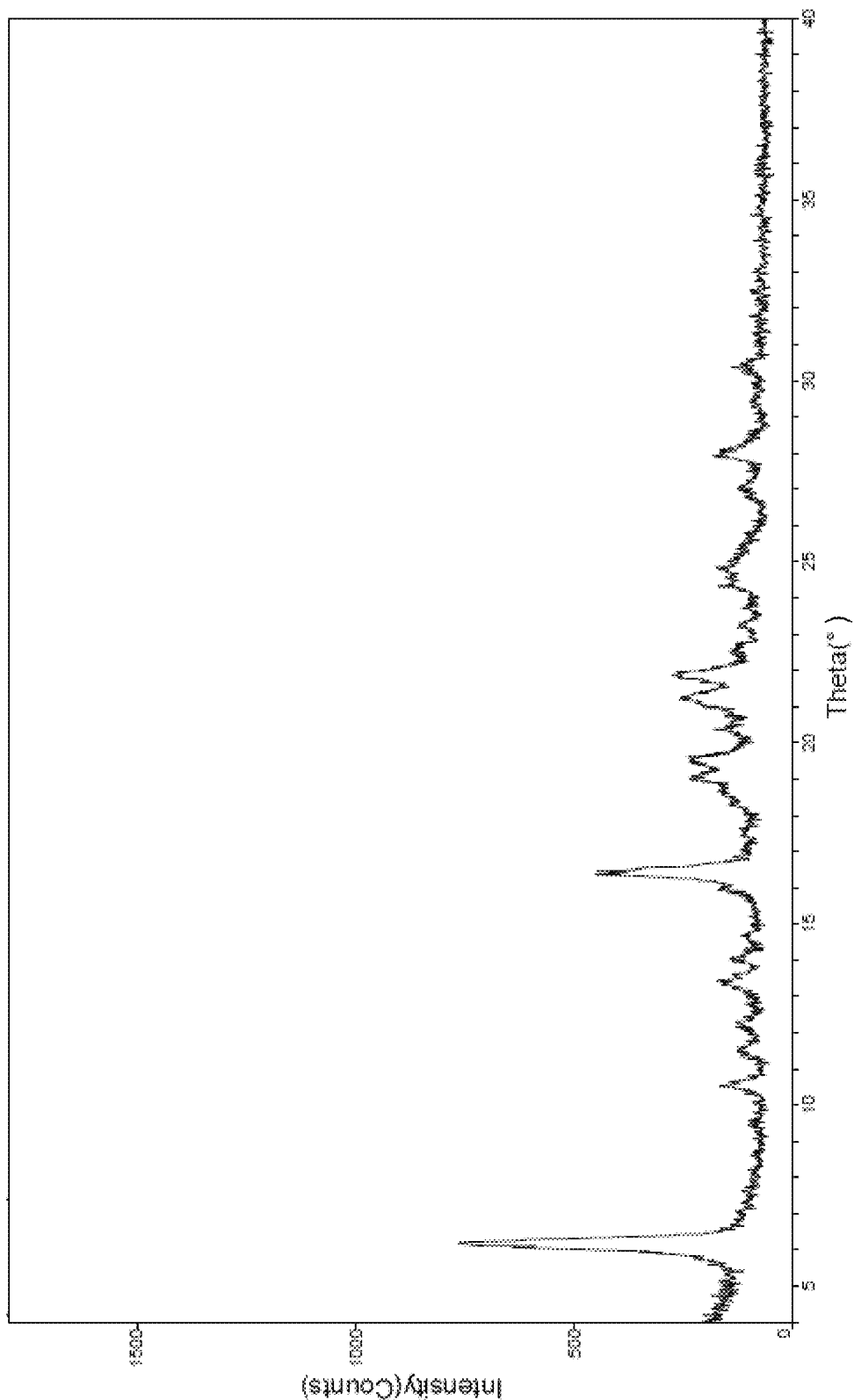

FIG. 154 is an XRPD pattern of Compound 1 hydrochloride crystalline Form LII.

Figure 155:
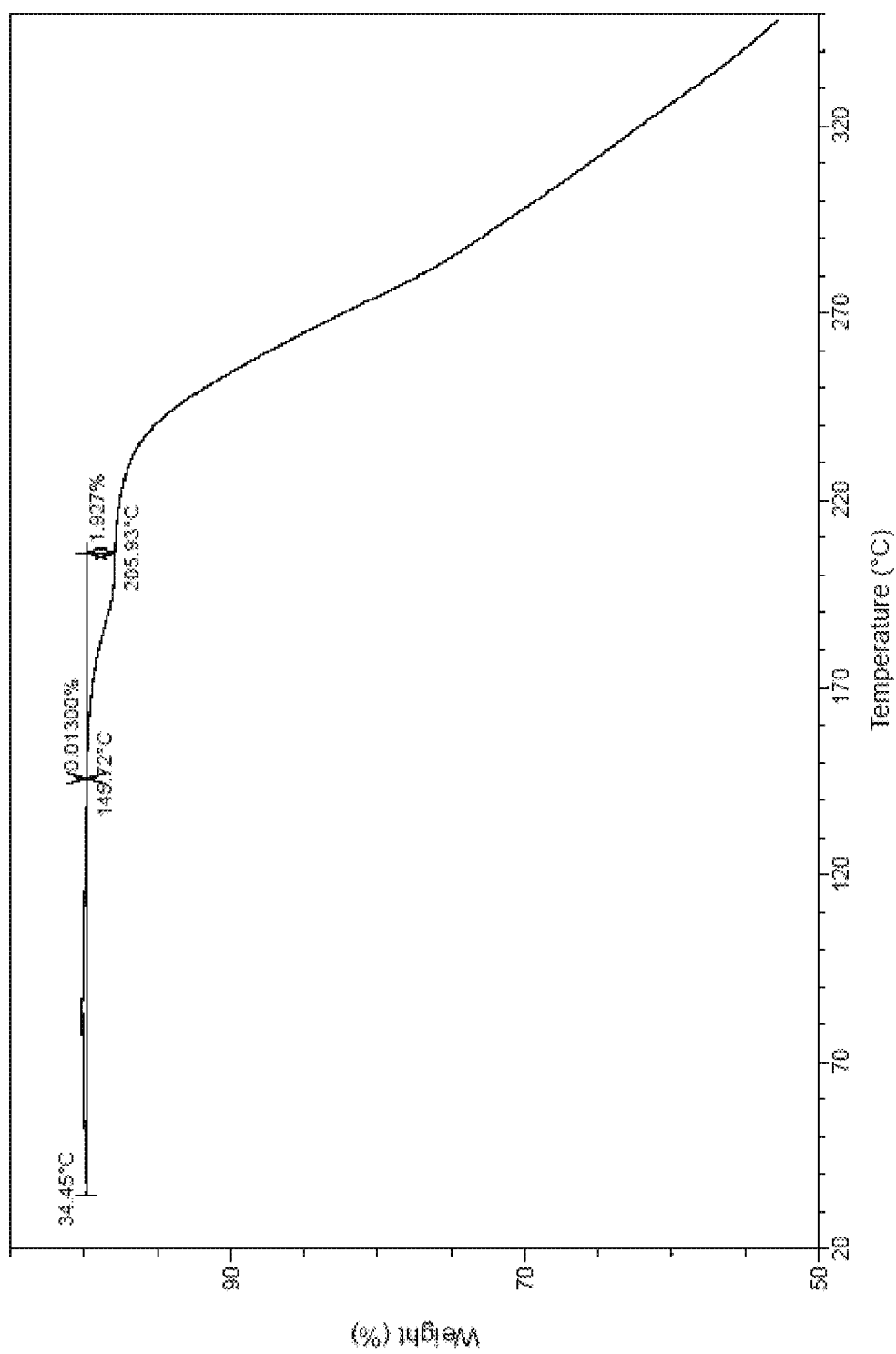

FIG. 155 is a TGA plot of Compound 1 hydrochloride crystalline Form LII.

Figure 156:
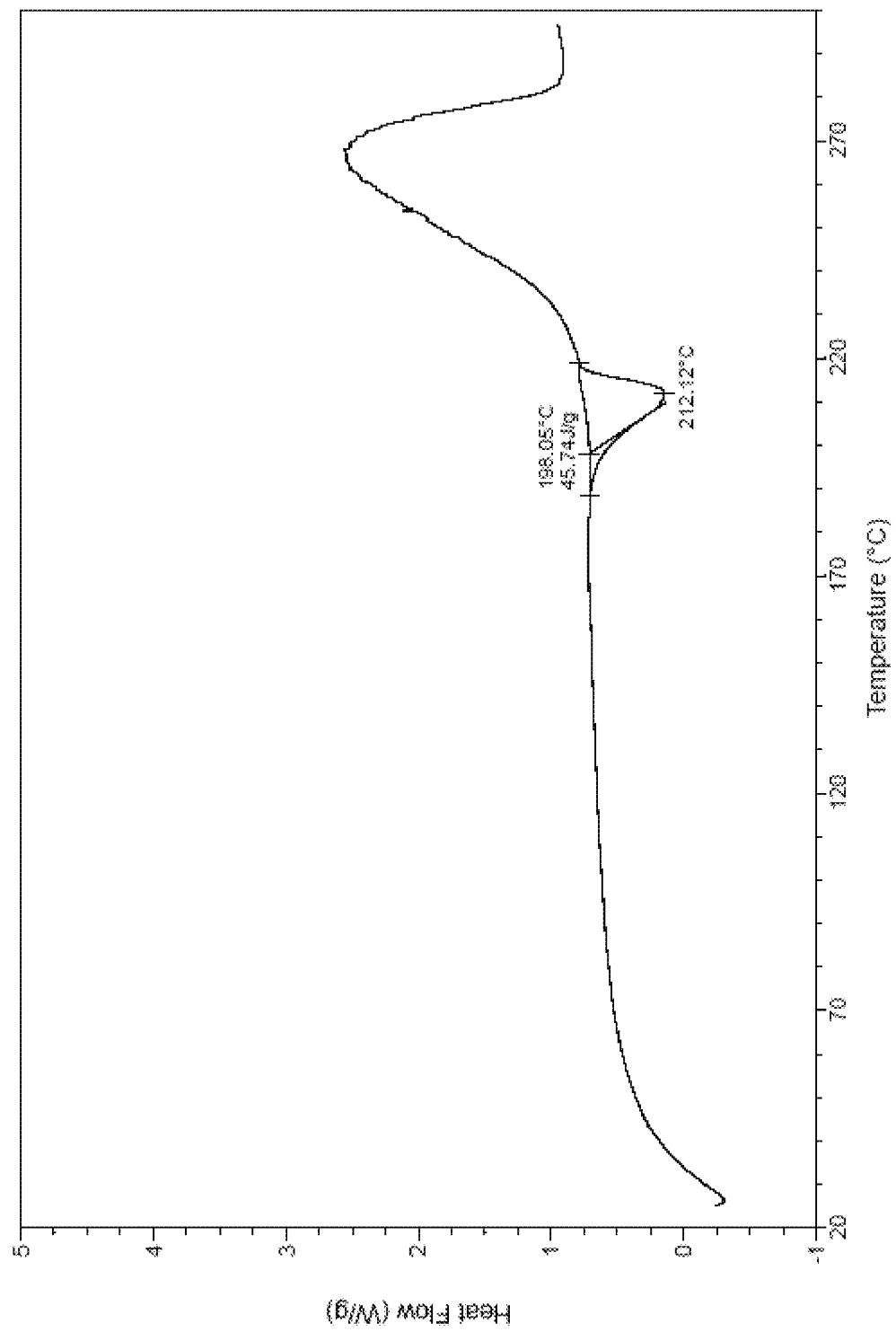

FIG. 156 is a DSC curve of Compound 1 hydrochloride crystalline Form LII.

Figure 157:
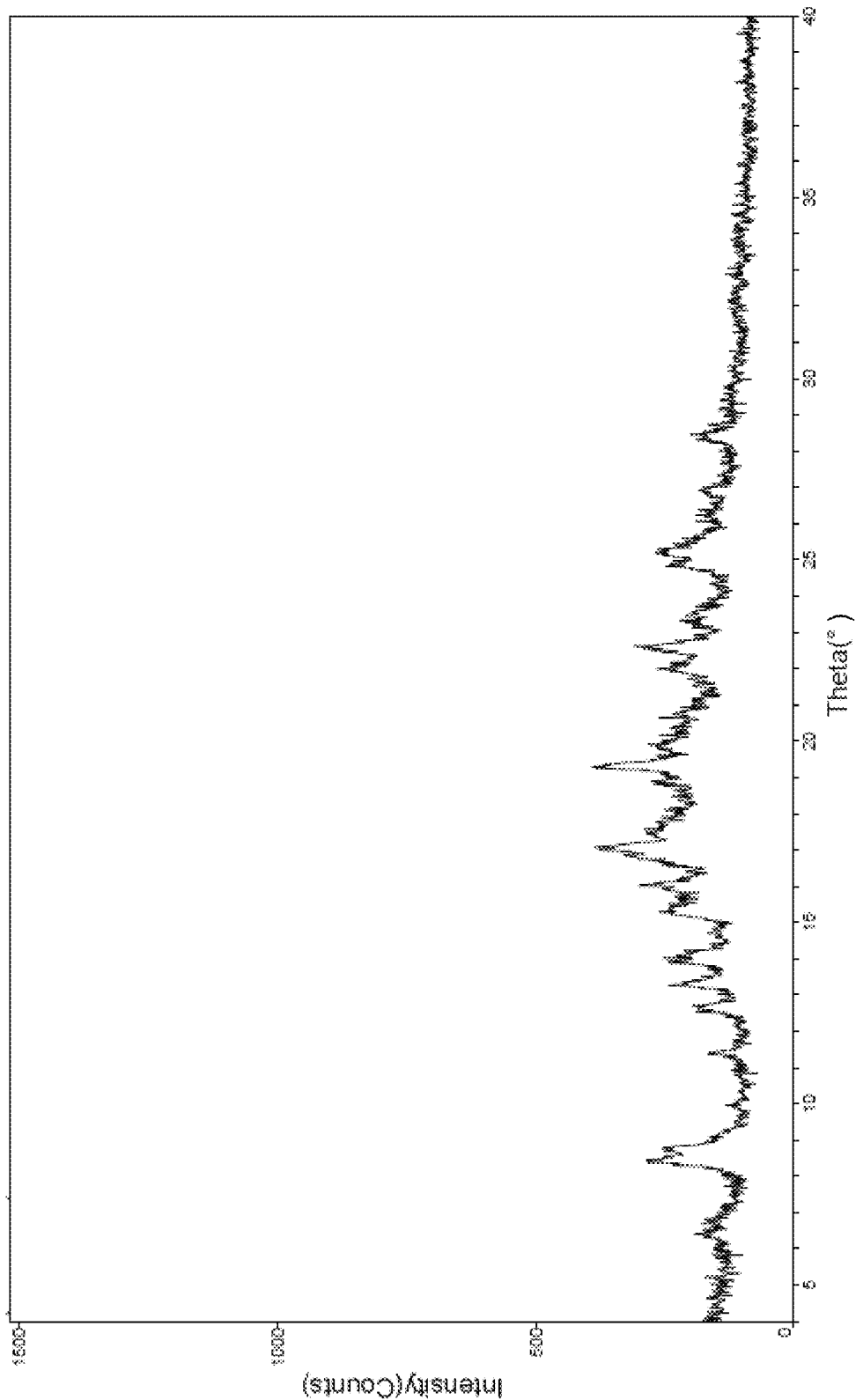

FIG. 157 is an XRPD pattern of Compound 1 hydrochloride crystalline Form LIII.

Figure 158:
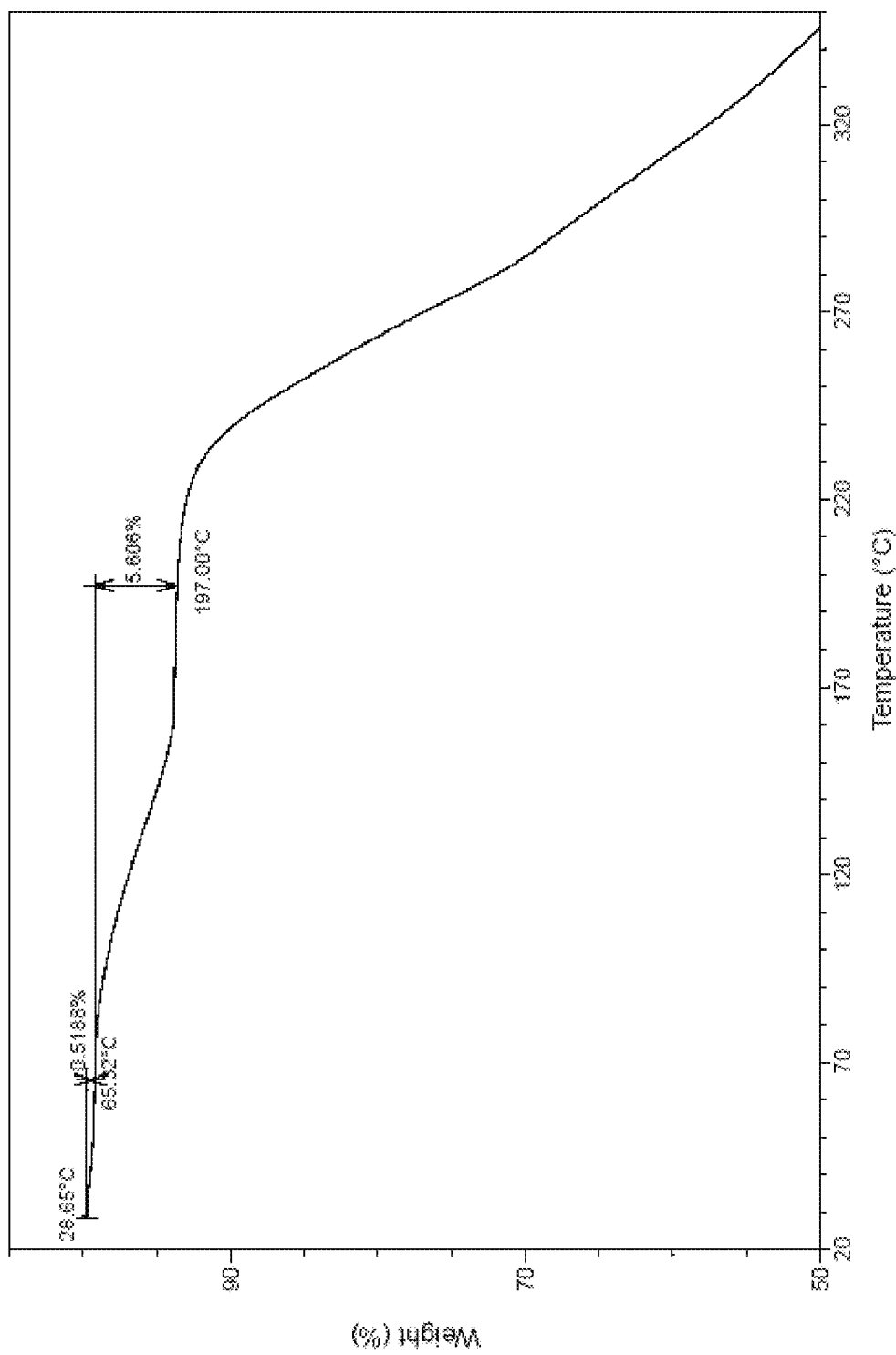

FIG. 158 is a TGA plot of Compound 1 hydrochloride crystalline Form LIII.

Figure 159:
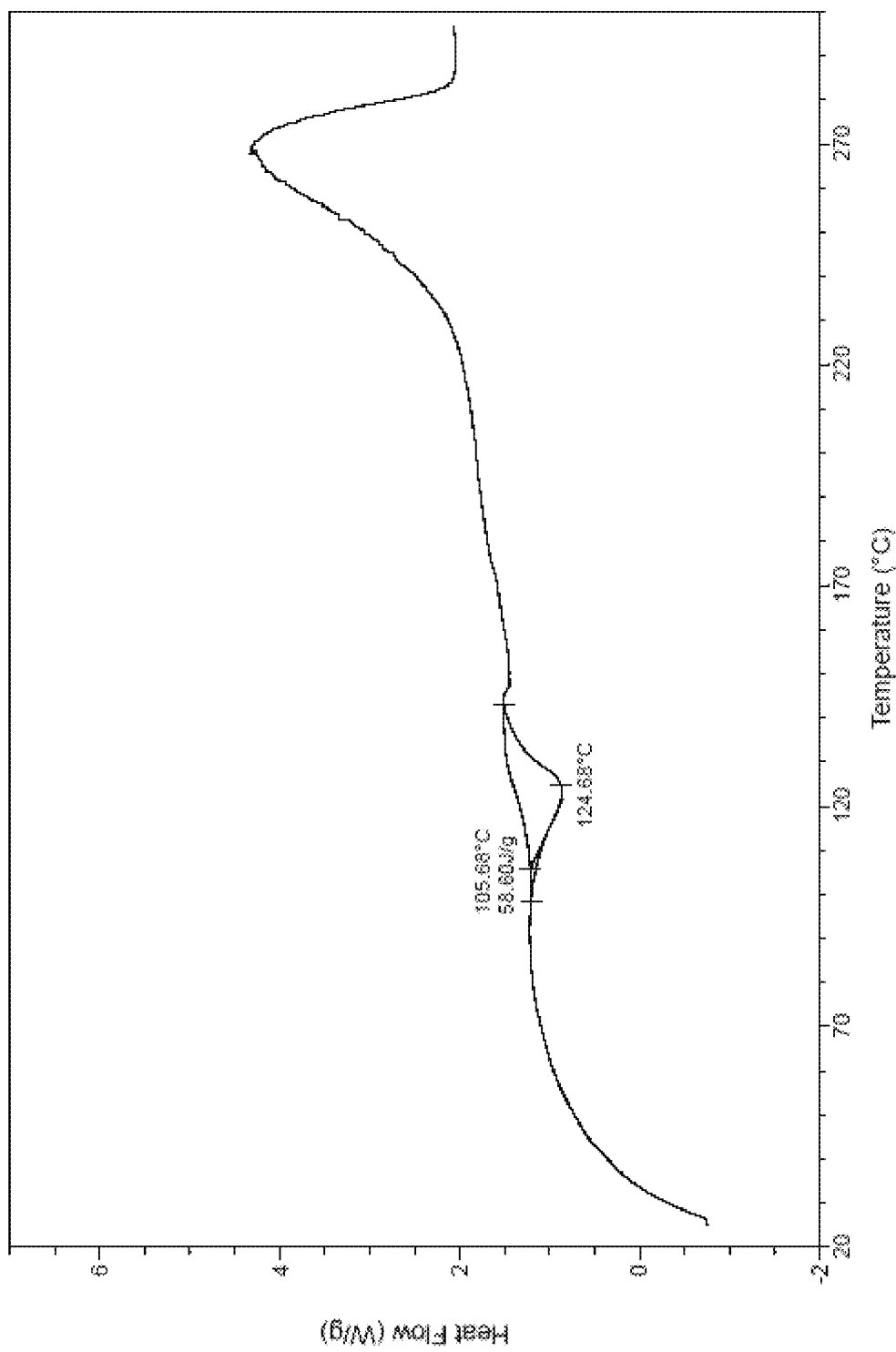

FIG. 159 is a DSC curve of Compound 1 hydrochloride crystalline Form LIII.

Figure 160:
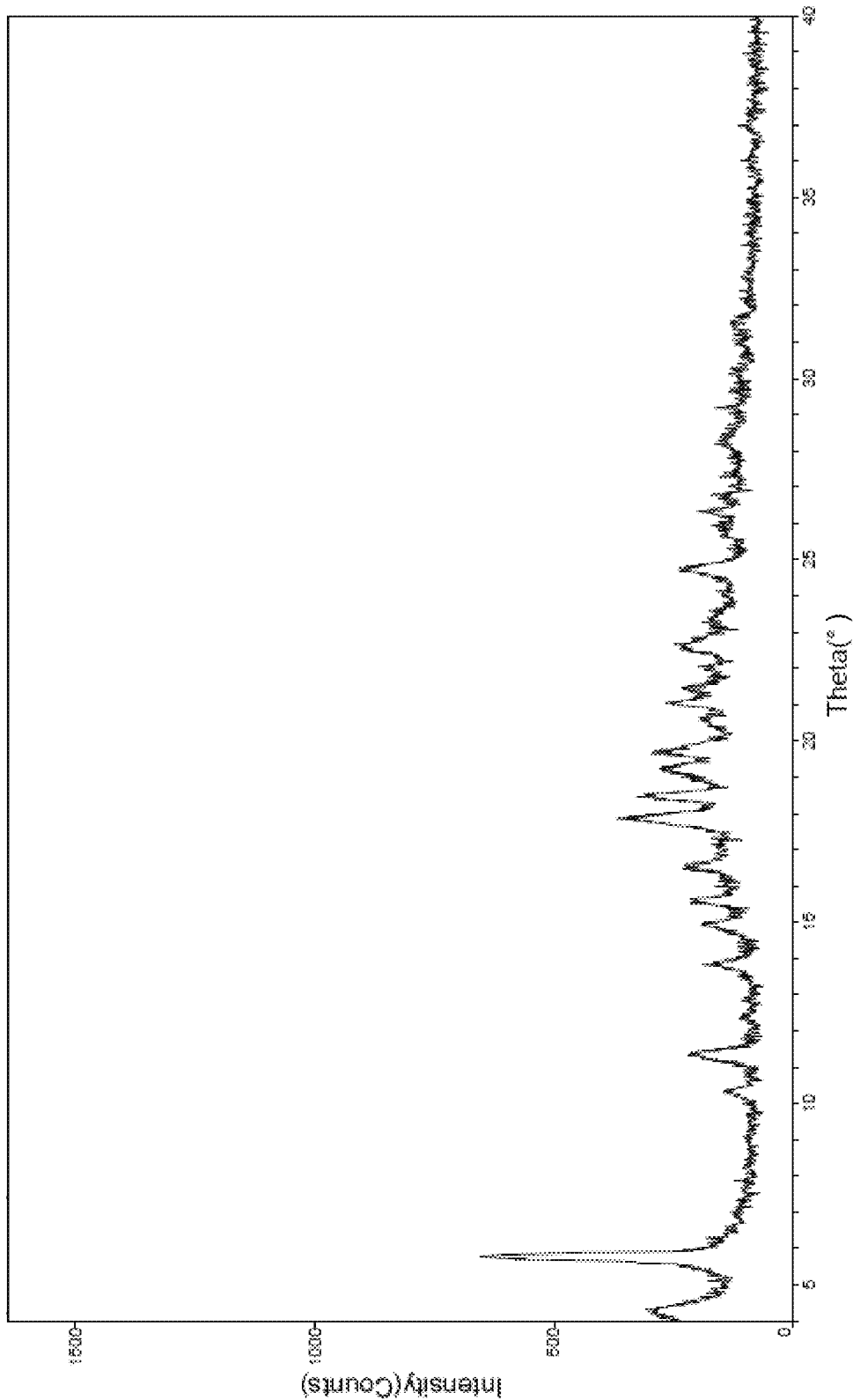

FIG. 160 is an XRPD pattern of Compound 1 hydrochloride crystalline Form LIV.

Figure 161:
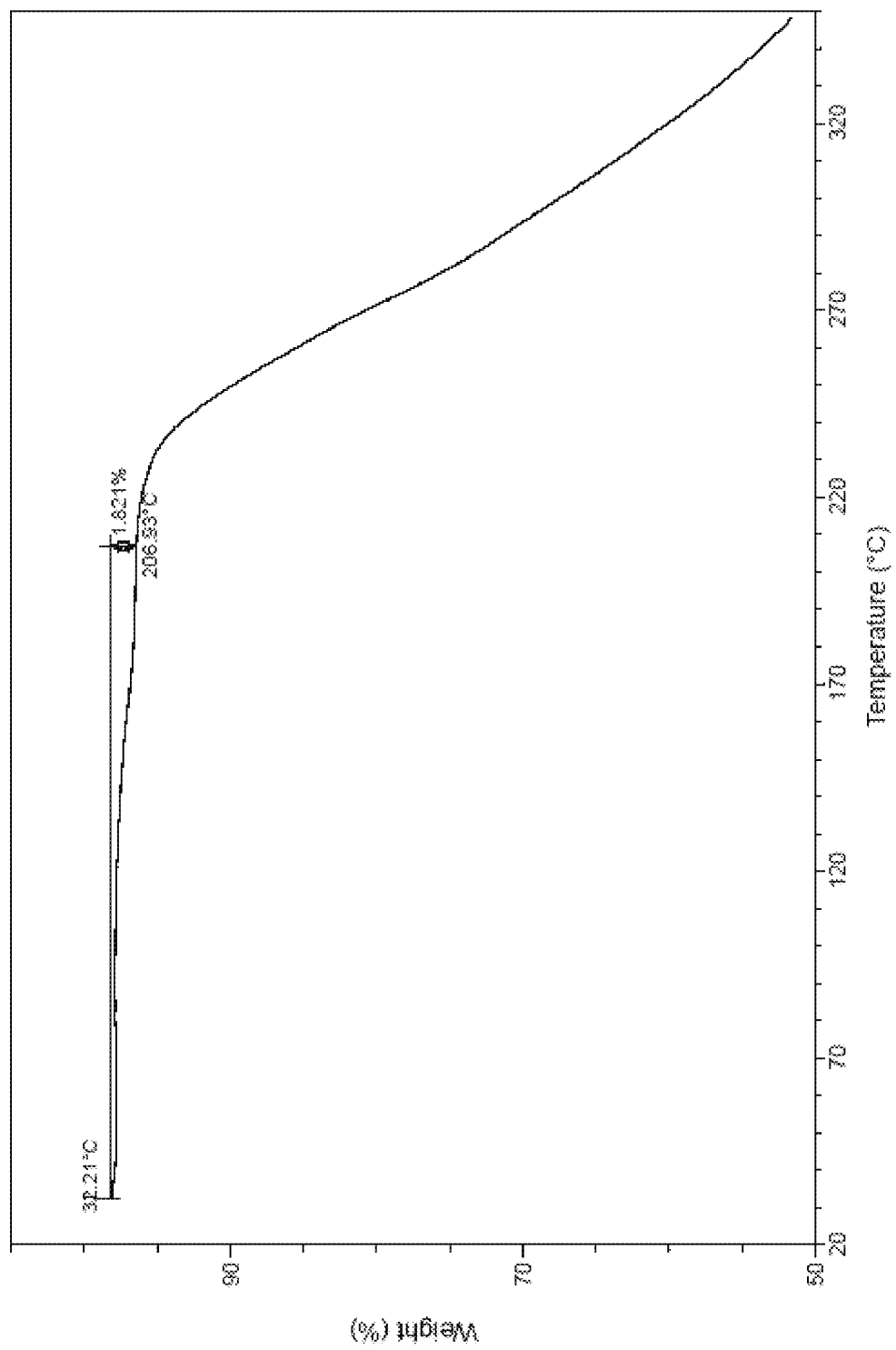

FIG. 161 is a TGA plot of Compound 1 hydrochloride crystalline Form LIV.

Figure 162:
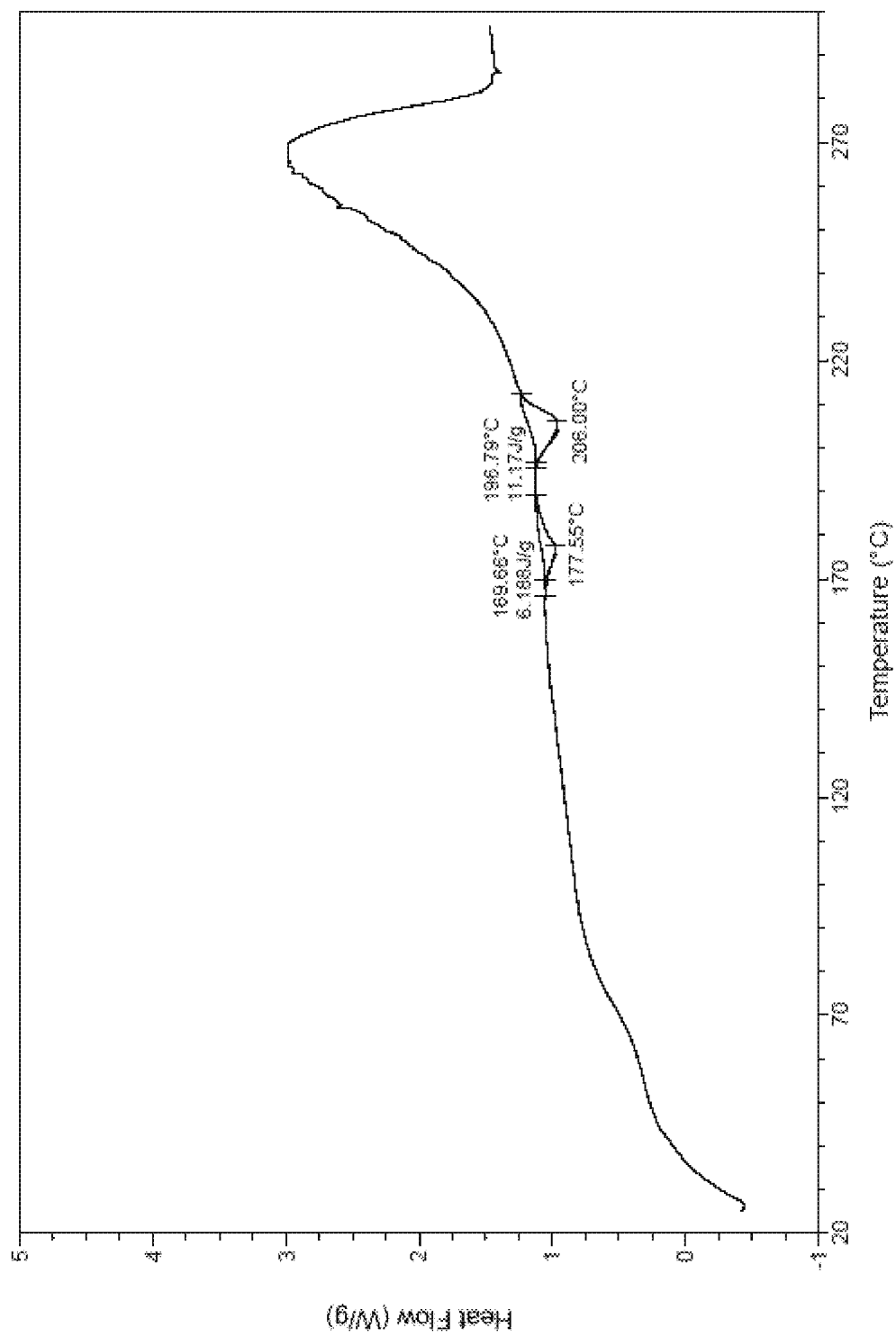

FIG. 162 is a DSC curve of Compound 1 hydrochloride crystalline Form LIV.

Figure 163:
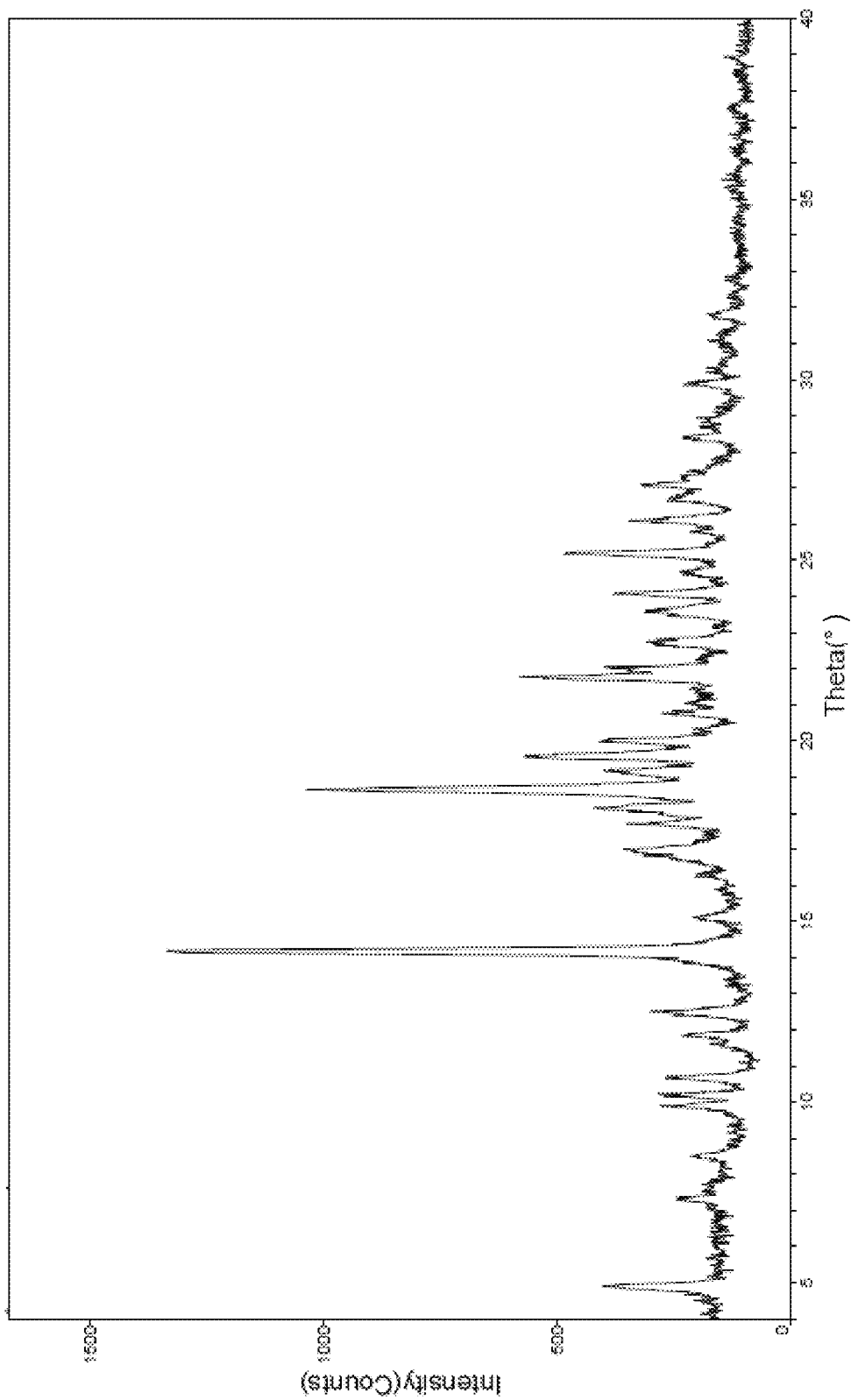

FIG. 163 is an XRPD pattern of Compound 1 hydrochloride crystalline Form LV.

Figure 164:
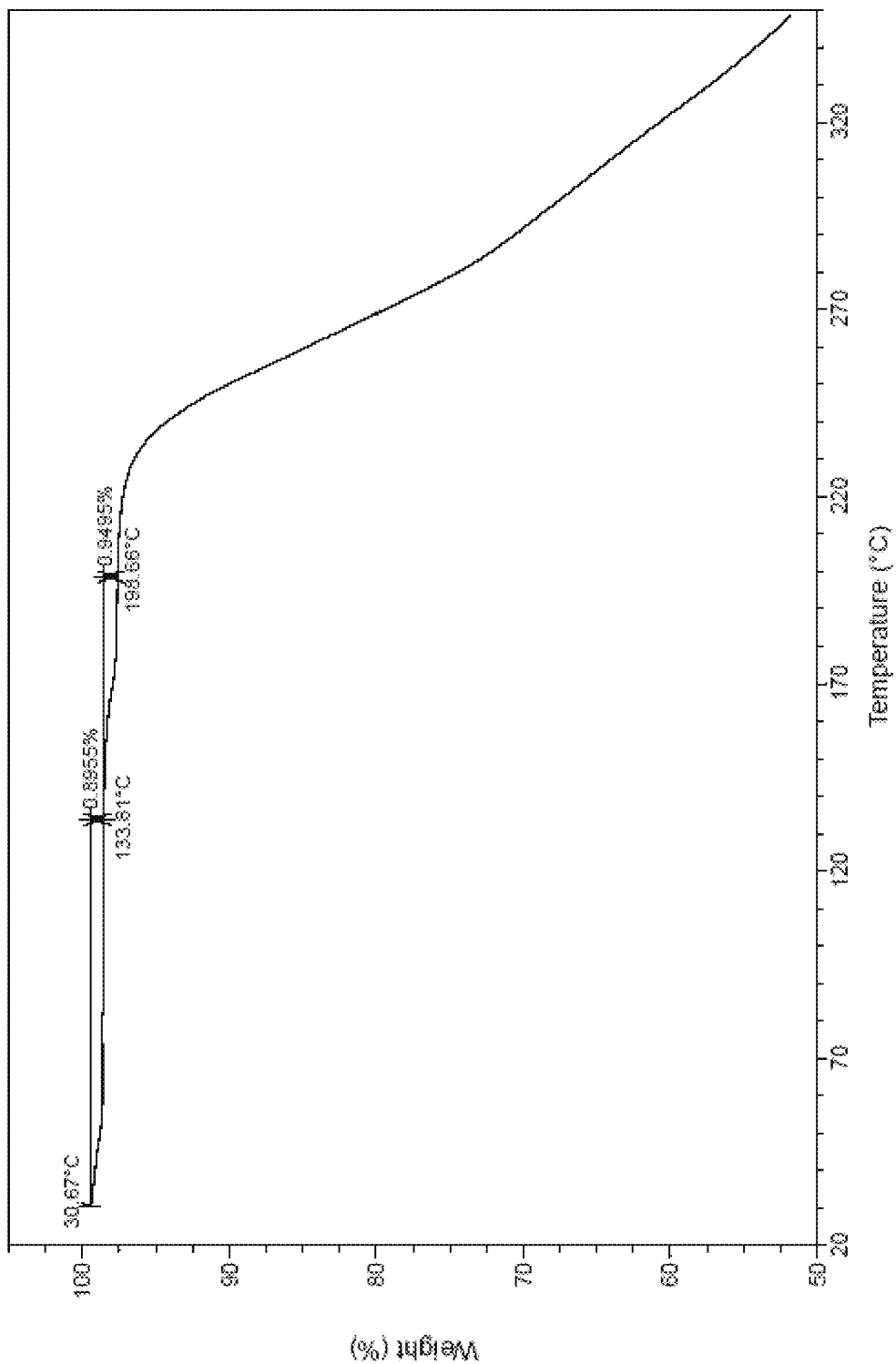

FIG. 164 is a TGA plot of Compound 1 hydrochloride crystalline Form LV.

Figure 165:
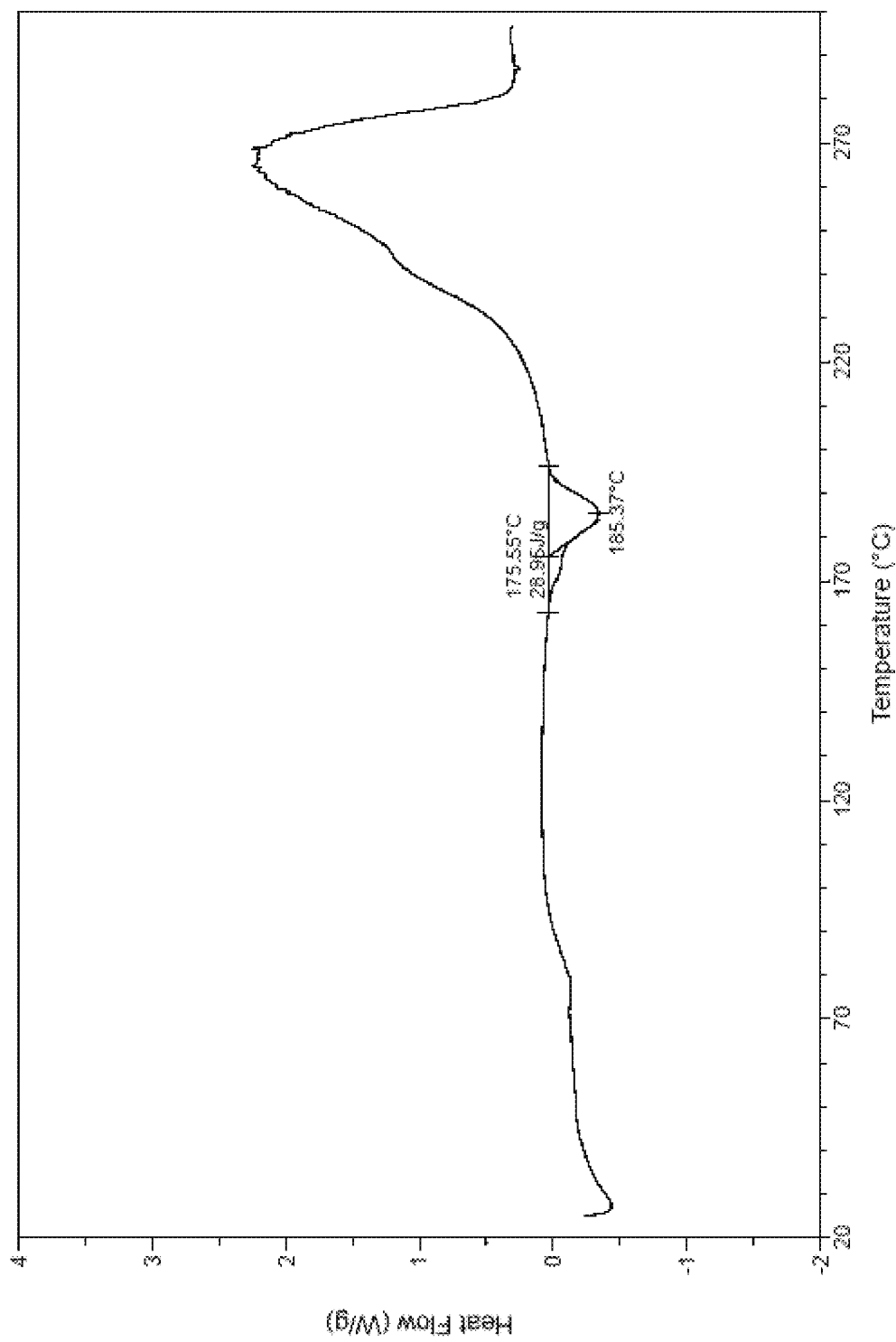

FIG. 165 is a DSC curve of Compound 1 hydrochloride crystalline Form LV.

Figure 166:
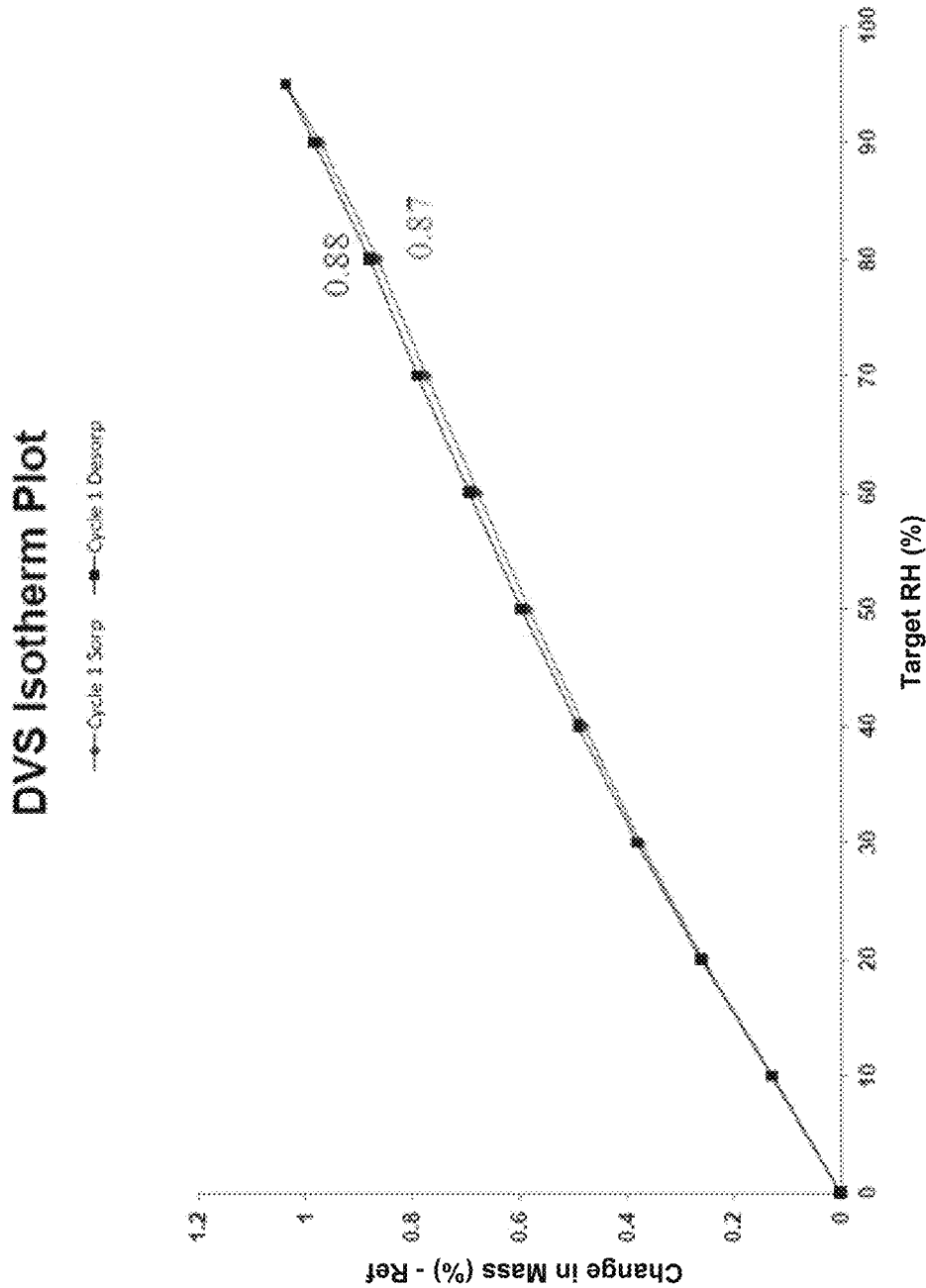

FIG. 166 is a DVS figure of Compound 1 crystalline Form III.

Figure 167:
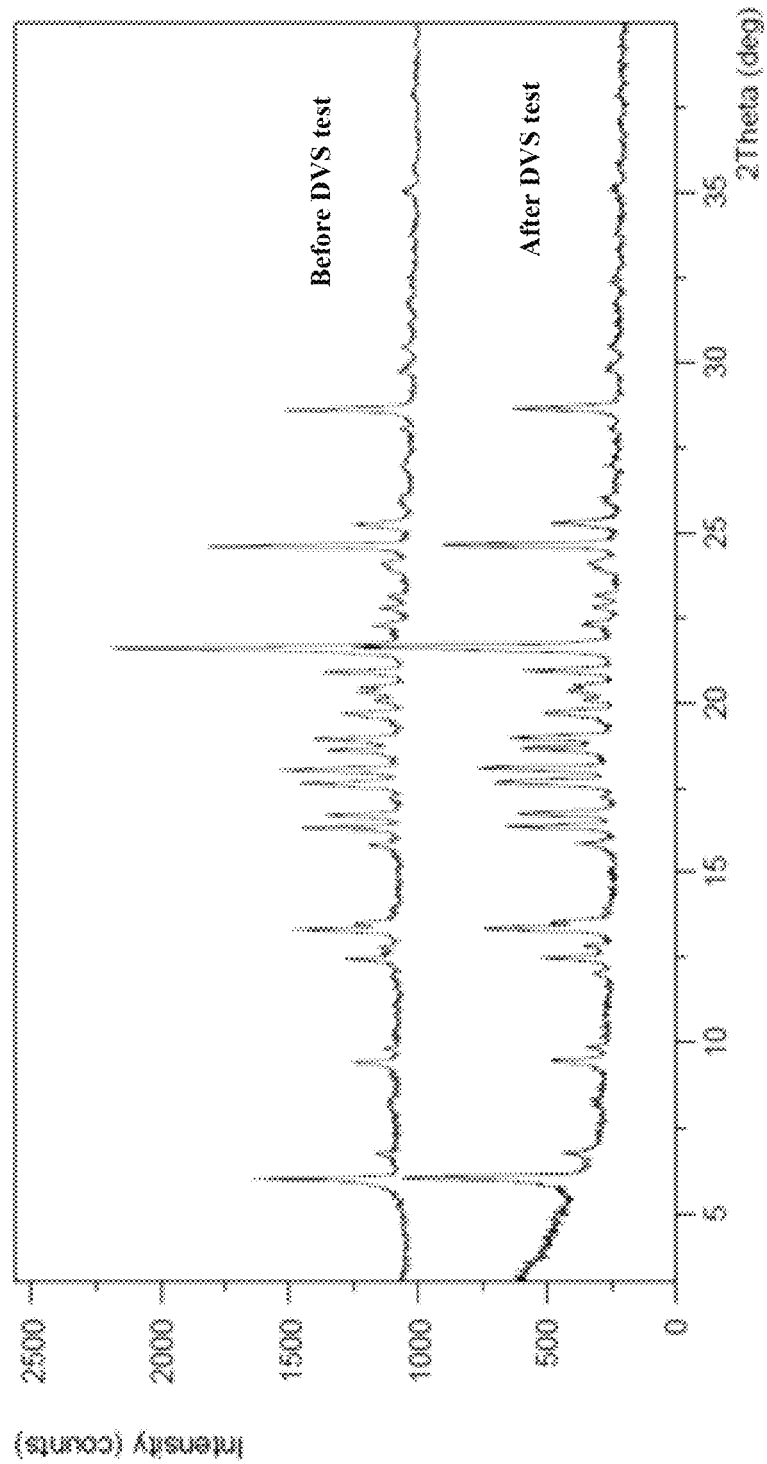

FIG. 167 is a comparison diagram of XRPD pattern of Compound 1 crystalline Form III before DVS test and after DVS test.

Figure 168:
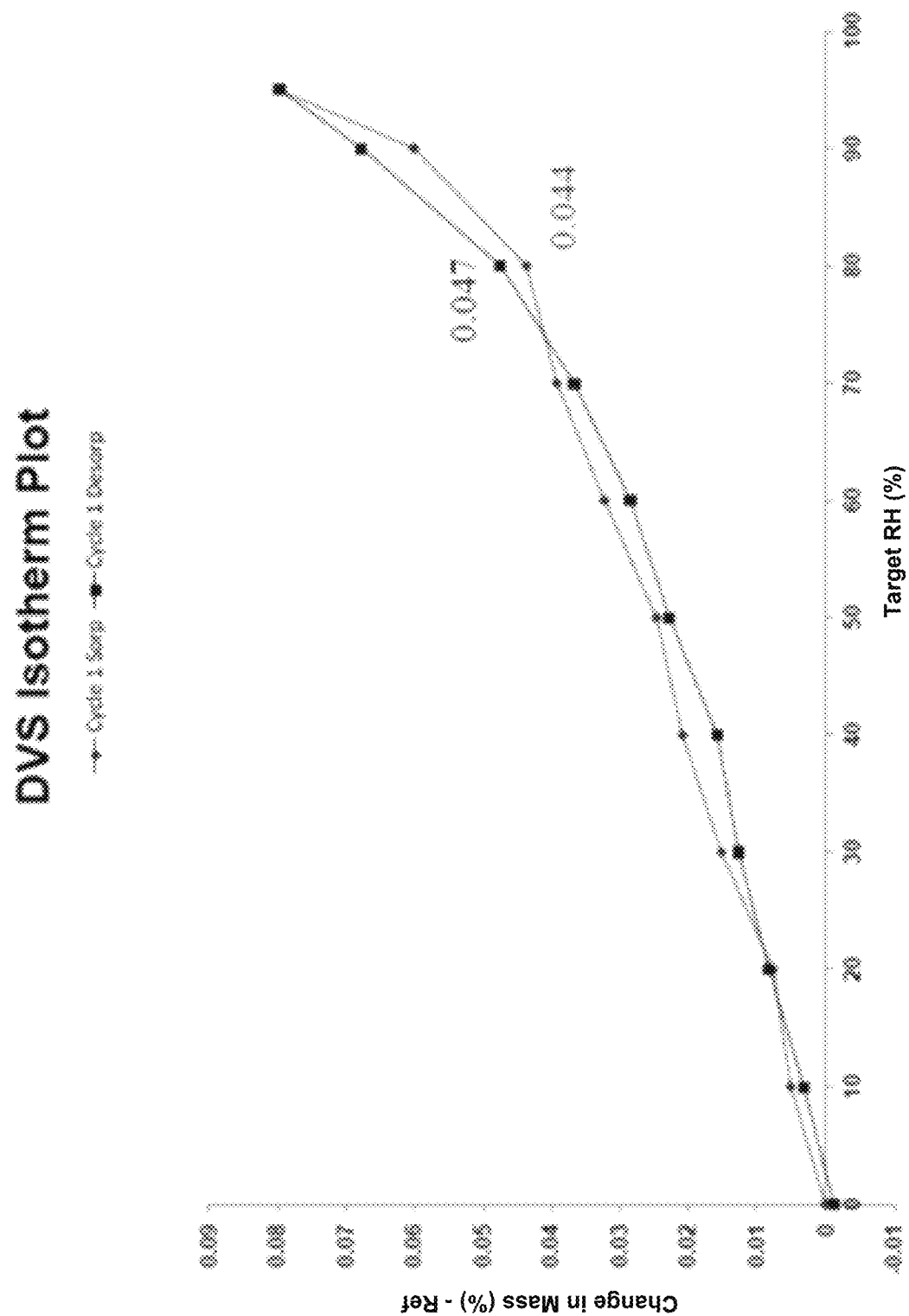
Figure 169:
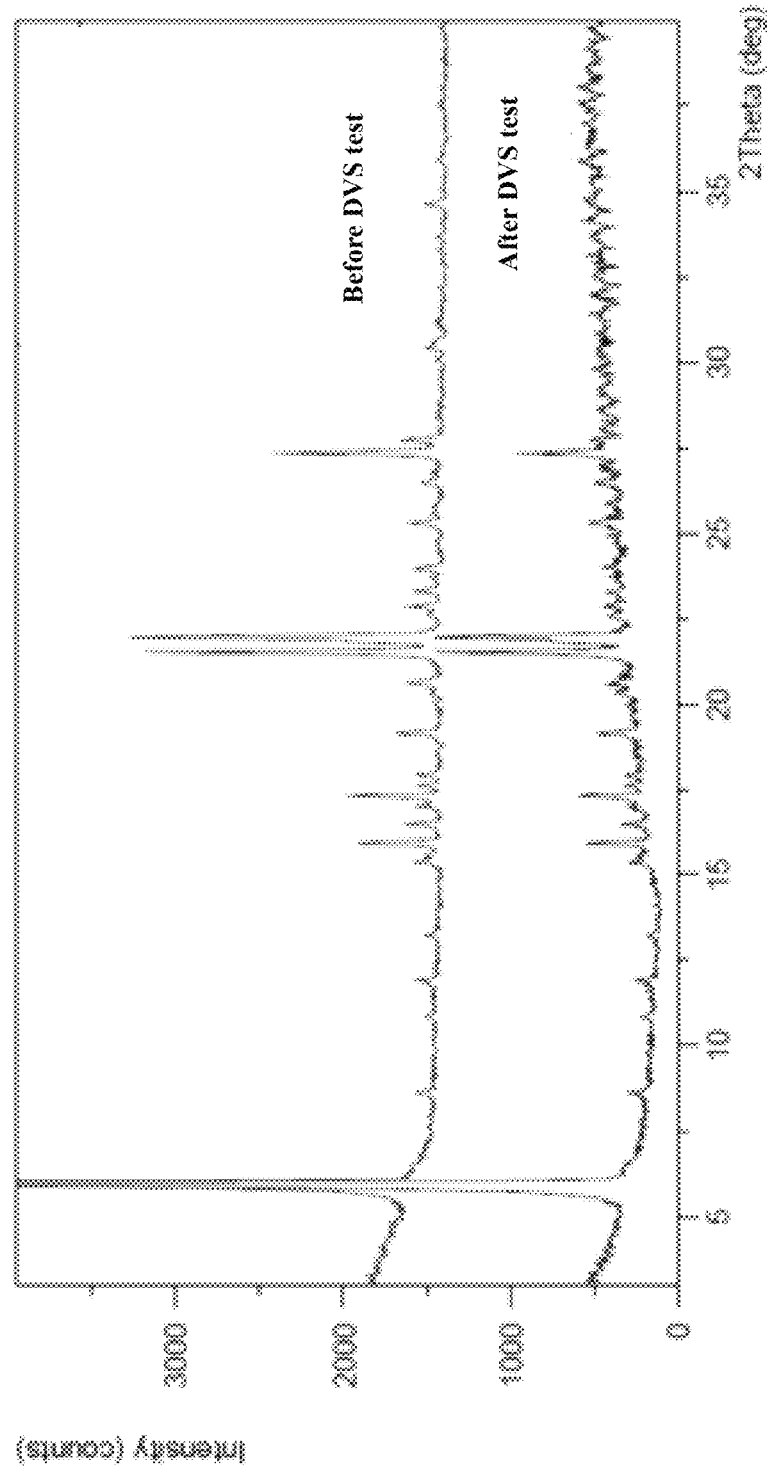

FIG. 168 is a DVS figure of Compound 1 crystalline Form XVIII FIG. 169 is a comparison diagram of XRPD pattern of Compound 1 crystalline Form XVIII before DVS test and after DVS test.

Figure 170:
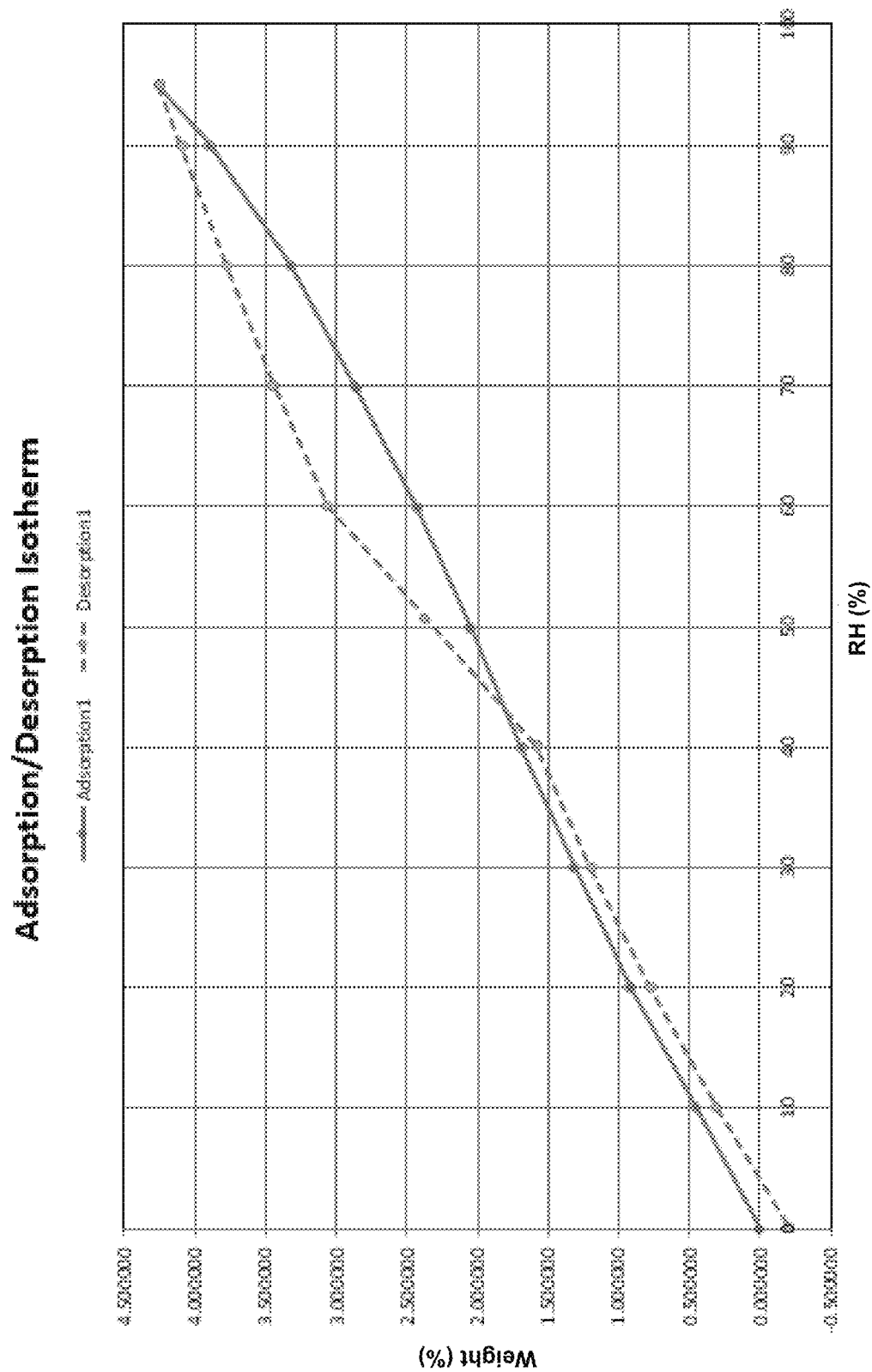
Figure 171:
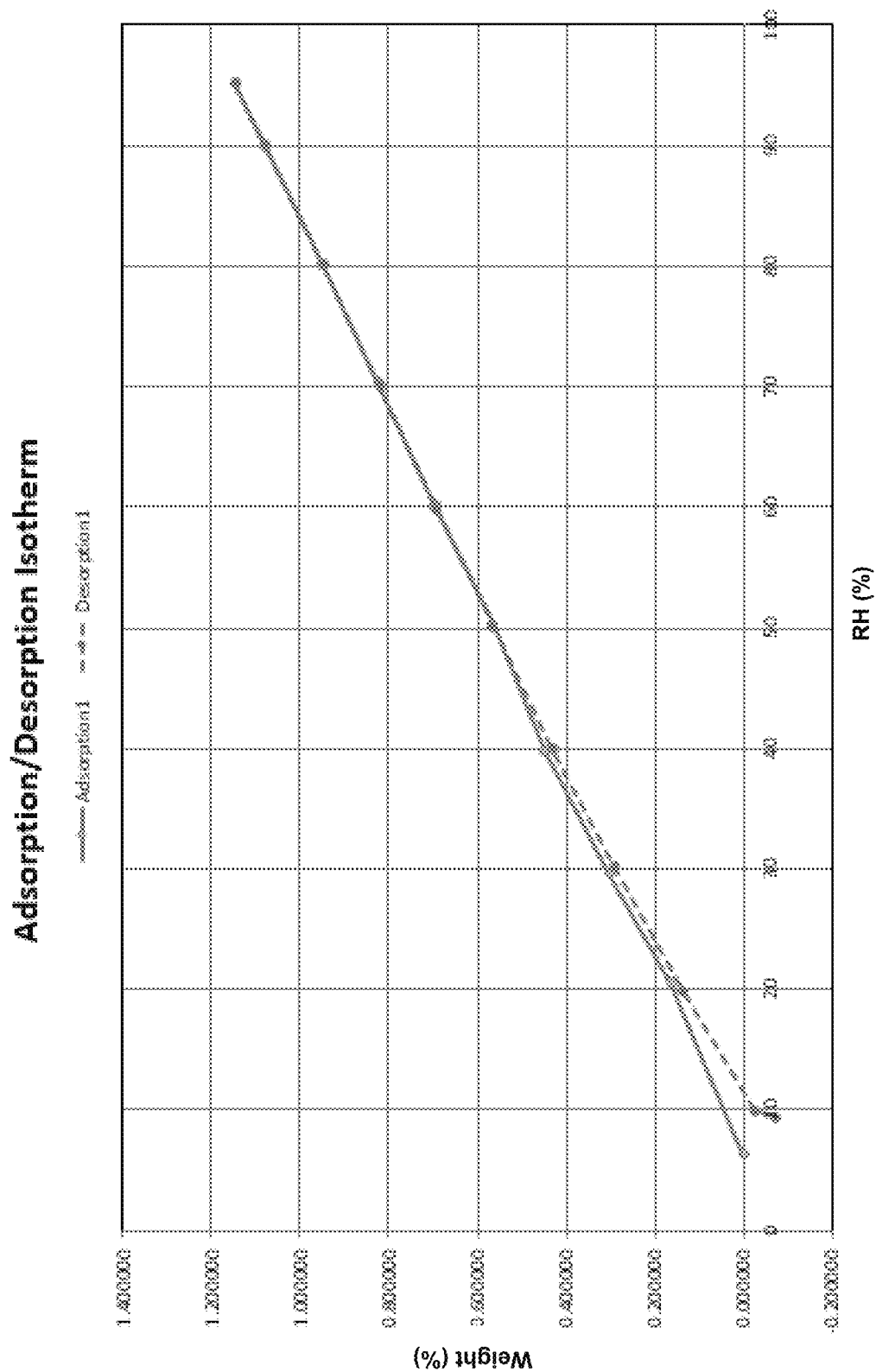

FIG. 170 is a DVS figure of Compound 1 benzene sulfonate crystalline Form XXVII FIG. 171 is a DVS figure of Compound 1 p-toluenesulfonate crystalline Form XXIX.

Figure 172:
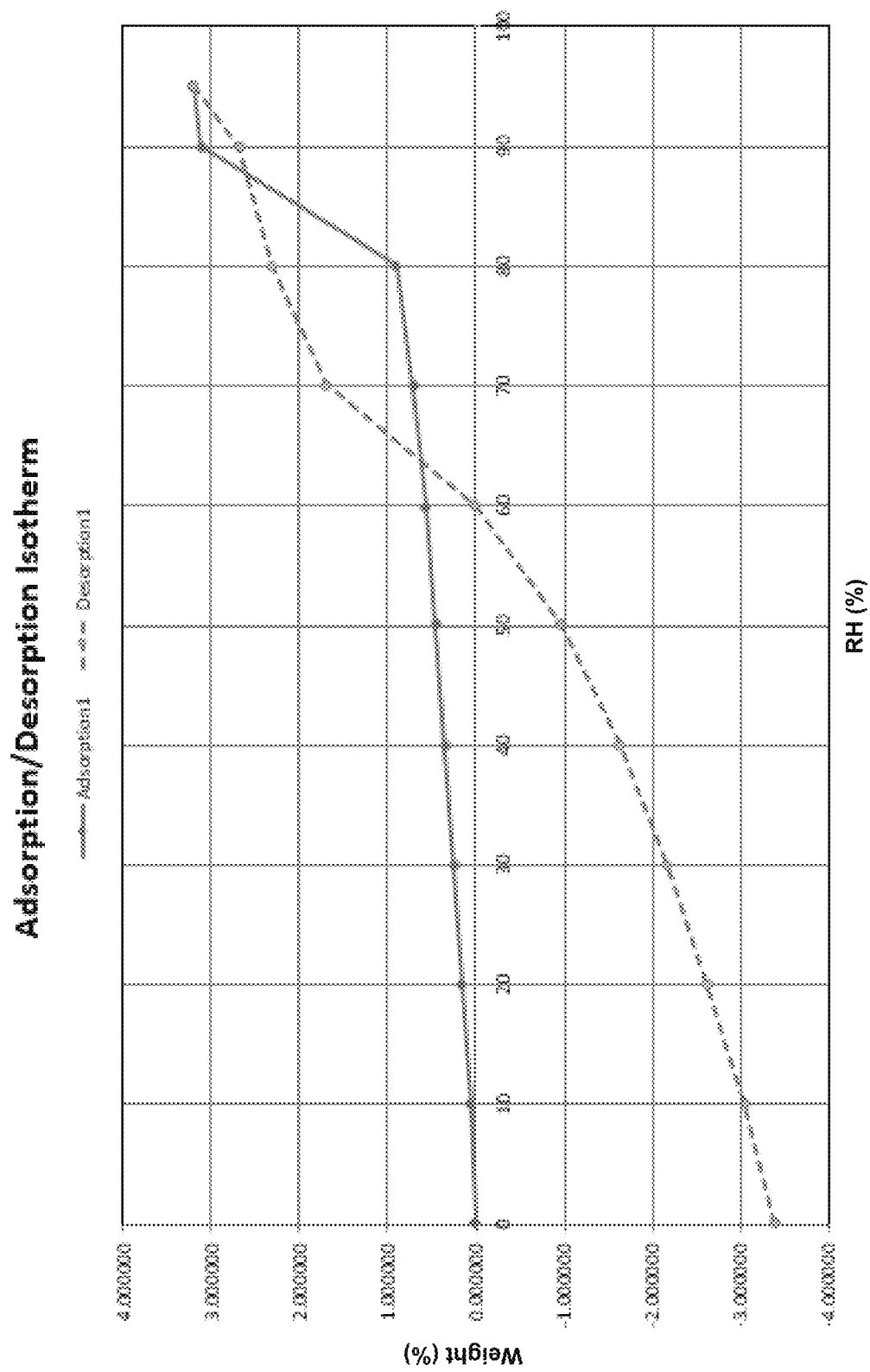

FIG. 172 is a DVS figure of Compound 1 sulphate crystalline Form XXX.

Figure 173:
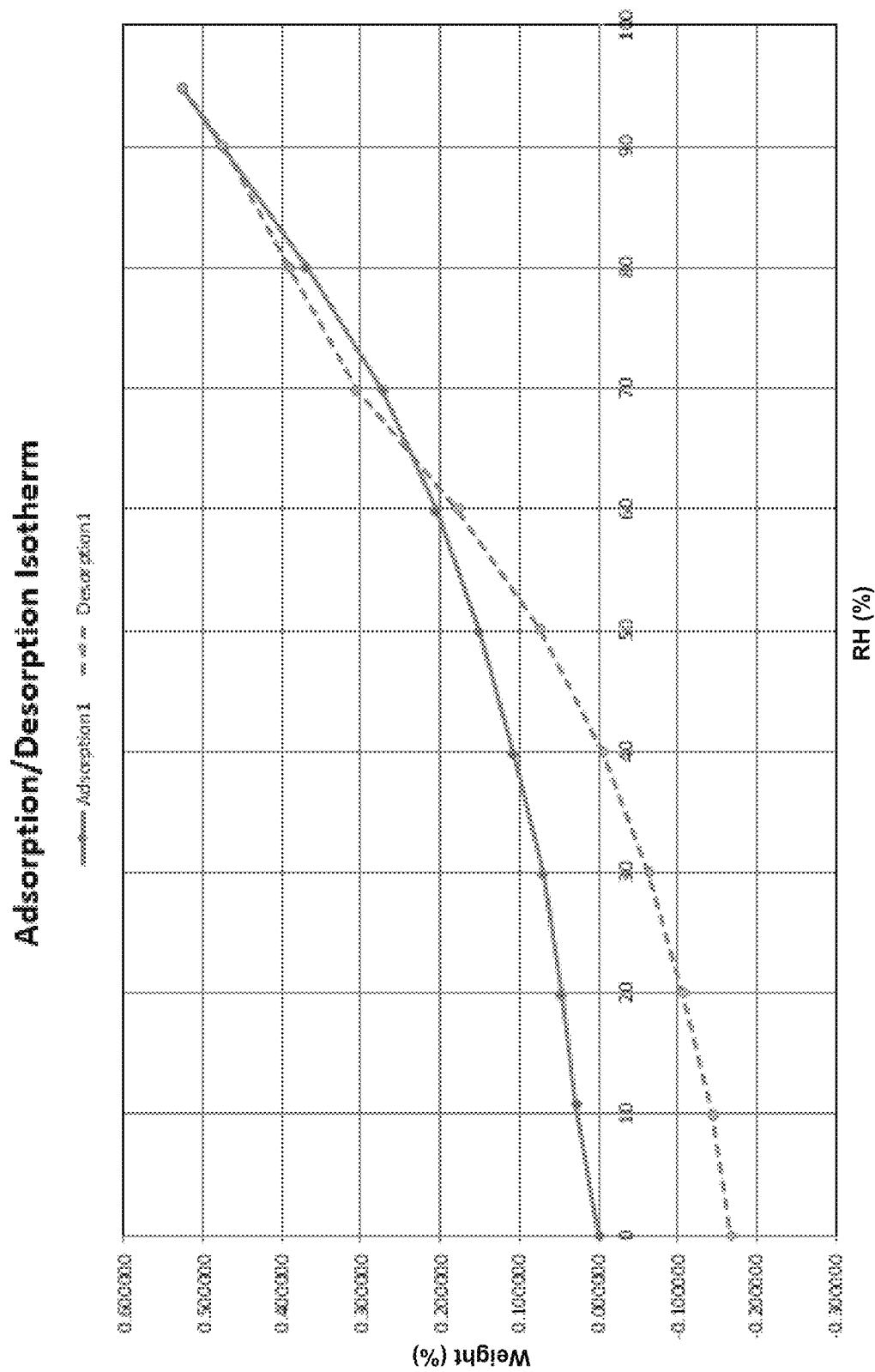

FIG. 173 is a DVS figure of Compound 1 citrate crystalline Form XXXIX.

Figure 174:
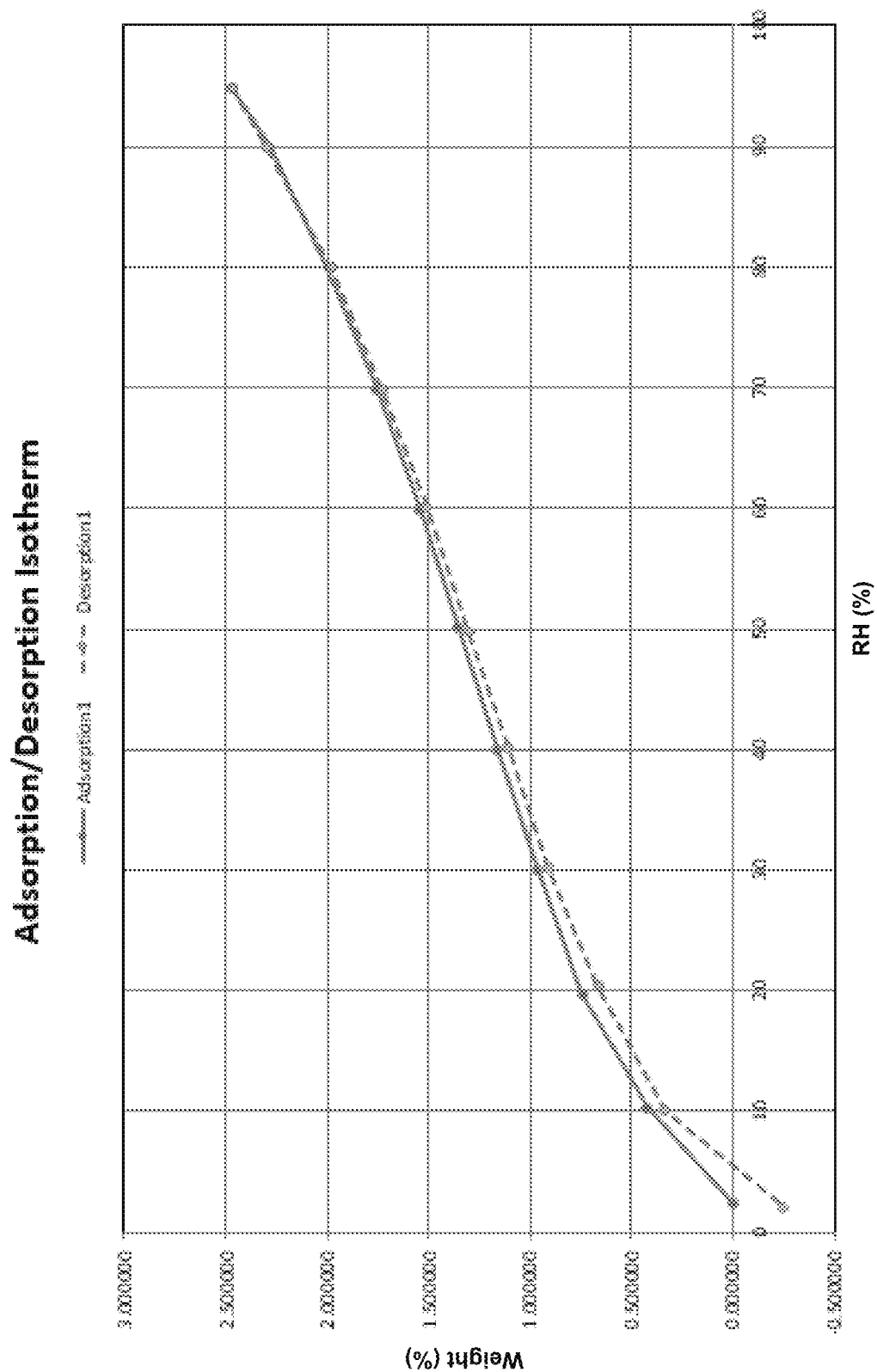

FIG. 174 is a DVS figure of Compound 1 citrate crystalline Form XXXVI.

Figure 175:
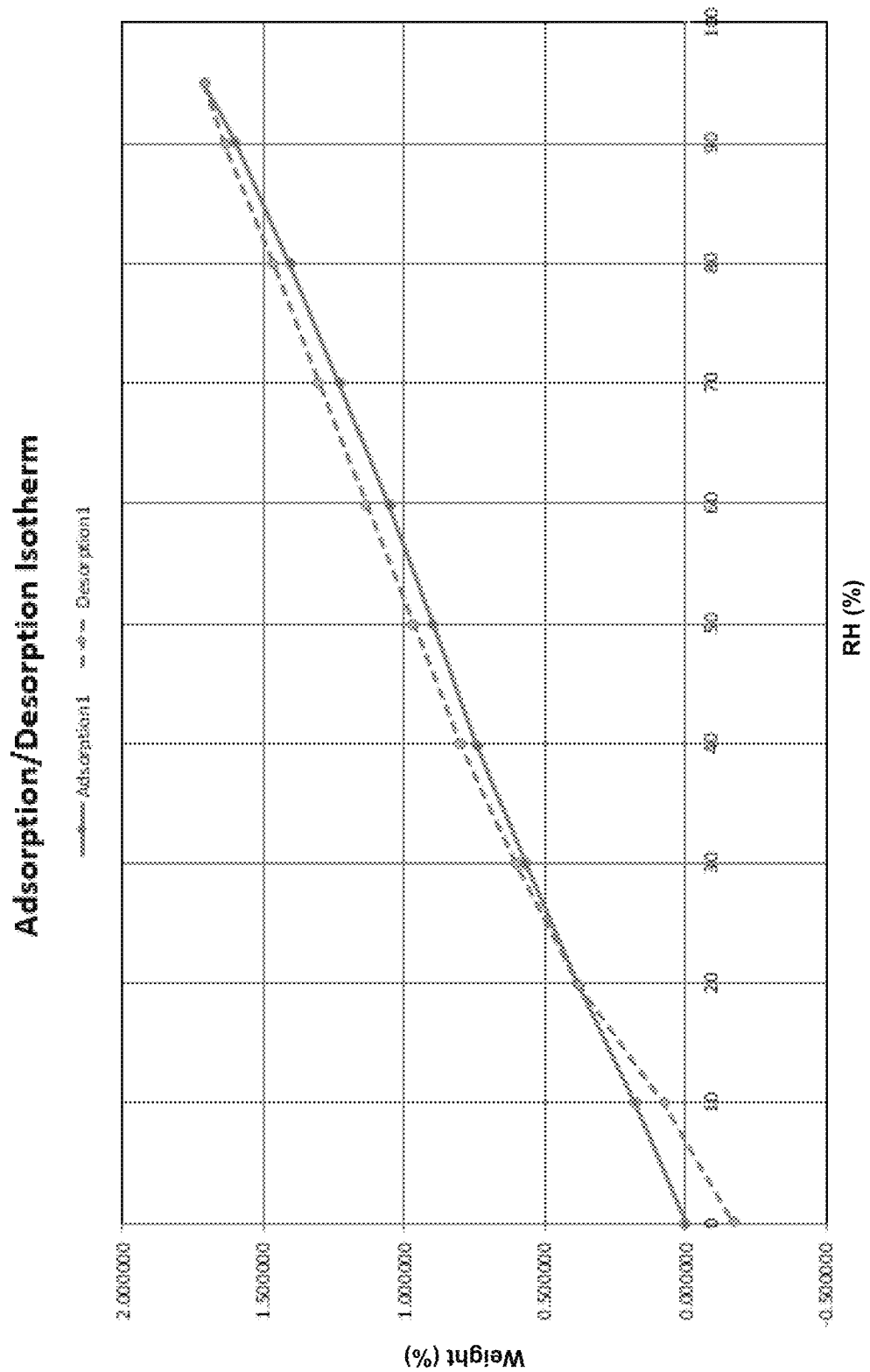

FIG. 175 is a DVS figure of Compound 1 maleate crystalline Form XL.

Figure 176:
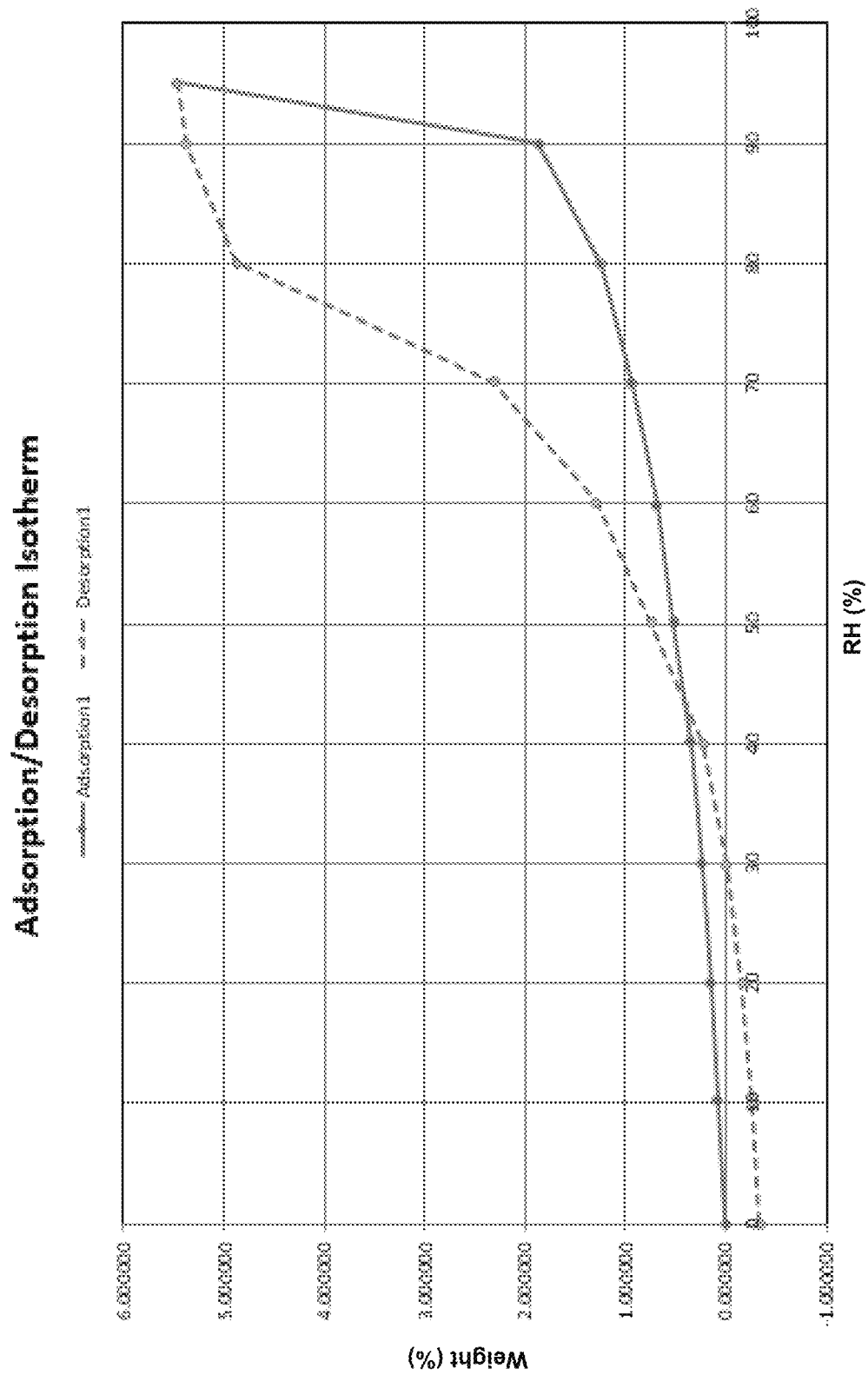

FIG. 176 is a DVS figure of Compound 1 maleate crystalline Form XXIV.

Figure 177:
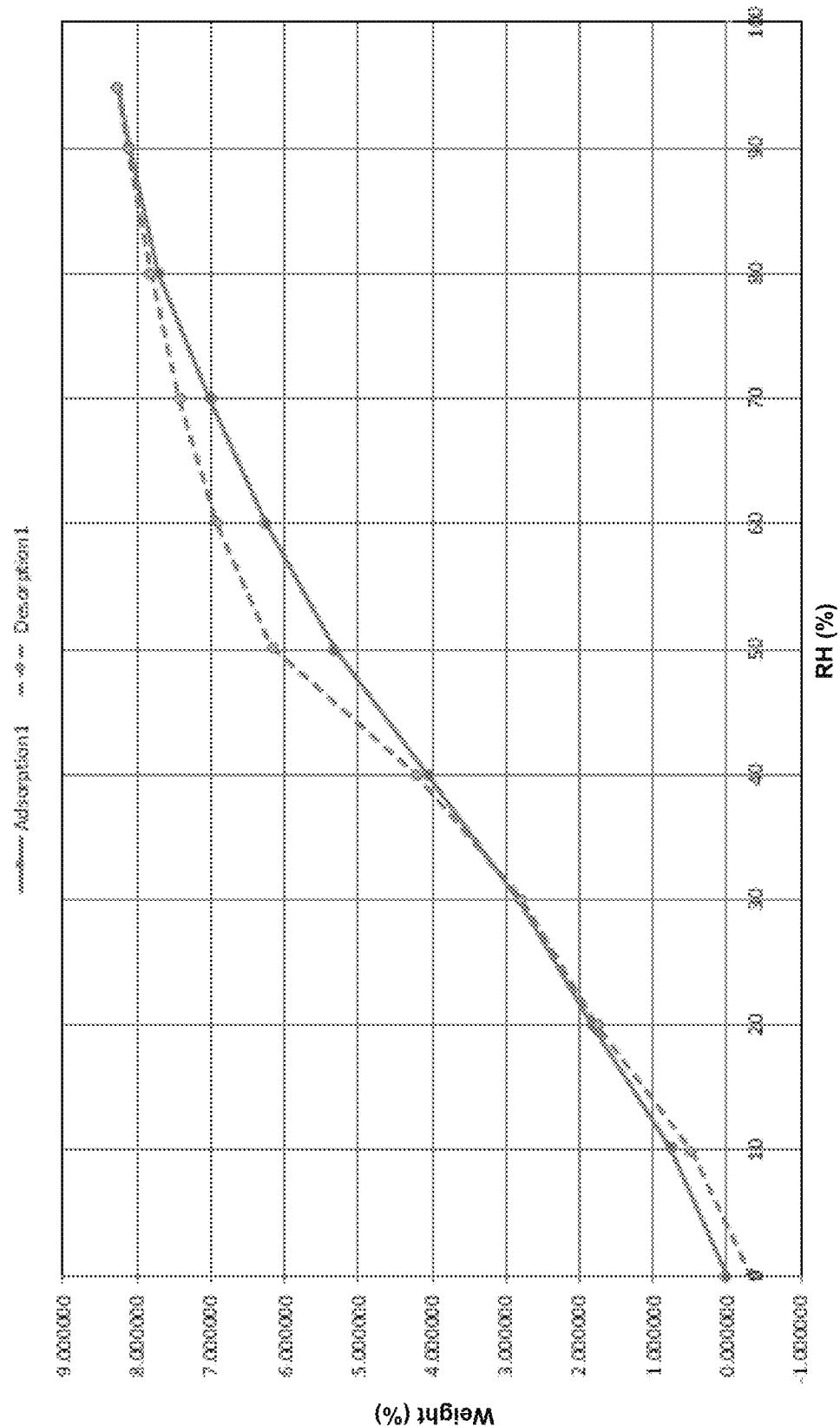

FIG. 177 is a DVS figure of Compound 1 mesylate crystalline Form XXXIII.

DETAILED DESCRIPTION OF THE INVENTION

Examples

In the following examples, the experimental methods are completed in accordance with conventional conditions or conventional test conditions, and the compounds used in the examples are commercially available or self-made.

Example 1: Preparation of Crystalline Form I of Compound 1

200 mg of compound 1 was weighed and placed in a 5 mL vial, added with 4 mL mixed solvent THF/H2O (1:9, V/V), stirred for 5 days at room temperature, centrifuged for separation that solids were dried at room temperature to obtain the crystalline form I.

Example 2: Preparation of Crystalline Form II of Compound 1

200 mg of compound 1 was weighed and placed in a 5 mL vial, added with 4 mL ethyl acetate, heated to reflux, cooled, separated that solids were dried at room temperature to obtain the crystalline form II.

Example 3: Preparation of Crystalline Form III of Compound 1

200 mg of compound 1 was weighed and placed in a 5 mL vial, added with 4 mL EtOAc, stirred for 5 days at 70° C., centrifuged for separation that solids were dried at room temperature to obtain the crystalline form III.

Example 4: Preparation of 1,4-Dioxane Solvate Crystalline Form IV of Compound 1

50 mg of compound 1 was weighed and placed in a 3 mL vial which was placed in a 20 mL vial containing 3 mL of solvent 1, 4-dioxane. The sample was allowed to stand at room temperature for 3 days, centrifuged for separation that solids were dried at room temperature to obtain the 1,4-dioxane solvate crystalline Form IV.

Example 5: Preparation of Ethyl Acetate Solvate Crystalline Form V of Compound 1

50 mg of compound 1 was weighed and placed in a HPLC vial, added with 1 mL EtOAc, stirred at room temperature for 8 days, centrifuged for separation that solids were dried at room temperature to obtain the ethyl acetate solvate crystalline form V.

Example 6: Preparation of Methylbenzene Solvate Crystalline Form VI of Compound 1

50 mg of compound 1 was weighed and placed in a 3 mL vial, added with 1 mL methylbenzene, stirred at room temperature for 22 hours, centrifuged for separation that solids were dried at room temperature to obtain the methylbenzene solvate crystalline form VI.

Example 7: Preparation of Crystalline Form VII of Compound 1

200 mg of compound 1 was weighed and placed in a 3 mL vial, added with 4.0 mL EtOH, stirred at room temperature for 5 days, centrifuged for separation that solids were dried at room temperature to obtain the crystalline Form VII.

Example 8: Preparation of Chloroform Solvate Crystalline Form VIII of Compound 1

15 mg of compound 1 was weighed and placed in a 3 mL vial, added with 0.5 mL CHCl3 for dissolved clarification of solids. The 3 mL vial was placed in a 20 mL vial containing 3 mL of solvent n-heptane. The sample was allowed to stand at room temperature for 1 day, centrifuged for separation that solids were dried at room temperature to obtain the chloroform solvate crystalline form VIII.

Example 9: Preparation of Methyl Tert-Butyl Ether Solvate Crystalline Form IX of Compound 1

50 mg of compound 1 was weighed and placed in a HPLC vial, added with 1.0 mL MTBE, stirred at room temperature for 6 days, centrifuged for separation that solids were dried at room temperature to obtain the methyl tert-butyl ether solvate crystalline form IX.

Example 10: Preparation of 2-Methyltetrahydrofuran Solvate Crystalline Form X of Compound 1

40 mg of compound 1 was weighed and placed in a HPLC vial, added with 0.8 mL solvent 2-MeTHF, stirred at room temperature for 1 hour, centrifuged for separation that solids were dried at room temperature to obtain the 2-methyltetrahydrofuran solvate crystalline form X.

Example 11: Preparation of Crystalline Form XI of Compound 1

16 mg of compound 1 was weighed and placed in a HPLC vial, added with 0.5 mL ACN, stirred at room temperature for 5 days, centrifuged for separation that solids were dried at room temperature to obtain the crystalline Form XI.

Example 12: Preparation of Acetone Solvate Crystalline Form XII of Compound 1

11 mg of crystalline Form VII was weighed and placed in a HPLC vial, added with 1.0 mL solvent acetone, stirred at room temperature for 1.5 hours, centrifuged for separation that solids were dried at room temperature to obtain the acetone solvate crystalline form XII.

Example 13: Preparation of Crystalline Form XIII of Compound 1

50 mg of compound 1 was weighed and placed in a 20 mL vial, added with 6 mL solvent acetone for dissolved clarification of solids, 5.0 ml anti-solvent $H_2O$ was added dropwise while stirring at room temperature, solid precipitated, continue to stir at room temperature for 4 days centrifuged for separation that solids were dried at room temperature to obtain the crystalline Form XIII.

Example 14: Preparation of Crystalline Form XIV of Compound 1

15 mg of compound 1 was weighed and placed in a 20 mL vial, added with 0.4 mL solvent DCM for dissolved clarification of solids, 15.0 mL of anti-solvent toluene was added dropwise while stirring at room temperature. The sample was clear. After stirring at 5° C., no solid precipitated.

The sample was transfered to room temperature for open volatilization, centrifuged for separation that solids were dried at room temperature to obtain the crystalline Form XIV.

Example 15: Preparation of Crystalline Form XV of Compound 1

50 mg of compound 1 was weighed and placed in a 3 mL vial which was placed in a 20 mL vial containing 3 mL of solvent EtOH. The sample was allowed to stand at room temperature for 5 days, centrifuged for separation that solids were dried at room temperature to obtain the crystalline Form XV.

Example 16: Preparation of N,N-Dimethylformamide Solvate Crystalline Form XVI of Compound 1

50 mg of compound 1 was weighed and placed in a 3 mL vial which was placed in a 20 mL vial containing 3 mL of solvent DMF. The sample was allowed to stand at room temperature for 5 days, centrifuged for separation that solids were dried at room temperature to obtain the N,N-dimethylformamide solvate crystalline form XVI.

Example 17: Preparation of Crystalline Form XVII of Compound 1

15 mg of compound 1 was weighed and placed in a 3 mL vial, added with 0.5 mL solvent THF for dissolved clarification of solids. The 3 mL vial was placed in a 20 mL vial containing 3 mL of solvent EtOH. The sample was allowed to stand at room temperature for 2 days, centrifuged for separation that solids were dried at room temperature to obtain the crystalline Form XVII.

Example 18: Preparation of Crystalline Form XVIII of Compound 1

The crystalline Form IV of Compound 1 was heated to 150° C. and cooled down to room temperature to obtain the crystalline Form XVIII.

Example 19: Preparation of Hydrochloride Crystalline Form XIX of Compound 1

16 mg of Compound 1 was weighed and placed in a HPLC vial, added with 0.5 mL solvent EtOH, added with 34.0 μL 1M hydrochloric acid, stirred at room temperature for 4 days, centrifuged for separation that solids were dried at room temperature to obtain the hydrochloride crystalline form XIX.

Example 20: Preparation of Sulphate Crystalline Form XX of Compound 1

15 mg of Compound 1 was weighed and placed in a HPLC vial, added with 0.5 mL solvent EtOH, added with 17.0 μL 1M sulfuric acid, stirred at room temperature for 4 days, centrifuged for separation that solids were dried at room temperature to obtain the sulphate crystalline form XX.

Example 21: Preparation of the Mesylate Crystalline Form XXI of Compound 1

1.7 mg of mesylate was weighed and placed in a HPLC vial, added with 0.5 mL solvent EtOAc, added with 15 mg of Compound 1, stirred at room temperature for 4 days, centrifuged for separation that solids were dried at room temperature to obtain the mesylate crystalline form XXI.

Example 22: Preparation of the Mesylate Crystalline Form XXII of Compound 1

1.7 mg of mesylate was weighed and placed in a HPLC vial, added with 0.5 mL solvent EtOH, added with 15 mg of Compound 1, stirred at room temperature for 4 days, centrifuged for separation that solids were dried at room temperature to obtain the mesylate crystalline form XXII.

Example 23: Preparation of the Maleate Crystalline Form XXIII of Compound 1

15 mg of Compound 1 and 2.0 mg of maleic acid was weighed and placed in a HPLC vial, added with 0.5 mL solvent EtOAc, stirred at room temperature for 4 days, centrifuged for separation that solids were dried at room temperature to obtain the maleate crystalline form XXIII.

Example 24: Preparation of the Maleate Crystalline Form XXIV of Compound 1

15 mg of Compound 1 and 2.2 mg of maleic acid was weighed and placed in a HPLC vial, added with 0.5 mL solvent EtOH, stirred at room temperature for 4 days, centrifuged for separation that solids were dried at room temperature to obtain the maleate crystalline form XXIV.

Example 25: Preparation of the Amorphous Form XXV of Compound 1

6 g of Compound 1 was added in a 250 mL bottle, added with 200 mL solvent DCM for dissolved clarification of solids. The solution was spray dried for about 30 minutes and the injection temperature was 90° C. to obtain the amorphous form of the compound 1.

Example 26: Preparation of the Acetone Solvate Crystalline Form XXVI of Compound 1

About 40 mg of the sample (crystalline form XVIII) was weighed and placed in a 4 mL glass bottle. Then 0.4 mL acetone was gradually added into the glass bottle to make a turbid sample. After adding magnetons, the sample was stirred (40° C., 600 rpm). After stirring over the weekend, the sample was still turbid. After the sample was centrifuged, the residual solids were dried in a vacuum drying oven at 25° C. to obtain the acetone solvate crystalline form XXVI.

Example 27: Preparation of the Compound 1 Benzene Sulfonate Crystalline Form XXVII The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then phenylsulfonic acid was added in the amount that the molar ratio of API to acid was 1:1 (the acid was first dissolved with 1.5 mL EtOH), stirred overnight at room temperature, centrifuged, and the residual solids were dried in a vacuum drying oven at 25° C. to obtain the Compound 1 benzene sulfonate crystalline form XXVII.

Example 28: Preparation of the Compound 1 p-Toluenesulfonate Crystalline Form XXVIII The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then p-toluenesulfonic acid was added in the amount that the molar ratio of API to acid was 1:1 (the acid was first dissolved with 1.5 mL EtOH), stirred overnight at room temperature, centrifuged, and the residual solids were dried in a vacuum drying oven at 25° C. to obtain the Compound 1 p-toluenesulfonate crystalline form XXVIII.

Example 29: Preparation of the Compound 1 p-Toluenesulfonate Crystalline Form XXIX The sample (Compound 1 p-toluenesulfonate crystalline form XXVIII) was accurately weighed about 40 mg, and placed in a 4 mL glass bottle, gradually added with 0.4 mL single or mixed solvents (methanol, acetonitrile, acetone, ethyl acetate, methanol:water 3:1 (v:v), ethanol:water 3:1 (v:v), acetonitrile:water 1:1 (v:v) or acetone:water 1:2 (v:v)) into the glass bottle to get suspension sample. After adding with magnetons, the suspension sample was stirred at 40° C. for 3 days, centrifuged, and the residual solids were dried in a vacuum drying oven at 25° C. to obtain the Compound 1 p-toluenesulfonate crystalline form XXIX.

Example 30: Preparation of the Compound 1 Sulphate Crystalline Form XXX

The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then sulfuric acid was added in the amount that the molar ratio of API to acid was 1:1 (the sulfuric acid was diluted with THF 10 times before use), stirred overnight at room temperature, centrifuged, and the residual solids were dried in a vacuum drying oven at 25° C. to obtain the Compound 1 sulphate crystalline form XXX.

Example 31: Preparation of the Compound 1 Sulphate Crystalline Form XXXI

The sample (sulphate crystalline form XXX) was accurately weighed about 40 mg, and placed in a 4 mL glass bottle, gradually added with 0.4 mL ethyl acetate into the glass bottle to get suspension sample. After adding with magnetons, the suspension sample was stirred at 40° C. for 3 days, centrifuged, and the residual solids were dried in a vacuum drying oven at 25° C. to obtain the Compound 1 sulphate crystalline form XXXI.

Example 32: Preparation of the Compound 1 Sulphate Crystalline Form XXXII

The sample (sulphate crystalline form XXX) was accurately weighed about 40 mg, and placed in a 4 mL glass bottle, gradually added with 0.4 mL acetonitrile-water (v:v 1:1) into the glass bottle to get suspension sample. After adding with magnetons, the suspension sample was stirred at 40° C. for 3 days, centrifuged, and the residual solids were dried in a vacuum drying oven at 25° C. to obtain the Compound 1 sulphate crystalline form XXXII.

Example 33: Preparation of the Compound 1 Mesylate Crystalline Form XXXIII

The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then methanesulfonic acid was added in the amount that the molar ratio of API to acid was 1:1 (the methanesulfoni acid was diluted with THF times before use), stirred overnight at room temperature, centrifuged, and the residual solids were dried in a vacuum drying oven at 25° C. to obtain the Compound 1 mesylate crystalline form XXXIII.

Example 34: Preparation of the Compound 1 Mesylate Crystalline Form XXXIV

The sample (mesylate crystalline form XXXII) was accurately weighed about 40 mg, and placed in a 4 mL glass bottle, gradually added with 0.4 mL methanol into the glass bottle to get suspension sample. After adding with magnetons, the suspension sample was stirred at 40° C. for 3 days, centrifuged, and the residual solids were dried in a vacuum drying oven at 25° C. to obtain the Compound 1 mesylate crystalline form XXXIV.

Example 35: Preparation of the Compound 1 Mesylate Crystalline Form XXXV

The sample (mesylate crystalline form XXXII) was accurately weighed about 40 mg, and placed in a 4 mL glass bottle, gradually added with 0.4 mL 1,4-dioxane into the glass bottle to get suspension sample. After adding with magnetons, the suspension sample was stirred at 40° C. for 3 days, centrifuged, and the residual solids were dried in a vacuum drying oven at 25° C. to obtain the Compound 1 mesylate crystalline form XXXV.

Example 36: Preparation of the Compound 1 Citrate Crystalline Form XXXVI

The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then citric acid was added in the amount that the molar ratio of API to acid was 1:1, stirred overnight at room temperature, centrifuged, and the residual solids were dried in a vacuum drying oven at 25° C. to obtain the Compound 1 citrate crystalline form XXXVI.

Example 37: Preparation of the Compound 1 Citrate Crystalline Form XXXVII

The sample (XXXVI) was accurately weighed about 40 mg, and placed in a 4 mL glass bottle, gradually added with 0.4 mL methanol or ethanol into the glass bottle to get suspension sample. After adding with magnetons, the suspension sample was stirred at 40° C. for 3 days, centrifuged, and the residual solids were dried in a vacuum drying oven at 25° C. to obtain the Compound 1 citrate crystalline form XXXVII.

Example 38: Preparation of the Compound 1 Citrate Crystalline Form XXXVIII

The sample (XXXVI) was accurately weighed about 40 mg, and placed in a 4 mL glass bottle, gradually added with 0.4 mL acetonitrile into the glass bottle to get suspension sample. After adding with magnetons, the suspension sample was stirred at 40° C. for 3 days, centrifuged, and the residual solids were dried in a vacuum drying oven at 25° C. to obtain the Compound 1 citrate crystalline form XXXVIII.

Example 39: Preparation of the Compound 1 Citrate Crystalline Form XXXIX

The sample (XXXVI) was accurately weighed about 40 mg, and placed in a 4 mL glass bottle, gradually added with 0.4 mL tetrahydrofuran or 1, 4-dioxane into the glass bottle to get suspension sample. After adding with magnetons, the suspension sample was stirred at 40° C. for 3 days, centrifuged, and the residual solids were dried in a vacuum drying oven at 25° C. to obtain the Compound 1 citrate crystalline form XXXIX.

Example 40: Preparation of the Compound 1 Maleate Crystalline Form XL

The sample (crystalline form XVIII) was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then maleic acid was added in the amount that the molar ratio of API to acid was 1:1, stirred overnight at room temperature, centrifuged, and the residual solids were dried in a vacuum drying oven at 25° C. to obtain the Compound 1 maleate crystalline form XL.

Example 41: Preparation of the Compound 1 Maleate Crystalline form XLI

The sample (XL) was accurately weighed about 40 mg, and placed in a 4 mL glass bottle, gradually added with 0.4 mL acetonitrile or acetonitrile-water (v:v 1:1) into the glass bottle to get suspension sample. After adding with magnetons, the suspension sample was stirred at 40° C. for 3 days, centrifuged, and the residual solids were dried in a vacuum drying oven at 25° C. to obtain the Compound 1 maleate crystalline form XLI.

Example 42: Preparation of the Compound 1 Maleate Crystalline Form XLII

The sample (XL) was accurately weighed about 40 mg, and placed in a 4 mL glass bottle, gradually added with 0.4 mL n-heptane into the glass bottle to get suspension sample. After adding with magnetons, the suspension sample was stirred at 40° C. for 3 days, centrifuged, and the residual solids were dried in a vacuum drying oven at 25° C. to obtain the Compound 1 maleate crystalline form XLII.

Example 43: Preparation of the Compound 1 Maleate Crystalline Form XLIII

The sample (XL) was accurately weighed about 40 mg, and placed in a 4 mL glass bottle, gradually added with 0.4 mL 1,4-dioxane into the glass bottle to get suspension sample. After adding with magnetons, the suspension sample was stirred at 40° C. for 3 days, centrifuged, and the residual solids were dried in a vacuum drying oven at 25° C. to obtain the Compound 1 maleate crystalline form XLIII.

Example 44: Preparation of the Compound 1 Maleate Crystalline Form XLIV

The sample (XL) was accurately weighed about 40 mg, and placed in a 4 mL glass bottle, gradually added with 0.4 mL water into the glass bottle to get suspension sample. After adding with magnetons, the suspension sample was stirred at 40° C. for 3 days, centrifuged, and the residual solids were dried in a vacuum drying oven at 25° C. to obtain the Compound 1 maleate crystalline form XLIV.

Example 45: Preparation of the Compound 1 Tartrate Crystalline Form XLV

The crystalline form XVIII was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then tartaric acid was added in the amount that the molar ratio of API to acid was 1:1, stirred overnight at room temperature, centrifuged, and the residual solids were dried in a vacuum drying oven at 25° C. to obtain the Compound 1 tartrate crystalline form XLV.

Example 46: Preparation of the Compound 1 Hydrochloride Crystalline Form XLVI The crystalline form XVIII was accurately weighed about 176.5 mg, and placed in a 4 mL glass bottle. Then 1 mL DCM and 2 mL THF were added to dissolve and heated to help dissolve. After adding with magnetons, the sample was placed on a stirrer for stirring. Then hydrochloric acid was added in the amount that the molar ratio of API to acid was 1:1 (the hydrochloric acid was diluted with THF 10 times before use), stirred overnight at room temperature, centrifuged, and the residual solids were dried in a vacuum drying oven at 25° C. to obtain the Compound 1 hydrochloride crystalline form XLVI.

Example 47: Preparation of the Compound 1 Hydrochloride Crystalline Form XLVII The crystalline form XVIII was accurately weighed about 1058.9 mg, and placed in a 20 mL glass bottle. Then 6 mL DCM and 12 mL THF were added to dissolve and heated to help dissolve. After adding with magnetons, the sample was placed on a stirrer for stirring. Then hydrochloric acid was added in the amount that the molar ratio of API to acid was 1:1 (the hydrochloric acid was diluted with THF 10 times before use), stirred overnight at room temperature, centrifuged, and the residual solids were dried in a vacuum drying oven at 25° C. to obtain the Compound 1 hydrochloride crystalline form XLVII.

Example 48: Preparation of the Compound 1 Hydrochloride Crystalline Form XLVIII The sample (XLVII) was accurately weighed about 40 mg, and placed in a 4 mL glass bottle, gradually added with 0.4 mL methyl alcohol into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form XLVIII.

Example 49: Preparation of the Compound 1 Hydrochloride Crystalline Form XLIX The sample (XLVII) was accurately weighed about 40 mg, and placed in a 4 mL glass bottle, gradually added with 0.4 mL ethanol or n-heptane into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form XLIX.

Example 50: Preparation of the Compound 1 Hydrochloride Crystalline Form L

The sample (XLVII) was accurately weighed about 40 mg, and placed in a 4 mL glass bottle, gradually added with 0.4 mL acetonitrile into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form L.

Example 51: Preparation of the Compound 1 Hydrochloride Crystalline Form LI

The sample (XLVII) was accurately weighed about 40 mg, and placed in a 4 mL glass bottle, gradually added with 0.4 mL acetone (or acetone-water 1:2, ethanol-water 3:1) into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form LI.

Example 52: Preparation of the Compound 1 Hydrochloride Crystalline Form LII The sample (XLVII) was accurately weighed about 40 mg, and placed in a 4 mL glass bottle, gradually added with 0.4 mL ethyl acetate into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form LII.

Example 53: Preparation of the Compound 1 Hydrochloride Crystalline Form LIII The sample (XLVII) was accurately weighed about 40 mg, and placed in a 4 mL glass bottle, gradually added with 0.4 mL 1,4-dioxane into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form LIII.

Example 54: Preparation of the Compound 1 Hydrochloride Crystalline Form LIV The sample (XLVII) was accurately weighed about 40 mg, and placed in a 4 mL glass bottle, gradually added with 0.4 mL water into the glass bottle to get suspension sample. After adding with magnetons, the suspension sample was stirred at 40° C. for 3 days, centrifuged, and the residual solids were dried in a vacuum drying oven at 25° C. to obtain the Compound 1 hydrochloride crystalline form LIV.

Example 55: Preparation of the Compound 1 Hydrochloride Crystalline Form LV

The sample (XLVII) was accurately weighed about 40 mg, and placed in a 4 mL glass bottle, gradually added with 0.4 mL methanol-water 3:1 into the glass bottle to get suspension sample. After adding with magnetons, the suspension sample was stirred at 40° C. for 3 days, centrifuged, and the residual solids were dried in a vacuum drying oven at 25° C. to obtain the Compound hydrochloride crystalline form LV.

Example 56: Identification and Characterization of Compound 1 Form I-LV and DVS Test of Compound 1

The used instruments and their parameters are described as follows:
1. XRPD X-Ray Powder Diffraction

TABLE 55

| X rays Cu, Kα, | Kα1 (Å): 1.540598, Kα2 (Å): 1.544426 Kα2/Kα1 intensity ratio: 0.50 | Kα1 (Å): 1.540598, Kα2 (Å): 1.544426 Kα2/Kα1 intensity ratio: 0.50 | Kα1 (Å): 1.5406 Kα2 (Å): 1.54439 Kα2/Kα1 intensity ratio: 0.50 | Kα(Å): 1.5406 |
|---|---|---|---|---|
| Setting of X-ray tube | 45 kV, 40 mA | 45 kV, 40 mA | 30 kV, 10 mA | 40 KV, 40 mA |
| Divergence slit | Auto | 1/8° | 0.6 mm | 1.0 mm |
| Scanning range (°2Theta) | 3°-40° | 3°-40° | 3°-40° | 3°-40° |
| Scanning time per step (s) | 17.8 | 46.7 | 0.1 | 0.1 |
| Scanning step size (°2Theta) | 0.0167 | 0.0263 | 0.0201 | 0.02 |

2. TGA—Thermogravimetric Analysis and DSC—Differential Scanning Calorimetry

TABLE 56-1

| Parameter | TA Instruments TGA | TA Instruments DSC |
|---|---|---|
| Method | Linear temperature | Linear temperature |
| Sample plate | Platinum plate, open | Aluminum plate, Gland/Ungland |
| Temperature range | Room temperature-set the end temperature | 25° C. - set the end temperature |
| Scanning rate (° C./min) | 10 | 10 |
| Shielding gas | Nitrogen | Nitrogen |

TABLE 56-2

| mDSC | |
|---|---|
| Parameter | Set value |
| Test mode | Conventional mDSC |
| Amplitude (° C.) | 1.0 |
| Modulation period (sec.) | 60 |
| Scanning rate (° C./Minute) | 3.0 |
| Shielding gas | Nitrogen |

3. DVS

TABLE 57

| Parameter | Set value |
|---|---|
| Temperature | 25° C. |
| Amount of sample | 10-20 mg |
| Shielding gas and rate of flow | N₂, 200 ml/minute |
| dm/dt | 0.002%/minute |
| Minimum equilibrium time | 10 minute |
| Maximum equilibrium time | 180 minute |
| RH range | 0% RH-90% RH-0% RH |
| RH gradient | 10%(0% RH-90% RH, 90% RH-0% RH) 5%(90% RH-95% RH, 95% RH-90% RH) |

Example 57: Anti-Solvent Method was Used to Prepare Forms of Compound 1

15 mg of Compound 1 was weighed into a 20 mL vial, and added with 0.4-2.0 mL of solvent to completely dissolve the solids. Anti-solvent was added dropwise to the clarifying solution while stirring until solids were precipitated, or when the total volume of anti-solvent was increased to 15 mL, the sample without solid precipitation was suspended and stirred at 5° C. for 20 hours. If there was still no solid precipitation, the sample was evaporated at room temperature, and the precipitated solids were separated and XRPD test was performed. The related results are shown in Table 58 below.

TABLE 58

| No. | Solvent | Anti-solvent | Solid Form |
|---|---|---|---|
| 1 | THF | Water | Crystalline Form XVII |
| 2 | | n-Heptane | Crystalline Form XVII |
| 3 | | Methanol | Crystalline Form VII |
| 4 | | Methyl tert-butyl ether | Amorphous Form |
| 5 | Acetone | Ethyl Alcohol | Crystalline Form XVII |
| 6 | | n-Heptane | Crystalline Form XVII |
| 7 | | Water | Crystalline Form XIII |
| 8 | 1,4-dioxane | Isopropanol | Crystalline Form XVII |
| 9 | | Isopropyl Acetate | Crystalline Form I |
| 10 | | Methyl tert-butyl ether | Crystalline Form VII |
| 11 | | Water | Crystalline Form IV |

Example 58: Slow Evaporation Method was Used to Prepare Forms of Compound 1

15 mg of Compound 1 was weighed into a 3 mL vial, and added with 0.5-3.0 mL of solvent to dissolve respectively (the undissolved sample was filtered by 0.45 μm PTFE filter head). The vial was sealed with the Parafilm® sealing film, poked 4 pinholes in the top, and evaporated slowly at room temperature, and the solids were collected and XRPD test was performed. The related results are shown in Table 59 below.

TABLE 59

| No. | Solvent | Solid Form |
| --- | --- | --- |
| 1 | Acetone | Crystalline Form I + Crystalline Form XVII |
| 2 | THF | Crystalline Form X |
| 3 | 1,4-Dioxane | Crystalline Form IV |
| 4 | Dichloromethane | Crystalline Form V |
| 5 | Ethyl acetate | Crystalline Form V |
| 6 | 2-Methyltetrahydrofuran/ Methyl tert-butyl ether (1:1) | Crystalline Form IX |
| 7 | Dichloromethane/Heptane (1:1) | Crystalline Form XVII |
| 8 | THF/Methanol (1:1) | Crystalline Form VII |

Example 59: Gas-Liquid Diffusion Method was Used to Prepare Forms of Compound 1

15 mg of Compound 1 was weighed into a 3 mL vial, and added with 0.5-2.0 mL of solvent to dissolve (the undissolved sample was filtered by 0.45 μm PTFE filter head). Another 20 mL bottle was taken to add with 3 mL of anti-solvent. The 3 mL open vial containing the clear liquid was put into the 20 mL bottle. The 20 mL bottle was sealed and standed at room temperature for 1-7 days, and the solids were collected and XRPD test was performed. The related results are shown in Table 60 below.

TABLE 60

| No. | Solvent | Anti-solvent | Solid Form |
| --- | --- | --- | --- |
| 1 | THF | Ethyl Alcohol | Crystalline Form XVII |
| 2 | | Water | Crystalline Form XVII |
| 3 | | Methyl tert-butyl ether | Crystalline Form XVII |
| 4 | 2-Methyl-tetrahydrofuran | n-Heptane | Crystalline Form XVII |
| 5 | | Methyl tert-butyl ether | Crystalline Form XVII |
| 6 | 1,4-Dioxane | Isopropanol | Crystalline Form IV |
| 7 | | n-Heptane | Crystalline Form IV |
| 8 | | Isopropyl Acetate | Crystalline Form IV |
| 9 | Acetone | Toluene | Crystalline Form II and Crystalline Form XVII |
| 10 | Trichloromethane | n-Heptane | Crystalline Form VIII |
| 11 | | Methanol | Crystalline Form VIII |
| 12 | | Acetonitrile | Crystalline Form VIII |

Example 60: Suspension Stirring Method at Room Temperature was Used to Prepare Forms of Compound 1

15 mg of Compound 1 was weighed into a 1.5 mL glass vial, and added with 0.5 mL of solvent respectively to get turbid liquid, and standed at room temperature under magnetic stirring for 5 days, and the centrifugal solids were collected and XRPD test was performed. The related results are shown in Table 61 below.

TABLE 61

| No. | Solvent | Solid Form |
| --- | --- | --- |
| 1 | Ethyl Alcohol | Crystalline Form VII |
| 2 | Methyl isobutyl ketone | Crystalline Form V |
| 3 | Ethyl acetate | Crystalline Form V |
| 4 | Methyl tert-butyl ether | Crystalline Form IX |
| 5 | Acetonitrile | Crystalline Form XI |
| 6 | n-Heptane | Crystalline Form I |

TABLE 61-continued

| No. | Solvent | Solid Form |
| --- | --- | --- |
| 7 | Water | Amorphous Form |
| 8 | THF/Water (1:9) | Crystalline Form I |

Example 61: Suspension Stirring Method at 50° C. was Used to Prepare Forms of Compound 1

15 mg of Compound 1 was weighed into a 1.5 mL glass vial, and added with 0.5 mL of solvent respectively to get turbid liquid, and standed at 50° C. under magnetic stirring for 5 days, and the centrifugal solids were collected and XRPD test was performed. The related results are shown in Table 62 below.

TABLE 62

| No. | Solvent | Solid Form |
| --- | --- | --- |
| 1 | Ethyl Alcohol | Crystalline Form VI |
| 2 | Methyl isobutyl ketone | Crystalline Form III |
| 3 | Ethyl acetate | Crystalline Form V |
| 4 | Methyl tert-butyl ether | Crystalline Form VIII |
| 5 | Acetonitrile | Crystalline Form IX |
| 6 | Water | Amorphous Form |
| 7 | THF/Water (1:9) | Crystalline Form III |

Example 62: Slow Cooling Method was Used to Prepare Forms of Compound 1

15 mg of Compound 1 was weighed into a 3 mL glass vial, and added with 1.0 mL of solvent, and standed at 50° C. under stirring for 1 hour to filter to obtain the supernatant. The resulting supernatant was cooled from 50° C. to 5° C. at 0.1° C./min and kept in a bio-incubator at a constant temperature at 5° C. The precipitated solids were collected and XRPD test was performed. The samples without precipitated solids were transferred to room temperature for volatilization. The related results are shown in Table 63 below.

TABLE 63

| No. | Solvent | Solid Form |
| --- | --- | --- |
| 1 | Ethyl acetate | Crystalline Form V |
| 2 | Acetonitrile | Amorphous Form |
| 3 | Toluene | Amorphous Form |
| 4 | THF/Water (1:1) | Crystalline Form XIV |
| 5 | Trichloromethane/Heptane(1:1) | Amorphous Form |

Example 63: Gas-Solid Penetration Method was Used to Prepare Forms of Compound 1

15 mg of Compound 1 was weighed into a 3 mL vial. Another 20 mL bottle was taken to add with 2 mL of solvent. The 3 mL open vial was put into the 20 mL bottle. The 20 mL bottle was sealed and standed at room temperature for 7 days, and the solids were collected and XRPD test was performed. The related results are shown in Table 64 below.

TABLE 64

| No. | Solvent | Solid Form |
| --- | --- | --- |
| 1 | Water | Crystalline Form I |
| 2 | Ethyl Alcohol | Crystalline Form XV |
| 3 | Acetone | Crystalline Form XVII |
| 4 | Ethyl acetate | Crystalline Form V |
| 5 | Methyl tert-butyl ether | Crystalline Form IX |
| 6 | Acetonitrile | Crystalline Form XI |
| 7 | 2-Methyltetrahydrofuran | Crystalline Form XVII |
| 8 | 1,4-Dioxane | Crystalline Form IV |
| 9 | Methanol | Crystalline Form VII |
| 10 | DMF | Crystalline Form XVI |

Example 64: Competitive Experiment

To study the stability relationship between anhydrous Crystalline Forms of the compound 1, suspension competitive agitation tests were carried out at different temperatures and in different solvents. With crystalline form I, crystalline form III, crystalline form XV, crystalline form XVII and crystalline form XVIII as raw materials, the suspension samples were suspended and stirred for 3 days in the saturated solution of IPA and MTBE at different temperatures (room temperature, 50° C. and 70° C.), and then the samples were centrifuged to separate and the solid XRPD was tested. The results were summarized in Table 65 below.

TABLE 65

| Starting Material | Solvent | Temperature | Crystalline Form |
| --- | --- | --- | --- |
| Crystalline Form I, Crystalline Form III, Crystalline Form XV, Crystalline Form XVII, Crystalline Form XVIII | IPA | Room temperature | Crystalline Form III |
| | | 50° C. | Crystalline Form III |
| | | 70° C. | Crystalline Form III |
| | MTBE | Room temperature | Crystalline Form III |
| | | 50° C. | Crystalline Form III |
| | | 70° C. | Crystalline Form III |

To study the stability relationship between Crystalline Form III and Crystalline Form XVIII, using Crystalline Form III and Crystalline Form XVIII as raw materials, suspension samples were suspended and stirred in a saturated solution of 3 solvents (EtOAc, MTBE and n-butyl alcohol) at different temperatures (room temperature, 50° C. and 70° C.) for 7 days, and then the samples were centrifuged to separate and the XRPD of solid was tested. The results were summarized in Table 66 below.

TABLE 66

| Starting Material | Slovent | Temperature | Crystalline Form |
| --- | --- | --- | --- |
| Crystalline Form III and Crystalline Form XVIII | EtOAc | Room temperature | Crystalline Form V |
| | | 50° C. | Crystalline Form III |
| | | 70° C. | Crystalline Form III |
| | MTBE | Room temperature | Crystalline Form III + Crystalline Form XVIII |
| | | 50° C. | Crystalline Form III |
| | | 70° C. | Crystalline Form III |
| | n-Butyl alcohol | Room temperature | Crystalline Form III + Crystalline Form XVIII |
| | | 50° C. | Crystalline Form III |
| | | 70° C. | Crystalline Form III |

The interconversion rate of crystalline form III and crystalline form XVIII at room temperature is relatively slow, and the stability of crystalline form III and crystalline form XVIII at room temperature is similar.

Example 65: Stability Test (1) The crystalline form III, crystalline form XVIII and amorphous form XXV was placed at 80° C. (sealed) for 24 hours, at 40° C./75% RH and 25° C./60% RH (open) for 1 week, respectively. The physical and chemical stability of the samples were tested by XRPD and HPLC. The test data are listed in Table 67. The crystalline form of the three samples did not change after being placed under the three conditions, showing good physical stability. The HPLC purity results showed that the three samples did not degrade after being placed under the three conditions, showing good chemical stability.

TABLE 67

| Form at starting point | Condition | purity (area %) | Form |
| --- | --- | --- | --- |
| Crystalline Form III | starting point | 98.65 | Crystalline Form III |
| | 80° C. 24 hours | 98.64 | Crystalline Form III |
| | 25° C./60% RH 1 week | 98.66 | Crystalline Form III |
| | 40° C./75% RH 1 week | 98.67 | Crystalline Form III |
| Crystalline Form XVIII | starting point | 99.48 | Crystalline Form XVIII |
| | 80° C. 24 hours | 99.61 | Crystalline Form XVIII |
| | 25° C./60% RH 1 week | 99.60 | Crystalline Form XVIII |
| | 40° C./75% RH 1 week | 99.61 | Crystalline Form XVIII |
| Amorphous form XXV | starting point | 99.43 | Amorphous form XXV |
| | 80° C. 24 hours | 99.42 | Amorphous form XXV |
| | 25° C./60% RH 1 week | 99.42 | Amorphous form XXV |
| | 40° C./75% RH 1 week | 99.45 | Amorphous form XXV |

(2) Weigh 20~30 mg of the salt crystalline form of the compound 1 into an 8 mL glass bottle, and then place it at high temperature (60° C., open), high humidity (room temperature/75RH, open) and light (room temperature, white light: 6980 lux, UV 282 µW/cm2), samples were taken on the 5th, 10th, and 30th day for detection (HPLC, XRPD). The results are shown in Table 68-75.

TABLE 68

| Sample | Test condition | Time point | total impurities (%) | XPRD |
| --- | --- | --- | --- | --- |
| XXVII | The initial sample | 0 day | 1.19 | XXVII |
| | 60° C. | 5 days | 1.26 | No change |
| | RT/75% RH | | 1.22 | No change |
| | light | | 1.20 | No change |
| | 60° C. | 10 days | 1.37 | No change |
| | RT/75% RH | | 1.25 | No change |
| | light | | 1.28 | No change |
| | 60° C. | 30 days | 1.33 | No change |
| | RT/75% RH | | 1.27 | No change |

TABLE 69

| Sample | Test condition | Time point | total impurities (%) | XPRD |
|---|---|---|---|---|
| XXIX | The initial sample | 0 day | 0.65 | XXIX |
| | 60° C. | 5 days | 0.64 | No change |
| | RT/75% RH | | 0.65 | No change |
| | light | | 0.64 | No change |
| | 60° C. | 10 days | 0.65 | No change |
| | RT/75% RH | | 0.65 | No change |
| | light | | 0.59 | No change |
| | 60° C. | 30 days | 0.66 | No change |
| | RT/75% RH | | 0.60 | No change |

TABLE 70

| Sample | Test condition | Time point | total impurities (%) | XPRD |
|---|---|---|---|---|
| XXX | The initial sample | 0 day | 0.80 | XXX |
| | 60° C. | 5 days | 0.89 | No change |
| | RT/75% RH | | 0.82 | No change |
| | light | | 0.82 | No change |
| | 60° C. | 10 days | 0.92 | No change |
| | RT/75% RH | | 0.86 | No change |
| | light | | 1.02 | No change |
| | 60° C. | 30 days | 0.83 | No change |
| | RT/75% RH | | 0.74 | No change |

TABLE 71

| Sample | Test condition | Time point | total impurities (%) | XPRD |
|---|---|---|---|---|
| XXXIX | The initial sample | 0 day | 0.76 | XXXIX |
| | 60° C. | 5 days | 0.90 | No change |
| | RT/75% RH | | 0.80 | No change |
| | light | | 0.88 | No change |
| | 60° C. | 10 days | 0.89 | No change |
| | RT/75% RH | | 0.82 | No change |
| | light | | 1.02 | No change |
| | 60° C. | 30 days | 0.86 | No change |
| | RT/75% RH | | 0.81 | No change |

TABLE 72

| Sample | Test condition | Time point | total impurities (%) | XPRD |
|---|---|---|---|---|
| XXXVI | The initial sample | 0 day | 1.02 | XXXVI |
| | 60° C. | 5 days | 0.97 | changed |
| | RT/75% RH | | 0.95 | XXXVI A slight change |
| | light | | 1.06 | no change |
| | 60° C. | 10 days | 1.01 | changed |
| | RT/75% RH | | 0.95 | XXXVI A slight change |
| | light | | 1.36 | no change |
| | 60° C. | 30 days | 0.98 | changed |
| | RT/75% RH | | 1.00 | XXXVI A slight change |

TABLE 73

| Sample | Test condition | Time point | total impurities (%) | XPRD |
|---|---|---|---|---|
| XL | The initial sample | 0 day | 0.91 | XL |
| | 60° C. | 5 days | 1.15 | No change |
| | RT/75% RH | | 0.93 | No change |
| | light | | 1.08 | No change |
| | 60° C. | 10 days | 1.18 | No change |
| | RT/75% RH | | 1.06 | No change |
| | light | | 1.18 | No change |
| | 60° C. | 30 days | 1.28 | No change |
| | RT/75% RH | | 0.90 | XL A slight change |

TABLE 74

| Sample | Test condition | Time point | total impurities (%) | XPRD |
|---|---|---|---|---|
| XXIV | The initial sample | 0 day | 0.50 | XXIV |
| | 60° C. | 5 days | 0.48 | No change |
| | RT/75% RH | | 0.50 | No change |
| | light | | 0.73 | No change |
| | 60° C. | 10 days | 0.48 | No change |
| | RT/75% RH | | 0.50 | No change |
| | light | | 0.72 | No change |
| | 60° C. | 30 days | 0.61 | No change |
| | RT/75% RH | | 0.50 | No change |

TABLE 75

| Sample | Test condition | Time point | total impurities (%) | XPRD |
|---|---|---|---|---|
| XXXIII | The initial sample | 0 day | 0.67 | XXXIII |
| | 60° C. | 5 days | 0.90 | XXXIII A slight change |
| | RT/75% RH | | 0.67 | XXXIII A slight change |
| | light | | 0.84 | No change |
| | 60° C. | 10 days | 0.91 | XXXIII A slight change |
| | RT/75% RH | | 0.71 | XXXIII A slight change |
| | light | | 1.09 | No change |
| | 60° C. | 30 days | 1.11 | XXXIII A slight change |
| | RT/75% RH | | 0.70 | XXXIII A slight change |

Example 66. The Evaluation of Hygroscopicity

Started with 0 humidity (0% RH) through the Dynamic Moisture Sorption Analyzer (DVS), under constant temperature conditions, when the humidity changed (0% RH-95% RH-0% RH), the moisture adsorption of the crystalline form III at 80% RH/25° C. is 0.9%, showing slight hygroscopicity. The XRPD characterization result of the sample after the DVS test indicated that the crystalline form III did not change after the DVS test (FIGS. 166-167).

The test results of the crystalline form XVIII are shown in FIGS. 168-169. The moisture adsorption of the crystalline form XVIII at 80% RH/25° C. is 0.04%, showing almost no moisture absorption. The XRPD characterization result of the sample after the DVS test indicates that the crystalline form XVIII did not change after the DVS test.

The DVS diagrams, weight increase by hygroscopy and XRPD results before and after DVS of some salt crystalline forms are shown in Table 76 and FIGS. 170-177.

TABLE 76

| Form | weight increase by hygroscopy (80% RH) | XRPD change |
| --- | --- | --- |
| XXVII | 3.32% | no change |
| XXIX | 0.948% | no change |
| XXX | 0.90% | no change |
| XXXIX | 0.37% | no change |
| XXXVI | 2.00% | no change |
| XL | 1.41% | no change |
| XXIV | 1.246% | changed |
| XXXIII | 7.82% | changed |

Each reference, including all patents, patent applications and publications referenced in this application, is incorporated herein by reference in its entirety as if each of them were incorporated separately. In addition, it is understood that in the teaching of the present invention, the technicians in the art may make certain changes or modifications to the present invention and that these equivalents will remain within the scope of the present invention as limited by the claims appended to the application.

What is claimed is:

1. The methylbenzene solvate crystalline form VI of Compound (1) or its salt or solvate:

compound 1

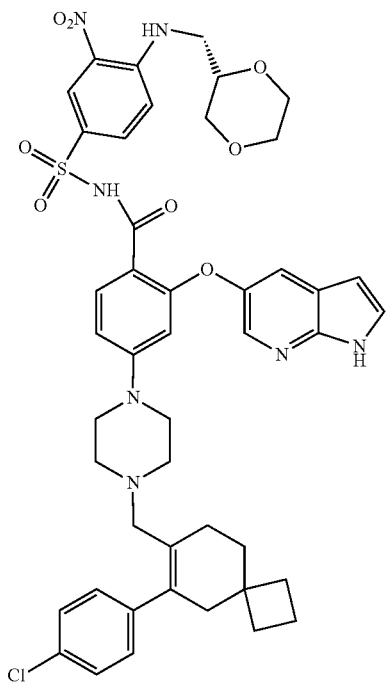

having characteristic peaks at positions in the XRPD pattern represented by angles 2θ: 7.16±0.2°, 18.02±0.2°, 18.76±0.2°, 19.97±0.2° and 20.64±0.2°.

2. The form according to claim 1, which has the following characteristics:

1) in the TGA plot, there is a weight loss of 3.7±0.2% by weight before 150° C.; and/or 2) in the DSC curve, there are two endothermic peaks at the initial temperatures of 140.9±2.0° C. and 181.3±2.0° C.

3. A pharmaceutical composition, comprising a crystalline form or amorphous form of the Compound (1) selected from a group consisting of:

1) the methylbenzene solvate crystalline form VI of Compound (1) or its salt;

2) the acetone solvate crystalline form XII of Compound (1) or its salt;

3) the crystalline form XVIII of Compound (1) or its salt or solvate;

4) the amorphous form XXV of Compound (1) or its salt or solvate; and 5) the acetone solvate crystalline form XXVI of Compound (1) or its salt.

4. A method of treating a hyperproliferative disease, comprising administering to a patient in need thereof a crystalline form or amorophous form of Compound (1) selected from a group consisting of:

1) the methylbenzene solvate crystalline form VI of Compound (1) or its salt;

2) the acetone solvate crystalline form XII of Compound (1) or its salt;

3) the crystalline form XVIII of Compound (1) or its salt or solvate;

4) the amorphous form XXV of Compound (1) or its salt or solvate; and 5) the acetone solvate crystalline form XXVI of Compound (1) or its salt, wherein the disease is selected from: acute mononuclear leukemia, acute myelogenous leukemia, chronic myelogenous leukemia, chronic lymphocytic leukemia, mixed lineage leukemia, the NUT midline carcinoma, multiple myeloma, small cell lung cancer, neuroblastoma, burkitt lymphoma, cervical cancer, esophageal cancer, ovarian cancer, colorectal cancer, prostate cancer and breast cancer.

5. The acetone solvate crystalline form XII of Compound (1) or its salt:

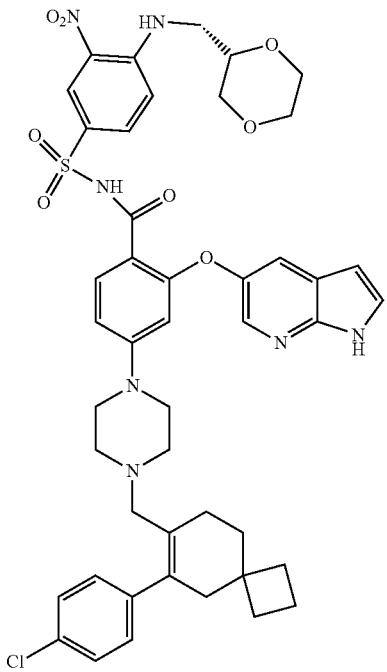

Compound (1)

having characteristic peaks at positions in the XRPD pattern represented by angles 2θ: 5.42±0.2°, 13.62±0.20° 15.64±0.2°, 21.62±0.2° and 22.19±0.2°.

6. The form according to claim 5, which has the following characteristics:
 1) in the TGA plot, there is a weight loss of 1.0±0.2% by weight before 90° C., and a weight loss of 3.6±0.2% by weight between 90° C. and 150° C.; and/or
 2) in the DSC curve, there are two endothermic peaks at the peak temperature of 59.1±2.0° C., and the initial temperature of 146.2±2.0° C.

7. The crystalline form XVIII of Compound (1) or its salt or solvate:

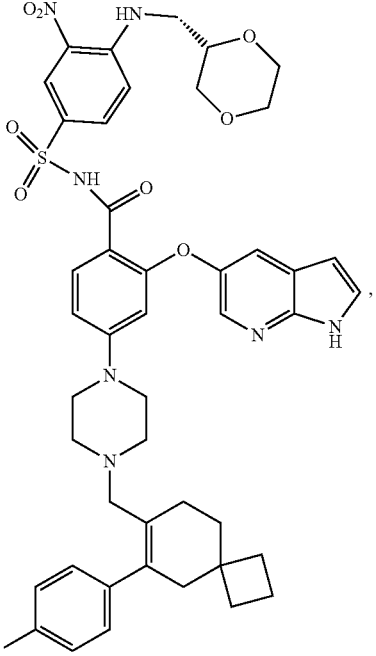

Compound (1)

having characteristic peaks at positions in the XRPD pattern represented by angles 2θ: 5.93±0.2°, 8.61±0.2°, 17.28±0.2°, 20.60±0.2°, 21.45±0.2° and 21.76±0.2°.126.

8. The form according to claim 7, which has the following characteristics:
 1) in the TGA plot, there is a weight loss of 0.3±0.2% by weight before 150° C.; and/or
 2) in the DSC curve, there is an endothermic peak at the initial temperature of 206.7±2.0° C.

9. The amorphous form XXV of Compound (1) or its salt or solvate:

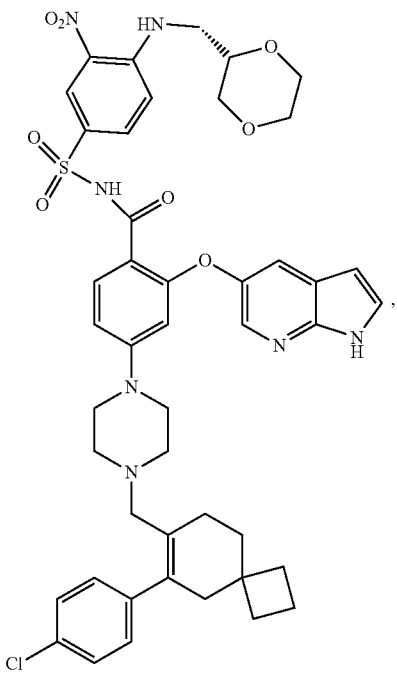

Compound (1)

having the following characteristics:
1) in the TGA plot, there is a weight loss of 3.0±0.2% by weight before 150° C.; and/or
2) in the DSC curve, there is a glassy transition temperature at the midpoint temperature of 121.5±2.0° C.

10. The acetone solvate crystalline form XXVI of Compound (1) or its salt or solvate:

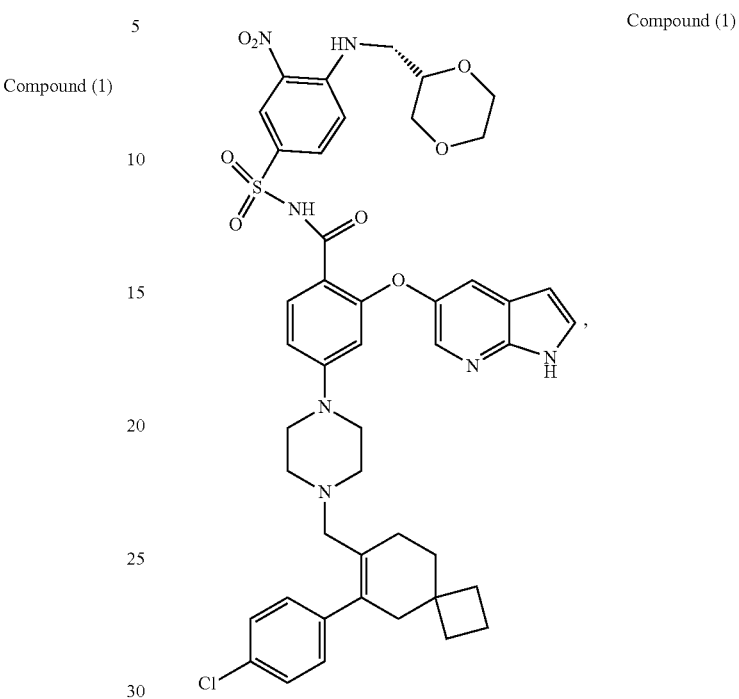

Compound (1)

having characteristic peaks at positions in the XRPD pattern represented by angles 2θ: 6.12±0.2°, 8.07±0.2°, 16.79±0.2°, 17.90±0.2°, 19.09±0.2° and 22.39±0.2°.

11. The form according to claim 10, which has the following characteristics:
1) in the TGA plot, there is a weight loss of 0.18±0.02% by weight before 74.2° C., and a weight loss of 5.0±0.2% by weight between 74.2° C. and 168.55° C.; and/or
2) in the DSC curve, there is an endothermic peaks at the initial temperature of 137.1±2.0° C.

* * * * *